US008889670B2

(12) United States Patent
Bartolozzi et al.

(10) Patent No.: US 8,889,670 B2
(45) Date of Patent: Nov. 18, 2014

(54) HETEROCYCLIC COMPOUNDS WHICH MODULATE THE CB2 RECEPTOR

(75) Inventors: Alessandra Bartolozzi, Norwalk, CT (US); Angela Berry, Gaylordsville, CT (US); Pier Francesco Cirillo, Woodbury, CT (US); Eugene Richard Hickey, Danbury, CT (US); Doris Riether, Biberach an der Riss (DE); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 194 days.

(21) Appl. No.: 13/147,432

(22) PCT Filed: Feb. 16, 2010

(86) PCT No.: PCT/US2010/024270
§ 371 (c)(1),
(2), (4) Date: Aug. 23, 2011

(87) PCT Pub. No.: WO2010/096371
PCT Pub. Date: Aug. 26, 2010

(65) Prior Publication Data
US 2011/0312944 A1 Dec. 22, 2011

Related U.S. Application Data

(60) Provisional application No. 61/153,333, filed on Feb. 18, 2009.

(51) Int. Cl.
*A61K 31/4545* (2006.01)
*C07D 211/60* (2006.01)
*C07D 401/12* (2006.01)
*C07D 405/04* (2006.01)
*C07D 413/12* (2006.01)
*C07D 417/12* (2006.01)
*C07D 417/14* (2006.01)

(52) U.S. Cl.
CPC ............ *C07D 413/12* (2013.01); *C07D 211/60* (2013.01); *C07D 401/12* (2013.01); *C07D 405/04* (2013.01); *C07D 417/12* (2013.01); *C07D 417/14* (2013.01)
USPC .................. 514/227.8; 514/237.2; 514/253.1; 514/316; 514/318; 514/321; 514/326; 544/58.2; 544/60; 544/129; 544/364; 546/187; 546/193; 546/194; 546/198; 546/207; 546/209; 546/210

(58) Field of Classification Search
USPC ........ 514/227.8, 237.2, 253.1, 316, 318, 321, 514/326; 544/58.2, 60, 129, 364; 546/187, 546/193, 194, 198, 207, 209, 210
See application file for complete search history.

(56) References Cited

U.S. PATENT DOCUMENTS

| 4,734,125 | A | 3/1988 | Gehring et al. |
|---|---|---|---|
| 5,491,170 | A | 2/1996 | Lee et al. |
| 5,834,490 | A * | 11/1998 | Verde-Casanova et al. .. 514/330 |
| 5,958,940 | A | 9/1999 | Rane et al. |
| 6,756,404 | B2 | 6/2004 | Livinghouse |
| 6,930,115 | B2 | 8/2005 | Fujii et al. |
| 7,585,881 | B2 | 9/2009 | Edwards et al. |
| 7,595,397 | B2 | 9/2009 | Zindell et al. |
| 7,776,897 | B2 | 8/2010 | Murakami et al. |
| 7,928,123 | B2 | 4/2011 | Berry et al. |
| 7,935,715 | B2 | 5/2011 | Berry et al. |
| 8,048,899 | B2 | 11/2011 | Bartolozzi et al. |
| 8,173,638 | B2 | 5/2012 | Berry et al. |
| 8,178,568 | B2 | 5/2012 | Regan et al. |
| 8,299,103 | B2 | 10/2012 | Bartolozzi et al. |
| 8,299,111 | B2 | 10/2012 | Berry et al. |
| 8,329,735 | B2 | 12/2012 | Ermann et al. |
| 8,546,563 | B2 | 10/2013 | Berry et al. |
| 2004/0152747 | A1 | 8/2004 | Chen et al. |
| 2004/0242666 | A1 | 12/2004 | Chen |
| 2005/0222219 | A1 | 10/2005 | Chen |
| 2006/0009491 | A1 | 1/2006 | Yao et al. |
| 2006/0173022 | A1 | 8/2006 | Schaper |
| 2007/0191340 | A1 | 8/2007 | Zindell et al. |
| 2007/0270426 | A1 | 11/2007 | Chen |
| 2008/0039464 | A1 | 2/2008 | Berry et al. |
| 2008/0081822 | A1 | 4/2008 | Berry et al. |
| 2008/0227781 | A1 | 9/2008 | Brodney et al. |
| 2009/0275611 | A1 | 11/2009 | Riether et al. |
| 2010/0009964 | A1 | 1/2010 | Berry et al. |
| 2010/0029644 | A1 | 2/2010 | Riether et al. |
| 2010/0081644 | A1 | 4/2010 | Bartolozzi et al. |
| 2010/0261708 | A1 | 10/2010 | Cirillo et al. |
| 2010/0331304 | A1 | 12/2010 | Berry et al. |
| 2011/0071127 | A1 | 3/2011 | Berry et al. |
| 2011/0071196 | A1 | 3/2011 | Bartolozzi et al. |
| 2011/0124696 | A1 | 5/2011 | Regan et al. |
| 2011/0130431 | A1 | 6/2011 | Berry et al. |
| 2011/0136869 | A1 | 6/2011 | Bartolozzi et al. |
| 2011/0190256 | A1 | 8/2011 | Cirillo et al. |

(Continued)

FOREIGN PATENT DOCUMENTS

| DE | 36 36 278 | * | 5/1988 |
|---|---|---|---|
| GB | 1237126 A | | 6/1971 |

(Continued)

OTHER PUBLICATIONS

Stalberg et al., Capillary Electrophoretic Separation of Basic Drugs Using Surface-Modified C8 Capillaries and Derivatized Cyclodextrins as Structural/Chiral Selectors, Chromatographia, vol. 40, No. 11/12, pp. 697-704, Jun. 1995.*

(Continued)

*Primary Examiner* — Brenda Coleman
(74) *Attorney, Agent, or Firm* — Michael P. Morris; Anthony P. Bottino

(57) ABSTRACT

Compounds which modulate the CB2 receptor are disclosed. Compounds according to the invention bind to and are agonists of the CB2 receptor, and are useful for treating inflammation. Those compounds which are agonists are additionally useful for treating pain.

13 Claims, No Drawings

(56) References Cited

U.S. PATENT DOCUMENTS

| | | |
|---|---|---|
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |

FOREIGN PATENT DOCUMENTS

| | | | |
|---|---|---|---|
| JP | 2006504796 A | | 2/2006 |
| JP | 2006-143667 | * | 6/2006 |
| JP | 2006525990 A | | 11/2006 |
| JP | 2007502828 A | | 2/2007 |
| JP | 2007530525 A | | 11/2007 |
| JP | 2007530661 A | | 11/2007 |
| WO | 9811097 A1 | | 3/1998 |
| WO | 9965889 A1 | | 12/1999 |
| WO | 0008015 A2 | | 2/2000 |
| WO | 02088089 A1 | | 7/2002 |
| WO | 03074493 A1 | | 9/2003 |
| WO | 2004014370 A2 | | 2/2004 |
| WO | 2004014902 A2 | | 2/2004 |
| WO | 2004026301 A1 | | 4/2004 |
| WO | 2004042351 A2 | | 5/2004 |
| WO | 2005044797 A1 | | 5/2005 |
| WO | 2005068448 A1 | | 7/2005 |
| WO | 2005077345 A1 | | 8/2005 |
| WO | 2005077368 A2 | | 8/2005 |
| WO | 2005077373 A2 | | 8/2005 |
| WO | 200600031 A1 | | 1/2006 |
| WO | 2006030805 A1 | | 3/2006 |
| WO | 2006074445 A2 | | 7/2006 |
| WO | 2007070760 A2 | | 6/2007 |
| WO | 2007118041 A1 | | 10/2007 |
| WO | 2007140385 A2 | | 12/2007 |
| WO | 2008014199 A2 | | 1/2008 |
| WO | 2008039645 A1 | | 4/2008 |
| WO | 2008048914 A1 | | 4/2008 |
| WO | 2008064054 A2 | | 5/2008 |
| WO | 2008098025 A1 | | 8/2008 |
| WO | 2009055357 A1 | | 4/2009 |
| WO | 2009061652 A1 | | 5/2009 |
| WO | 2009086303 A2 | | 7/2009 |
| WO | 2009105509 A1 | | 8/2009 |
| WO | 2009140089 A2 | | 11/2009 |
| WO | 2010005782 A1 | | 1/2010 |
| WO | 2010036630 A2 | | 4/2010 |
| WO | 2010036631 A2 | | 4/2010 |
| WO | 2010077836 A2 | | 7/2010 |
| WO | 2010096371 A2 | | 8/2010 |
| WO | 2010147791 A1 | | 12/2010 |
| WO | 2010147792 A2 | | 12/2010 |
| WO | 2011035159 A1 | | 3/2011 |
| WO | 2011037795 | | 3/2011 |
| WO | 2011088015 A1 | | 7/2011 |
| WO | 2011109324 A1 | | 9/2011 |
| WO | 2012012307 A1 | | 1/2012 |

OTHER PUBLICATIONS

Hauske et al., Design and Synthesis of Novel FKBP Inhibitors, Journal of Medicinal Chemistry, vol. 35, No. 23, pp. 4284-4296, 1992.*
CAS printout of Kunieda et al., Optically Active Amino Acids. XIII. Racemization of N-Benzoylanilides or Optically Acitve Proline and Pipecolic Acid, Chemical Pharmaceutical Bulletin, vol. 15, No. 3, pp. 350-351, 1967.*
Ho et al., Synthesis and Structure-Activity Relationships of Potential Anticonvulsants Based on 2-Piperidinecarboxylic Acid and Related Pharmacophores, European Journal of Medicinal Chemistry, vol. 36, No. 3, pp. 265-286, 2001.*
Wei et al., Solid-Phase Synthesis of FKBP12 Inhibitors: N-Sulfonyl and N-Carbamoylprolyl/Pipecolyl Amides, Bioorganic & Medicinal Chemistry Letters, vol. 12, No. 10, pp. 1429-1433, 2002.*

Catalano, A. et al., "Constrained analogues of tocainide as potent skeletal muscle sodium channel blockers toward the development of antimyotonic agents". European Journal of Medicinal Chemistry, vol. 43, No. 11, 2008, p. 2535-2540.
Iwakubo, M. et al., "Design and synthesis of Rho kinase inhibitors (II)". Biorganic and Medicinal Chemistry, Vo. 15, No. 1, Nov. 15, 2006, p. 350-364.
Kulkarni, S.S. et al., "Design and synthesis of noncompetitive metabotropic glutamate receptor subtype 5 antagonists." Bioorganic and Medicinal Chemistry Letters, Vo. 16, No. 13, Jul. 1, 2006, p. 3371-3375.
International Search Report and Written Opinion for PCT/US2010/024270 mailed Sep. 17, 2010.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.
Beilstein Database—Beilstein Registry No. 1084348. CAS Registry No. 6125-38-8. Beilstein Institute for Organic Chemistry. 1966, Abstract.
Beilstein Database—Beilstein Registry No. 1179643. CAS Registry No. 54890-73-2. Beilstein Institute for Organic Chemistry. 1974, Abstract.
Beilstein Database—Beilstein Registry No. 5396840. CAS Registry No. 54890-82-3. Beilstein Institute for Organic Chemistry. 1974, Abstract.
Beilstein Database—Beilstein Registry No. 5398283. CAS Registry No. 68558-02-01. Beilstein Institute for Organic Chemistry. 1978, Abstract.
Beilstein Database—Beilstein Registry No. 857451. CAS Registry No. 37901-58-9. Beilstein Institute for Organic Chemistry. 1972, Abstract.
Carenzi, A, et al., "New Isoxazole Derivatives Provided with Antihypertensive Activity". Arzneimittel-Forschung, vol. 39, No. 6, 1989, p. 624-646.
Chem Abstract—Accession No. 126:89390, Abstract of JP8311026, Kumaiai Chemical Industry Co., Nov. 26, 1996.
ChemAbstracts: 693218-49-4 and 402562-90-7. 2004, 2009.
Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60.
International Search Report and Written Opinion for PCT/US2009/042665 mailed Sep. 17, 2009.
International Search Report and Written Opinion for PCT/US2009/057776 mailed Mar. 11, 2010.
International Search Report and Written Opinion for PCT/US2010/037696 mailed Sep. 13, 2010.
International Search Report and Written Opinion for PCT/US2010/037697 mailed Jul. 1, 2011.
International Search Report and Written Opinion for PCT/US2010/048883 mailed Feb. 15, 2011.
International Search Report and Written Opinion for PCT/US2011/020767 mailed Jun. 22, 2011.
International Search Report and Written Opinion for PCT/US2011/026574 mailed Apr. 11, 2011.
International Search Report for PCT/US2008/081680 mailed Feb. 17, 2009.
International Search Report for PCT/US2009/048392 mailed Sep. 8, 2009.
International Search Report for PCT/US2009057777 mailed Mar. 11, 2010.
Kano, S. et al., Formation of Some Heterocyles through Ring Transformation of 1-Arylaxetidin-2-Ones. Heterocycles, vol. 8, No. 1, Dec. 30, 1977, p. 411-416.
LeBerre, A. et al., No. 150—Alpha-sulfocarboxylic acids and derivatives. V.-Acyclic sulfamoyl carboxyesters and carboxamides. 1,2-Thiazetidine 3-one 1,1-dioxides. National Conservatory of Skills and Trades, Laborator of Industrial Chemistry. Manuscript received Sep. 17, 1974, p. 807-811.

(56) References Cited

OTHER PUBLICATIONS

Li, S. et al., "The Synthesis and Preliminary Activity Assay In Vitro of Peptide-like Derivatives as APN Inhibitors." Archives of Pharmacal Research, 2008, vol. 31, No. 10, pp. 1231-1239.

Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35.

Office Action mailed Jan. 13, 2012 for U.S. Appl. 12/882,328, filed Sep. 15, 2010. Inventor: Alessandra Bartolozzi.

Office Action mailed Jan. 27, 2012 for U.S. Appl. 12/741,260, filed Jun. 17, 2010 Inventor: Angela Berry.

Sheehan, J.C. The Synthesis and Reactions of Some Substitued Beta-Lactams, 1951, Journal of the American Chemical Society, 73, 1761-1765.

STN results for Dorme et al., Bulletin de la Societe Chimique de France; 1959; No. 9; pp. 2582-2588.

U.S. Appl. No. 13/022,866, filed Feb. 8, 2011, Inventor: Angela Berry.

U.S. Appl. No. 13/037,422, filed Mar. 1, 2011, Inventor: Monika Ermann.

Venkov, A.P. et al., "A new synthesis of 1,2,3,40tetrahydro-2-methyl-4-phenylisoquinolines". Dept of Chemistry, University of Plovdiv, Bulgaria, pp. 253-255, Mar. 1990.

White, J.D. et al., "Conversion of Carbamates to Amidosulphones and Amides. Synthesis of the [ 14 C]-Labeled Antiobestity Agent Ro23-7637", Organice Letters, vol. 4. No. 10, Apr. 17, 2002, pp. 1803-1806.

Database Pubchem Substance, 2005, Retrieved online from <http://www.ncbi.nlm.nih.gov/pcsubstance>.

International Search Report and Written Opinion for PCT/US2011/044309 mailed Sep. 1, 2011.

Silverman, Richard B., The Organic Chemistry of Drug Design and Drug Action, 2nd Edition, 2004, Elsevier, pp. 29-34.

Wermuth, C. G., The Practice of Medicinal Chemistry, 2008, Third Edition, Ch. 17, pp. 363-379.

* cited by examiner

HETEROCYCLIC COMPOUNDS WHICH MODULATE THE CB2 RECEPTOR

APPLICATION DATA

This application claims benefit to U.S. provisional application Ser. No. 61/153,333 filed Feb. 18, 2009.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of *cannabis* is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of *cannabis*.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of *cannabis*, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB 1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J. Pharmacol. (2005) 520:164-171 and Smith et al., The anti-inflammatory activities of cannabinoid receptor ligands in mouse peritonitis models Eur J. Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J. Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In one generic aspect of the invention there is provided a compound of the formula (IA)

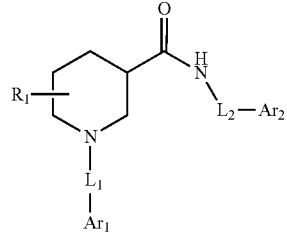

(IA)

wherein:
Ar$_1$ is chosen from carbocycle, heterocyclyl and heteroaryl each optionally substituted by 1-3 C$_{1-10}$ alkyl which is optionally substituted by halogens, C$_{1-10}$ alkoxy, CN, halogen, NO$_2$, —S(O)$_m$—C$_{1-10}$ alkyl, —CO$_2$—C$_{1-10}$ alkyl, —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl, carbocycle and heterocyclyl;
Ar$_2$ is chosen from carbocycle, heterocyclyl and heteroaryl each optionally substituted by 1-3 C$_{1-10}$ alkyl which is optionally substituted by halogens, C$_{3-10}$ cycloalkyl, carbocycle, C$_{1-10}$ alkylcarbocycle, heteroaryl, CN or halogen, wherein the C$_{1-10}$ alkyl and carbocycle may be additionally optionally substituted by hydroxyl, C$_{1-5}$ alkoxycarbonyl or C$_{1-5}$ alkoxy;
L$_1$ and L$_2$ are each independently chosen from a bond or C$_{1-10}$ alkyl chain wherein each —CH$_2$— of said chain is optionally replaced by —O—, C(O), or S(O)$_m$;
wherein each L$_1$ and L$_2$ where possible is optionally substituted by halogen or C$_{1-3}$ alkyl;
R$_1$ is chosen from hydrogen, oxo (=O) and OH;
m is 0, 1 or 2;
or a pharmaceutically acceptable salt thereof.

The compound according to the embodiment described immediately above and wherein:
Ar$_1$ is chosen from phenyl, C$_{3-6}$ cycloalkyl, dioxanyl, tetrahydrofuranyl, tetrahydropyranyl, thiomorpholinyl, 1,1-Dioxo-1λ$^6$-thiomorpholinyl, morpholinyl and pyridinyl, each optionally substituted by 1-3 C$_{1-6}$ alkyl which is optionally substituted with halogens, or halogen,
Ar$_2$ is chosen from oxazolyl, isoxazolyl, thiazoyl, thiadiazoyl, benzothiazoyl, triazoyl, isothiazoyl, phenyl, pyrimidinyl, pyridizinyl, pyrazinyl and pyridinyl, each optionally substituted by 1-3 C$_{1-6}$ alkyl which is optionally substituted by halogens, phenyl, halogen or C$_{3-8}$ cycloalkyl;
R$_1$ is hydrogen;
L$_1$ is a bond, or C$_{1-3}$ alkyl chain wherein each —CH$_2$— of said chain is optionally replaced by C(O) or S(O)$_m$;
L$_2$ is a bond The compound according to the embodiment described immediately above and wherein:
Ar$_1$ is chosen from phenyl, C$_{3-6}$ cycloalkyl, tetrahydropyranyl, 1-Dioxo-1λ$^6$-thiomorpholinyl, morpholinyl and pyridinyl, each optionally substituted by 1-3 C$_{1-6}$ alkyl, trifluoromethyl or halogen;
Ar$_2$ is chosen from isoxazolyl, pyridinyl, each optionally substituted by C$_{1-6}$ alkyl or trifluoromethyl;
L$_1$ is a bond, —CH$_2$—, C(O) or S(O)$_2$;

The compound according to the embodiment described immediately above and wherein:
Ar$_1$ is chosen from phenyl, cyclohexyl, tetrahydropyranyl, 1-Dioxo-1λ$^6$-thiomorpholinyl, morpholinyl and pyridinyl, each optionally substituted by 1-3 C$_{1-3}$ alkyl, trifluoromethyl or halogen;

The compound according to the embodiment described immediately above and wherein:
Ar$_2$ is chosen from

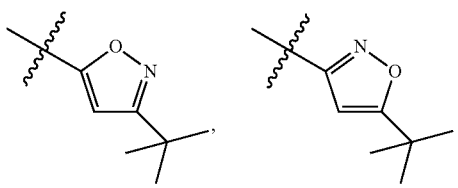

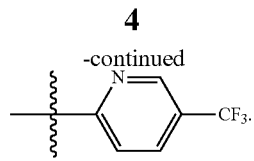

The compound according to the embodiment described immediately above and wherein:
Ar$_2$ is chosen from

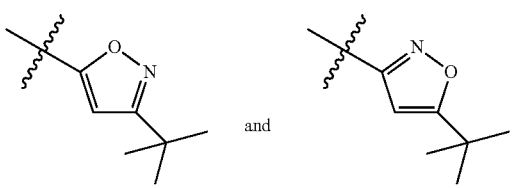

In another generic aspect of the invention there is provided a compound of the formula (IIA)

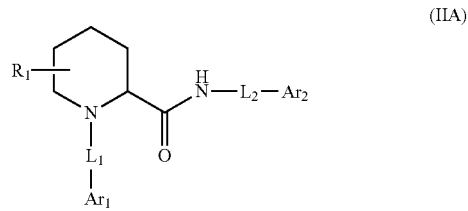

(IIA)

wherein
Ar$_1$ is chosen from C$_{1-6}$ alkyl which is optionally substituted by halogens, C$_{1-6}$ alkoxy, carbocycle, heterocyclyl and heteroaryl each optionally substituted by 1-3 C$_{1-10}$ alkyl which is optionally substituted by halogens, C$_{1-10}$ alkoxy, CN, halogen, NO$_2$, —S(O)$_m$—C$_{1-10}$ alkyl, —C(O)—C$_{1-10}$ alkyl, —CO$_2$—C$_{1-10}$ alkyl, C$_{1-10}$ acyl, oxo (=O), —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_n$—C$_{1-10}$ alkyl and heterocyclyl the heterocyclyl being further optionally substituted by C$_{1-5}$ alkyl;
Ar$_2$ is chosen from C$_{1-6}$ alkyl, carbocycle, heterocyclyl and heteroaryl each optionally substituted by 1-3 C$_{1-10}$ alkyl which is optionally substituted by halogens alkoxy or hydroxy, carbocycle optionally substituted by $C_{1-3}$ alkyl, aryl which is optionally substituted by halogen, heteroaryl, CN, halogen, $C_{1-10}$ acyl or oxo (=O), wherein the $C_{1-6}$ alkyl and carbocycle may be additionally optionally substituted by hydroxyl;

$L_1$ and $L_2$ are each independently chosen from a bond or $C_{1-10}$ alkyl chain wherein each —$CH_2$— of said chain is optionally replaced by —O—, C(O), $S(O)_m$ or —NH—;

$R_1$ is chosen from hydrogen, hydroxyl and oxo (=O);

m is 0, 1 or 2;

or a pharmaceutically acceptable salt thereof.

The compound according to the embodiment described immediately above and wherein:

$Ar_1$ is chosen from $C_{1-6}$ alkyl which is optionally substituted by halogens, $C_{1-6}$ alkoxyl, phenyl, $C_{3-8}$ cycloalkyl, dioxanyl, tetrahydrofuranyl, tetrahydropyranyl, tetrahydrothiopyranyl, tetrahydrothiopyran-1,1-dioxide, tetrahydrothiofuranyl, tetrahydrothiofuran-1,1-dioxide, thiomorpholinyl, 1-Oxo-1%$^4$-thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl and piperazinyl, each optionally substituted by 1-3 $C_{1-6}$ alkyl which is optionally substituted by halogens, $C_{1-6}$ alkoxy, CN, halogen, oxo, —C(O)—$C_{1-10}$ alkyl, —$S(O)_2$—$C_{1-3}$ alkyl or —$CO_2$—$C_{1-4}$ alkyl;

$Ar_2$ is chosen from $C_{1-6}$ alkyl, cyclohexyl, phenyl, benzoxazolyl, benzothiazolyl, benzimidazolyl, oxazolyl, isoxazolyl, thiazolyl, isothiazolyl, pyrazolyl, pyrrolyl, imidazolyl, thienyl, thiadiazolyl, triazolyl, pyridinyl, pyrimidinyl, pyridazinyl, pyrazinyl, triazinyl, benzofuranyl and benzothienyl, each optionally substituted by 1-3 $C_{1-6}$ alkyl which is optionally substituted by halogen, cyclopropyl, cyclobutyl, cyclopentyl, cyclohexyl, cycloheptyl, phenyl optionally substituted by halogens, CN, halogens, $C_{1-6}$ alkoxy or hydroxy;

$R_1$ is hydrogen, hydroxyl and oxo (=O);

$L_1$ is bond or $C_{1-3}$ alkyl chain wherein each —$CH_2$— of said chain is optionally replaced by C(O) or $S(O)_m$;

$L_2$ is chosen bond or $C_{1-5}$ alkyl chain wherein each —$CH_2$— of said chain is optionally replaced by —O— or $S(O)_m$;

The compound according to the embodiment described immediately above and wherein:

$Ar_1$ is chosen from $C_{1-6}$ alkyl which is optionally substituted by halogens, $C_{1-6}$ alkoxyl, phenyl, cyclopropyl, cyclobutyl, cyclopentyl, cyclohexyl, cycloheptyl, tetrahydrofuranyl, tetrahydropyranyl, tetrahydrothiopyranyl, tetrahydrothiopyran-1,1-dioxide, tetrahydrothiofuranyl, tetrahydrothiofuran-1,1-dioxide, thiomorpholinyl, 1-Oxo-1$\lambda^4$-thiomorpholinyl, 1,1-Dioxo-1$\lambda^6$-thiomorpholinyl, morpholinyl, pyridinyl, pyrrolidinyl, piperidinyl and piperazinyl, each optionally substituted by 1-3 $C_{1-6}$ alkyl, trifluoromethyl, $C_{1-2}$ alkoxy, CN, halogen, oxo, —C(O)—$C_{1-10}$ alkyl, —$S(O)_2$—$C_{1-3}$ alkyl or —$CO_2$—$C_{1-4}$ alkyl;

$Ar_2$ is chosen from $C_{1-6}$ alkyl, cyclohexyl, phenyl, benzoxazolyl, benzothiazolyl, benzimidazolyl, oxazolyl, isoxazolyl, thiazolyl, isothiazolyl, thiadiazolyl, triazolyl and pyridinyl, each optionally substituted by 1-3 $C_{1-6}$ alkyl, trifluoromethyl, cyclopropyl, cyclopentyl, cyclohexyl, phenyl optionally substituted by halogens, CN, halogen, $C_{1-6}$ alkoxy or $C_{1-6}$ hydroxy;

$L_1$ is bond or $C_{1-3}$ alkyl chain wherein each —$CH_2$— of said chain is optionally replaced by C(O) or $SO_2$;

$L_2$ is chosen bond or $C_{1-5}$ alkyl chain wherein each —$CH_2$— of said chain is optionally replaced by —O— or S;

The compound according to the embodiment described immediately above and wherein:

$Ar_1$ is chosen from phenyl, cyclopropyl, cyclobutyl, cyclopentyl, cyclohexyl, cycloheptyl, tetrahydrofuranyl, tetrahydropyranyl, tetrahydrothiopyranyl, tetrahydrothiopyran-1,1-dioxide, tetrahydrothiofuranyl, tetrahydrothiofuran-1,1-dioxide, thiomorpholinyl, 1-oxo-1$\lambda^4$-thiomorpholinyl, 1,1-dioxo-1$\lambda^6$-thiomorpholinyl, pyridinyl, pyrrolidinyl, piperidinyl and piperazinyl, each optionally substituted by 1-3 $C_{1-6}$ alkyl, trifluoromethyl, $C_{1-2}$ alkoxy, halogen, oxo, —C(O)—$C_{1-10}$ alkyl, —$S(O)_2$—$C_{1-3}$ alkyl or —$CO_2$—$C_{1-4}$ alkyl;

$Ar_2$ is chosen from cyclohexyl, phenyl, benzothiazolyl, benzimidazolyl, oxazolyl, isoxazolyl, isothiazolyl, thiadiazolyl, triazolyl and pyridinyl, each optionally substituted by 1-3 $C_{1-6}$ alkyl, trifluoromethyl, cyclopropyl, cyclopentyl, cyclohexyl, phenyl optionally substituted by halogens, CN, halogen or $C_{1-6}$ alkoxy;

$R_1$ is hydrogen or oxo;

$L_2$ is chosen bond or $C_{1-3}$ alkyl chain wherein each —$CH_2$— of said chain is optionally replaced by S;

The compound according to the embodiment described immediately above and wherein:

$R_1$ is hydrogen;

In another generic aspect of the invention there is provided a compound of the formula (IIIA)

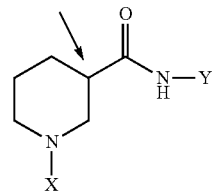

(IIIA)

wherein of the formula (IIIA) is chosen from A1-A9 of Table I, and

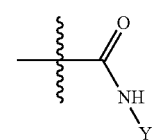

of the formula (IIIA) is chosen from B1-B2 of Table I,
TABLE I
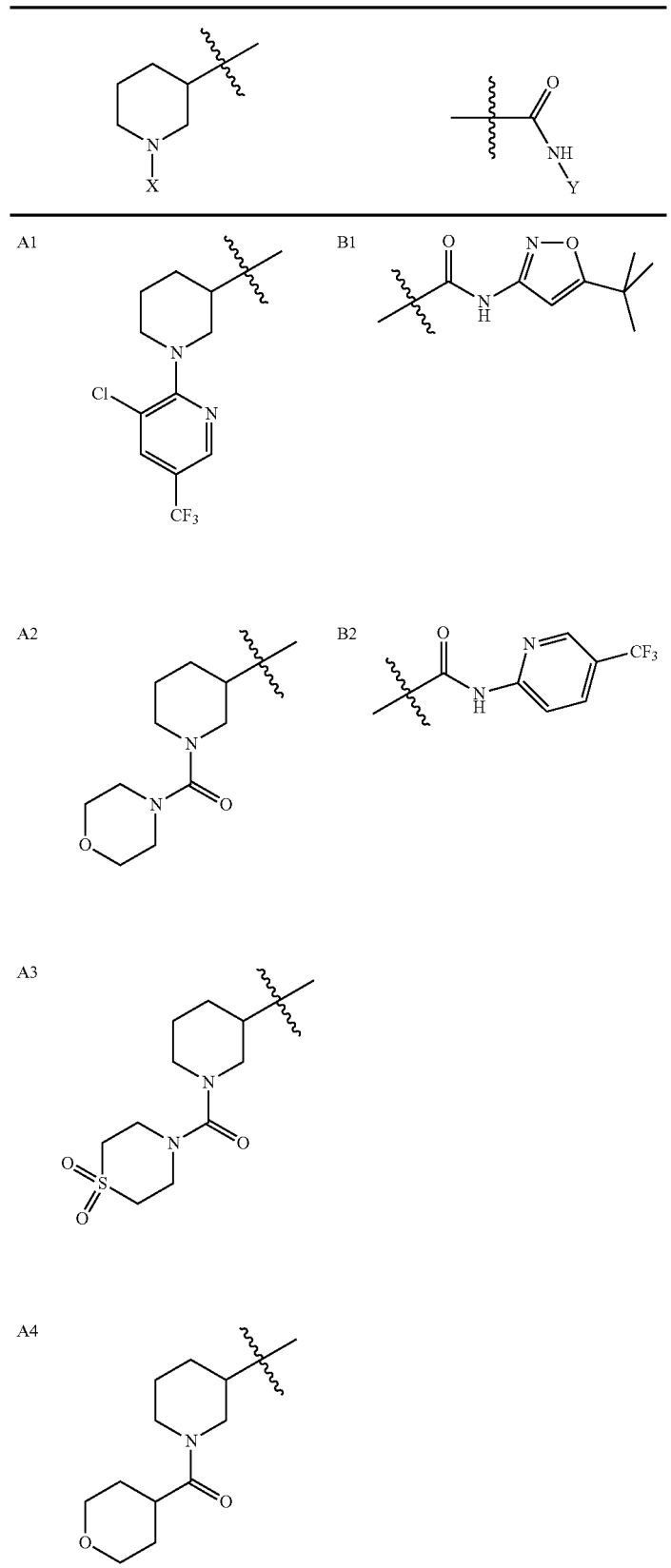

TABLE I-continued
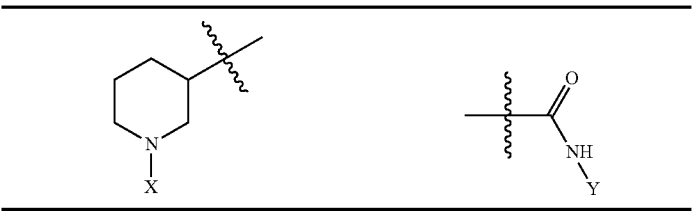
| | | |
|---|---|---|
| A5 | 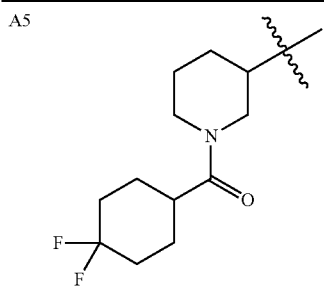 | |
| A6 | 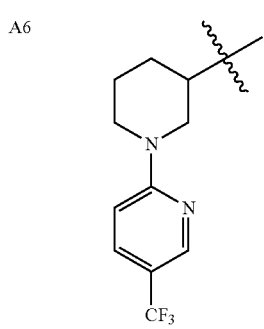 | |
| A7 | 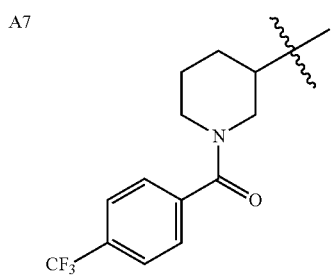 | |
| A8 | 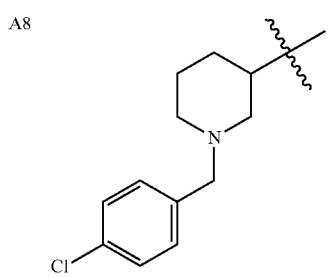 | |
| A9 | 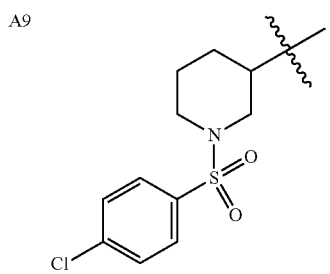 | | or a pharmaceutically acceptable salt thereof;

In another embodiment of the invention, the compounds in Table I, the stereogenic carbon indicated with an arrow is in the (R) configuration.

In another generic aspect of the invention there is provided a compound of the formula (IVA)

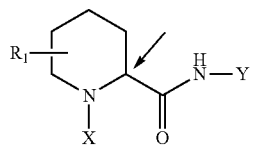
(IVA)

wherein

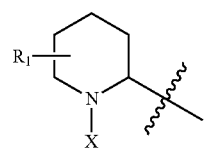

of the formula (IVA) is chosen from A1-A53 of Table II, and

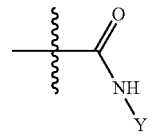

of the formula (IVA) is chosen from B1-B40 of Table II,

TABLE II

| <br> | <br> |
|---|---|
| A1 | B1 |
| A2 | B2 |
| A3 | B3 |
| A4 | B4 |

TABLE II-continued
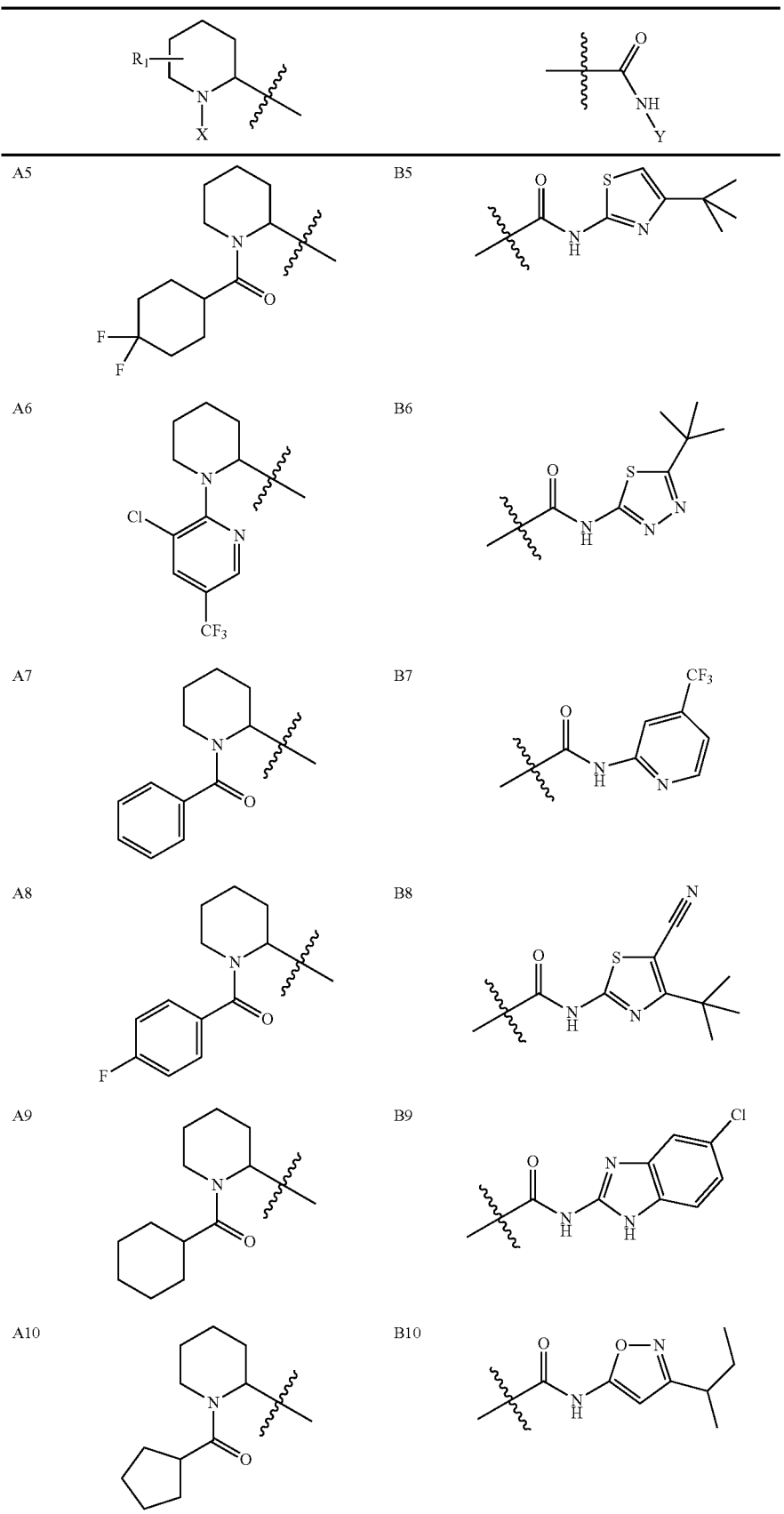

TABLE II-continued
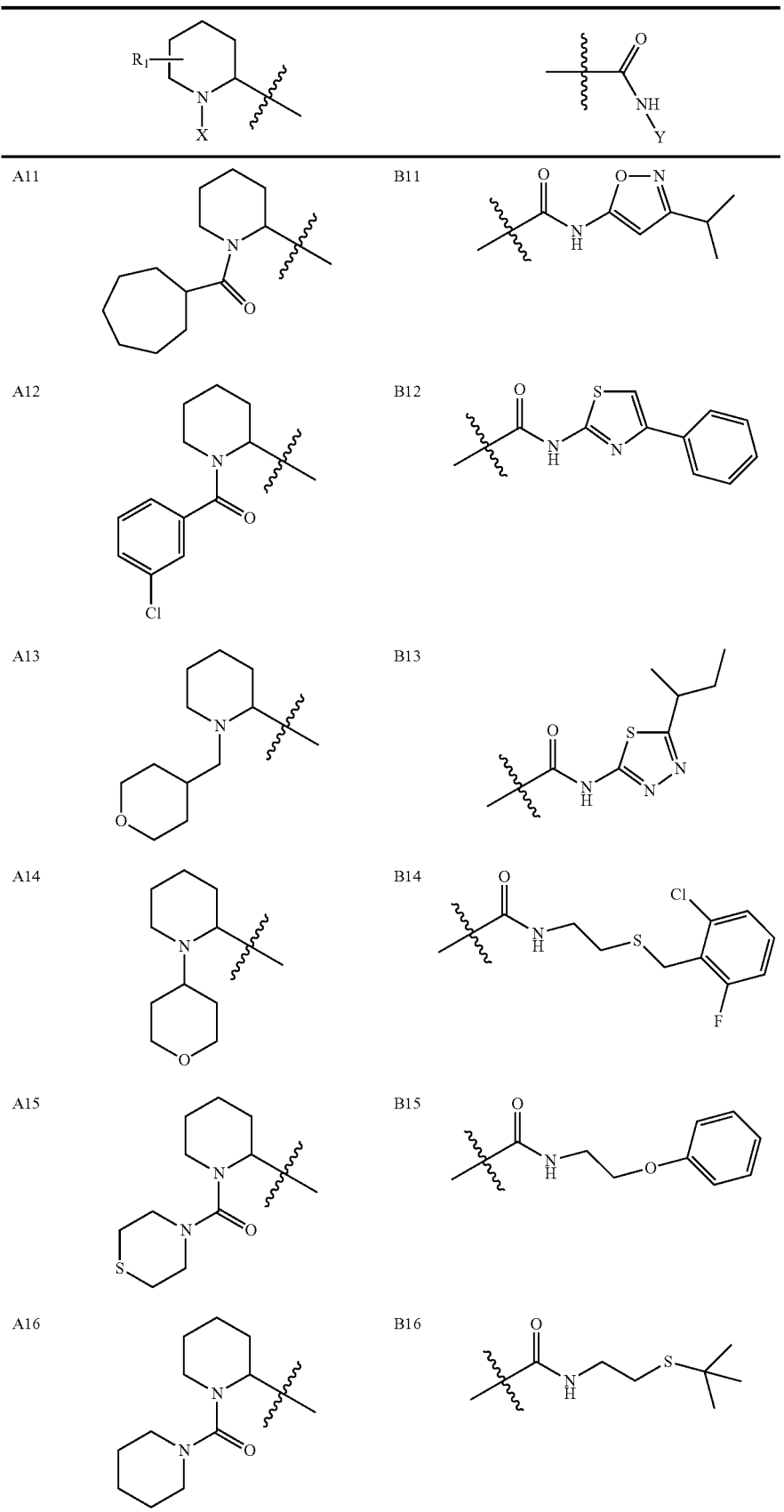

TABLE II-continued
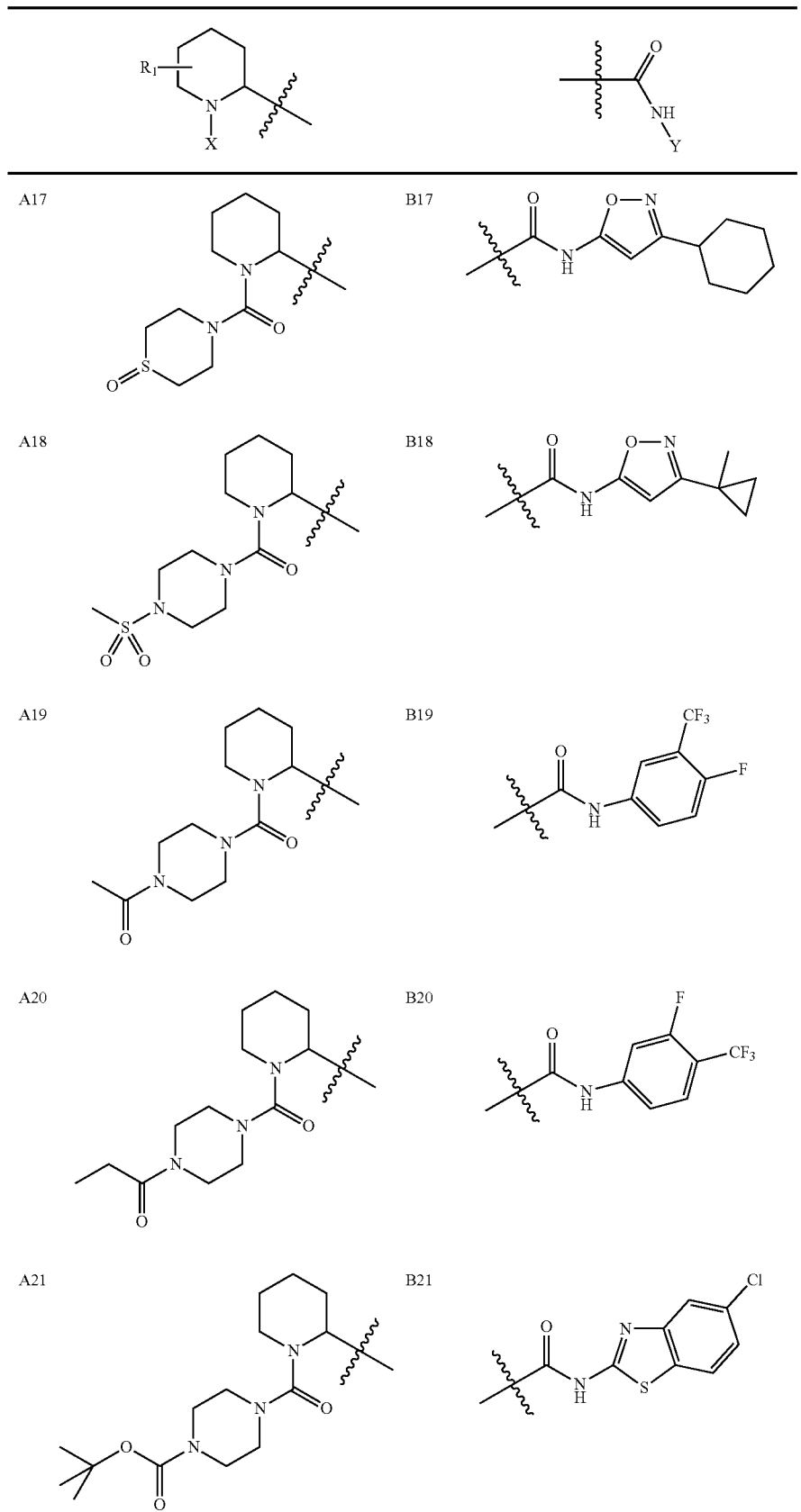

TABLE II-continued
| | | | |
|---|---|---|---|
| A22 | 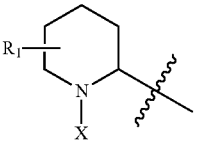 | B22 | 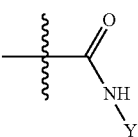 |
| A23 | 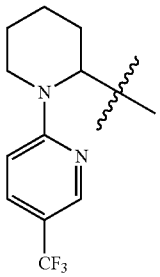 [SMILES: *C1CCCCN1c1ccc(C(F)(F)F)cn1] | B23 | 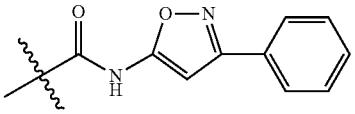 [SMILES: *C(=O)Nc1cc(-c2ccccc2)no1] |
| A24 | 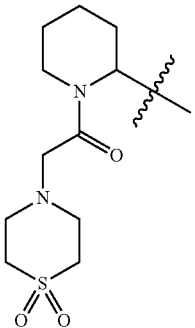 [SMILES: *C1CCCCN1C(=O)CN1CCS(=O)(=O)CC1] | B24 | 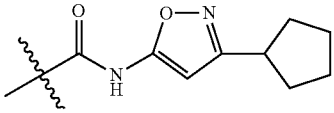 [SMILES: *C(=O)Nc1cc(C2CCCC2)no1] |
| A25 | 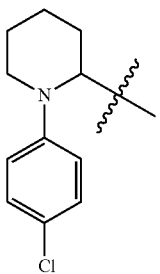 [SMILES: *C1CCCCN1c1ccc(Cl)cc1] | B25 | 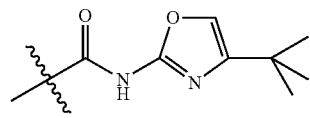 [SMILES: *C(=O)Nc1nc(C(C)(C)C)co1] |
| A26 | 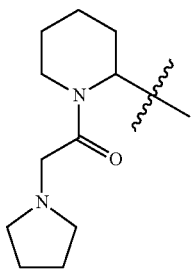 [SMILES: *C1CCCCN1C(=O)CN1CCCC1] | B26 | 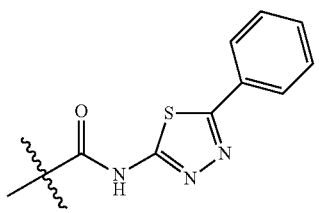 [SMILES: *C(=O)Nc1nnc(-c2ccccc2)s1] |

TABLE II-continued
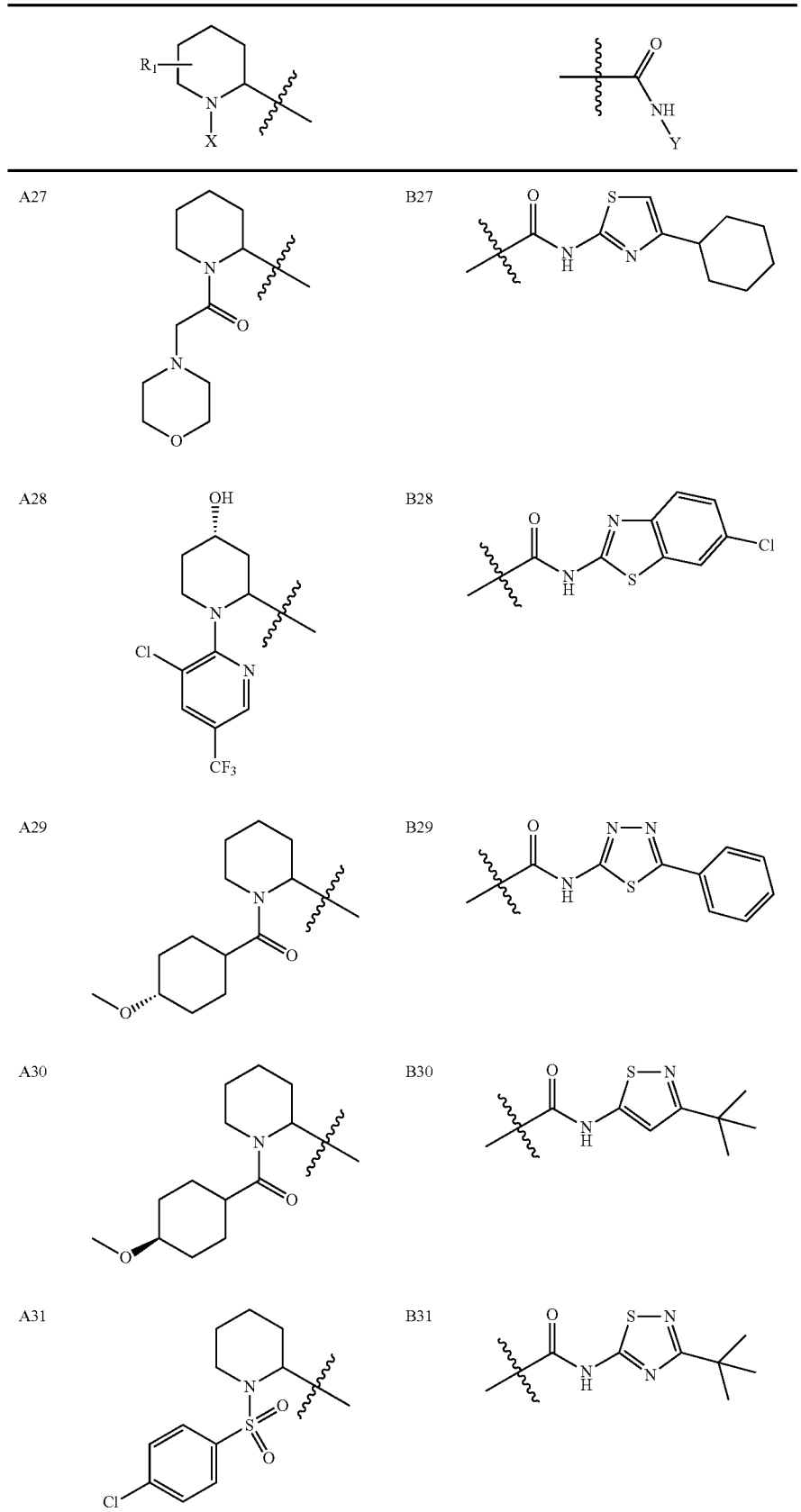

TABLE II-continued

| | | | |
|---|---|---|---|
| A32 | [4,4-difluoropiperidinyl-CH2-C(O)- on piperidine N] | B32 | -C(O)NH-(4-tert-butylthiazol-2-yl) |
| A33 | [tetrahydropyran-4-yl-CH2-C(O)- on piperidine N] | B33 | -C(O)NH-[4-(3,4-difluorophenyl)thiazol-2-yl] |
| A34 | [tetrahydrofuran-2-yl-CH2-C(O)- on piperidine N] | B34 | -C(O)NH-(4-fluorobenzothiazol-2-yl) |
| A35 | [4-chlorobenzoyl on piperidine N] | B35 | -C(O)NH-(5-ethyl-4-phenylthiazol-2-yl) |
| A36 | [4,4-difluoropiperidine-1-carbonyl on piperidine N] | B36 | -C(O)NH-(5-ethyl-1-phenyl-1,2,4-triazol-3-yl) |

TABLE II-continued
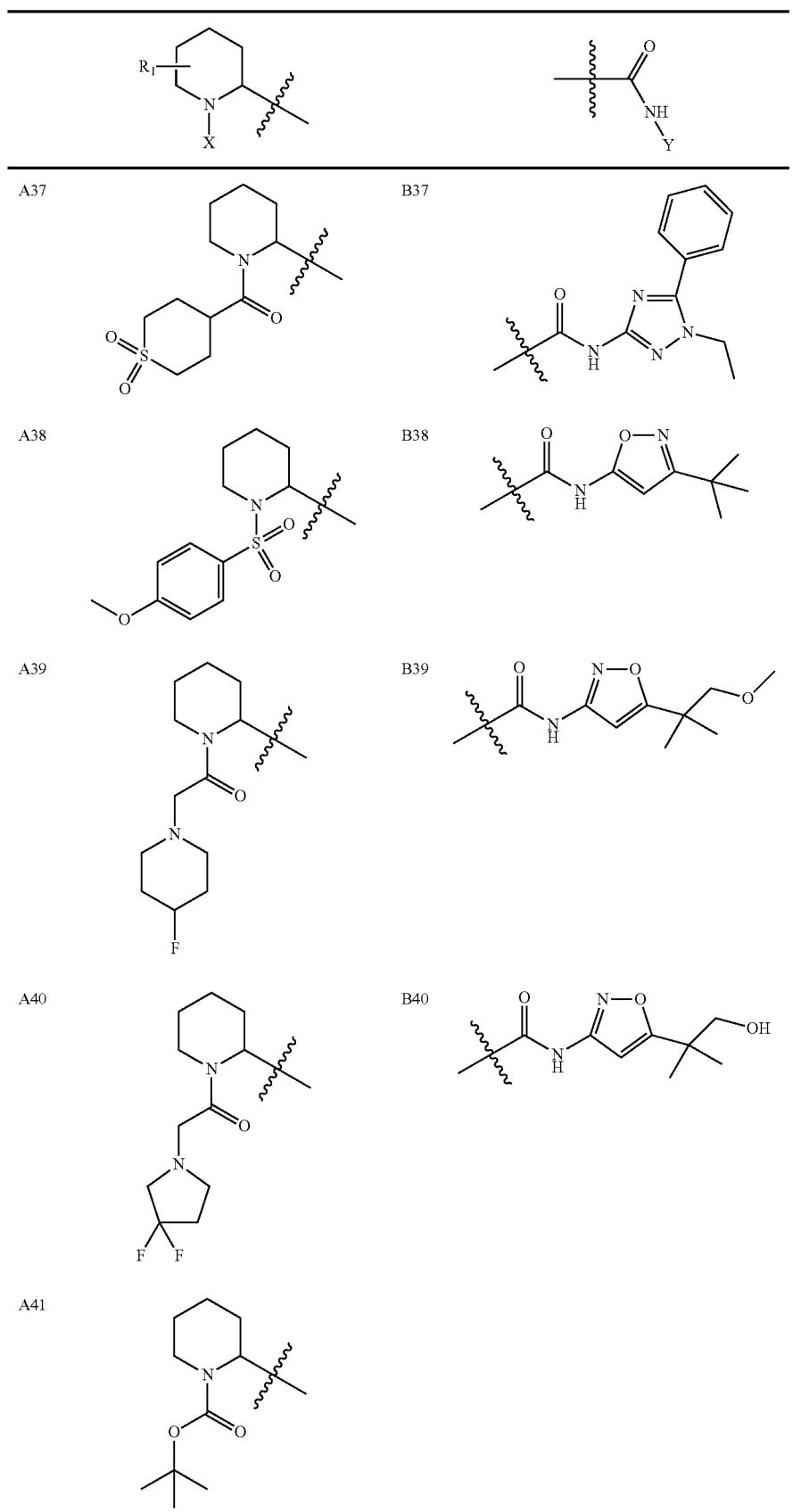

TABLE II-continued
| | 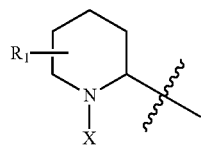 | 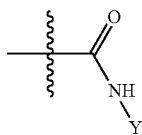 |
|---|---|---|
A42 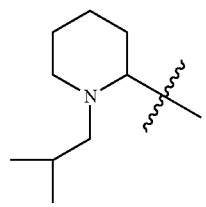 [SMILES: *C1CCCCN1CC(C)C]
A43 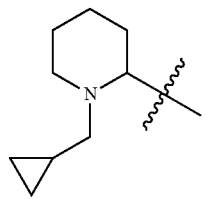 [SMILES: *C1CCCCN1CC1CC1]
A44 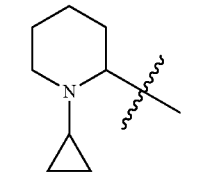 [SMILES: *C1CCCCN1C1CC1]
A45 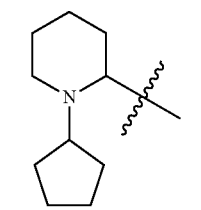 [SMILES: *C1CCCCN1C1CCCC1]
A46 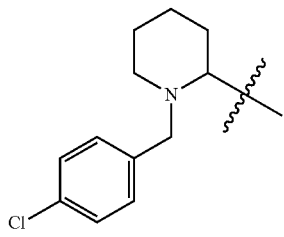 [SMILES: *C1CCCCN1Cc1ccc(Cl)cc1]
A47 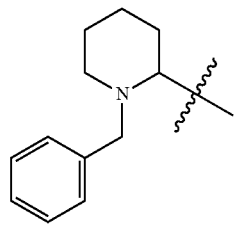 [SMILES: *C1CCCCN1Cc1ccccc1]

TABLE II-continued
| | | |
|---|---|---|
| | 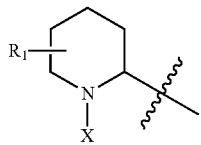 | 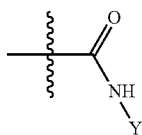 |
| A48 | 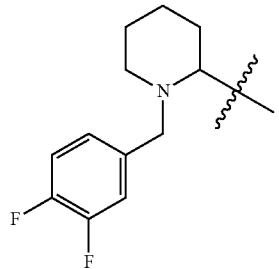 [SMILES: *C1CCCCN1Cc1ccc(F)c(F)c1] |
| A49 | 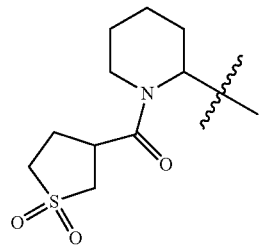 [SMILES: *C1CCCCN1C(=O)C1CCS(=O)(=O)C1] |
| A50 | 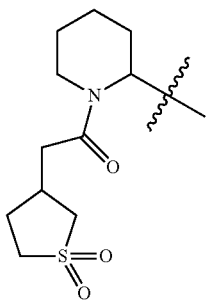 [SMILES: *C1CCCCN1C(=O)CC1CCS(=O)(=O)C1] |
| A51 | 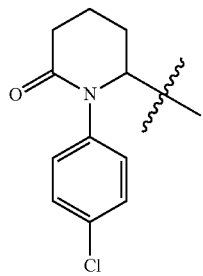 [SMILES: *C1CCCC(=O)N1c1ccc(Cl)cc1] |
| A52 | 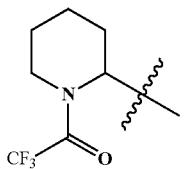 |

TABLE II-continued

| | |
|---|---|
| 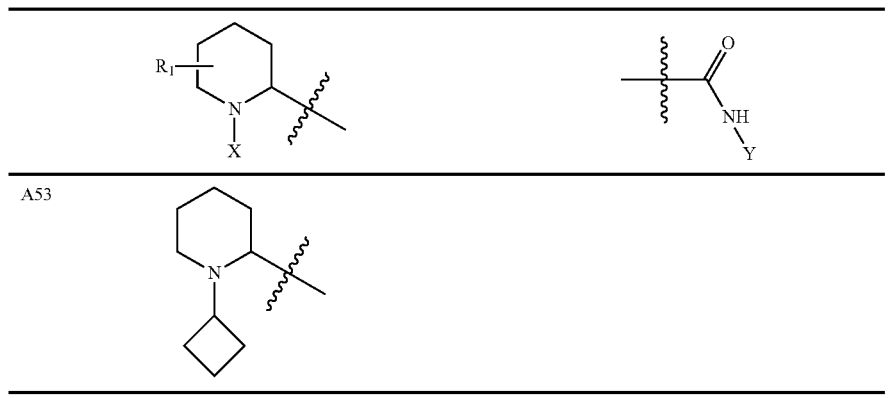 | |
| A53 | | or a pharmaceutically acceptable salt thereof.

In another embodiment of the invention, the compounds in Table II, the stereogenic carbon indicated with an arrow is in the (S) configuration.

In another embodiment of the invention, there is provided compounds in Table III, which can be made by the methods and examples shown herein and methods known in the art.

TABLE III

| Structure | Name |
|---|---|
| 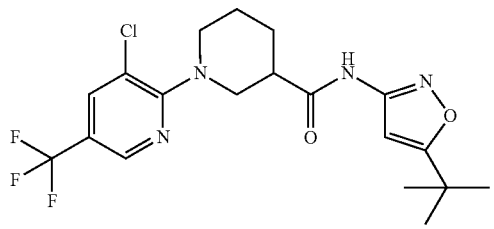 [SMILES: CC(C)(C)c1cc(NC(=O)C2CCCN(c3ncc(C(F)(F)F)cc3Cl)C2)no1] | 3'-Chloro-5'-trifluoromethyl-3,4,5,6-tetrahydro-2H-[1,2']bipyridinyl-3-carboxylic acid (5-tert-butyl-isoxazol-3-yl)-amide |
| 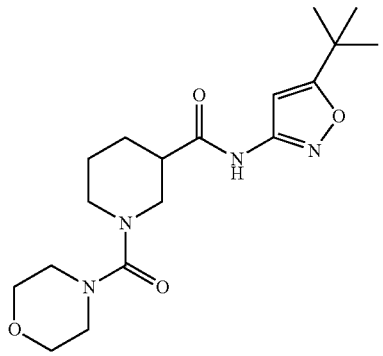 [SMILES: CC(C)(C)c1cc(NC(=O)C2CCCN(C(=O)N3CCOCC3)C2)no1] | 1-(Morpholine-4-carbonyl)-piperidine-3-carboxylic acid (5-tert-butyl-isoxazol-3-yl)-amide |
| 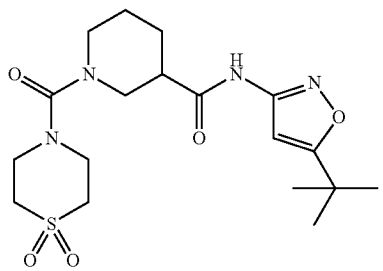 [SMILES: CC(C)(C)c1cc(NC(=O)C2CCCN(C(=O)N3CCS(=O)(=O)CC3)C2)no1] | 1-(1,1-Dioxo-1λ6-thiomorpholine-4-carbonyl)-piperidine-3-carboxylic acid (5-tert-butyl-isoxazol-3-yl)-amide |

TABLE III-continued

| Structure | Name |
|---|---|
| 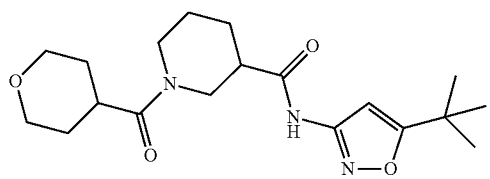 [SMILES: CC(C)(C)c1cc(NC(=O)C2CCCN(C(=O)C3CCOCC3)C2)no1] | 1-(Tetrahydro-pyran-4-carbonyl)-piperidine-3-carboxylic acid (5-tert-butyl-isoxazol-3-yl)-amide |
| 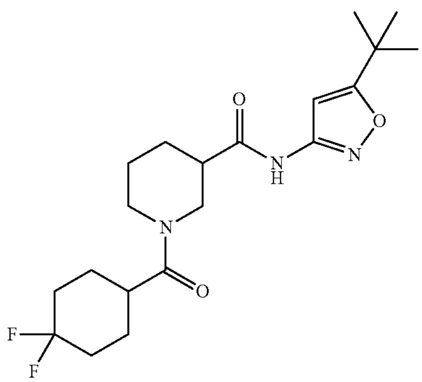 | 1-(4,4-Difluoro-cyclohexanecarbonyl)-piperidine-3-carboxylic acid (5-tert-butyl-isoxazol-3-yl)-amide |
| 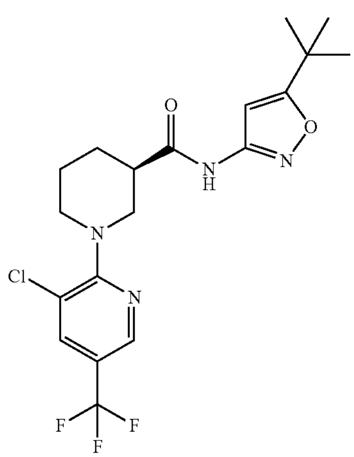 [SMILES: CC(C)(C)c1cc(NC(=O)[C@@H]2CCCN(c3ncc(C(F)(F)F)cc3Cl)C2)no1] | (R)-3'-Chloro-5'-trifluoromethyl-3,4,5,6-tetrahydro-2H-[1,2']bipyridinyl-3-carboxylic acid (5-tert-butyl-isoxazol-3-yl)-amide |
| 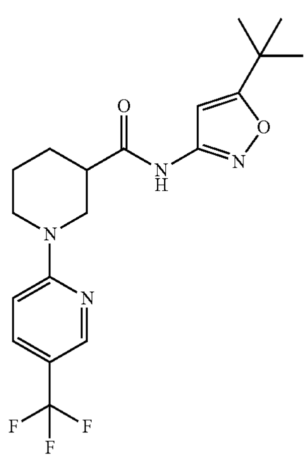 | 5'-Trifluoromethyl-3,4,5,6-tetrahydro-2H-[1,2']bipyridinyl-3-carboxylic acid (5-tert-butyl-isoxazol-3-yl)-amide |

TABLE III-continued

| Structure | Name |
| --- | --- |
| 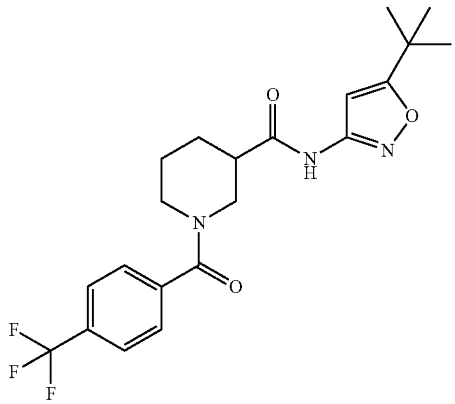 [SMILES: CC(C)(C)c1cc(NC(=O)C2CCCN(C(=O)c3ccc(C(F)(F)F)cc3)C2)no1] | 1-(4-Trifluoromethyl-benzoyl)-piperidine-3-carboxylic acid (5-tert-butyl-isoxazol-3-yl)-amide |
| 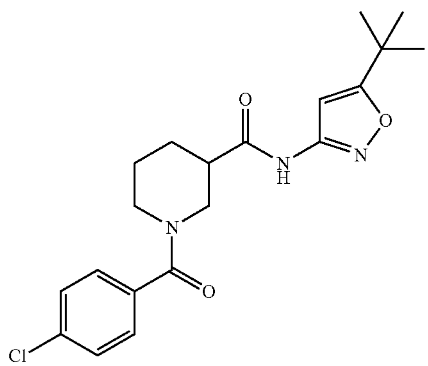 [SMILES: CC(C)(C)c1cc(NC(=O)C2CCCN(C(=O)c3ccc(Cl)cc3)C2)no1] | 1-(4-Chloro-benzyl)-piperidine-3-carboxylic acid (5-tert-butyl-isoxazol-3-yl)-amide |
| 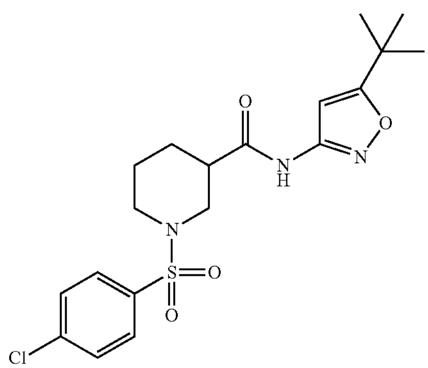 [SMILES: CC(C)(C)c1cc(NC(=O)C2CCCN(S(=O)(=O)c3ccc(Cl)cc3)C2)no1] | 1-(4-Chloro-benzenesulfonyl)-piperidine-3-carboxylic acid (5-tert-butyl-isoxazol-3-yl)-amide |
| 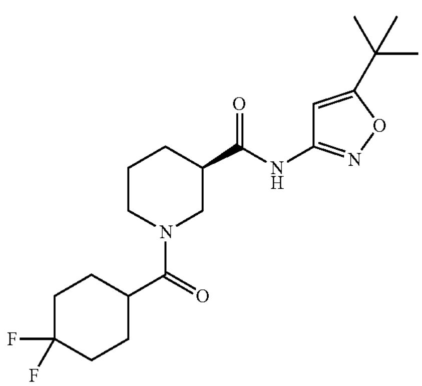 [SMILES: CC(C)(C)c1cc(NC(=O)[C@@H]2CCCN(C(=O)C3CCC(F)(F)CC3)C2)no1] | (R)-1-(4,4-Difluoro-cyclohexanecarbonyl)-piperidine-3-carboxylic acid (5-tert-butyl-isoxazol-3-yl)-amide |

TABLE III-continued

| Structure | Name |
|---|---|
| 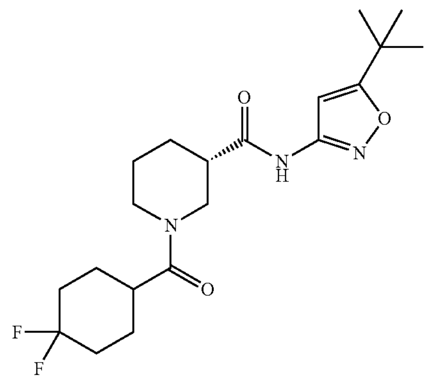 [SMILES: CC(C)(C)c1cc(NC(=O)[C@H]2CCCN(C(=O)C3CCC(F)(F)CC3)C2)no1] | (S)-1-(4,4-Difluoro-cyclohexanecarbonyl)-piperidine-3-carboxylic acid (5-tert-butyl-isoxazol-3-yl)-amide |
| 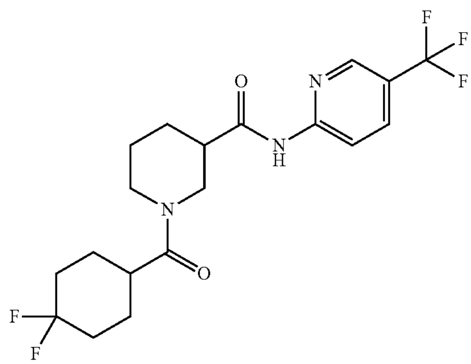 [SMILES: O=C(Nc1ccc(C(F)(F)F)cn1)C1CCCN(C(=O)C2CCC(F)(F)CC2)C1] | 1-(4,4-Difluoro-cyclohexanecarbonyl)-piperidine-3-carboxylic acid (5-trifluoromethyl-pyridin-2-yl)-amide |
| | 1-(1,1-Dioxo-1λ6-thiomorpholine-4-carbonyl)-piperidine-2-carboxylic acid (5-tert-butyl-isoxazol-3-yl)-amide |
| 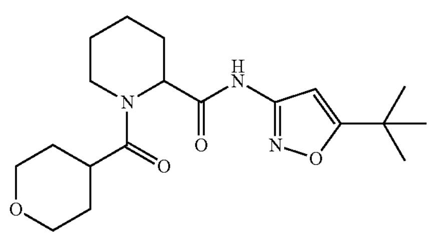 [SMILES: CC(C)(C)c1cc(NC(=O)C2CCCCN2C(=O)C2CCOCC2)no1] | 1-(Tetrahydro-pyran-4-carbonyl)-piperidine-2-carboxylic acid (5-tert-butyl-isoxazol-3-yl)-amide |
| | 1-(1,1-Dioxo-1λ6-thiomorpholine-4-carbonyl)-piperidine-2-carboxylic acid (5-tert-butyl-isoxazol-3-yl)-amide |

TABLE III-continued

| Structure | Name |
|---|---|
| 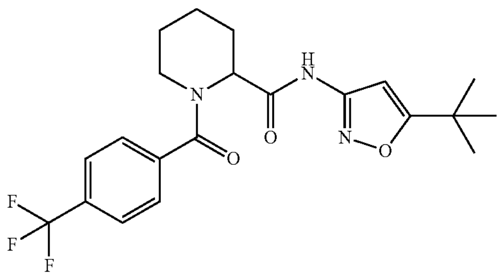 [SMILES: CC(C)(C)c1cc(NC(=O)C2CCCCN2C(=O)c2ccc(C(F)(F)F)cc2)no1] | 1-(4-Trifluoromethyl-benzoyl)-piperidine-2-carboxylic acid (5-tert-butyl-isoxazol-3-yl)-amide |
| 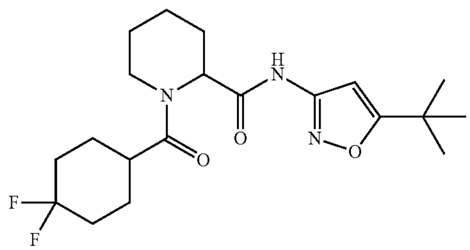 [SMILES: CC(C)(C)c1cc(NC(=O)C2CCCCN2C(=O)C2CCC(F)(F)CC2)no1] | 1-(4,4-Difluoro-cyclohexanecarbonyl)-piperidine-2-carboxylic acid (5-tert-butyl-isoxazol-3-yl)-amide |
| 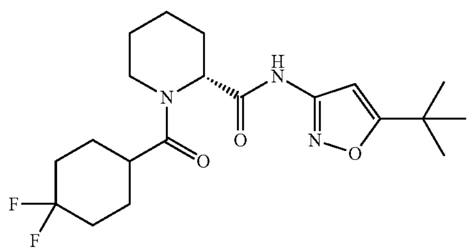 [SMILES: CC(C)(C)c1cc(NC(=O)[C@H]2CCCCN2C(=O)C2CCC(F)(F)CC2)no1] | (R)-1-(4,4-Difluoro-cyclohexanecarbonyl)-piperidine-2-carboxylic acid (5-tert-butyl-isoxazol-3-yl)-amide |
| 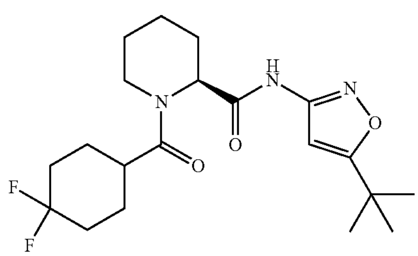 [SMILES: CC(C)(C)c1cc(NC(=O)[C@@H]2CCCCN2C(=O)C2CCC(F)(F)CC2)no1] | (S)-1-(4,4-Difluoro-cyclohexanecarbonyl)-piperidine-2-carboxylic acid (5-tert-butyl-isoxazol-3-yl)-amide |
| 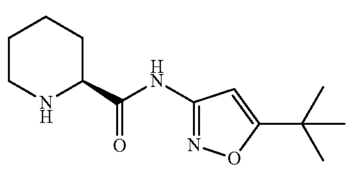 [SMILES: CC(C)(C)c1cc(NC(=O)[C@@H]2CCCCN2)no1] | (S)-Piperidine-2-carboxylic acid (5-tert-butyl-isoxazol-3-yl)-amide |
| 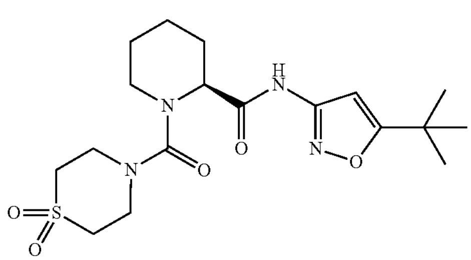 [SMILES: CC(C)(C)c1cc(NC(=O)[C@@H]2CCCCN2C(=O)N2CCS(=O)(=O)CC2)no1] | (S)-1-(1,1-Dioxo-1λ6-thiomorpholine-4-carbonyl)-piperidine-2-carboxylic acid (5-tert-butyl-isoxazol-3-yl)-amide |

TABLE III-continued

| Structure | Name |
|---|---|
| 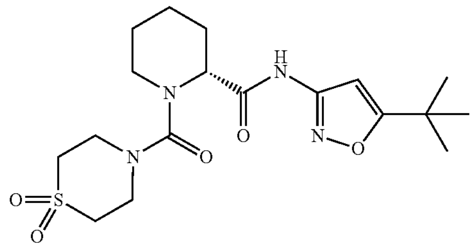 [SMILES: CC(C)(C)c1cc(NC(=O)[C@H]2CCCCN2C(=O)N2CCS(=O)(=O)CC2)no1] | (R)-1-(1,1-Dioxo-1λ6-thiomorpholine-4-carbonyl)-piperidine-2-carboxylic acid (5-tert-butyl-isoxazol-3-yl)-amide |
| 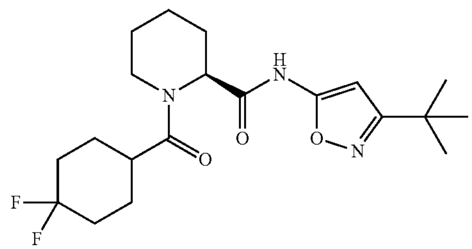 [SMILES: CC(C)(C)c1cc(NC(=O)[C@@H]2CCCCN2C(=O)C2CCC(F)(F)CC2)on1] | (S)-1-(4,4-Difluoro-cyclohexanecarbonyl)-piperidine-2-carboxylic acid (3-tert-butyl-isoxazol-5-yl)-amide |
| 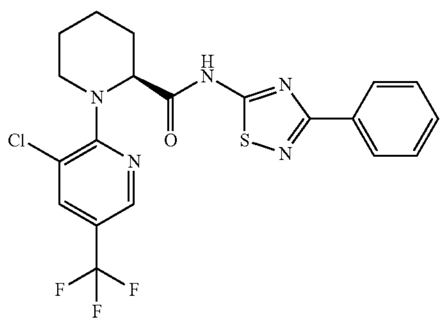 [SMILES: O=C(Nc1nc(-c2ccccc2)ns1)[C@@H]1CCCCN1c1ncc(C(F)(F)F)cc1Cl] | (S)-3'-Chloro-5'-trifluoromethyl-3,4,5,6-tetrahydro-2H-1,2'-bipyridinyl-2-carboxylic acid (3-phenyl-1,2,4-thiadiazol-5-yl)-amide |
| 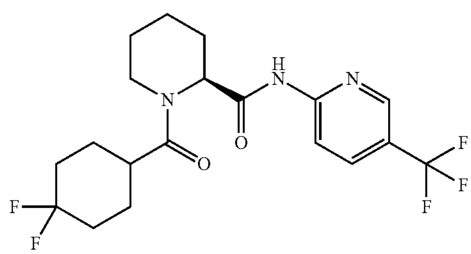 [SMILES: O=C(Nc1ccc(C(F)(F)F)cn1)[C@@H]1CCCCN1C(=O)C1CCC(F)(F)CC1] | (S)-1-(4,4-Difluoro-cyclohexanecarbonyl)-piperidine-2-carboxylic acid (5-trifluoromethyl-pyridin-2-yl)-amide |
| 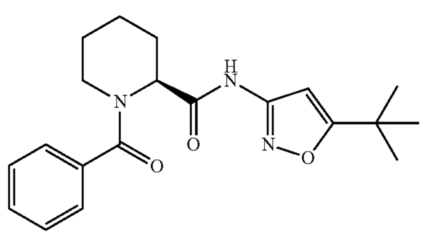 [SMILES: CC(C)(C)c1cc(NC(=O)[C@@H]2CCCCN2C(=O)c2ccccc2)no1] | (S)-1-Benzoyl-piperidine-2-carboxylic acid (5-tert-butyl-isoxazol-3-yl)-amide |
| 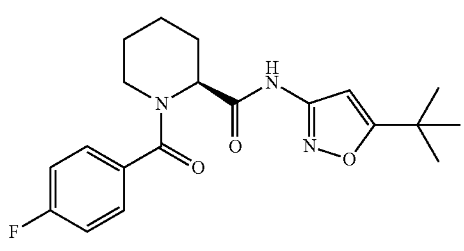 [SMILES: CC(C)(C)c1cc(NC(=O)[C@@H]2CCCCN2C(=O)c2ccc(F)cc2)no1] | (S)-1-(4-Fluoro-benzoyl)-piperidine-2-carboxylic acid (5-tert-butyl-isoxazol-3-yl)-amide |

TABLE III-continued

| Structure | Name |
|---|---|
| 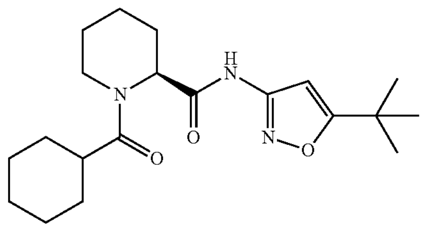 [SMILES: CC(C)(C)c1cc(NC(=O)[C@@H]2CCCCN2C(=O)C2CCCCC2)no1] | (S)-1-Cyclohexanecarbonyl-piperidine-2-carboxylic acid (5-tert-butyl-isoxazol-3-yl)-amide |
| 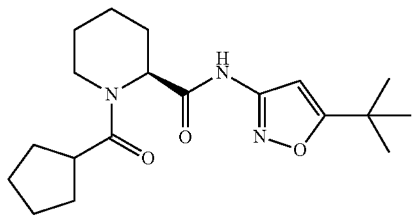 [SMILES: CC(C)(C)c1cc(NC(=O)[C@@H]2CCCCN2C(=O)C2CCCC2)no1] | (S)-1-Cyclopentanecarbonyl-piperidine-2-carboxylic acid (5-tert-butyl-isoxazol-3-yl)-amide |
| 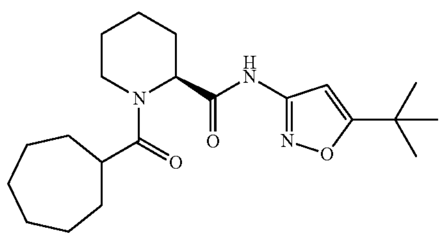 [SMILES: CC(C)(C)c1cc(NC(=O)[C@@H]2CCCCN2C(=O)C2CCCCCC2)no1] | (S)-1-Cycloheptanecarbonyl-piperidine-2-carboxylic acid (5-tert-butyl-isoxazol-3-yl)-amide |
| 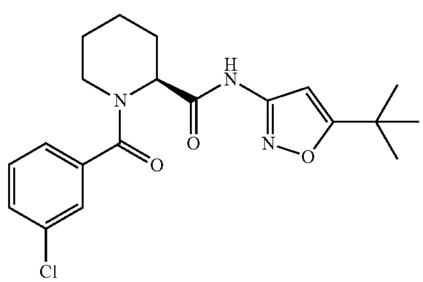 [SMILES: CC(C)(C)c1cc(NC(=O)[C@@H]2CCCCN2C(=O)c2cccc(Cl)c2)no1] | (S)-1-(3-Chloro-benzoyl)-piperidine-2-carboxylic acid (5-tert-butyl-isoxazol-3-yl)-amide |
| 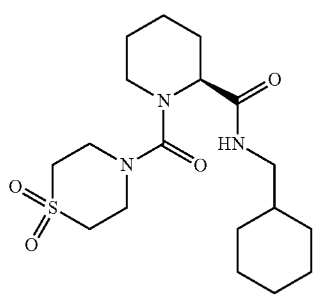 [SMILES: O=C(NCC1CCCCC1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid cyclohexylmethyl-amide |
| 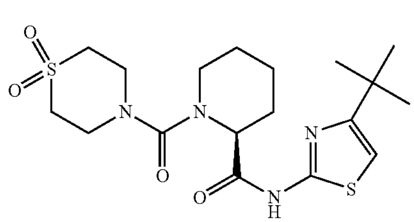 [SMILES: CC(C)(C)c1csc(NC(=O)[C@@H]2CCCCN2C(=O)N2CCS(=O)(=O)CC2)n1] | (S)-1-(1,1-Dioxo-1λ6-thiomorpholine-4-carbonyl)-piperidine-2-carboxylic acid (4-tert-butyl-thiazol-2-yl)-amide |

TABLE III-continued

| Structure | Name |
|---|---|
| 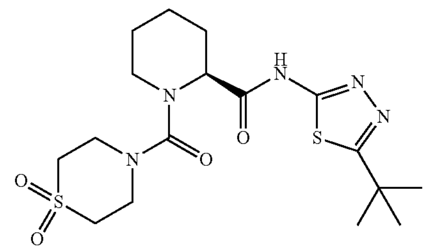 [SMILES: CC(C)(C)c1nnc(NC(=O)[C@@H]2CCCCN2C(=O)N2CCS(=O)(=O)CC2)s1] | (S)-1-(1,1-Dioxo-1λ6-thiomorpholine-4-carbonyl)-piperidine-2-carboxylic acid (5-tert-butyl-1,3,4-thiadiazol-2-yl)-amide |
| 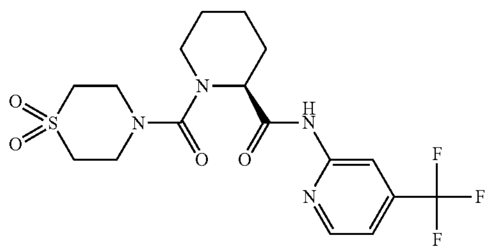 [SMILES: O=C(Nc1cc(C(F)(F)F)ccn1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (4-trifluoromethyl-pyridin-2-yl)-amide |
| 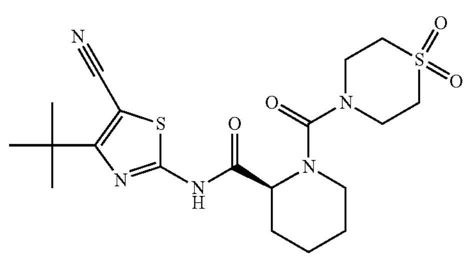 [SMILES: CC(C)(C)c1nc(NC(=O)[C@@H]2CCCCN2C(=O)N2CCS(=O)(=O)CC2)sc1C#N] | (S)-1-(1,1-Dioxo-1λ6-thiomorpholine-4-carbonyl)-piperidine-2-carboxylic acid (4-tert-butyl-5-cyano-thiazol-2-yl)-amide |
| 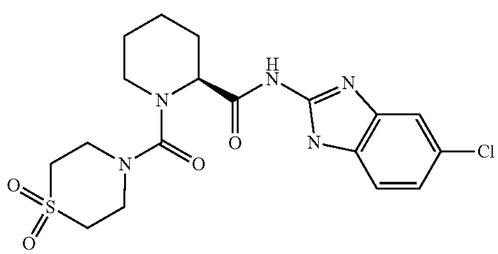 [SMILES: O=C(Nc1nc2cc(Cl)ccc2[nH]1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (5-chloro-1H-benzimidazol-2-yl)-amide |
| 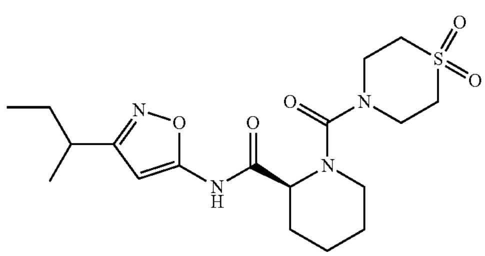 [SMILES: CCC(C)c1cc(NC(=O)[C@@H]2CCCCN2C(=O)N2CCS(=O)(=O)CC2)on1] | (S)-1-(1,1-Dioxo-1λ6-thiomorpholine-4-carbonyl)-piperidine-2-carboxylic acid (3-sec-butyl-isoxazol-5-yl)-amide |
| 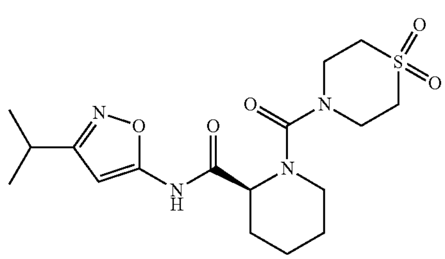 [SMILES: CC(C)c1cc(NC(=O)[C@@H]2CCCCN2C(=O)N2CCS(=O)(=O)CC2)on1] | (S)-1-(1,1-Dioxo-1λ6-thiomorpholine-4-carbonyl)-piperidine-2-carboxylic acid (3-isopropyl-isoxazol-5-yl)-amide |

TABLE III-continued

| Structure | Name |
|---|---|
| 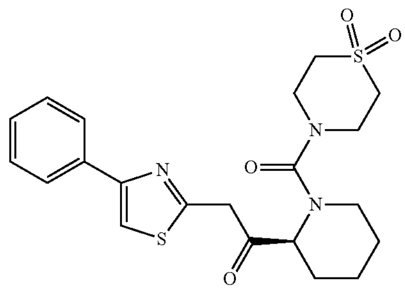 [SMILES: O=C(Cc1nc(-c2ccccc2)cs1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (4-phenyl-thiazol-2-yl)-amide |
| 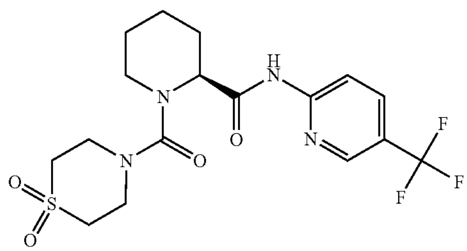 [SMILES: O=C(Nc1ccc(C(F)(F)F)cn1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (5-trifluoromethyl-pyridin-2-yl)-amide |
| 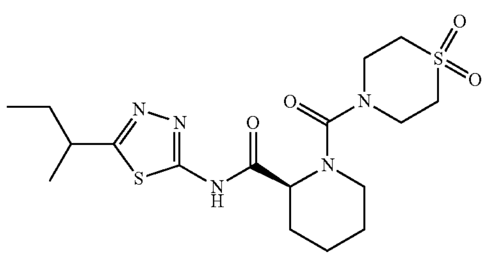 [SMILES: CCC(C)c1nnc(NC(=O)[C@@H]2CCCCN2C(=O)N2CCS(=O)(=O)CC2)s1] | (S)-1-(1,1-Dioxo-1λ6-thiomorpholine-4-carbonyl)-piperidine-2-carboxylic acid (5-sec-butyl-1,3,4-thiadiazol-2-yl)-amide |
| 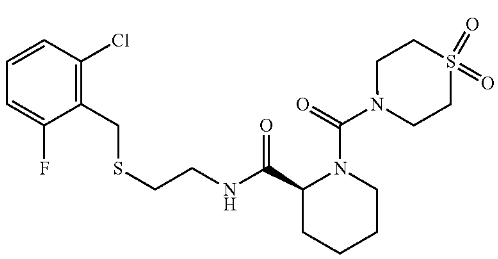 [SMILES: O=C(NCCSCc1c(F)cccc1Cl)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid [2-(2-chloro-6-fluoro-benzylsulfanyl)-ethyl]-amide |
|  | (S)-1-(1,1-Dioxo-1λ6-thiomorpholine-4-carbonyl)-piperidine-2-carboxylic acid (2-phenoxy-ethyl)-amide |

TABLE III-continued

| Structure | Name |
|---|---|
| 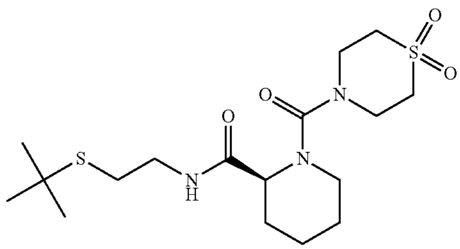 [SMILES: CC(C)(C)SCCNC(=O)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (2-tert-butylsulfanyl-ethyl)-amide |
| 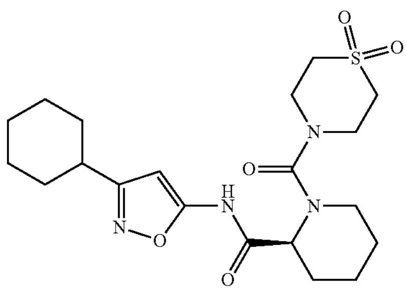 [SMILES: O=C(Nc1cc(C2CCCCC2)no1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-cyclohexyl-isoxazol-5-yl)-amide |
| 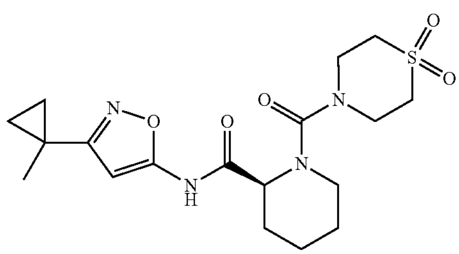 [SMILES: CC1(c2cc(NC(=O)[C@@H]3CCCCN3C(=O)N3CCS(=O)(=O)CC3)on2)CC1] | (S)-1-(1,1-Dioxo-1λ6-thiomorpholine-4-carbonyl)-piperidine-2-carboxylic acid [3-(1-methyl-cyclopropyl)-isoxazol-5-yl]-amide |
| 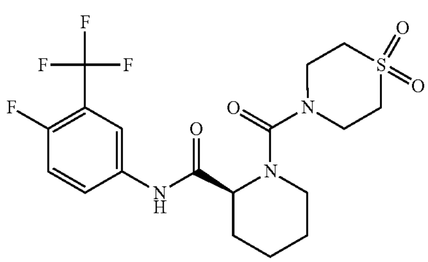 [SMILES: O=C(Nc1ccc(F)c(C(F)(F)F)c1)[C@@H]1CCCCN1C(=O)N1CCS(=O)(=O)CC1] | (S)-1-(1,1-Dioxo-1λ6-thiomorphone-4-carbonyl)-piperidine-2-carboxylic acid (4-fluoro-3-trifluoromethyl-phenyl)-amide |
| 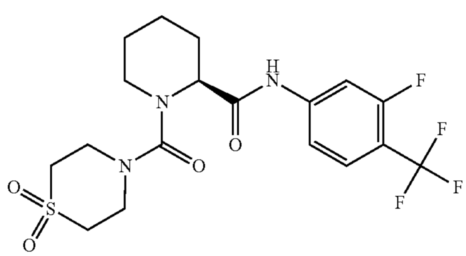 [SMILES: O=C(Nc1ccc(C(F)(F)F)c(F)c1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-fluoro-4-trifluoromethyl-phenyl)-amide |
| 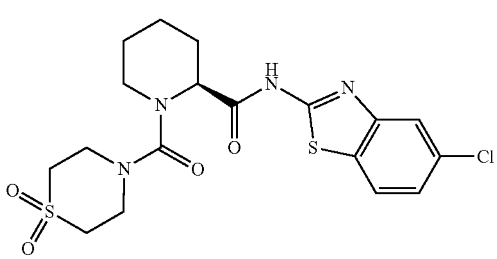 | (S)-1-(1,1-Dioxo-1λ6-thiomorpholine-4-carbonyl)-piperidine-2-carboxylic acid (5-chloro-benzothiazol-2-yl)-amide |

TABLE III-continued

| Structure | Name |
|---|---|
| 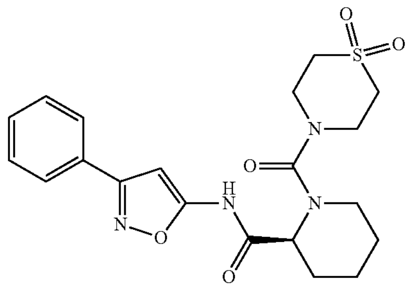 [SMILES: O=C(Nc1cc(-c2ccccc2)no1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-phenyl-isoxazol-5-yl)-amide |
| 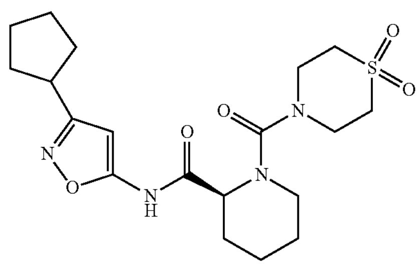 [SMILES: O=C(Nc1cc(C2CCCC2)no1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-cyclopentyl-isoxazol-5-yl)-amide |
| 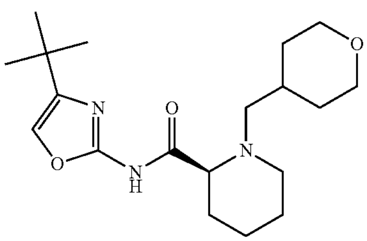 [SMILES: CC(C)(C)c1coc(NC(=O)[C@@H]2CCCCN2CC2CCOCC2)n1] | (S)-1-(Tetrahydro-pyran-4-ylmethyl)-piperidine-2-carboxylic acid (4-tert-butyl-oxazol-2-yl)-amide |
| 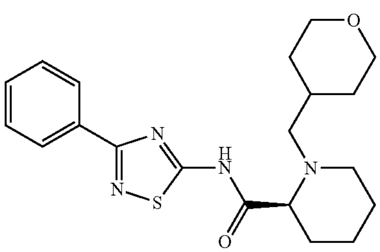 [SMILES: O=C(Nc1nc(-c2ccccc2)ns1)[C@@H]1CCCCN1CC1CCOCC1] | (S)-1-(Tetrahydro-pyran-4-ylmethyl)-piperidine-2-carboxylic acid (3-phenyl-1,2,4-thiadiazol-5-yl)-amide |
| 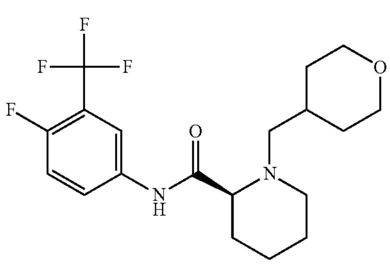 [SMILES: O=C(Nc1ccc(F)c(C(F)(F)F)c1)[C@@H]1CCCCN1CC1CCOCC1] | (S)-1-(Tetrahydro-pyran-4-ylmethyl)-piperidine-2-carboxylic acid (4-fluoro-3-trifluoromethyl-phenyl)-amide |
| 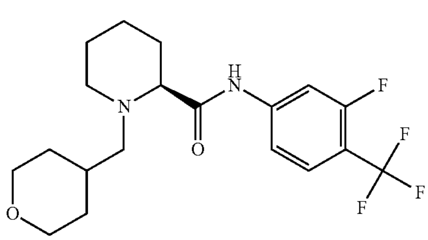 [SMILES: O=C(Nc1ccc(C(F)(F)F)c(F)c1)[C@@H]1CCCCN1CC1CCOCC1] | (S)-1-(Tetrahydro-pyran-4-ylmethyl)-piperidine-2-carboxylic acid (3-fluoro-4-trifluoromethyl-phenyl)-amide |

TABLE III-continued

| Structure | Name |
|---|---|
| 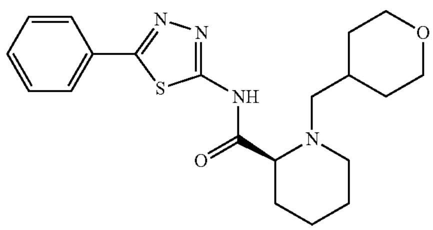 [SMILES: O=C(Nc1nnc(-c2ccccc2)s1)[C@@H]1CCCCN1CC1CCOCC1] | (S)-1-(Tetrahydro-pyran-4-ylmethyl)-piperidine-2-carboxylic acid (5-phenyl-1,3,4-thiadiazol-2-yl)-amide |
| 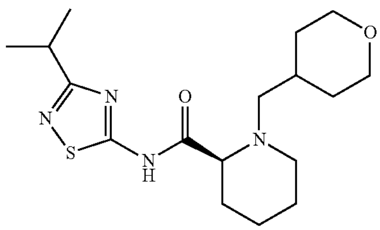 [SMILES: CC(C)c1nsc(NC(=O)[C@@H]2CCCCN2CC2CCOCC2)n1] | (S)-1-(Tetrahydro-pyran-4-ylmethyl)-piperidine-2-carboxylic acid (3-isopropyl-1,2,4-thiadiazol-5-yl)-amide |
| 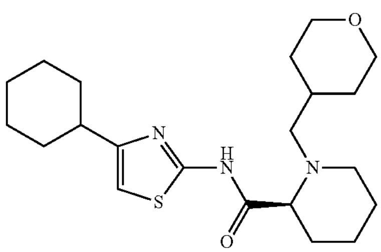 [SMILES: O=C(Nc1nc(C2CCCCC2)cs1)[C@@H]1CCCCN1CC1CCOCC1] | (S)-1-(Tetrahydro-pyran-4-ylmethyl)-piperidine-2-carboxylic acid (4-cyclohexyl-thiazol-2-yl)-amide |
| 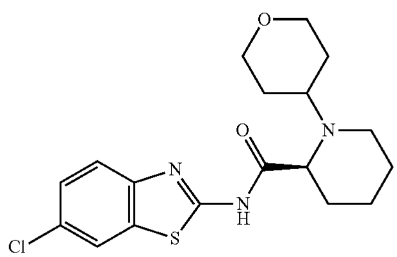 [SMILES: O=C(Nc1nc2ccc(Cl)cc2s1)[C@@H]1CCCCN1C1CCOCC1] | (S)-1-(Tetrahydro-pyran-4-yl)-piperidine-2-carboxylic acid (6-chloro-benzothiazol-2-yl)-amide |
| 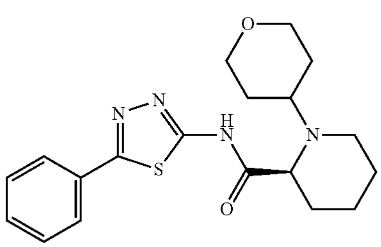 [SMILES: O=C(Nc1nnc(-c2ccccc2)s1)[C@@H]1CCCCN1C1CCOCC1] | (S)-1-(Tetrahydro-pyran-4-yl)-piperidine-2-carboxylic acid (5-phenyl-1,3,4-thiadiazol-2-yl)-amide |
| 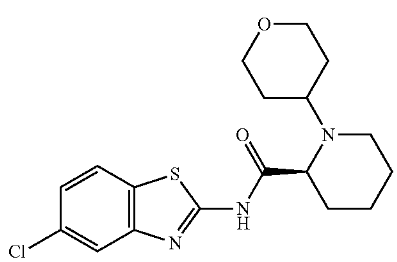 [SMILES: O=C(Nc1nc2cc(Cl)ccc2s1)[C@@H]1CCCCN1C1CCOCC1] | (S)-1-(Tetrahydro-pyran-4-yl)-piperidine-2-carboxylic acid (5-chloro-benzothiazol-2-yl)-amide |

TABLE III-continued

| Structure | Name |
|---|---|
| 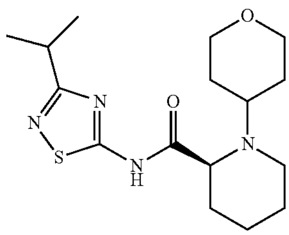 [SMILES: CC(C)c1nsc(NC(=O)[C@@H]2CCCCN2C2CCOCC2)n1] | (S)-1-(Tetrahydro-pyran-4-yl)-piperidine-2-carboxylic acid (3-isopropyl-1,2,4-thiadiazol-5-yl)-amide |
| 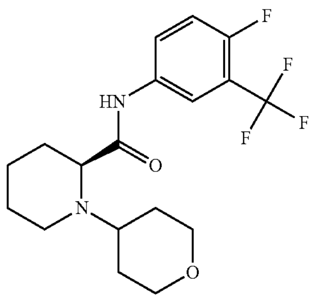 [SMILES: O=C(Nc1ccc(F)c(C(F)(F)F)c1)[C@@H]1CCCCN1C1CCOCC1] | (S)-1-(Tetrahydro-pyran-4-yl)-piperidine-2-carboxylic acid (4-fluoro-3-trifluoromethyl-phenyl)-amide |
| 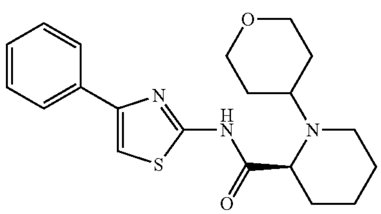 [SMILES: O=C(Nc1nc(-c2ccccc2)cs1)[C@@H]1CCCCN1C1CCOCC1] | (S)-1-(Tetrahydro-pyran-4-yl)-piperidine-2-carboxylic acid (4-phenyl-thiazol-2-yl)-amide |
| 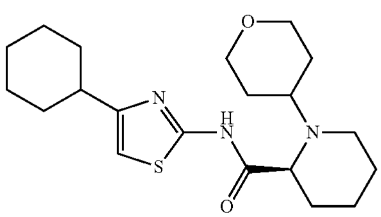 [SMILES: O=C(Nc1nc(C2CCCCC2)cs1)[C@@H]1CCCCN1C1CCOCC1] | (S)-1-(Tetrahydro-pyran-4-yl)-piperidine-2-carboxylic acid (4-cyclohexyl-thiazol-2-yl)-amide |
| 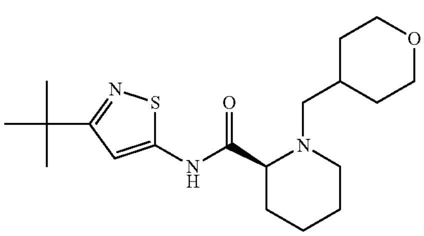 [SMILES: CC(C)(C)c1cc(NC(=O)[C@@H]2CCCCN2CC2CCOCC2)sn1] | (S)-1-(Tetrahydro-pyran-4-ylmethyl)-piperidine-2-carboxylic acid (3-tert-butyl-isothiazol-5-yl)-amide |
| 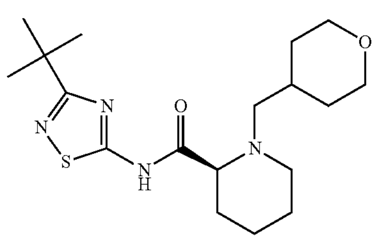 [SMILES: CC(C)(C)c1nsc(NC(=O)[C@@H]2CCCCN2CC2CCOCC2)n1] | (S)-1-(Tetrahydro-pyran-4-ylmethyl)-piperidine-2-carboxylic acid (3-tert-butyl-1,2,4-thiadiazol-5-yl)-amide |

TABLE III-continued

| Structure | Name |
|---|---|
| 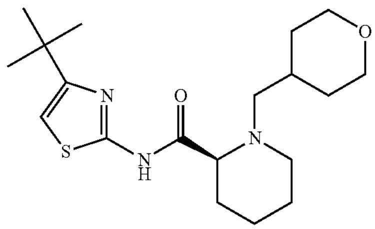 [SMILES: CC(C)(C)c1csc(NC(=O)[C@@H]2CCCCN2CC2CCOCC2)n1] | (S)-1-(Tetrahydro-pyran-4-ylmethyl)-piperidine-2-carboxylic acid (4-tert-butyl-thiazol-2-yl)-amide |
| 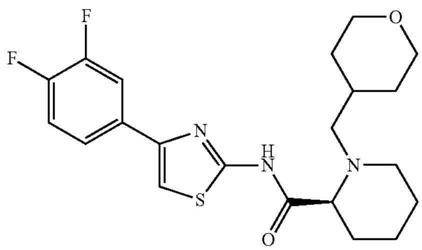 [SMILES: O=C(Nc1nc(-c2ccc(F)c(F)c2)cs1)[C@@H]1CCCCN1CC1CCOCC1] | (S)-1-(Tetrahydro-pyran-4-ylmethyl)-piperidine-2-carboxylic acid [4-(3,4-difluoro-phenyl)-thiazol-2-yl]-amide |
| 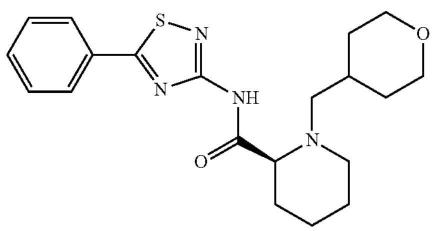 [SMILES: O=C(Nc1nsc(-c2ccccc2)n1)[C@@H]1CCCCN1CC1CCOCC1] | (S)-1-(Tetrahydro-pyran-4-ylmethyl)-piperidine-2-carboxylic acid (5-phenyl-1,2,4-thiadiazol-3-yl)-amide |
| 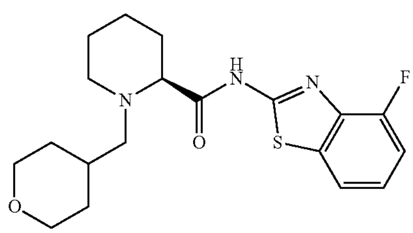 [SMILES: O=C(Nc1nc2c(F)cccc2s1)[C@@H]1CCCCN1CC1CCOCC1] | (S)-1-(Tetrahydro-pyran-4-ylmethyl)-piperidine-2-carboxylic acid (4-fluoro-benzothiazol-2-yl)-amide |
| 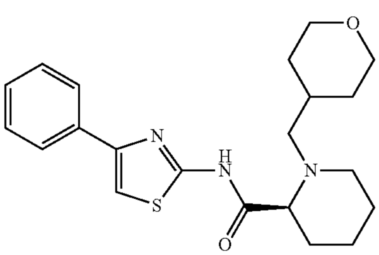 | (S)-1-(Tetrahydro-pyran-4-ylmethyl)-piperidine-2-carboxylic acid (4-phenyl-thiazol-2-yl)-amide |
| 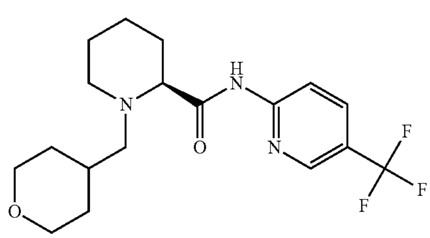 [SMILES: O=C(Nc1ccc(C(F)(F)F)cn1)[C@@H]1CCCCN1CC1CCOCC1] | (S)-1-(Tetrahydro-pyran-4-ylmethyl)-piperidine-2-carboxylic acid (5-trifluoromethyl-pyridin-2-yl)-amide |

TABLE III-continued

| Structure | Name |
|---|---|
| 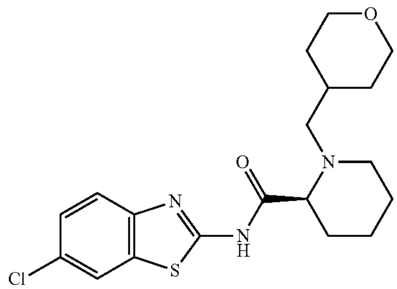 [SMILES: O=C(Nc1nc2ccc(Cl)cc2s1)[C@@H]1CCCCN1CC1CCOCC1] | (S)-1-(Tetrahydro-pyran-4-ylmethyl)-piperidine-2-carboxylic acid (6-chloro-benzothiazol-2-yl)-amide |
| 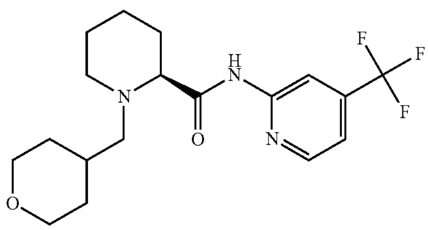 [SMILES: O=C(Nc1cc(C(F)(F)F)ccn1)[C@@H]1CCCCN1CC1CCOCC1] | (S)-1-(Tetrahydro-pyran-4-ylmethyl)-piperidine-2-carboxylic acid (4-trifluoromethyl-pyridin-2-yl)-amide |
| 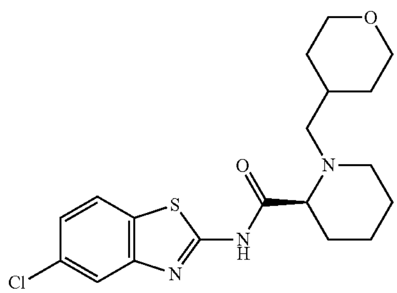 [SMILES: O=C(Nc1nc2cc(Cl)ccc2s1)[C@@H]1CCCCN1CC1CCOCC1] | (S)-1-(Tetrahydro-pyran-4-ylmethyl)-piperidine-2-carboxylic acid (5-chloro-benzothiazol-2-yl)-amide |
| 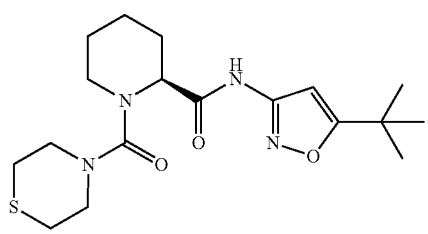 [SMILES: CC(C)(C)c1cc(NC(=O)[C@@H]2CCCCN2C(=O)N2CCSCC2)no1] | (S)-1-(Thiomorpholine-4-carbonyl)-piperidine-2-carboxylic acid (5-tert-butyl-isoxazol-3-yl)-amide |
| 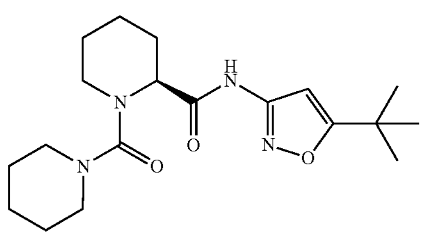 [SMILES: CC(C)(C)c1cc(NC(=O)[C@@H]2CCCCN2C(=O)N2CCCCC2)no1] | (S)-1-(Piperidine-1-carbonyl)-piperidine-2-carboxylic acid (5-tert-butyl-isoxazol-3-yl)-amide |
| 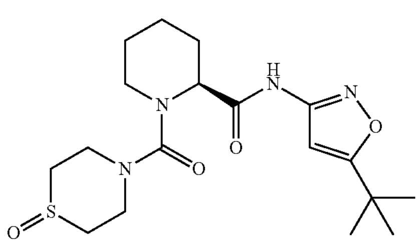 [SMILES: CC(C)(C)c1cc(NC(=O)[C@@H]2CCCCN2C(=O)N2CCS(=O)CC2)no1] | (S)-1-(1-Oxo-1λ4-thiomorpholine-4-carbonyl)-piperidine-2-carboxylic acid (5-tert-butyl-isoxazol-3-yl)-amide |

TABLE III-continued

| Structure | Name |
|---|---|
| 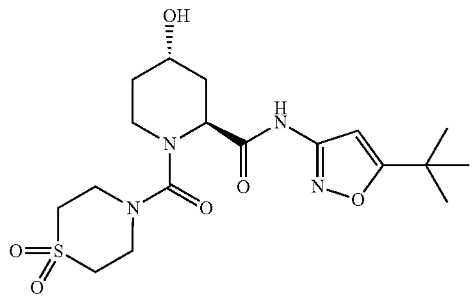 [SMILES: CC(C)(C)c1cc(NC(=O)[C@@H]2C[C@@H](O)CCN2C(=O)N2CCS(=O)(=O)CC2)no1] | (2S,4S)-1-(1,1-Dioxo-1λ6-thiomorpholine-4-carbonyl)-4-hydroxy-piperidine-2-carboxylic acid (5-tert-butyl-isoxazol-3-yl)-amide |
| 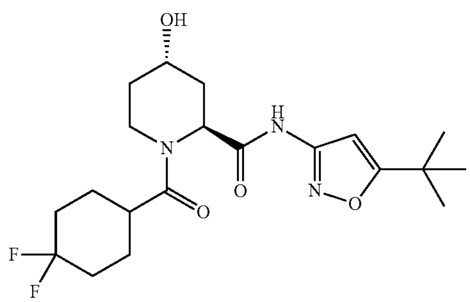 [SMILES: CC(C)(C)c1cc(NC(=O)[C@@H]2C[C@@H](O)CCN2C(=O)C2CCC(F)(F)CC2)no1] | (2S,4S)-1-(4,4-Difluoro-cyclohexanecarbonyl)-4-hydroxy-piperidine-2-carboxylic acid (5-tert-butyl isoxazol-3-yl)-amide |
| 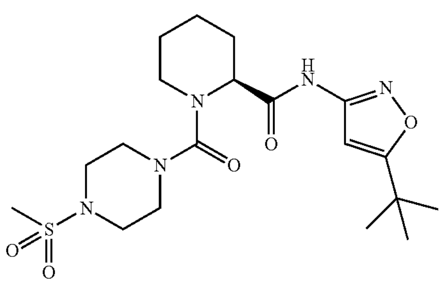 [SMILES: CC(C)(C)c1cc(NC(=O)[C@@H]2CCCCN2C(=O)N2CCN(S(C)(=O)=O)CC2)no1] | (S)-1-(4-Methanesulfonyl-piperazine-1-carbonyl)-piperidine-2-carboxylic acid (5-tert-butyl-isoxazol-3-yl)-amide |
| 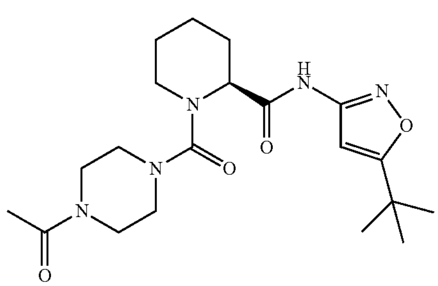 [SMILES: CC(=O)N1CCN(C(=O)N2CCCC[C@H]2C(=O)Nc2cc(C(C)(C)C)on2)CC1] | (S)-1-(4-Acetyl-piperazine-1-carbonyl)-piperidine-2-carboxylic acid (5-tert-butyl-isoxazol-3-yl)-amide |
| 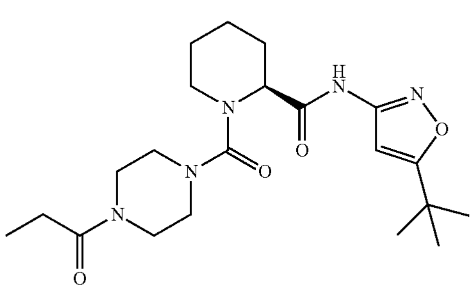 [SMILES: CCC(=O)N1CCN(C(=O)N2CCCC[C@H]2C(=O)Nc2cc(C(C)(C)C)on2)CC1] | (S)-1-(4-Propionyl-piperazine-1-carbonyl)-piperidine-2-carboxylic acid (5-tert-butyl-isoxazol-3-yl)-amide |

TABLE III-continued

| Structure | Name |
|---|---|
| 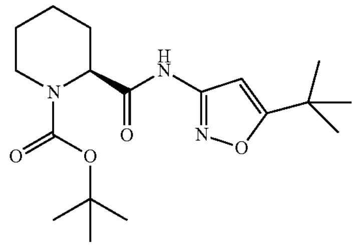 [SMILES: CC(C)(C)OC(=O)N1CCCC[C@H]1C(=O)Nc1cc(C(C)(C)C)on1] | (S)-2-(5-tert-Butyl-isoxazol-3-ylcarbamoyl)-piperidine-1-carboxylic acid tert-butyl ester |
| 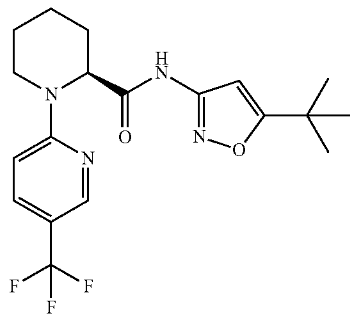 [SMILES: CC(C)(C)c1cc(NC(=O)[C@@H]2CCCCN2c2ccc(C(F)(F)F)cn2)no1] | (S)-5'-trifluoromethyl-3,4,5,6-tetrahydro-2H-[1,2']bipyridinyl-2-carboxylic acid (5-tert-butyl-isoxazol-3-yl)-amide |
| 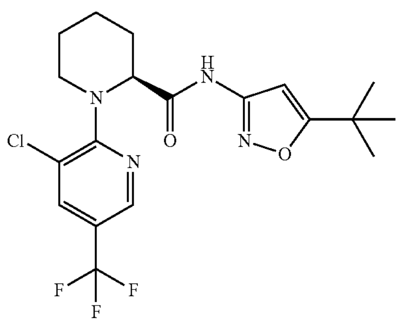 [SMILES: CC(C)(C)c1cc(NC(=O)[C@@H]2CCCCN2c2ncc(C(F)(F)F)cc2Cl)no1] | (S)-3'-Chloro-5'-trifluoromethyl-3,4,5,6-tetrahydro-2H-[1,2']bipyridinyl-2-carboxylic acid (5-tert-butyl-isoxazol-3-yl)-amide |
| 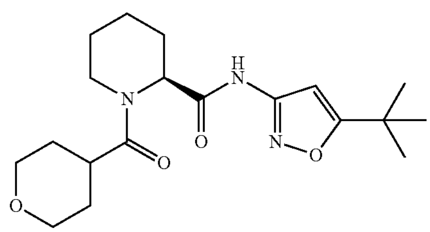 [SMILES: CC(C)(C)c1cc(NC(=O)[C@@H]2CCCCN2C(=O)C2CCOCC2)no1] | (S)-1-(Tetrahydro-pyran-4-carbonyl)-piperidine-2-carboxylic acid (5-tert-butyl-isoxazol-3-yl)-amide |
| 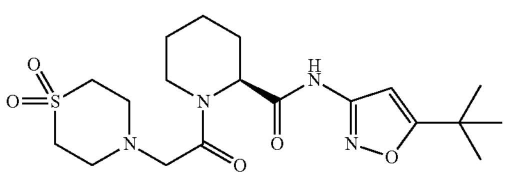 [SMILES: CC(C)(C)c1cc(NC(=O)[C@@H]2CCCCN2C(=O)CN2CCS(=O)(=O)CC2)no1] | (S)-1-[2-(1,1-Dioxo-1λ6-thiomorpholin-4-yl)-acetyl]-piperidine-2-carboxylic acid (5-tert-butyl-isoxazol-3-yl)-amide |
| 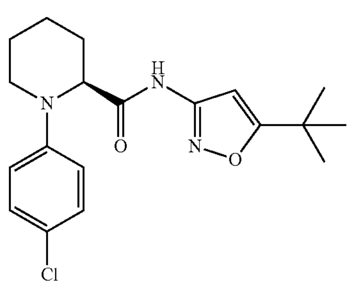 [SMILES: CC(C)(C)c1cc(NC(=O)[C@@H]2CCCCN2c2ccc(Cl)cc2)no1] | (S)-1-(4-Chloro-phenyl)-piperidine-2-carboxylic acid (5-tert-butyl-isoxazol-3-yl)-amide |

TABLE III-continued

| Structure | Name |
|---|---|
| 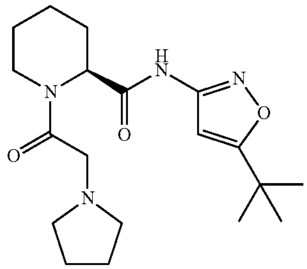 [SMILES: CC(C)(C)c1cc(NC(=O)[C@@H]2CCCCN2C(=O)CN2CCCC2)no1] | (S)-1-(2-Pyrrolidin-1-yl-acetyl)-piperidine-2-carboxylic acid (5-tert-butyl-isoxazol-3-yl)-amide |
| 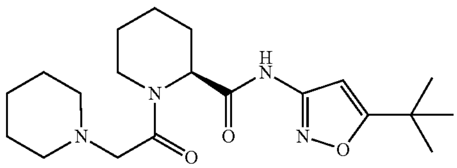 [SMILES: CC(C)(C)c1cc(NC(=O)[C@@H]2CCCCN2C(=O)CN2CCCCC2)no1] | (S)-1-(2-Piperidinyl-acetyl)-piperidine-2-carboxylic acid (5-tert-butyl-isoxazol-3-yl)-amide |
| 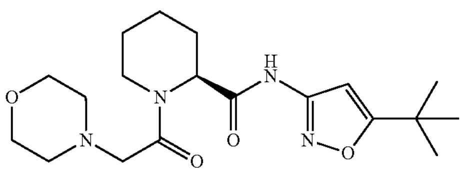 [SMILES: CC(C)(C)c1cc(NC(=O)[C@@H]2CCCCN2C(=O)CN2CCOCC2)no1] | (S)-1-(2-Morpholin-4-yl-acetyl)-piperidine-2-carboxylic acid (5-tert-butyl-isoxazol-3-yl)-amide |
| 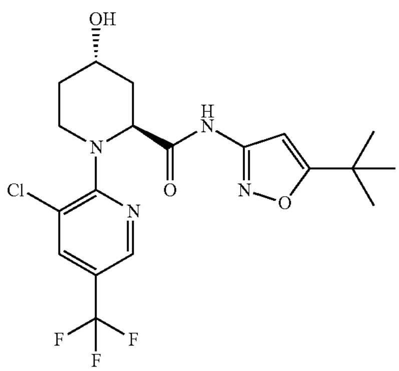 [SMILES: CC(C)(C)c1cc(NC(=O)[C@@H]2C[C@@H](O)CCN2c2ncc(C(F)(F)F)cc2Cl)no1] | (2S,4S)-3'-Chloro-4-hydroxy-5'-trifluoromethyl-3,4,5,6-tetrahydro-2H-[1,2']bipyridinyl-2-carboxylic acid (5-tert-butyl-isoxazol-3-yl)-amide |
| 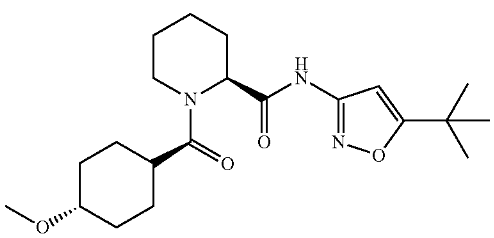 | (S)-1-(4-trans-Methoxy-cyclohexanecarbonyl)-piperidine-2-carboxylic acid (5-tert-butyl-isoxazol-3-yl)-amide |
| 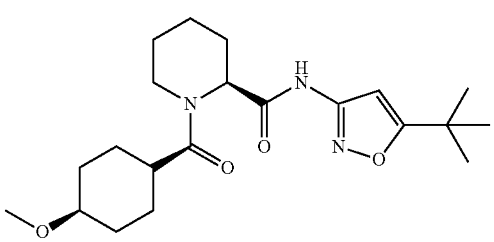 | (S)-1-(4-cis-Methoxy-cyclohexanecarbonyl)-piperidine-2-carboxylic acid (5-tert-butyl-isoxazol-3-yl)-amide |

TABLE III-continued

| Structure | Name |
|---|---|
| 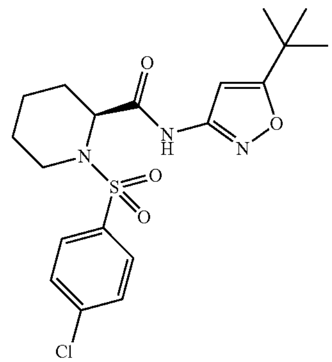 [SMILES: CC(C)(C)c1cc(NC(=O)[C@@H]2CCCCN2S(=O)(=O)c2ccc(Cl)cc2)no1] | (S)-1-(4-Chloro-benzenesulfonyl)-piperidine-2-carboxylic acid (5-tert-butyl-isoxazol-3-yl)-amide |
| 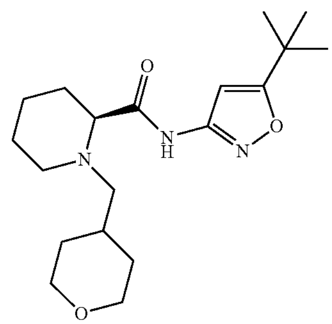 [SMILES: CC(C)(C)c1cc(NC(=O)[C@@H]2CCCCN2CC2CCOCC2)no1] | (S)-1-(Tetrahydro-pyran-4-ylmethyl)-piperidine-2-carboxylic acid (5-tert-butyl-isoxazol-3-yl)-amide |
| 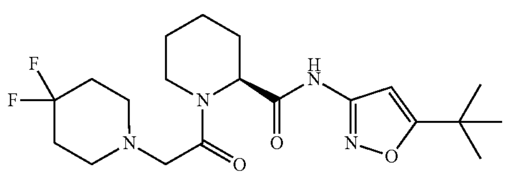 [SMILES: CC(C)(C)c1cc(NC(=O)[C@@H]2CCCCN2C(=O)CN2CCC(F)(F)CC2)no1] | (S)-1-[2-(4,4-Difluoro-piperidin-1-yl)-acetyl]-piperidine-2-carboxylic acid (5-tert-butyl-isoxazol-3-yl)-amide |
| 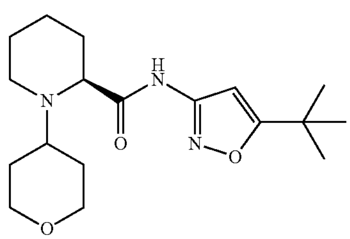 [SMILES: CC(C)(C)c1cc(NC(=O)[C@@H]2CCCCN2C2CCOCC2)no1] | (S)-1-(Tetrahydro-pyran-4-yl)-piperidine-2-carboxylic acid (5-tert-butyl-isoxazol-3-yl)-amide |
| 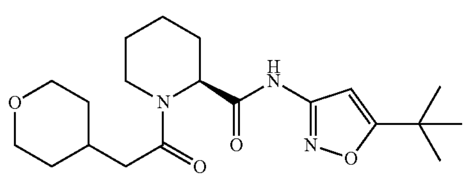 [SMILES: CC(C)(C)c1cc(NC(=O)[C@@H]2CCCCN2C(=O)CC2CCOCC2)no1] | (S)-1-(2-Tetrahydro-pyran-4-yl-acetyl)-piperidine-2-carboxylic acid (5-tert-butyl-isoxazol-3-yl)-amide |
| 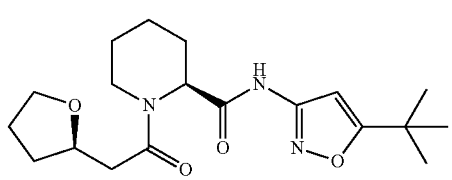 [SMILES: CC(C)(C)c1cc(NC(=O)[C@@H]2CCCCN2C(=O)C[C@H]2CCCO2)no1] | (S)-1-((R)-2-Tetrahydro-furan-2-yl-acetyl)-piperidine-2-carboxylic acid (5-tert-butyl-isoxazol-3-yl)-amide |

TABLE III-continued

| Structure | Name |
|---|---|
| 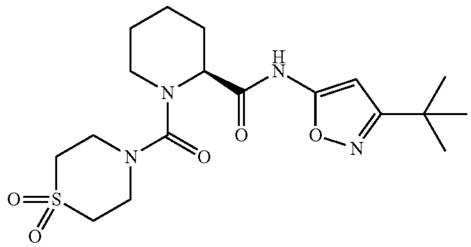 [SMILES: CC(C)(C)c1cc(NC(=O)[C@@H]2CCCCN2C(=O)N2CCS(=O)(=O)CC2)on1] | (S)-1-(1,1-Dioxo-1λ6-thiomorpholine-4-carbonyl)-piperidine-2-carboxylic acid (3-tert-butyl-isoxazol-5-yl)-amide |
| 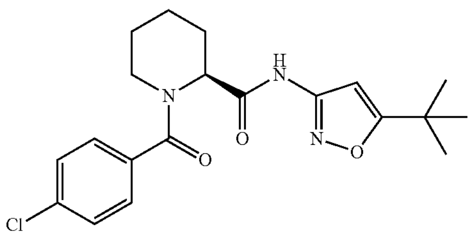 [SMILES: CC(C)(C)c1cc(NC(=O)[C@@H]2CCCCN2C(=O)c2ccc(Cl)cc2)no1] | (S)-1-(4-Chloro-benzoyl)-piperidine-2-carboxylic acid (5-tert-butyl-isoxazol-3-yl)-amide |
| 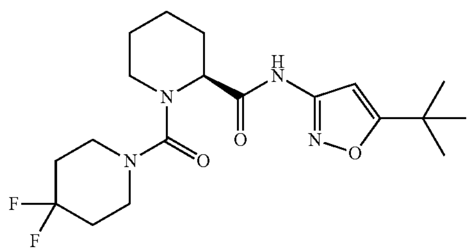 [SMILES: CC(C)(C)c1cc(NC(=O)[C@@H]2CCCCN2C(=O)N2CCC(F)(F)CC2)no1] | (S)-1-(4,4-Difluoro-piperidine-1-carbonyl)-piperidine-2-carboxylic acid (5-tert-butyl-isoxazol-3-yl)-amide |
| 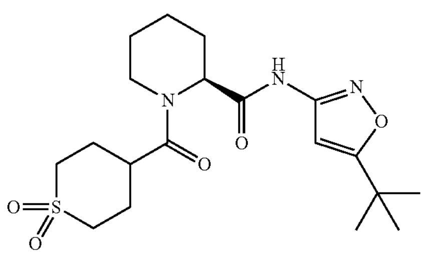 [SMILES: CC(C)(C)c1cc(NC(=O)[C@@H]2CCCCN2C(=O)C2CCS(=O)(=O)CC2)no1] | (S)-1-(1,1-Dioxo-hexahydro-1λ6-thiopyran-4-carbonyl)-piperidine-2-carboxylic acid (5-tert-butyl-isoxazol-3-yl)-amide |
| 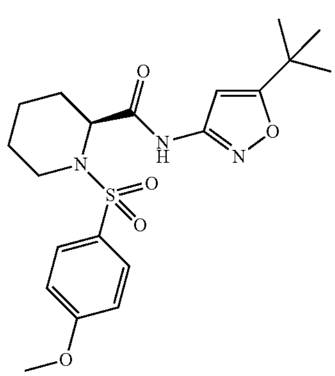 [SMILES: COc1ccc(S(=O)(=O)N2CCCC[C@H]2C(=O)Nc2cc(C(C)(C)C)on2)cc1] | (S)-1-(4-Methoxy-benzenesulfonyl)-piperidine-2-carboxylic acid (5-tert-butyl-isoxazol-3-yl)-amide |
| 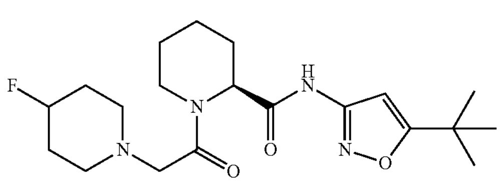 [SMILES: CC(C)(C)c1cc(NC(=O)[C@@H]2CCCCN2C(=O)CN2CCC(F)CC2)no1] | (S)-1-[2-(4-Fluoro-piperidin-1-yl)acetyl]-piperidine-2-carboxylic acid (5-tert-butyl-isoxazol-3-yl)-amide |

TABLE III-continued

| Structure | Name |
|---|---|
| 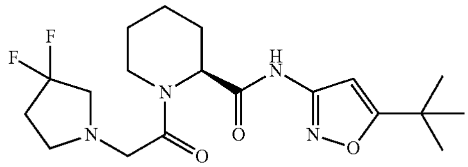 [SMILES: CC(C)(C)c1cc(NC(=O)[C@@H]2CCCCN2C(=O)CN2CCC(F)(F)C2)no1] | (S)-1-[2-(3,3-Difluoro-pyrrolidin-1-yl)-acetyl]-piperidine-2-carboxylic acid (5-tert-butyl-isoxazol-3-yl)-amide |
| 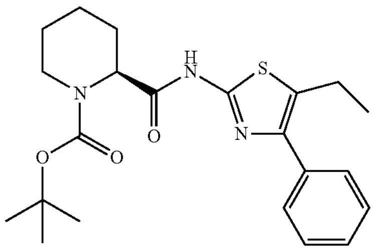 [SMILES: CCc1sc(NC(=O)[C@@H]2CCCCN2C(=O)OC(C)(C)C)nc1-c1ccccc1] | (S)-2-(5-Ethyl-4-phenyl-thiazol-2-ylcarbamoyl)-piperidine-1-carboxylic acid tert-butyl ester |
| 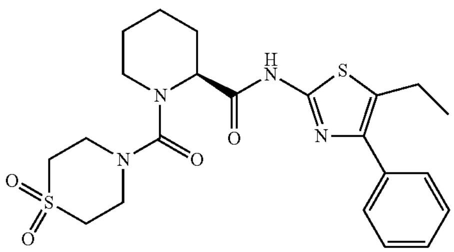 [SMILES: CCc1sc(NC(=O)[C@@H]2CCCCN2C(=O)N2CCS(=O)(=O)CC2)nc1-c1ccccc1] | (S)-1-(1,1-Dioxo-1λ6-thiomorpholine-4-carbonyl)-piperidine-2-carboxylic acid (5-ethyl-4-phenyl-thiazol-2-yl)-amide |
| 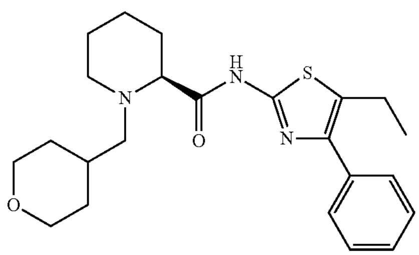 [SMILES: CCc1sc(NC(=O)[C@@H]2CCCCN2CC2CCOCC2)nc1-c1ccccc1] | (S)-1-(Tetrahydro-pyran-4-ylmethyl)-piperidine-2-carboxylic acid (5-ethyl-4-phenyl-thiazol-2-yl)-amide |
| 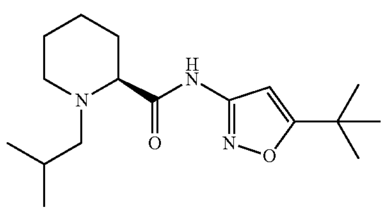 [SMILES: CC(C)CN1CCCC[C@H]1C(=O)Nc1cc(C(C)(C)C)on1] | (S)-1-Isobutyl-piperidine-2-carboxylic acid (5-tert-butyl-isoxazol-3-yl)-amide |
| 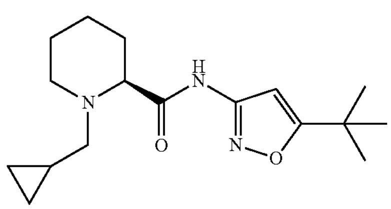 [SMILES: CC(C)(C)c1cc(NC(=O)[C@@H]2CCCCN2CC2CC2)no1] | (S)-1-Cyclopropylmethyl-piperidine-2-carboxylic acid (5-tert-butyl-isoxazol-3-yl)-amide |
| 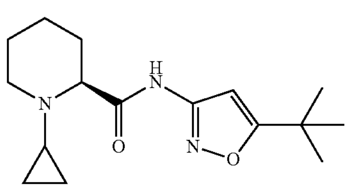 [SMILES: CC(C)(C)c1cc(NC(=O)[C@@H]2CCCCN2C2CC2)no1] | (S)-1-Cyclopropyl-piperidine-2-carboxylic acid (5-tert-butyl-isoxazol-3-yl)-amide |

TABLE III-continued

| Structure | Name |
|---|---|
| 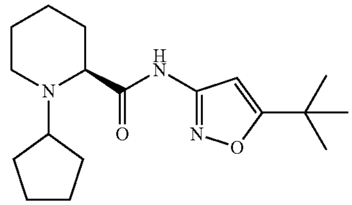 [SMILES: CC(C)(C)c1cc(NC(=O)[C@@H]2CCCCN2C2CCCC2)no1] | (S)-1-Cyclopentyl-piperidine-2-carboxylic acid (5-tert-butyl-isoxazol-3-yl)-amide |
| 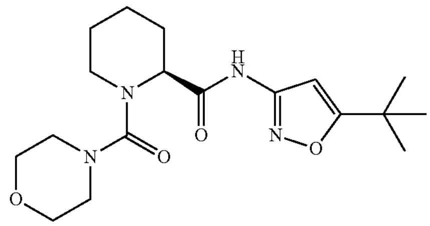 | (S)-1-(Morpholine-4-carbonyl)-piperidine-2-carboxylic acid (5-tert-butyl-isoxazol-3-yl)-amide |
| 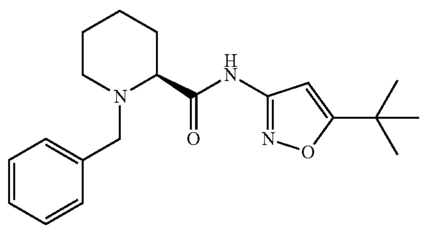 [SMILES: CC(C)(C)c1cc(NC(=O)[C@@H]2CCCCN2Cc2ccccc2)no1] | (S)-1-(benzyl)-piperidine-2-carboxylic acid (5-tert-butyl-isoxazol-3-yl)-amide |
| 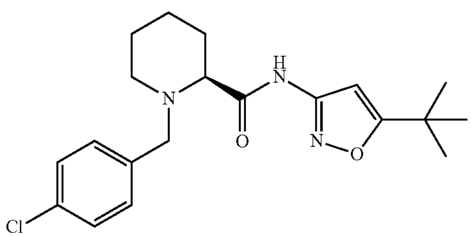 [SMILES: CC(C)(C)c1cc(NC(=O)[C@@H]2CCCCN2Cc2ccc(Cl)cc2)no1] | (S)-1-(4-Chloro-benzyl)-piperidine-2-carboxylic acid (5-tert-butyl-isoxazol-3-yl)-amide |
| 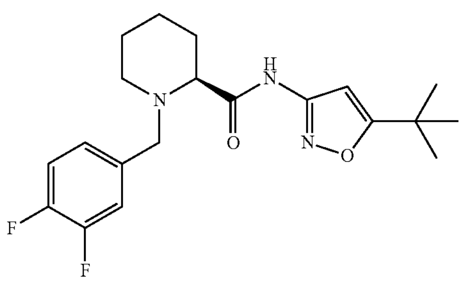 [SMILES: CC(C)(C)c1cc(NC(=O)[C@@H]2CCCCN2Cc2ccc(F)c(F)c2)no1] | (S)-1-(3,4-Difluoro-benzyl)-piperidine-2-carboxylic acid (5-tert-butyl-isoxazol-3-yl)-amide |
| 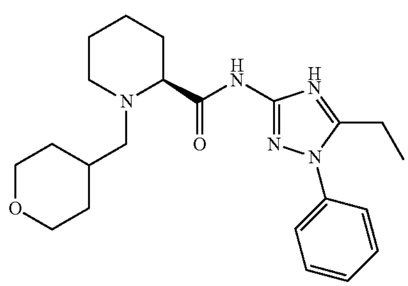 | (S)-1-(Tetrahydro-pyran-4-ylmethyl)-piperidine-2-carboxylic acid (5-ethyl-1-phenyl-1H-1,2,4-triazol-3-yl)-amide |

TABLE III-continued

| Structure | Name |
|---|---|
| 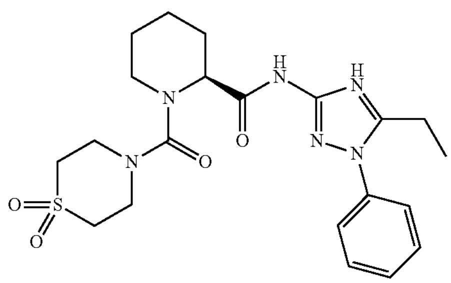 | (S)-1-(1,1-Dioxo-1λ6-thiomorpholine-4-carbonyl)-piperidine-2-carboxylic acid (5-ethyl-1-phenyl-1H-1,2,4-triazol-3-yl)-amide |
| 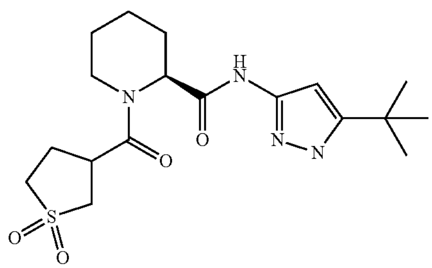 [SMILES: CC(C)(C)c1cc(NC(=O)[C@@H]2CCCCN2C(=O)C2CCS(=O)(=O)C2)n[nH]1] | (S)-1-(1,1-Dioxo-tetrahydro-1λ6-thiophene-3-carbonyl)-piperidine-2-carboxylic acid (5-tert-butyl-isoxazol-3-yl)-amide |
| 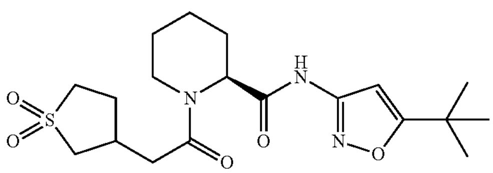 [SMILES: CC(C)(C)c1cc(NC(=O)[C@@H]2CCCCN2C(=O)CC2CCS(=O)(=O)C2)no1] | (S)-1-[2-(1,1-Dioxo-tetrahydro-1λ6-thiophen-3-yl)-acetyl]-piperidine-2-carboxylic acid (5-tert-butyl-isoxazol-3-yl)-amide |
| 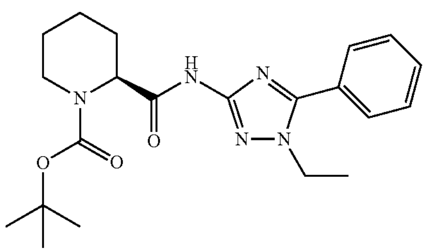 [SMILES: CCn1nc(NC(=O)[C@@H]2CCCCN2C(=O)OC(C)(C)C)nc1-c1ccccc1] | (S)-2-(1-Ethyl-5-phenyl-1H-1,2,4-triazol-3-ylcarbamoyl)-piperidine-1-carboxylic acid tert-butyl ester |
| 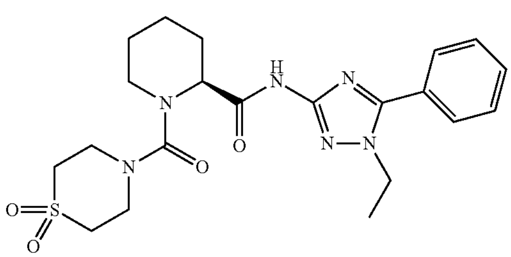 [SMILES: CCn1nc(NC(=O)[C@@H]2CCCCN2C(=O)N2CCS(=O)(=O)CC2)nc1-c1ccccc1] | (S)-1-(1,1-Dioxo-1λ6-thiomorpholine-4-carbonyl)-piperidine-2-carboxylic acid (1-ethyl-5-phenyl-1H-1,2,4-triazol-3-yl)-amide |
| 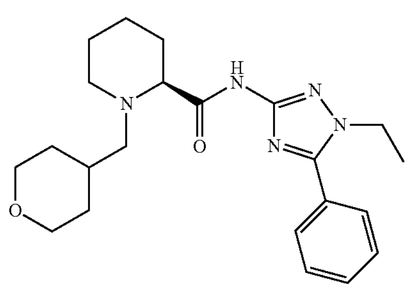 [SMILES: CCn1nc(NC(=O)[C@@H]2CCCCN2CC2CCOCC2)nc1-c1ccccc1] | (S)-1-(Tetrahydro-pyran-4-ylmethyl)-piperidine-2-carboxylic acid (1-ethyl-5-phenyl-1H-1,2,4-triazol-3-yl)-amide |

TABLE III-continued

| Structure | Name |
|---|---|
| 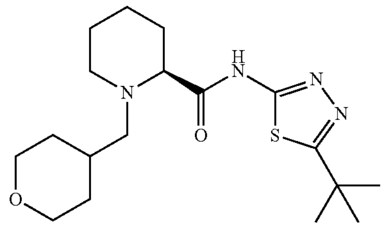 [SMILES: CC(C)(C)c1nnc(NC(=O)[C@@H]2CCCCN2CC2CCOCC2)s1] | (S)-1-(Tetrahydro-pyran-4-ylmethyl)-piperidine-2-carboxylic acid (5-tert-butyl-1,3,4-thiadiazol-2-yl)-amide |
| 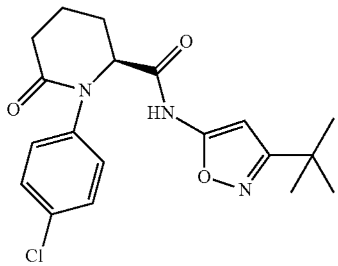 [SMILES: CC(C)(C)c1cc(NC(=O)[C@@H]2CCCC(=O)N2c2ccc(Cl)cc2)on1] | (S)-1-(4-Chloro-phenyl)-6-oxo-piperidine-2-carboxylic acid (3-tert-butyl-isoxazol-5-yl)-amide |
| 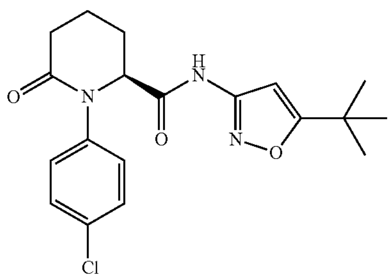 [SMILES: CC(C)(C)c1cc(NC(=O)[C@@H]2CCCC(=O)N2c2ccc(Cl)cc2)no1] | (S)-1-(4-Chloro-phenyl)-6-oxo-piperidine-2-carboxylic acid (5-tert-butyl-isoxazol-3-yl)-amide |
| 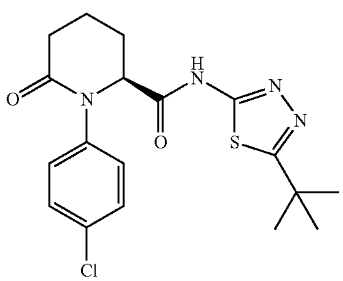 [SMILES: CC(C)(C)c1nnc(NC(=O)[C@@H]2CCCC(=O)N2c2ccc(Cl)cc2)s1] | (S)-1-(4-Chloro-phenyl)-6-oxo-piperidine-2-carboxylic acid (5-tert-butyl-1,3,4-thiadiazol-2-yl)-amide |
| 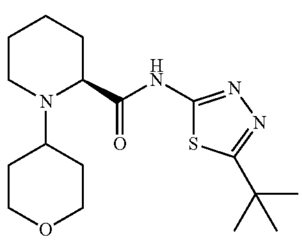 [SMILES: CC(C)(C)c1nnc(NC(=O)[C@@H]2CCCCN2C2CCOCC2)s1] | (S)-1-(Tetrahydro-pyran-4-yl)-piperidine-2-carboxylic acid (5-tert-butyl-1,3,4-thiadiazol-2-yl)-amide |
| 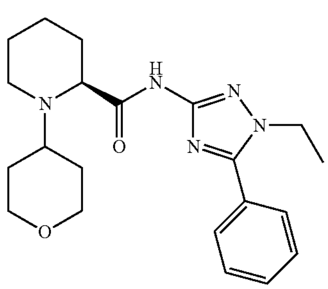 [SMILES: CCn1nc(NC(=O)[C@@H]2CCCCN2C2CCOCC2)nc1-c1ccccc1] | (S)-1-(Tetrahydro-pyran-4-yl)-piperidine-2-carboxylic acid (1-ethyl-5-phenyl-1H-1,2,4-triazol-3-yl)-amide |

TABLE III-continued

| Structure | Name |
|---|---|
| 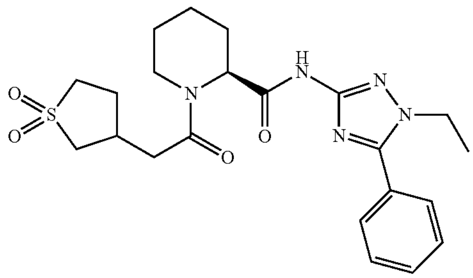 [SMILES: CCn1nc(NC(=O)[C@@H]2CCCCN2C(=O)CC2CCS(=O)(=O)C2)nc1-c1ccccc1] | (S)-1-[2-(1,1-Dioxo-tetrahydro-1λ6-thiophen-3-yl)-acetyl]-piperidine-2-carboxylic acid (1-ethyl-5-phenyl-1H-1,2,4-triazol-3-yl)-amide |
| 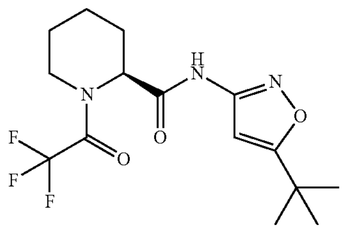 [SMILES: CC(C)(C)c1cc(NC(=O)[C@@H]2CCCCN2C(=O)C(F)(F)F)no1] | (S)-1-(2,2,2-Trifluoro-acetyl)-piperidine-2-carboxylic acid (5-tert-butyl-isoxazol-3-yl)-amide |
| 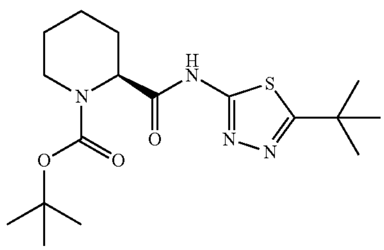 [SMILES: CC(C)(C)OC(=O)N1CCCC[C@H]1C(=O)Nc1nnc(C(C)(C)C)s1] | (S)-2-(5-tert-Butyl-1,3,4-thiadiazol-2-ylcarbamoyl)-piperidine-1-carboxylic acid tert-butyl ester |
| 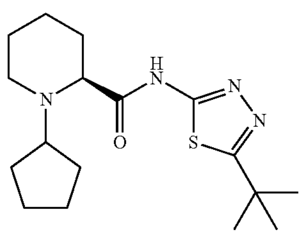 [SMILES: CC(C)(C)c1nnc(NC(=O)[C@@H]2CCCCN2C2CCCC2)s1] | (S)-1-Cyclopentyl-piperidine-2-carboxylic acid (5-tert-butyl-1,3,4-thiadiazol-2-yl)-amide |
| 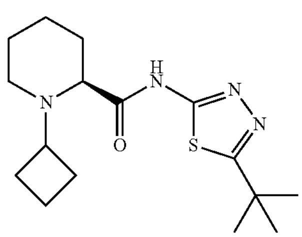 [SMILES: CC(C)(C)c1nnc(NC(=O)[C@@H]2CCCCN2C2CCC2)s1] | (S)-1-Cyclobutyl-piperidine-2-carboxylic acid (5-tert-butyl-1,3,4-thiadiazol-2-yl)-amide |
| 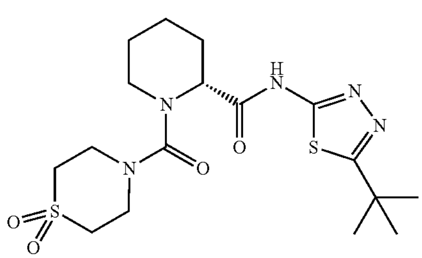 [SMILES: CC(C)(C)c1nnc(NC(=O)[C@H]2CCCCN2C(=O)N2CCS(=O)(=O)CC2)s1] | (R)-1-(1,1-Dioxo-1λ6-thiomorpholine-4-carbonyl)-piperidine-2-carboxylic acid (5-tert-butyl-1,3,4-thiadiazol-2-yl)-amide |

TABLE III-continued

| Structure | Name |
|---|---|
| 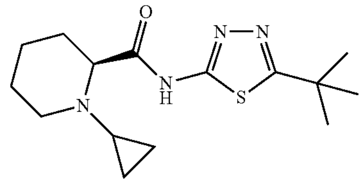 [SMILES: CC(C)(C)c1nnc(NC(=O)[C@@H]2CCCCN2C2CC2)s1] | (S)-1-Cyclopropyl-piperidine-2-carboxylic acid (5-tert-butyl-1,3,4-thiadiazol-2-yl)-amide |
| 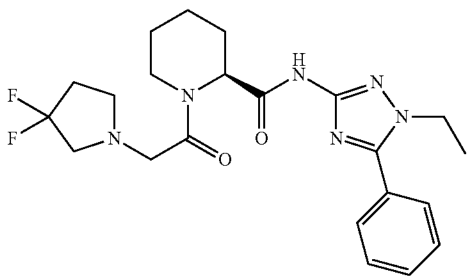 [SMILES: CCn1nc(NC(=O)[C@@H]2CCCCN2C(=O)CN2CCC(F)(F)C2)nc1-c1ccccc1] | (S)-1-[2-(3,3-Difluoro-pyrrolidin-1-yl)-acetyl]-piperidine-2-carboxylic acid (1-ethyl-5-phenyl-1H-1,2,4-triazol-3-yl)-amide |
| 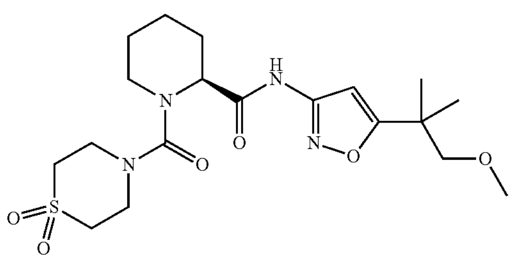 [SMILES: COCC(C)(C)c1cc(NC(=O)[C@@H]2CCCCN2C(=O)N2CCS(=O)(=O)CC2)no1] | (S)-1-(1,1-Dioxo-1λ6-thiomorpholine-4-carbonyl)-piperidine-2-carboxylic acid [5-(2-methoxy-1,1-dimethyl-ethyl)-isoxazol-3-yl]-amide |
| 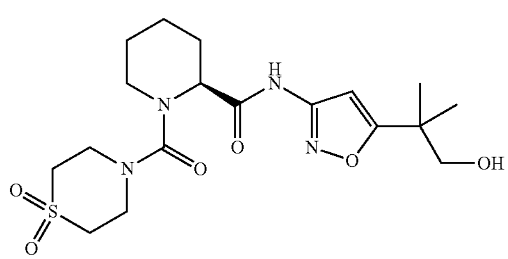 [SMILES: CC(C)(CO)c1cc(NC(=O)[C@@H]2CCCCN2C(=O)N2CCS(=O)(=O)CC2)no1] | (S)-1-(1,1-Dioxo-1λ6-thiomorpholine-4-carbonyl)-piperidine-2-carboxylic acid [5-(2-hydroxy-1,1-dimethyl-ethyl)-isoxazol-3-yl]-amide |
| | (S)-1-(1,1-Dioxo-1λ6-thiomorpholine-4-carbonyl)-piperidine-2-carboxylic acid (3-phenyl-1,2,4-thiadiazol-5-yl)-amide | or a pharmaceutically acceptable salt thereof.

In another generic aspect of the invention there is provided a compound of the formula (IB)

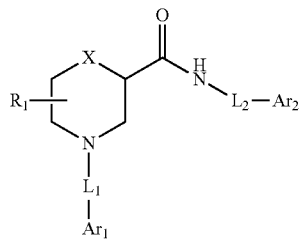

(IB)

wherein:
X is O, S, —S(O)— or —SO$_2$;
Ar$_1$ is chosen from carbocycle, heterocyclyl and heteroaryl each optionally substituted by 1-3 C$_{1-10}$ alkyl which is optionally substituted by halogens, C$_{1-10}$ alkoxy, CN, halogen, NO$_2$, —S(O)$_m$—C$_{1-10}$ alkyl, —CO$_2$—C$_{1-10}$ alkyl, —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl, carbocycle or heterocyclyl;
Ar$_2$ is chosen from carbocycle, heterocyclyl and heteroaryl each optionally substituted by 1-3 C$_{1-10}$ alkyl which is optionally substituted by halogens, C$_{3-10}$ cycloalkyl, carbocycle, C$_{1-10}$ alkylcarbocycle, heteroaryl, CN or halogen, wherein the C$_{1-10}$ alkyl and carbocycle may be additionally optionally substituted by hydroxyl, C$_{1-5}$ alkoxycarbonyl or C$_{1-5}$ alkoxy;
L$_1$ and L$_2$ are each independently chosen from a bond or C$_{1-10}$ alkyl chain wherein each —CH$_2$— of said chain is optionally replaced by —O—, C(O), or S(O)$_m$;
wherein each L$_1$ and L$_2$ where possible is optionally substituted by halogen or C$_{1-3}$ alkyl;
R$_1$ is chosen from hydrogen, oxo (=O) and OH;
m is 0, 1 or 2;
or a pharmaceutically acceptable salt thereof.

The compound according to the embodiment described immediately above and wherein:
X is O
Ar$_1$ is chosen from phenyl, C$_{3-6}$ cycloalkyl, tetrahydrofuranyl, tetrahydropyranyl, and pyridinyl, each optionally substituted by 1-3 C$_{1-6}$ alkyl which is optionally substituted by halogens, or halogen;
Ar$_2$ is chosen from oxazolyl, isoxazolyl and pyridinyl, each optionally substituted by 1-3 C$_{1-6}$ alkyl which is optionally substituted by halogens, or halogen.

The compound according to the embodiment described immediately above and wherein:
Ar$_1$ is chosen from phenyl, cyclohexyl, tetrahydropyranyl and pyridinyl, each optionally substituted by 1-3 C$_{1-6}$ alkyl, halogen or trifluoromethyl;
Ar$_2$ is chosen from isoxazolyl substituted by C$_{1-6}$ alkyl;
L$_1$ is a bond or C(O);

The compound according to the embodiment described immediately above and wherein:
Ar$_2$ is chosen from

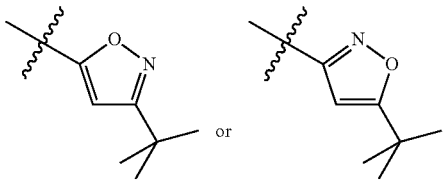

In another generic aspect of the invention there is provided a compound of the formula (IIB)

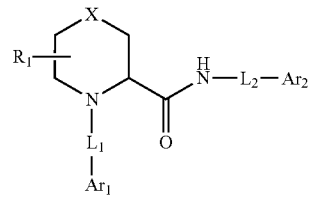

(IIB)

wherein
X is O, S, —S(O)— or —SO$_2$;
Ar$_1$ is chosen from C$_{1-6}$ alkyl which is optionally substituted by halogens, C$_{1-6}$ alkoxy, carbocycle, heterocyclyl and heteroaryl each optionally substituted by 1-3 C$_{1-10}$ alkyl which is optionally substituted by halogens, C$_{1-10}$ alkoxy, CN, halogen, NO$_2$, —S(O)$_m$—C$_{1-10}$ alkyl, —C(O)—C$_{1-10}$ alkyl, —CO$_2$—C$_{1-10}$ alkyl, C$_{1-10}$ acyl, oxo (=O), —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl or heterocyclyl the heterocyclyl being further optionally substituted by C$_{1-5}$ alkyl;
Ar$_2$ is chosen from C$_{1-6}$ alkyl, carbocycle, heterocyclyl and heteroaryl each optionally substituted by halogen, 1-3 C$_{1-10}$ alkyl which is optionally substituted by halogens, alkoxy or hydroxy, carbocycle optionally substituted by C$_{1-3}$ alkyl, aryl which is optionally substituted by halogen, heteroaryl, CN, halogen, C$_{1-10}$ acyl or oxo (=O);
L$_1$ and L$_2$ are each independently chosen from a bond or C$_{1-10}$ alkyl chain wherein each —CH$_2$— of said chain is optionally replaced by —O—, C(O), S(O)$_m$ or —NH—;
R$_1$ is chosen from hydrogen, hydroxyl and oxo (=O);
m is 0, 1 or 2;
or a pharmaceutically acceptable salt thereof.

The compound according to the embodiment described immediately above and wherein:
X is O;
Ar$_1$ is chosen from phenyl, C$_{3-6}$ cycloalkyl, tetrahydrofuranyl, tetrahydropyranyl, and pyridinyl, each optionally substituted by 1-3 C$_{1-6}$ alkyl which is optionally substituted with halogens, or halogen;

Ar₂ is chosen from oxazolyl, isoxazolyl and pyridinyl, each optionally substituted by 1-3 C₁₋₆ alkyl which is optionally substituted by halogens or halogen;
R₁ is hydrogen;
L₁ is a bond, C(O) or S(O)₂;
L₂ is a bond.
The compound according to the embodiment described immediately above and wherein:
Ar₁ is chosen from phenyl or cyclohexyl, each optionally substituted by 1-3 C₁₋₆ alkyl or halogen;
Ar₂ is chosen from isoxazolyl substituted by C₁₋₆ alkyl;
L₁ is C(O) or SO₂,
The compound according to the embodiment described immediately above and wherein:

Ar₂ is chosen from

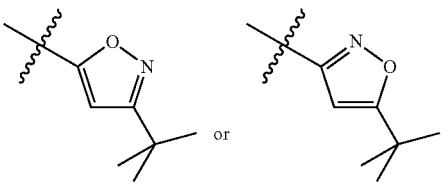

or

In another embodiment of the invention, there is provided compounds in Table IV, which can be made by the methods and examples shown herein and methods known in the art.

TABLE IV

| Structure | Name |
|---|---|
| 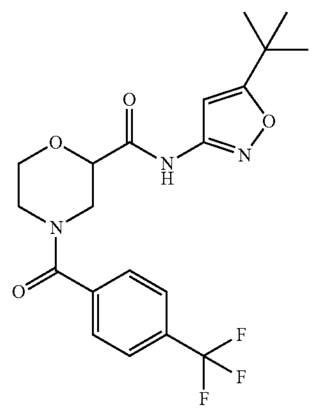 [SMILES: CC(C)(C)c1cc(NC(=O)C2CN(C(=O)c3ccc(C(F)(F)F)cc3)CCO2)no1] | 4-(4-Trifluoromethyl-benzoyl)-morpholine-2-carboxylic acid (5-tert-butyl-isoxazol-3-yl)-amide |
| 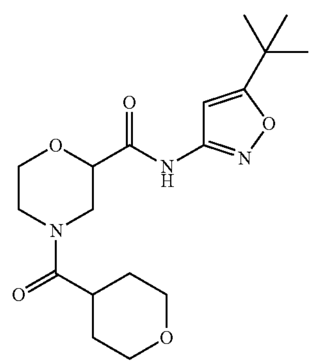 [SMILES: CC(C)(C)c1cc(NC(=O)C2CN(C(=O)C3CCOCC3)CCO2)no1] | 4-(Tetrahydro-pyran-4-carbonyl)-morpholine-2-carboxylic acid (5-tert-butyl-isoxazol-3-yl)-amide |
| 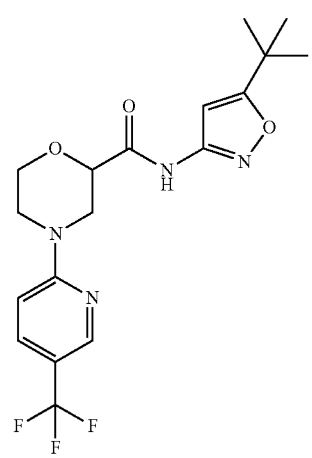 [SMILES: CC(C)(C)c1cc(NC(=O)C2CN(c3ccc(C(F)(F)F)cn3)CCO2)no1] | 4-(5-Trifluoromethyl-pyridin-2-yl)-morpholine-2-carboxylic acid (5-tea-butyl-isoxazol-3-yl)-amide |

TABLE IV-continued

| Structure | Name |
| --- | --- |
| 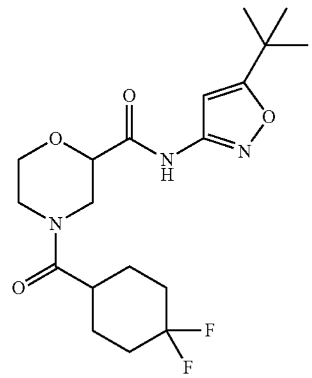 [SMILES: CC(C)(C)c1cc(NC(=O)C2CN(C(=O)C3CCC(F)(F)CC3)CCO2)no1] | 4-(4,4-Difluoro-cyclohexanecarbonyl)-morpholine-2-carboxylic acid (5-tert-butyl-isoxazol-3-yl)-amide |
| 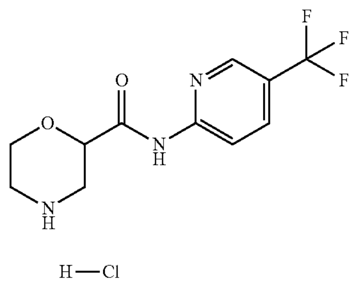 [SMILES: O=C(Nc1ccc(C(F)(F)F)cn1)C1CNCCO1 ; Cl] | Morpholine-2-carboxylic acid (5-trifluoromethyl-pyridin-2-yl)-amide; hydrochloride |
| 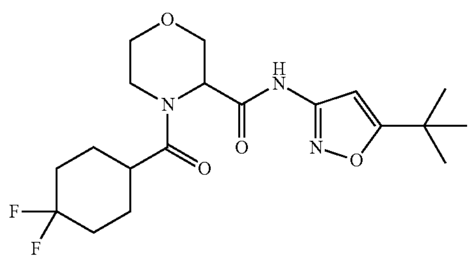 [SMILES: CC(C)(C)c1cc(NC(=O)C2COCCN2C(=O)C2CCC(F)(F)CC2)no1] | 4-(4,4-Difluoro-cyclohexanecarbonyl)-morpholine-3-carboxylic acid (5-tert-butyl-isoxazol-3-yl)-amide |
| 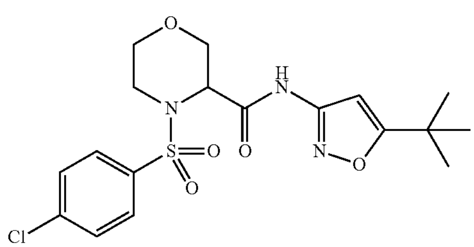 [SMILES: CC(C)(C)c1cc(NC(=O)C2COCCN2S(=O)(=O)c2ccc(Cl)cc2)no1] | 4-(4-Chloro-benzenesulfonyl)-morpholine-3-carboxylic acid (5-tert-butyl-isoxazol-3-yl)-amide |

In another generic aspect of the invention there is provided a compound of the formula (IC)

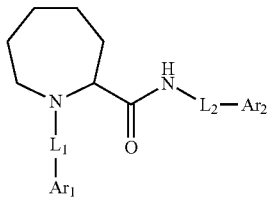

(IC)

wherein

Ar$_1$ is chosen from C$_{1-6}$ alkyl which is optionally substituted by halogens, C$_{1-6}$ alkoxy, carbocycle, heterocyclyl and heteroaryl each optionally substituted by 1-3 C$_{1-10}$ alkyl which is optionally substituted by halogens, C$_{1-10}$ alkoxy, CN, halogen, NO$_2$, —S(O)$_m$—C$_{1-10}$ alkyl, —C(O)—C$_{1-10}$ alkyl, —CO$_2$—C$_{1-10}$ alkyl, C$_{1-10}$ acyl, oxo (=O), —NH(C$_{1-5}$ alkyl)-CO$_2$—C$_{1-10}$ alkyl, —C(O)—NH(C$_{1-5}$ alkyl), —C(O)—N(C$_{1-5}$ alkyl)$_2$, —NH(C$_{1-5}$ alkyl), —N(C$_{1-5}$ alkyl)-C(O)—C$_{1-10}$ alkyl, —N(C$_{1-5}$ alkyl)-S(O)$_m$—C$_{1-10}$ alkyl and heterocyclyl the heterocyclyl being further optionally substituted by C$_{1-5}$ alkyl;

Ar$_2$ is chosen from C$_{1-6}$ alkyl, carbocycle, heterocyclyl and heteroaryl each optionally substituted by 1-3 C$_{1-10}$ alkyl which is optionally substituted by halogens, alkoxy or hydroxy, carbocycle which is optionally substituted by C$_{1-3}$ alkyl, aryl which is optionally substituted by halogen, heteroaryl, CN, halogen, C$_{1-10}$ acyl or oxo (=O), wherein the C$_{1-6}$ alkyl and carbocycle may be additionally optionally substituted by hydroxyl;

$L_1$ and $L_2$ are each independently chosen from a bond or $C_{1-10}$ alkyl chain wherein each —$CH_2$— of said chain is optionally replaced by —O—, C(O), $S(O)_m$ or —NH—;
m is 0, 1 or 2;
or a pharmaceutically acceptable salt thereof.

The compound according to the embodiment described immediately above and wherein:
$Ar_1$ is chosen from $C_{1-6}$ alkyl which is optionally substituted by halogens, $C_{1-6}$ alkoxyl, phenyl, $C_{3-8}$ cycloalkyl, dioxanyl, tetrahydrofuranyl, tetrahydropyranyl, tetrahydrothiopyranyl, tetrahydrothiopyran-1,1-dioxide, tetrahydrothiofuranyl, tetrahydrothiofuran-1,1-dioxide, thiomorpholinyl, 1-oxo-1$\lambda^4$-thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl and piperazinyl, each optionally substituted by 1-3 $C_{1-6}$ alkyl which is optionally substituted by halogens, $C_{1-6}$ alkoxy, CN, halogen, oxo, —C(O)—$C_{1-10}$ alkyl, —$S(O)_2$—$C_{1-3}$ alkyl or —$CO_2$—$C_{1-4}$ alkyl;
$Ar_2$ is chosen from $C_{1-6}$ alkyl, cyclohexyl, phenyl, benzoxazolyl, benzothiazolyl, benzimidazolyl, oxazolyl, isoxazolyl, thiazolyl, isothiazolyl, pyrazolyl, pyrrolyl, imidazolyl, thienyl, thiadiazolyl, triazolyl, pyridinyl, pyrimidinyl, pyridazinyl, pyrazinyl, triazinyl, benzofuranyl and benzothienyl, each optionally substituted by 1-3 $C_{1-6}$ alkyl which is optionally substituted by halogen, cyclopropyl, cyclobutyl, cyclopentyl, cyclohexyl, cycloheptyl, phenyl optionally substituted by halogens, CN, halogens, $C_{1-6}$ alkoxy or hydroxy;
$L_1$ is a bond or $C_{1-3}$ alkyl chain wherein each —$CH_2$— of said chain is optionally replaced by C(O) or $S(O)_m$;
$L_2$ is a bond or $C_{1-5}$ alkyl chain wherein each —$CH_2$— of said chain is optionally replaced by —O— or $S(O)_m$.

The compound according to any of the embodiments described above and wherein:
$Ar_1$ is chosen from phenyl, tetrahydropyranyl, thiomorpholinyl, 1-Oxo-1$\lambda^4$-thiomorpholinyl, and 1,1-dioxo-1$\lambda^6$-thiomorpholinyl, each optionally substituted halogen.

The compound according to any of the embodiments described above and wherein:
$Ar_2$ is isoxazolyl substituted by 1-3 $C_{1-6}$ alkyl group.

The compound according to any of the embodiments described above and wherein:
$L_1$ is a bond or $C_{1-3}$ alkyl chain wherein each —$CH_2$— of said chain is optionally replaced by C(O);
$L_2$ is a bond.

The compound according to any of the embodiments described above and wherein:
$Ar_1$ is chosen from phenyl, tetrahydropyranyl, thiomorpholinyl, 1-Oxo-1$\lambda^4$-thiomorpholinyl, and 1,1-dioxo-1$\lambda^6$-thiomorpholinyl, each optionally substituted chloro;
$Ar_2$ is isoxazolyl substituted by 1-3 $C_{1-6}$ alkyl group;
$L_1$ is a bond or $C_{1-2}$ alkyl chain wherein each —$CH_2$— of said chain is optionally replaced by C(O);
$L_2$ is a bond.

The compound according to any of the embodiments described above and wherein:
$Ar_2$ is

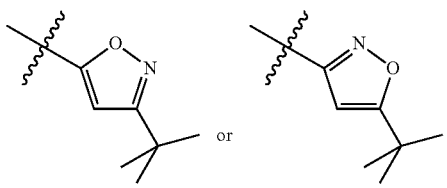

or

The compound according to any of the embodiments described above and wherein:
$Ar_1$ is chosen from phenyl optionally substituted chloro, tetrahydropyranyl, and 1,1-dioxo-1$\lambda^6$-thiomorpholinyl;
$L_1$ is a bond or —$CH_2$—;
$L_2$ is a bond.

In another embodiment of the invention, there is provided compounds in Table V, which can be made by the methods and examples shown herein and methods known in the art.

TABLE V

| Structure | Name |
|---|---|
| 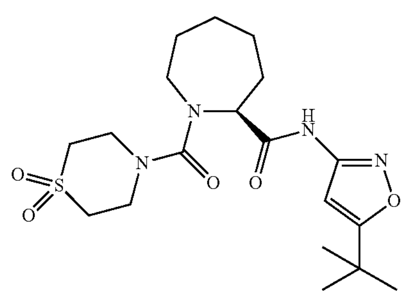 [SMILES: CC(C)(C)c1cc(NC(=O)[C@@H]2CCCCCN2C(=O)N2CCS(=O)(=O)CC2)no1] | (S)-1-(4-Chloro-phenyl)-azepane-2-carboxylic acid (5-tert-butyl-isoxazol-3-yl)-amide |
| 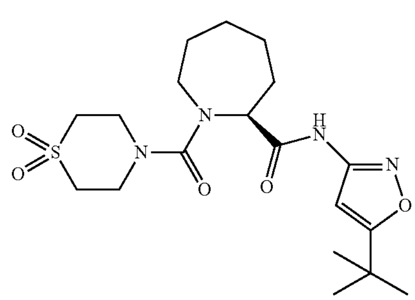 [SMILES: CC(C)(C)c1cc(NC(=O)[C@@H]2CCCCCN2C(=O)N2CCS(=O)(=O)CC2)no1] | (S)-1-(1,1-Dioxo-1$\lambda^6$-thiomorpholine-4-carbonyl)-azepane-2-carboxylic acid (5-tert-butyl-isoxazol-3-yl)-amide |

TABLE V-continued

| Structure | Name |
|---|---|
| 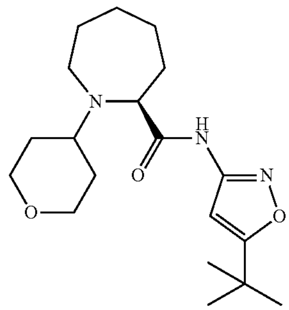 [SMILES: CC(C)(C)c1cc(NC(=O)[C@@H]2CCCCCN2C2CCOCC2)no1] | (S)-1-(Tetrahydro-pyran-4-yl)-azepane-2-carboxylic acid (5-tert-butyl-isoxazol-3-yl)-amide |
| 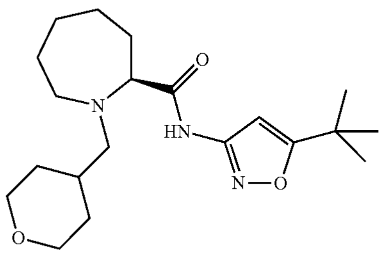 [SMILES: CC(C)(C)c1cc(NC(=O)[C@@H]2CCCCCN2CC2CCOCC2)no1] | (S)-1-(Tetrahydro-pyran-4-ylmethyl)-azepane-2-carboxylic acid (5-tert-butyl-isoxazol-3-yl)-amide |

Of the above compounds, the following are preferred CB2 agonists:

TABLE VI

| Compound | CB2 CAMP @ EC50 nM (mean) |
|---|---|
| 3'-Chloro-5'-trifluoromethyl-3,4,5,6-tetrahydro-2H-[1,2']bipyridinyl-3-carboxylic acid (5-tert-butyl-isoxazol-3-yl)-amide | 113 |
| 1-(1,1-Dioxo-1$\lambda^6$-thiomorpholine-4-carbonyl)-piperidine-3-carboxylic acid (5-tert-butyl-isoxazol-3-yl)-amide | 215 |
| 1-(Tetrahydro-pyran-4-carbonyl)-piperidine-3-carboxylic acid (5-tert-butyl-isoxazol-3-yl)-amide | 205 |
| 1-(4,4-Difluoro-cyclohexanecarbonyl)-piperidine-3-carboxylic acid (5-tert-butyl-isoxazol-3-yl)-amide | 23 |
| (R)-3'-Chloro-5'-trifluoromethyl-3,4,5,6-tetrahydro-2H-[1,2']bipyridinyl-3-carboxylic acid (5-tert-butyl-isoxazol-3-yl)-amide | 54 |
| 1-(4-Trifluoromethyl-benzoyl)-piperidine-3-carboxylic acid (5-tert-butyl-isoxazol-3-yl)-amide | 16 |
| 1-(4-Chloro-benzyl)-piperidine-3-carboxylic acid (5-tert-butyl-isoxazol-3-yl)-amide | 2.7 |
| 1-(4-Chloro-benzenesulfonyl)-piperidine-3-carboxylic acid (5-tert-butyl-isoxazol-3-yl)-amide | 12 |
| (R)-1-(4,4-Difluoro-cyclohexanecarbonyl)-piperidine-3-carboxylic acid (5-tert-butyl-isoxazol-3-yl)-amide | 42 |
| (S)-1-(4,4-Difluoro-cyclohexanecarbonyl)-piperidine-3-carboxylic acid (5-tert-butyl-isoxazol-3-yl)-amide | 119 |
| 1-(1,1-Dioxo-1$\lambda^6$-thiomorpholine-4-carbonyl)-piperidine-2-carboxylic acid (5-tert-butyl-isoxazol-3-yl)-amide | 18 |
| 1-(Tetrahydro-pyran-4-carbonyl)-piperidine-2-carboxylic acid (5-tert-butyl-isoxazol-3-yl)-amide | 274 |
| 1-(4-Trifluoromethyl-benzoyl)-piperidine-2-carboxylic acid (5-tert-butyl-isoxazol-3-yl)-amide | 395 |
| 1-(4,4-Difluoro-cyclohexanecarbonyl)-piperidine-2-carboxylic acid (5-tert-butyl-isoxazol-3-yl)-amide | 11 |
| (R)-1-(4,4-Difluoro-cyclohexanecarbonyl)-piperidine-2-carboxylic acid (5-tert-butyl-isoxazol-3-yl)-amide | 64 |
| (S)-1-(4,4-Difluoro-cyclohexanecarbonyl)-piperidine-2-carboxylic acid (5-tert-butyl-isoxazol-3-yl)-amide | 4.6 |
| (S)-1-(1,1-Dioxo-1$\lambda^6$-thiomorpholine-4-carbonyl)-piperidine-2-carboxylic acid (5-tert-butyl-isoxazol-3-yl)-amide | 7.9 |
| (R)-1-(1,1-Dioxo-1$\lambda^6$-thiomorpholine-4-carbonyl)-piperidine-2-carboxylic acid (5-tert-butyl-isoxazol-3-yl)-amide | 60 |

TABLE VI-continued

| Compound | CB2 CAMP @ EC50 nM (mean) |
|---|---|
| (S)-1-(4,4-Difluoro-cyclohexanecarbonyl)-piperidine-2-carboxylic acid (3-tert-butyl-isoxazol-5-yl)-amide | 1 |
| (S)-3'-Chloro-5'-trifluoromethyl-3,4,5,6-tetrahydro-2H-1,2'-bipyridinyl-2-carboxylic acid (3-phenyl-1,2,4-thiadiazol-5-yl)-amide | 11 |
| (S)-1-(4,4-Difluoro-cyclohexanecarbonyl)-piperidine-2-carboxylic acid (5-trifluoromethyl-pyridin-2-yl)-amide | 282 |
| (S)-1-Benzoyl-piperidine-2-carboxylic acid (5-tert-butyl-isoxazol-3-yl)-amide | 47 |
| (S)-1-(4-Fluoro-benzoyl)-piperidine-2-carboxylic acid (5-tert-butyl-isoxazol-3-yl)-amide | 2.2 |
| S)-1-Cyclohexanecarbonyl-piperidine-2-carboxylic acid (5-tert-butyl-isoxazol-3-yl)-amide | 15 |
| (S)-1-Cyclopentanecarbonyl-piperidine-2-carboxylic acid (5-tert-butyl-isoxazol-3-yl)-amide | 14 |
| S)-1-Cycloheptanecarbonyl-piperidine-2-carboxylic acid (5-tert-butyl-isoxazol-3-yl)-amide | 8.2 |
| (S)-1-(3-Chloro-benzoyl)-piperidine-2-carboxylic acid (5-tert-butyl-isoxazol-3-yl)-amide | 44 |
| (S)-1-(1,1-Dioxo-1$\lambda^6$-thiomorpholine-4-carbonyl)-piperidine-2-carboxylic acid (5-tert-butyl-1,3,4-thiadiazol-2-yl)-amide | 53 |
| (S)-1-(1,1-Dioxo-1$\lambda^6$-thiomorpholine-4-carbonyl)-piperidine-2-carboxylic acid (5-chloro-1H-benzimidazol-2-yl)-amide | 77 |
| (S)-1-(1,1-Dioxo-1$\lambda^6$-thiomorpholine-4-carbonyl)-piperidine-2-carboxylic acid (3-sec-butyl-isoxazol-5-yl)-amide | 105 |
| (S)-1-(1,1-Dioxo-1$\lambda^6$-thiomorpholine-4-carbonyl)-piperidine-2-carboxylic acid (3-isopropyl-isoxazol-5-yl)-amide | 170 |
| (S)-1-(1,1-Dioxo-1$\lambda^6$-thiomorpholine-4-carbonyl)-piperidine-2-carboxylic acid (4-phenyl-thiazol-2-yl)-amide | 17 |
| (S)-1-(1,1-Dioxo-1$\lambda^6$-thiomorpholine-4-carbonyl)-piperidine-2-carboxylic acid [2-(2-chloro-6-fluoro-benzylsulfanyl)-ethyl]-amide | 130 |
| (S)-1-(1,1-Dioxo-1$\lambda^6$-thiomorpholine-4-carbonyl)-piperidine-2-carboxylic acid (3-cyclohexyl-isoxazol-5-yl)-amide | 59 |
| (S)-1-(1,1-Dioxo-1$\lambda^6$-thiomorpholine-4-carbonyl)-piperidine-2-carboxylic acid [3-(1-methyl-cyclopropyl)-isoxazol-5-yl]-amide | 9.8 |
| (S)-1-(1,1-Dioxo-1$\lambda^6$-thiomorpholine-4-carbonyl)-piperidine-2-carboxylic acid (5-chloro-benzothiazol-2-yl)-amide | 23 |
| (S)-1-(1,1-Dioxo-1$\lambda^6$-thiomorpholine-4-carbonyl)-piperidine-2-carboxylic acid (3-cyclopentyl-isoxazol-5-yl)-amide | 42 |
| (S)-1-(Tetrahydro-pyran-4-ylmethyl)-piperidine-2-carboxylic acid (4-tert-butyl-oxazol-2-yl)-amide | 2.4 |
| (S)-1-(Tetrahydro-pyran-4-ylmethyl)-piperidine-2-carboxylic acid (3-phenyl-1,2,4-thiadiazol-5-yl)-amide | 1.2 |
| (S)-1-(Tetrahydro-pyran-4-ylmethyl)-piperidine-2-carboxylic acid (4-fluoro-3-trifluoromethyl-phenyl)-amide | 26 |
| (S)-1-(Tetrahydro-pyran-4-ylmethyl)-piperidine-2-carboxylic acid (3-fluoro-4-trifluoromethyl-phenyl)-amide | 1.8 |
| (S)-1-(Tetrahydro-pyran-4-ylmethyl)-piperidine-2-carboxylic acid (3-isopropyl-1,2,4-thiadiazol-5-yl)-amide | 208 |
| (S)-1-(Tetrahydro-pyran-4-ylmethyl)-piperidine-2-carboxylic acid (4-cyclohexyl-thiazol-2-yl)-amide | 9 |
| (S)-1-(Tetrahydro-pyran-4-yl)-piperidine-2-carboxylic acid (5-chloro-benzothiazol-2-yl)-amide | 206 |
| (S)-1-(Tetrahydro-pyran-4-yl)-piperidine-2-carboxylic acid (4-cyclohexyl-thiazol-2-yl)-amide | 65 |
| (S)-1-(Tetrahydro-pyran-4-ylmethyl)-piperidine-2-carboxylic acid (3-tert-butyl-isothiazol-5-yl)-amide | 0.3 |
| (S)-1-(Tetrahydro-pyran-4-ylmethyl)-piperidine-2-carboxylic acid (3-tert-butyl-1,2,4-thiadiazol-5-yl)-amide | 12 |
| (S)-1-(Tetrahydro-pyran-4-ylmethyl)-piperidine-2-carboxylic acid (4-tert-butyl-thiazol-2-yl)-amide | 13 |
| (S)-1-(Tetrahydro-pyran-4-ylmethyl)-piperidine-2-carboxylic acid [4-(3,4-difluoro-phenyl)-thiazol-2-yl]-amide | 3.6 |
| (S)-1-(Tetrahydro-pyran-4-ylmethyl)-piperidine-2-carboxylic acid (5-phenyl-1,2,4-thiadiazol-3-yl)-amide | 14 |
| (S)-1-(Tetrahydro-pyran-4-ylmethyl)-piperidine-2-carboxylic acid (4-fluoro-benzothiazol-2-yl)-amide | 1.3 |
| (S)-1-(Tetrahydro-pyran-4-ylmethyl)-piperidine-2-carboxylic acid (4-phenyl-thiazol-2-yl)-amide | 9.9 |
| (S)-1-(Tetrahydro-pyran-4-ylmethyl)-piperidine-2-carboxylic acid (5-trifluoromethyl-pyridin-2-yl)-amide | 69 |
| (S)-1-(Tetrahydro-pyran-4-ylmethyl)-piperidine-2-carboxylic acid (6-chloro-benzothiazol-2-yl)-amide | 131 |
| (S)-1-(Tetrahydro-pyran-4-ylmethyl)-piperidine-2-carboxylic acid (4-trifluoromethyl-pyridin-2-yl)-amide | 290 |
| (S)-1-(Tetrahydro-pyran-4-ylmethyl)-piperidine-2-carboxylic acid (5-chloro-benzothiazol-2-yl)-amide | 0.2 |

TABLE VI-continued

| Compound | CB2 CAMP @ EC50 nM (mean) |
|---|---|
| (S)-1-(Thiomorpholine-4-carbonyl)-piperidine-2-carboxylic acid (5-tert-butyl-isoxazol-3-yl)-amide | 7 |
| (S)-1-(Piperidine-1-carbonyl)-piperidine-2-carboxylic acid (5-tert-butyl-isoxazol-3-yl)-amide | 22 |
| (S)-1-(1-Oxo-1$\lambda^4$-thiomorpholine-4-carbonyl)-piperidine-2-carboxylic acid (5-tert-butyl-isoxazol-3-yl)-amide | 151 |
| (S)-1-(4-Acetyl-piperazine-1-carbonyl)-piperidine-2-carboxylic acid (5-tert-butyl-isoxazol-3-yl)-amide | 460 |
| (S)-1-(4-Propionyl-piperazine-1-carbonyl)-piperidine-2-carboxylic acid (5-tert-butyl-isoxazol-3-yl)-amide | 332 |
| (S)-2-(5-tert-Butyl-isoxazol-3-ylcarbamoyl)-piperidine-1-carboxylic acid tert-butyl ester | 279 |
| (S)-5'-trifluoromethyl-3,4,5,6-tetrahydro-2H-[1,2']bipyridinyl-2-carboxylic acid (5-tert-butyl-isoxazol-3-yl)-amide | 0.093 |
| (S)-3'-Chloro-5'-trifluoromethyl-3,4,5,6-tetrahydro-2H-[1,2']bipyridinyl-2-carboxylic acid (5-tert-butyl-isoxazol-3-yl)-amide | 0.18 |
| (S)-1-(Tetrahydro-pyran-4-carbonyl)-piperidine-2-carboxylic acid (5-tert-butyl-isoxazol-3-yl)-amide | 83 |
| (S)-1-[2-(1,1-Dioxo-1$\lambda^6$-thiomorpholin-4-yl)-acetyl]-piperidine-2-carboxylic acid (5-tert-butyl-isoxazol-3-yl)-amide | 161 |
| (S)-1-(4-Chloro-phenyl)-piperidine-2-carboxylic acid (5-tert-butyl-isoxazol-3-yl)-amide | 0.19 |
| (S)-1-(2-Pyrrolidin-1-yl-acetyl)-piperidine-2-carboxylic acid (5-tert-butyl-isoxazol-3-yl)-amide | 431 |
| (S)-1-(2-Morpholin-4-yl-acetyl)-piperidine-2-carboxylic acid (5-tert-butyl-isoxazol-3-yl)-amide | 188 |
| (2S,4S)-3'-Chloro-4-hydroxy-5'-trifluoromethyl-3,4,5,6-tetrahydro-2H-[1,2']bipyridinyl-2-carboxylic acid (5-tert-butyl-isoxazol-3-yl)-amide | 0.3 |
| (S)-1-(4-cis-Methoxy-cyclohexanecarbonyl)-piperidine-2-carboxylic acid (5-tert-butyl-isoxazol-3-yl)-amide | 43 |
| (S)-1-(4-Chloro-benzenesulfonyl)-piperidine-2-carboxylic acid (5-tert-butyl-isoxazol-3-yl)-amide | 21 |
| (S)-1-(Tetrahydro-pyran-4-ylmethyl)-piperidine-2-carboxylic acid (5-tert-butyl-isoxazol-3-yl)-amide | 0.41 |
| (S)-1-[2-(4,4-Difluoro-piperidin-1-yl)-acetyl]-piperidine-2-carboxylic acid (5-tert-butyl-isoxazol-3-yl)-amide | 34 |
| (S)-1-(Tetrahydro-pyran-4-yl)-piperidine-2-carboxylic acid (5-tert-butyl-isoxazol-3-yl)-amide | 33 |
| (S)-1-(2-Tetrahydro-pyran-4-yl-acetyl)-piperidine-2-carboxylic acid (5-tert-butyl-isoxazol-3-yl)-amide | 17 |
| (S)-1-((R)-2-Tetrahydro-furan-2-yl-acetyl)-piperidine-2-carboxylic acid (5-tert-butyl-isoxazol-3-yl)-amide | 94 |
| (S)-1-(1,1-Dioxo-1$\lambda^6$-thiomorpholine-4-carbonyl)-piperidine-2-carboxylic acid (3-tert-butyl-isoxazol-5-yl)-amide | 18 |
| (S)-1-(4-Chloro-benzoyl)-piperidine-2-carboxylic acid (5-tert-butyl-isoxazol-3-yl)-amide | 334 |
| (S)-1-(4,4-Difluoro-piperidine-1-carbonyl)-piperidine-2-carboxylic acid (5-tert-butyl-isoxazol-3-yl)-amide | 3.7 |
| (S)-1-(1,1-Dioxo-hexahydro-1$\lambda$6-thiopyran-4-carbonyl)-piperidine-2-carboxylic acid (5-tert-butyl-isoxazol-3-yl)-amide | 301 |
| (S)-1-(4-Methoxy-benzenesulfonyl)-piperidine-2-carboxylic acid (5-tert-butyl-isoxazol-3-yl)-amide | 27 |
| (S)-1-[2-(4-Fluoro-piperidin-1-yl)-acetyl]-piperidine-2-carboxylic acid (5-tert-butyl-isoxazol-3-yl)-amide | 75 |
| (S)-1-[2-(3,3-Difluoro-pyrrolidin-1-yl)-acetyl]-piperidine-2-carboxylic acid (5-tert-butyl-isoxazol-3-yl)-amide | 2.9 |
| (S)-2-(5-Ethyl-4-phenyl-thiazol-2-ylcarbamoyl)-piperidine-1-carboxylic acid tert-butyl ester | 180 |
| (S)-1-(1,1-Dioxo-1$\lambda^6$-thiomorpholine-4-carbonyl)-piperidine-2-carboxylic acid (5-ethyl-4-phenyl-thiazol-2-yl)-amide | 5.2 |
| (S)-1-(Tetrahydro-pyran-4-ylmethyl)-piperidine-2-carboxylic acid (5-ethyl-4-phenyl-thiazol-2-yl)-amide | 0.55 |
| (S)-1-Isobutyl-piperidine-2-carboxylic acid (5-tert-butyl-isoxazol-3-yl)-amide | 1.5 |
| (S)-1-Cyclopropylmethyl-piperidine-2-carboxylic acid (5-tert-butyl-isoxazol-3-yl)-amide | 0.94 |
| (S)-1-Cyclopropyl-piperidine-2-carboxylic acid (5-tert-butyl-isoxazol-3-yl)-amide | 8.5 |
| (S)-1-Cyclopentyl-piperidine-2-carboxylic acid (5-tert-butyl-isoxazol-3-yl)-amide | 9.4 |

TABLE VI-continued

| Compound | CB2 CAMP @ EC50 nM (mean) |
|---|---|
| (S)-1-(Morpholine-4-carbonyl)-piperidine-2-carboxylic acid (5-tert-butyl-isoxazol-3-yl)-amide | 132 |
| (S)-1-(benzyl)-piperidine-2-carboxylic acid (5-tert-butyl-isoxazol-3-yl)-amide | 1.9 |
| (S)-1-(4-Chloro-benzyl)-piperidine-2-carboxylic acid (5-tert-butyl-isoxazol-3-yl)-amide | 1.7 |
| (S)-1-(3,4-Difluoro-benzyl)-piperidine-2-carboxylic acid (5-tert-butyl-isoxazol-3-yl)-amide | 0.58 |
| (S)-1-(Tetrahydro-pyran-4-ylmethyl)-piperidine-2-carboxylic acid (5-ethyl-1-phenyl-1H-1,2,4-triazol-3-yl)-amide | 19 |
| (S)-1-(1,1-Dioxo-tetrahydro-1$\lambda^6$-thiophene-3-carbonyl)-piperidine-2-carboxylic acid (5-tert-butyl-isoxazol-3-yl)-amide | 17 |
| (S)-1-[2-(1,1-Dioxo-tetrahydro-1$\lambda^6$-thiophen-3-yl)-acetyl]-piperidine-2-carboxylic acid (5-tert-butyl-isoxazol-3-yl)-amide | 7.7 |
| (S)-1-(1,1-Dioxo-1$\lambda^6$-thiomorpholine-4-carbonyl)-piperidine-2-carboxylic acid (1-ethyl-5-phenyl-1H-1,2,4-triazol-3-yl)-amide | 135 |
| (S)-1-(Tetrahydro-pyran-4-ylmethyl)-piperidine-2-carboxylic acid (1-ethyl-5-phenyl-1H-1,2,4-triazol-3-yl)-amide | 8.6 |
| (S)-1-(Tetrahydro-pyran-4-ylmethyl)-piperidine-2-carboxylic acid (5-tert-butyl-1,3,4-thiadiazol-2-yl)-amide | 1.6 |
| (S)-1-(4-Chloro-phenyl)-6-oxo-piperidine-2-carboxylic acid (3-tert-butyl-isoxazol-5-yl)-amide | 181 |
| (S)-1-[2-(1,1-Dioxo-tetrahydro-1$\lambda^6$-thiophen-3-yl)-acetyl]-piperidine-2-carboxylic acid (1-ethyl-5-phenyl-1H-1,2,4-triazol-3-yl)-amide | 365 |
| (S)-1-(2,2,2-Trifluoro-acetyl)-piperidine-2-carboxylic acid (5-tert-butyl-isoxazol-3-yl)-amide | 48 |
| (S)-2-(5-tert-Butyl-1,3,4-thiadiazol-2-ylcarbamoyl)-piperidine-1-carboxylic acid tert-butyl ester | 495 |
| (S)-1-Cyclobutyl-piperidine-2-carboxylic acid (5-tert-butyl-1,3,4-thiadiazol-2-yl)-amide | 140 |
| (S)-1-Cyclopropyl-piperidine-2-carboxylic acid (5-tert-butyl-1,3,4-thiadiazol-2-yl)-amide | 485 |
| (S)-1-[2-(3,3-Difluoro-pyrrolidin-1-yl)-acetyl]-piperidine-2-carboxylic acid (1-ethyl-5-phenyl-1H-1,2,4-triazol-3-yl)-amide | 262 |
| (S)-1-(1,1-Dioxo-1$\lambda^6$-thiomorpholine-4-carbonyl)-piperidine-2-carboxylic acid [5-(2-methoxy-1,1-dimethyl-ethyl)-isoxazol-3-yl]-amide | 162 |
| (S)-1-(1,1-Dioxo-1$\lambda^6$-thiomorpholine-4-carbonyl)-piperidine-2-carboxylic acid (3-phenyl-1,2,4-thiadiazol-5-yl)-amide | 28 |
| 4-(4-Trifluoromethyl-benzoyl)-morpholine-2-carboxylic acid (5-tert-butyl-isoxazol-3-yl)-amide | 85 |
| 4-(4-Chloro-benzenesulfonyl)-morpholine-3-carboxylic acid (5-tert-butyl-isoxazol-3-yl)-amide | 34 |
| (S)-1-(1,1-Dioxo-1$\lambda^6$-thiomorpholine-4-carbonyl)-piperidine-2-carboxylic acid [3-(4-methoxy-phenyl)-[1,2,4]thiadiazol-5-yl]-amide | 20 |
| (S)-1-(1,1-Dioxo-1$\lambda^6$-thiomorpholine-4-carbonyl)-piperidine-2-carboxylic acid [3-(4-fluoro-phenyl)-[1,2,4]thiadiazol-5-yl]-amide | 22 |
| (S)-1-(1,1-Dioxo-1$\lambda^6$-thiomorpholine-4-carbonyl)-piperidine-2-carboxylic acid (5-fluoro-benzothiazol-2-yl)-amide | 56 |
| (S)-1-(1,1-Dioxo-1$\lambda^6$-thiomorpholine-4-carbonyl)-piperidine-2-carboxylic acid (5,6-difluoro-benzothiazol-2-yl)-amide | 448 |
| (S)-1-(1,1-Dioxo-1$\lambda^6$-thiomorpholine-4-carbonyl)-piperidine-2-carboxylic acid (4-chloro-benzothiazol-2-yl)-amide | 27 |
| (S)-1-(1,1-Dioxo-1$\lambda^6$-thiomorpholine-4-carbonyl)-piperidine-2-carboxylic acid [4-(4-chloro-phenyl)-thiazol-2-yl]-amide | 9.9 |
| (S)-1-(1,1-Dioxo-1$\lambda^6$-thiomorpholine-4-carbonyl)-piperidine-2-carboxylic acid [4-(3,4-difluoro-phenyl)-thiazol-2-yl]-amide | 26 |
| (S)-1-(1,1-Dioxo-1$\lambda^6$-thiomorpholine-4-carbonyl)-piperidine-2-carboxylic acid [4-(2,4-difluoro-phenyl)-thiazol-2-yl]-amide | 22 |
| (S)-1-(1,1-Dioxo-1$\lambda^6$-thiomorpholine-4-carbonyl)-piperidine-2-carboxylic acid [4-(4-fluoro-phenyl)-thiazol-2-yl]-amide | 38 |
| (S)-1-(1,1-Dioxo-1$\lambda^6$-thiomorpholine-4-carbonyl)-piperidine-2-carboxylic acid (4-fluoro-benzothiazol-2-yl)-amide | 59 |
| (S)-1-(4-Chloro-phenyl)-azepane-2-carboxylic acid (5-tert-butyl-isoxazol-3-yl)-amide | 0.4 |
| (S)-1-(1,1-Dioxo-1$\lambda^6$-thiomorpholine-4-carbonyl)-azepane-2-carboxylic acid (5-tert-butyl-isoxazol-3-yl)-amide | 15 |
| (S)-1-(Tetrahydro-pyran-4-yl)-azepane-2-carboxylic acid (5-tert-butyl-isoxazol-3-yl)-amide | 0.18 |
| (S)-1-(Tetrahydro-pyran-4-ylmethyl)-azepane-2-carboxylic acid (5-tert-butyl-isoxazol-3-yl)-amide | 0.03 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocyclic or cycloalkyl groups include hydrocarbon rings containing from three to twelve carbon atoms. These carbocyclic or cycloalkyl groups may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, tetrahydrothiopyranyl, tetrahydrothienyl, tetrahydrothiopyranyl 1,1-dioxide, tetrahydrothienyl 1,1-dioxide, oxazolyl, isoxazolyl, oxadiazolyl, triazolyl, thiazolyl, pyrazolyl, pyrrolyl, imidazolyl, thienyl, thiadiazolyl, thiomorpholinyl, 1,1-dioxo-1$\lambda^{6}$-thiomorpholinyl, morpholinyl, pyridinyl, pyrimidinyl, pyridazinyl, pyrazinyl, triazinyl, pyrrolidinyl, piperidinyl, piperazinyl, quinolinyl, Dihydro-2H-quinolinyl, isoquinolinyl, quinazolinyl, indazolyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle as defined herein. Each aryl unless otherwise specified includes it's partially or fully hydrogenated derivative. For example, naphthyl may include its hydrogenated derivatives such as tetrahydranaphthyl. Other partially or fully hydrogenated derivatives of the aryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention may be made using the general synthetic methods described below, which also constitute part of the invention.

General Synthetic Methods

The invention also provides processes for making compounds of Formula (IA), (IIA), (IIIA), (IVA), (IB), (IIB) and (IC). In all Schemes, unless specified otherwise, $R_1$, $L_1$, $L_2$, $Ar_1$, $Ar_2$ and X in the Formulas below shall have the meaning of $R_1$, $L_1$, $L_2$, $Ar_1$, $Ar_2$ and X in Formula (IA), (IIA), (IIIA), (IVA), (IB), (IIB) and (IC) of the invention described herein above. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

Compounds of Formula (IA) and (IIIA) may be synthesized by the method outlined in scheme 1.

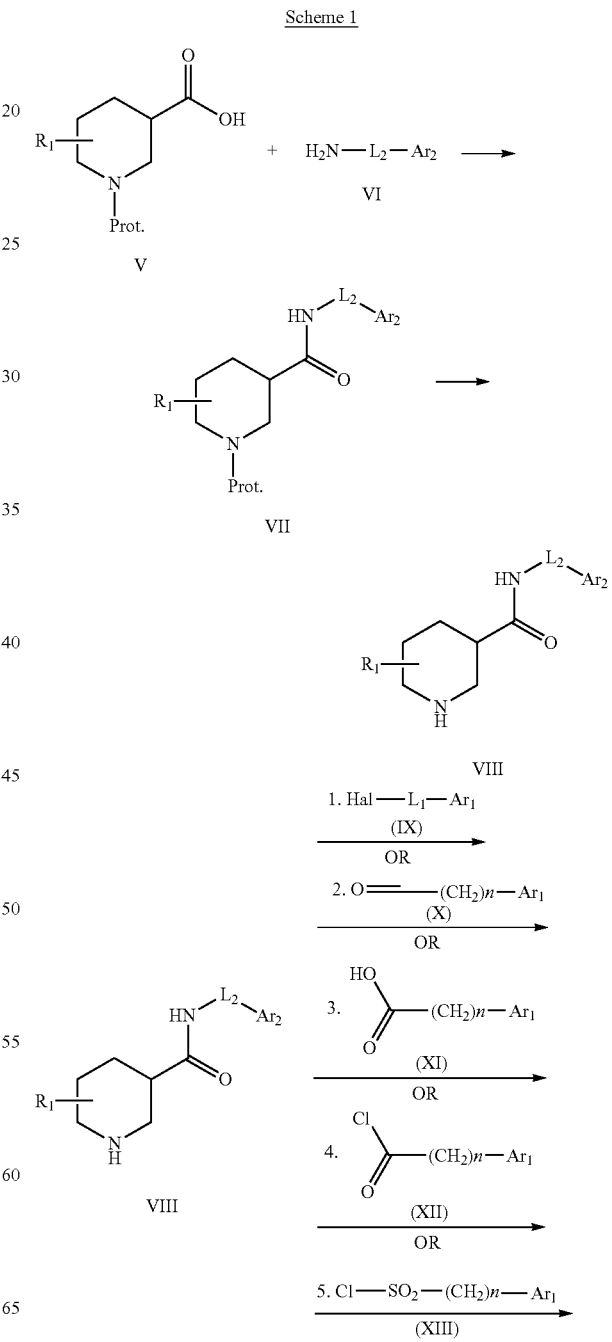

103
-continued

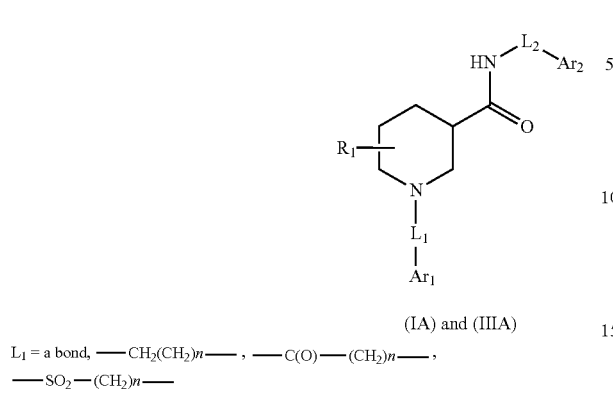

(IA) and (IIIA)

$L_1$ = a bond, —$CH_2(CH_2)n$—, —$C(O)$—$(CH_2)n$—,
—$SO_2$—$(CH_2)n$—
n = 0, 1, 2 or 3

As illustrated in scheme 1, reaction of an appropriately substituted piperidine-3-carboxylic acid (V) with an amine of formula (VI), under standard coupling conditions and as described in the examples, provides an amide of formula (VII). Prot.=amine protecting group, such as BOC. Reaction of the intermediate (VII) with an acid such as hydrochloric acid, in a suitable solvent, provides the deprotected amine intermediate (VIII). Reaction of the intermediate (VIII) with a suitable halide Hal-$L_1$-$Ar_1$ (IX), wherein Hal=F, Cl, Br or I, in a suitable solvent, in the presence of a suitable base, provides a compound of Formula (I). Intermediate (VIII) may also be reacted with a carbonyl compound of formula (X) under reductive amination conditions, to provide a compound of Formula (IA).

Alternatively, reaction of the intermediate (VIII) with an acid of formula (XI) under standard coupling conditions, provides a compound of Formula (I). Reaction of intermediate (VIII) with an acid chloride of formula (XII) or a sulfonyl chloride of formula (XIII), under standard reaction conditions, provides the corresponding compound of Formula (IA).

Compounds of Formula (IIA) and (IVA) may be synthesized using the procedure outlined in scheme 1, and as described in the examples, by using the appropriate piperidine-2-carboxylic acid staring material instead of the piperidine-3-carboxylic acid starting material (V).

Compounds of Formula (IIA) and (IVA) may be prepared according to scheme 2.

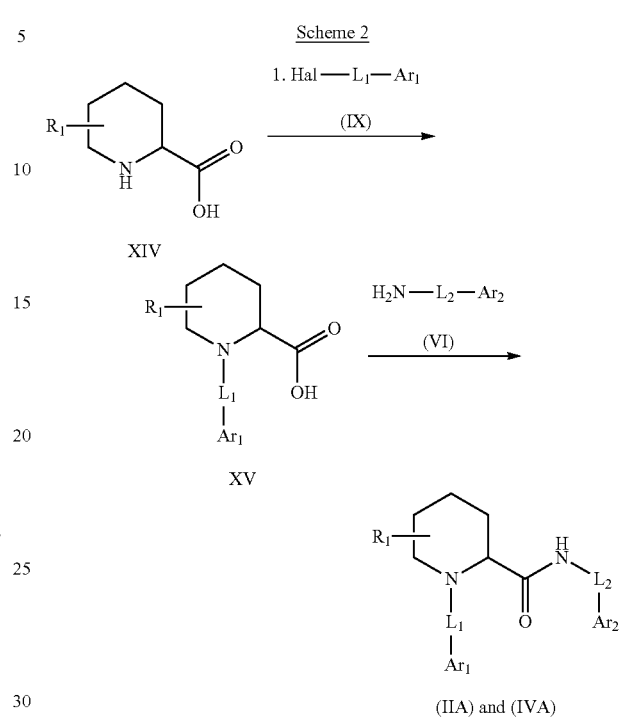

As outlined in scheme 2, reaction of the piperidine-2 carboxylic acid starting material of formula (XIV) with a suitable halide Hal-$L_1$-$Ar_1$ (IX), wherein Hal=F, Cl, Br or I, in a suitable solvent, in the presence of a suitable base, provides a compound of formula (XV). Reaction of intermediate (XV) with an amine of formula (VI), under standard coupling conditions and as described in coupling methods in examples, provides a compound of Formula (IIA).

Compounds of Formula (IA) and (IIIA) may be synthesized using the procedure outlined in scheme 2, by using the appropriate piperidine-3 carboxylic acid staring material instead of the piperidine-2 carboxylic acid starting material (XIV).

Compounds of Formula (IIA) and (IVA) may be made according to scheme 3.

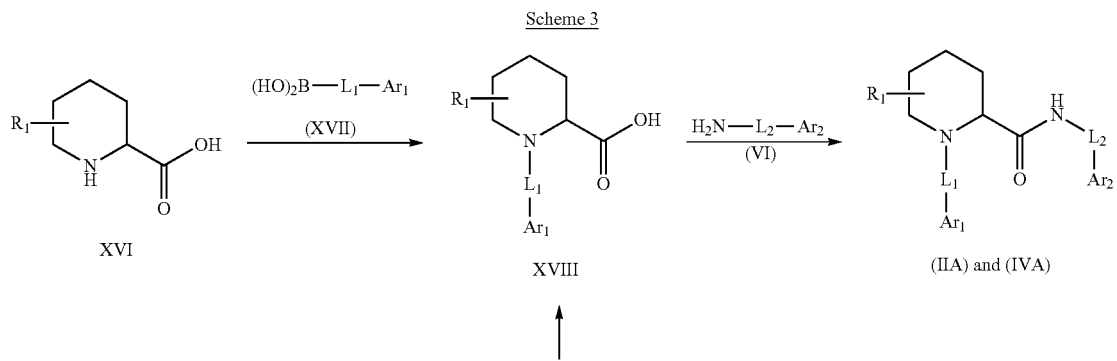

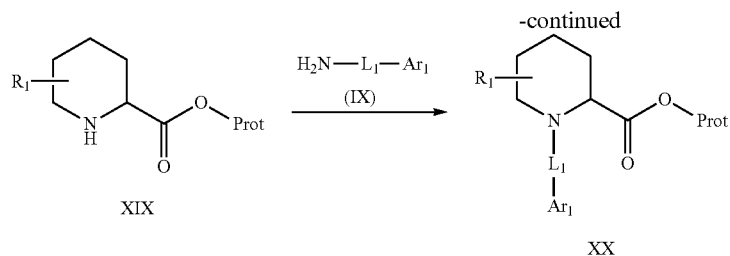

As illustrated in scheme 3, reaction of an appropriately substituted piperidine-2 carboxylic acid (XVI) with a boronic acid or ester of formula (XVII), under standard arylation conditions, provides an acid of formula (XVIII). Alternately, the intermediate of formula (XVIII) can be prepared by reacting a compound of formula (XIX) with a suitable halide Hal-$L_1$-$Ar_1$ (IX), wherein Hal=F, Cl, Br or I, in a suitable solvent, to afford ester of formula (XX). Prot=acid protecting group, such as tert-butyl ester. Hydrolysis of the compound of formula (XX) under standard conditions, provides an acid of formula (XVIII). Reaction of acid (XVIII) with an amine of formula (VI), under standard coupling conditions provides a compound of Formula (IIA).

Compounds of Formula (IVA) may also be prepared by scheme 3 by using the appropriately substituted starting material (XVI).

Compounds of Formula (IB) may be synthesized by the method outlined in scheme 4.

Scheme 4

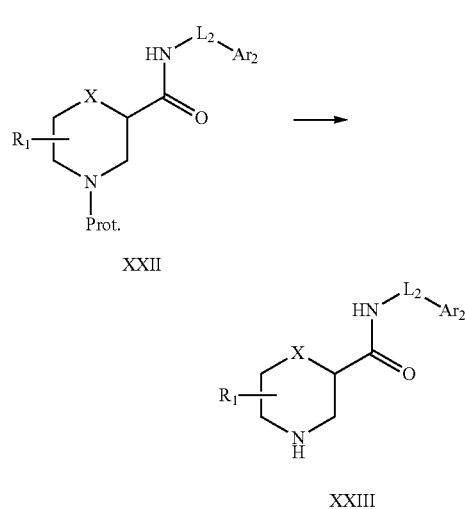

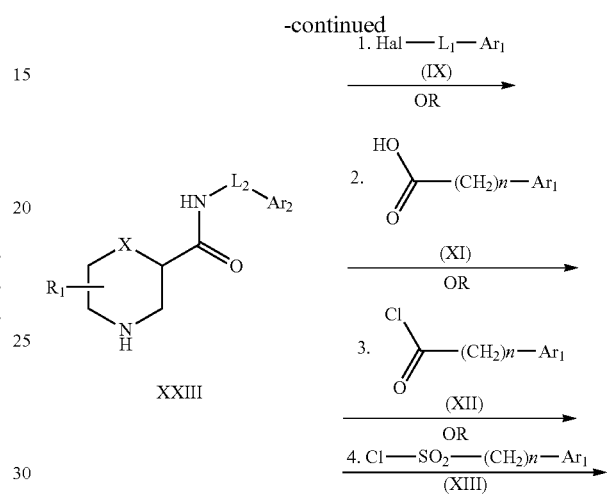

$L_1$ = a bond, —$CH_2(CH_2)n$—, —$C(O)$—$(CH_2)n$—, —$SO_2$—$(CH_2)n$— n = 0, 1, 2 or 3

As illustrated in scheme 4, reaction of an appropriately substituted morpholine-2-carboxylic acid (XXI) with an amine of formula (VI), under standard coupling conditions and as described in the examples, provides an amide of formula (XXII). Prot.=amine protecting group, such as BOC. Reaction of the intermediate (XXII) with an acid such as hydrochloric acid, in a suitable solvent, provides the deprotected amine intermediate (XXIII) Reaction of the intermediate (XXIII) with a suitable halide Hal-$L_1$-$Ar_1$ (IX), wherein Hal=F, Cl, Br or I, in a suitable solvent, in the presence of a suitable base, provides a compound of Formula (IB). Alternatively, reaction of the intermediate (XXIII) with an acid of formula (XI) under standard coupling conditions, provides a compound of Formula (IB). Reaction of intermediate (XXIII) with an acid chloride of formula (XII) or a sulfonyl chloride of formula (XIII), under standard reaction conditions, provides the corresponding compound of Formula (IB).

Compounds of Formula (IIB) may be synthesized using the procedure outlined in scheme 4, and as described in the examples, by using the appropriate morpholine-3-carboxylic acid staring material instead of the morpholine-2-carboxylic acid starting material (XXI).

Compounds of Formula IC may be prepared by the method outlined in scheme 5

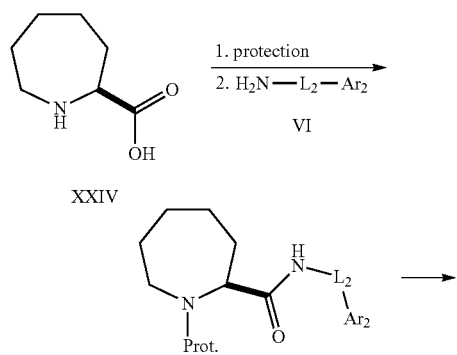

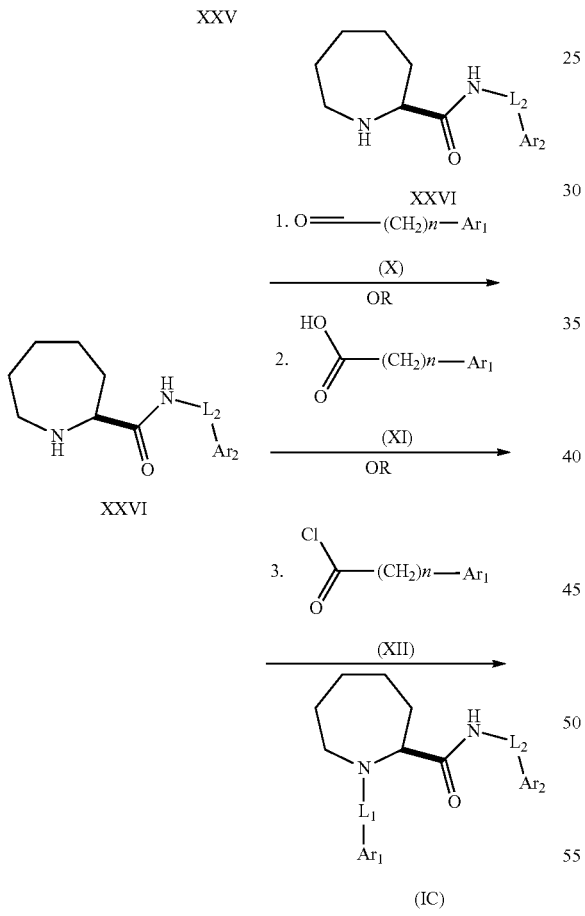

$L_1$ = a bond, —CH$_2$(CH$_2$)$n$—, —C(O)—(CH$_2$)$n$—
n = 0, 1, 2 or 3

Starting acid of formula XXIV is prepared by adaptation of the following literature: Dutton, F. E.; Lee, B. H.; Johnson, S. S.; Coscarelli, E. M.; Lee, P. H. J. Med. Chem. 2003, 46, 2057-2073

As illustrated in scheme 5, reaction of an azepine carboxylic acid of formula (XXIV), after protection of the nitrogen with standard groups, a with an amine of formula (VI), under standard coupling conditions and as described in the examples, provides an amide of formula (XXV). Prot.=amine protecting group, such as BOC. Reaction of the intermediate (XXV) with an acid such as hydrochloric acid, in a suitable solvent, provides the deprotected amine intermediate (XXVI). Reaction of the intermediate (XXVI) with a carbonyl compound of formula (X) under reductive amination conditions, provides a compound of Formula (IC). Alternatively, reaction of the intermediate (XXVI) with an acid of formula (XI) under standard coupling conditions, provides a compound of Formula (IC). Reaction of intermediate (XXVI) with an acid chloride of formula (XII), under standard reaction conditions, provides the corresponding compound of Formula (IC).

Compounds of Formula (IIA) and (IVA) may be prepared according to scheme 2.

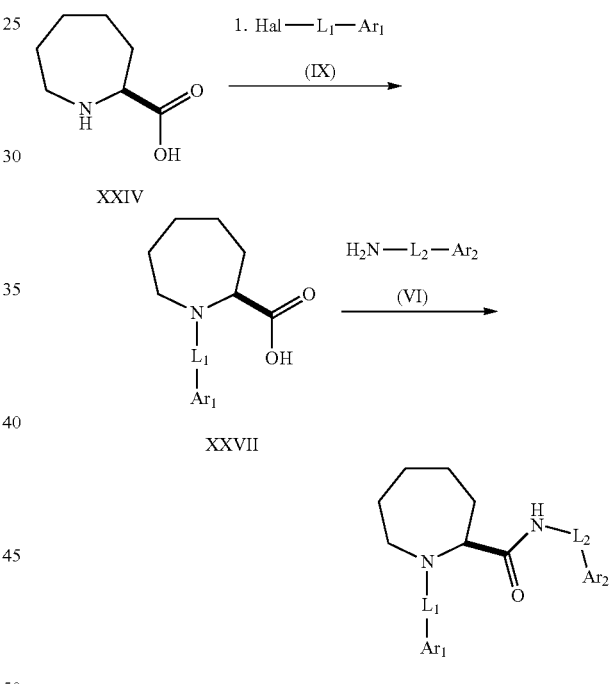

As outlined in scheme 6, reaction of the azepine carboxylic acid starting material of formula (XXIV) with a suitable halide Hal-$L_1$-Ar$_1$ (IX), wherein Hal=F, Cl, Br or I, in a suitable solvent, in the presence of a suitable base, provides a compound of formula (XXVII). Reaction of intermediate (XXVII) with an amine of formula (VI), under standard coupling conditions provides a compound of Formula (IC)

Further modification of the initial product of Formula (IA), (IIA), (IIIA), (IVA), (IB), (IIB) and (IC) by methods known to one skilled in the art and illustrated in the examples below, provides additional compounds of this invention.

EXAMPLES

Compounds of Formula (IA) and (IIIA)

Method A

Synthesis of 3'-Chloro-5'-trifluoromethyl-3,4,5,6-tetrahydro-2H-[1,2']bipyridinyl-3-carboxylic acid (5-tert-butyl-isoxazol-3-yl)-amide (Example 1)

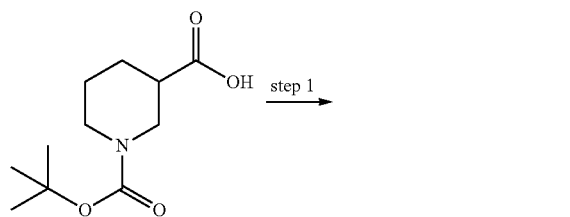

Step 1: Synthesis of 3-(5-tert-Butyl-isoxazol-3-ylcarbamoyl)-piperidine-1-carboxylic acid tert-butyl ester To a cold (5° C.) solution of piperidine-1,3-dicarboxylic acid 1-tert-butyl ester (1 g; 4.362 mmol) and 3-amino-5-t-butylisoxazole (589 mg; 4.2 mmol) in anhydrous pyridine (12 mL) is added phosphorus oxychloride (0.393 mL; 4.362 mmol). The reaction mixture is stirred at room temperature for 30 minutes. The mixture is quenched with saturated NH4Cl aqueous solution and extracted with ethyl acetate 3 times. The organics are combined and washed with brine, dried over Na2SO4, filtered and concentrated in vacuo. Purification by flash chromatography on silica using methanol/methylene chloride provides the title compound, m/z 352 [M+H$^+$].

Amide intermediates in Table 1 are made in a similar manner.

TABLE 1

| Structure | Name | m/z [M + H$^+$] |
|---|---|---|
| 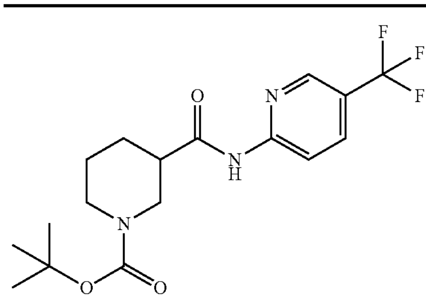 | 3-(5-Trifluoromethyl-pyridin-2-ylcarbamoyl)-piperidine-1-carboxylic acid tert-butyl ester | 374 |

TABLE 1-continued

| Structure | Name | m/z [M + H+] |
|---|---|---|
| (structure shown) | 3-(Morpholine-4-carbonyl)-piperidine-1-carboxylic acid tert-butyl ester | 299 |

Step 2: Synthesis of piperidine-3-carboxylic acid (5-tert-butyl-isoxazol-3-yl)-amide; hydrochloride To a solution of 3-(5-tert-Butyl-isoxazol-3-ylcarbamoyl)-piperidine-1-carboxylic acid tert-butyl ester (620 mg; 1.764 mmol) in methylene chloride (20 mL) is added 4N HCl in dioxanes (1.8 mL; 7.2 mmol). The reaction mixture is left stirring at room temperature for 1 hour. The mixture is concentrated in vacuo to provide the title compound, m/z 252 [M+H+].

Intermediates in Table 2 are made in a similar manner.

TABLE 2

| Structure | Name | m/z [M + H+] |
|---|---|---|
| (structure shown) | Piperidine-3-carboxylic acid (5-trifluoromethyl-pyridin-2-yl)-amide; hydrochloride | 274 |
| (structure shown) | Morpholin-4-yl-piperidin-3-yl-methanone; hydrochloride | 199 |

Step 3: Synthesis of 3'-Chloro-5'-trifluoromethyl-3,4,5,6-tetrahydro-2H-[1,2']bipyridinyl-3-carboxylic acid (5-tert-butyl-isoxazol-3-yl)-amide A microwave reaction vial is charged with piperidine-3-carboxylic acid (5-tert-butyl-isoxazol-3-yl)-amide; hydrochloride (94 mg; 0.327 mmol), 3-chloro-2-fluoro-5-trifluoromethylpyridine (0.043 mL; 0.33 mmol), triethylamine (0.092 mL; 0.66 mmol) and t-butanol (0.5 mL). The vial is heated in microwave at 175° C. for 1 hour then left standing at room temperature overnight. The reaction mixture is concentrated in vacuo. Purification by flash chromatography on silica using methanol/methylene chloride then recrystallization from hot methanol provides the title compound, m/z 431 [M+H+].

Compounds found in Table 3 Method A are prepared in a similar manner.

Method B

Synthesis of 1-(1,1-Dioxo-1λ⁶-thiomorpholine-4-carbonyl)-piperidine-3-carboxylic acid (5-tert-butyl-isoxazol-3-yl)-amide (Example 3)

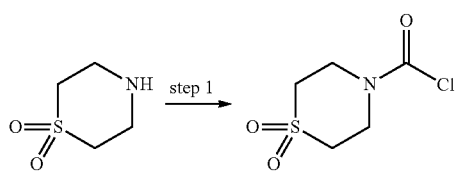

-continued

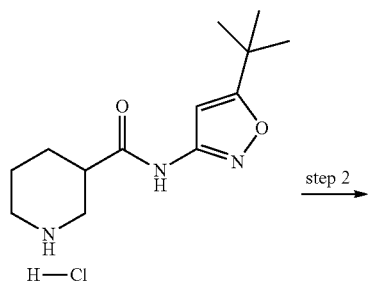

Step 1: Synthesis of 1,1-dioxo-1λ⁶-thiomorpholine-4-carbonyl chloride

Thiomorpholine 1,1-dioxide (1 g; 7.397 mmolline) is dispersed in THF (50 mL). Triethylamine (1.238 mL; 8.88 mmol) is added, followed by 20% phosgene in toluene (11.743 mL; 22.2 mmol). The reaction mixture is stirred at room temperature for 18 hours. The reaction mixture is diluted with diethyl ether and filtered through Celite®. The Celite® is washed with diethyl ether several times and the combined filtrates are concentrated in vacuo to afford the title compound. H NMR (400 MHz, CDCl$_3$): δ 3.1-3.2 (m; 4H), 4.1-4.3 (d, 4H).

Step 2: Synthesis of 1-(1,1-Dioxo-1λ⁶-thiomorpholine-4-carbonyl)-piperidine-3-carboxylic acid (5-tert-butyl-isoxazol-3-yl)-amide To a solution of piperidine-3-carboxylic acid (5-tert-butyl-isoxazol-3-yl)-amide; hydrochloride (100 mg; 0.347 mmol) in anhydrous THF (1 mL) is added triethylamine (0.098 mL; 0.7 mmol) and 1,1-dioxo-1λ⁶-thiomorpholine-4-carbonyl chloride (71.15 mg; 0.36 mmol). The reaction mixture is left stirring at room temperature overnight. The reaction mixture is diluted with water and extracted with ethyl acetate 3 times. The organics are combined and washed with brine, dried over Na2SO4, filtered and concentrated in vacuo.

Purification by flash chromatography on silica using methanol/methylene chloride then trituration from diethyl ether provides the title compound, m/z 412 [M+H⁺].

Compounds found in Table 3 Method B are prepared in a similar manner.

Method C:

Synthesis of 1-(Tetrahydro-pyran-4-carbonyl)-piperidine-3-carboxylic acid (5-tert-butyl-isoxazol-3-yl)-amide (Example 4)

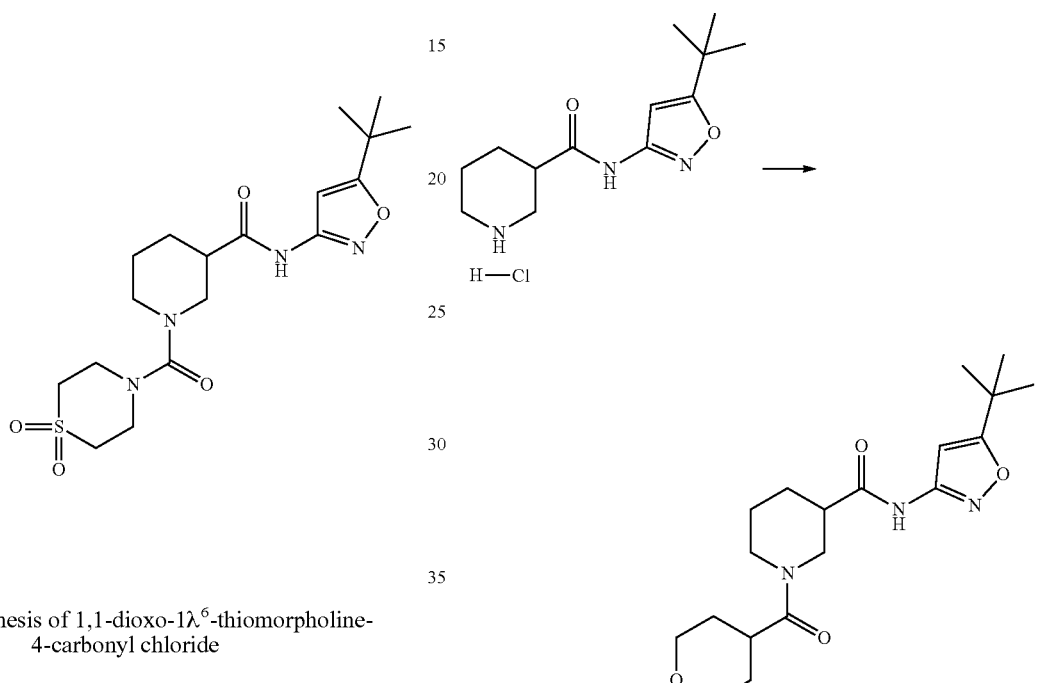

To a solution of tetrahydro-pyran-4-carboxylic acid (54.66 mg; 0.42 mmol) and 1-hydroxybenzotriazole hydrate (56.76 mg; 0.42 mmol) in anhydrous DMF (1.5 mL) is added 1-(3-dimethylaminopropyl)-3-ethylcarbodiimide hydrochloride (80.52 mg; 0.42 mmol) and the reaction mixture is stirred at room temperature for 15 minutes. After this time, piperidine-3-carboxylic acid (5-tert-butyl-isoxazol-3-yl)-amide; hydrochloride (90 mg; 0.313 mmol), triethylamine (0.044 mL; 0.313 mmol) and 4-dimethylaminopyridine (4.1 mg; 0.034 mmol) are added. The reaction mixture is stirred at room temperature for 18 hours. The mixture is diluted with ethyl acetate and then washed with water, saturated NaHCO3 aqueous solution then brine, dried over Na2SO4, filtered and concentrated in vacuo. Purification by flash chromatography on silica using methanol/methylene chloride then recrystallization from hot ethyl acetate provides the title compound, m/z 364 [M+H⁺].

Compounds found in Table 3 Method C are prepared in a similar manner.

Method D:

Synthesis 1-(4-Chloro-benzyl)-piperidine-3-carboxylic acid (5-tert-butyl-isoxazol-3-yl)-amide (Example 9)

Method E:

Synthesis of 1-(4-Chloro-benzenesulfonyl)-piperidine-3-carboxylic acid (5-tert-butyl-isoxazol-3-yl)-amide (Example 10)

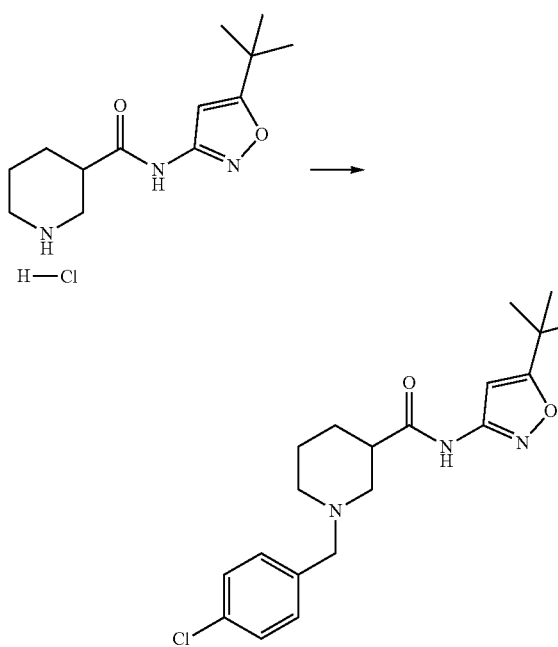

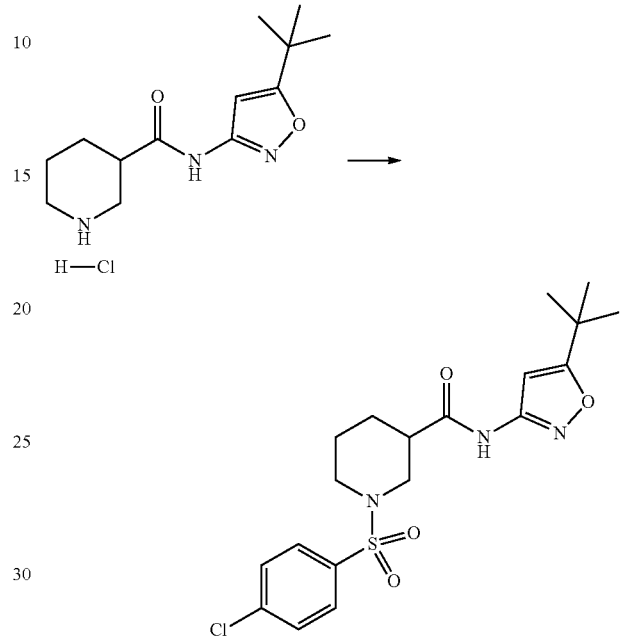

To a solution of 4-chlorobenzyl chloride (134 mg; 0.832 mmol) in DMF (3 mL) is added piperidine-3-carboxylic acid (5-tert-butyl-isoxazol-3-yl)-amide; hydrochloride (238.86 mg; 0.83 mmol) and N,N-diisopropylethylamine (0.331 mL; 1.9 mmol). The reaction mixture is left stirring at room temperature for 18 hours in the presence of catalytic amount of 4-dimethylaminopyridine (1 mg). The mixture is diluted with ethyl acetate and washed with water 3 times then brine, dried over Na2SO4, filtered and concentrated in vacuo. Purification by flash chromatography on silica using methanol/methylene chloride provides the title compound, m/z 376/378 [M+H$^+$].

To a solution of 4-chlorophenylsulfonyl chloride (117.35 mg; 0.556 mmol) in DMF (2 mL) is added piperidine-3-carboxylic acid (5-tert-butyl-isoxazol-3-yl)-amide; hydrochloride (160 mg; 0.556 mmol), N,N-diisopropylethylamine (0.261 mL; 1.5 mmol) and 4-dimethylaminopyridine (2 mg, 0.016 mmol). The reaction mixture is left stirring at room temperature for 18 hours. After this time, the mixture is diluted with ethyl acetate and washed with water 3 times, then brine, dried over Na2SO4, filtered and concentrated in vacuo. Purification by flash chromatography on silica using methanol/methylene chloride provides the title compound, m/z 426/428 [M+H$^+$].

TABLE 3

| Example | Structure | Name | m/z [M + H$^+$] | Patent Method |
|---|---|---|---|---|
| 1 | 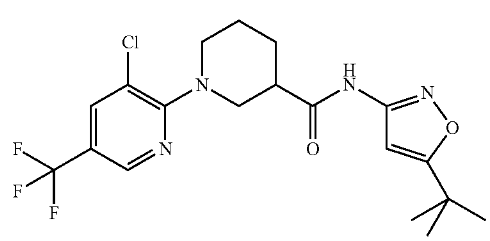 [SMILES: CC(C)(C)c1cc(NC(=O)C2CCCN(c3ncc(C(F)(F)F)cc3Cl)C2)no1] | 3'-Chloro-5'-trifluoromethyl-3,4,5,6-tetrahydro-2H-[1,2']bipyridinyl-3-carboxylic acid (5-tert-butyl-isoxazol-3-yl)-amide | 431 | A |

TABLE 3-continued

Examples

| Example | Structure | Name | m/z [M + H+] | Patent Method |
|---|---|---|---|---|
| 2 | 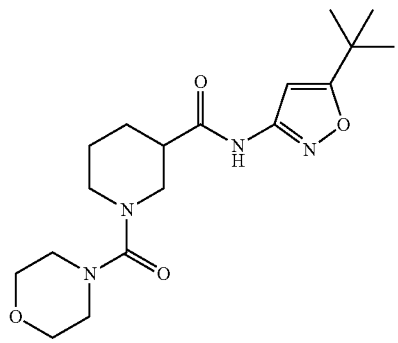 [SMILES: CC(C)(C)c1cc(NC(=O)C2CCCN(C(=O)N3CCOCC3)C2)no1] | 1-(Morpholine-4-carbonyl)-piperidine-3-carboxylic acid (5-tert-butyl-isoxazol-3-yl)-amide | 365 | B |
| 3 | 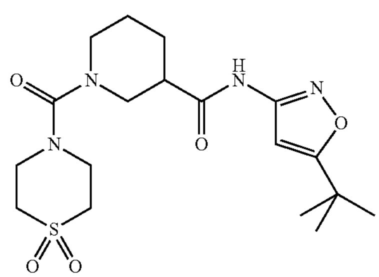 [SMILES: CC(C)(C)c1cc(NC(=O)C2CCCN(C(=O)N3CCS(=O)(=O)CC3)C2)no1] | 1-(1,1-Dioxo-1λ6-thiomorpholine-4-carbonyl)-piperidine-3-carboxylic acid (5-tert-butyl-isoxazol-3-yl)-amide | 412 | B |
| 4 | 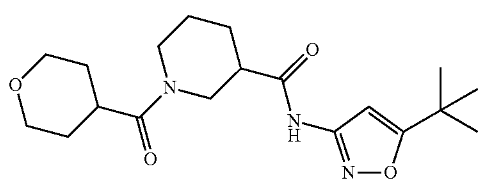 [SMILES: CC(C)(C)c1cc(NC(=O)C2CCCN(C(=O)C3CCOCC3)C2)no1] | 1-(Tetrahydro-pyran-4-carbonyl)-piperidine-3-carboxylic acid (5-tert-butyl-isoxazol-3-yl)-amide | 365 | C |
| 5 | 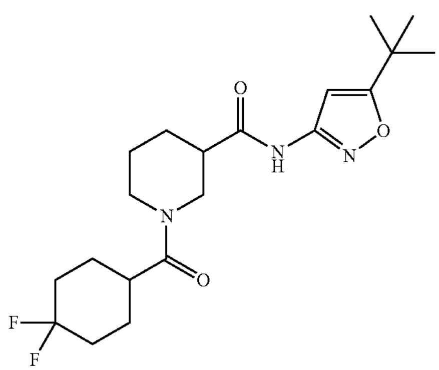 [SMILES: CC(C)(C)c1cc(NC(=O)C2CCCN(C(=O)C3CCC(F)(F)CC3)C2)no1] | 1-(4,4-Difluoro-cyclohexanecarbonyl)-piperidine-3-carboxylic acid (5-tert-butyl-isoxazol-3-yl)-amide | 398 | C |

TABLE 3-continued

| Example | Name | m/z [M + H+] | Patent Method |
|---|---|---|---|
| 6 | (R)-3'-Chloro-5'-trifluoromethyl-3,4,5,6-tetrahydro-2H-[1,2']bipyridinyl-3-carboxylic acid (5-tert-butyl-isoxazol-3-yl)-amide | 431 | A |
| 7 | 5'-Trifluoromethyl-3,4,5,6-tetrahydro-2H-[1,2']bipyridinyl-3-carboxylic acid (5-tert-butyl-isoxazol-3-yl)-amide | 397 | A |
| 8 | 1-(4-Trifluoromethyl-benzoyl)-piperidine-3-carboxylic acid (5-tert-butyl-isoxazol-3-yl)-amide | 424 | C |

TABLE 3-continued

Examples

| Example | Structure | Name | m/z [M + H⁺] | Patent Method |
|---|---|---|---|---|
| 9 | 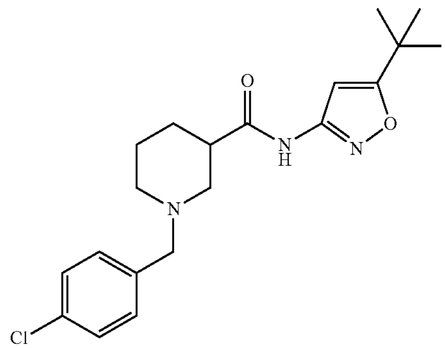 [SMILES: CC(C)(C)c1cc(NC(=O)C2CCCN(Cc3ccc(Cl)cc3)C2)no1] | 1-(4-Chloro-benzyl)-piperidine-3-carboxylic acid (5-tert-butyl-isoxazol-3-yl)-amide | 376/378 | D |
| 10 | 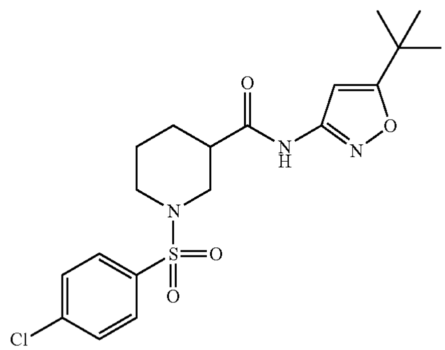 [SMILES: CC(C)(C)c1cc(NC(=O)C2CCCN(S(=O)(=O)c3ccc(Cl)cc3)C2)no1] | 1-(4-Chloro-benzenesulfonyl)-piperidine-3-carboxylic acid (5-tert-butyl-isoxazol-3-yl)-amide | 426/428 | E |
| 11 | 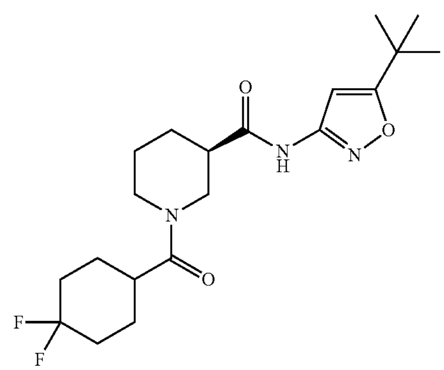 [SMILES: CC(C)(C)c1cc(NC(=O)[C@@H]2CCCN(C(=O)C3CCC(F)(F)CC3)C2)no1] | (R)-1-(4,4-Difluoro-cyclohexanecarbonyl)-piperidine-3-carboxylic acid (5-tert-butyl-isoxazol-3-yl)-amide | 398 | C |
| 12 | 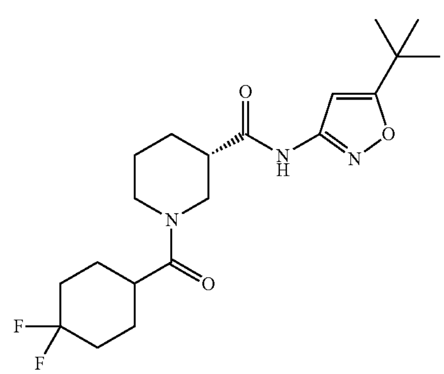 [SMILES: CC(C)(C)c1cc(NC(=O)[C@H]2CCCN(C(=O)C3CCC(F)(F)CC3)C2)no1] | (S)-1-(4,4-Difluoro-cyclohexanecarbonyl)-piperidine-3-carboxylic acid (5-tert-butyl-isoxazol-3-yl)-amide | 398 | C |

TABLE 3-continued

Examples

| Example | Structure | Name | m/z [M + H+] | Patent Method |
|---|---|---|---|---|
| 13 | 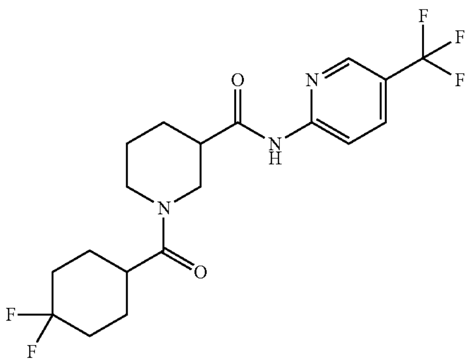 [SMILES: O=C(Nc1ccc(C(F)(F)F)cn1)C1CCCN(C(=O)C2CCC(F)(F)CC2)C1] | 1-(4,4-Difluoro-cyclohexanecarbonyl)-piperidine-3-carboxylic acid (5-trifluoromethyl-pyridin-2-yl)-amide | 420 | C |

Compounds of Formula (IIA) and (IVA)
Method F

Synthesis of (S)-1-(4,4-Difluoro-cyclohexanecarbonyl)-piperidine-2-carboxylic acid (5-tert-butyl-isoxazol-3-yl)-amide (Example 18)

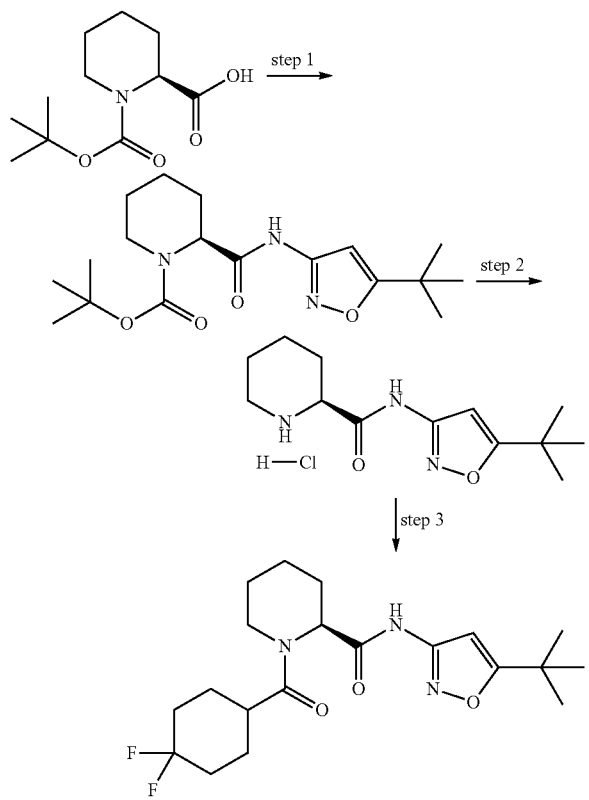

Step 1

Five different amide coupling procedures can be used for step 1. Amide intermediates and the coupling procedures 1-5 to synthesize them are listed in Table 4.

Amide coupling procedure 1: Synthesis of (S)-2-(5-tert-Butyl-isoxazol-3-ylcarbamoyl)-piperidine-1-carboxylic acid tert-butyl ester To a cold (5° C.) solution of (S)-piperidine-2-carboxylic acid (480 mg; 2.094 mmol) and 3-amino-5-t-butylisoxazole (300 mg; 2.14 mmol) in anhydrous pyridine (5 mL) is added phosphorus chloride (0.198 mL; 2.2 mmol). The reaction mixture is left stirring and allowed to warm to room temperature overnight. The reaction mixture is quenched with water and extracted with ethyl acetate twice. The combined organics are washed with brine, dried over Na2SO4, filtered and concentrated in vacuo. Purification by flash chromatography on silica using methanol/methylene chloride provides the title compound, m/z 352 [M+H+].

Amide coupling procedure 2: Synthesis of (S)-2-(3-tert-Butyl-isoxazol-5-ylcarbamoyl)-piperidine-1-carboxylic acid tert-butyl ester 2-Ethoxy-1-ethoxycarbonyl-1,2-dihydroquinoline (445 mg; 1.8 mmol) is added to a solution of (S)-piperidine-2-carboxylic acid (300 mg; 1.308 mmol) and 5-amino-3-t-butylisoxazole (183.4 mg; 1.308 mmol) in toluene (4.2 mL) at room temperature and the mixture is stirred for 18 hours. After this time, the mixture is concentrated in vacuo. Purification by flash chromatography on silica gel using methanol/methylene chloride provides the title compound, m/z 352 [M+H+].

Amide coupling procedure 3: Synthesis of (S)-2-(5-tert-Butyl-isoxazol-3-ylcarbamoyl)-piperidine-1-carboxylic acid tert-butyl ester To solution of the (S)-piperidine-2-carboxylic acid (5 g; 21.808 mmol), 3-amino-5-t-butylisoxazole (3.084 g; 22 mmol), and N,N-diisopropylethylamine (3.799 mL; 21.808 mmol) in anhydrous toluene (80 mL) is added 2-chloro-1-methylpyridinium iodide (6.132 g; 24 mmol). The mixture is left stirring for 2 hours at 75° C. After cooling to room temperature, the reaction mixture is diluted with ethyl acetate and washed with water twice then brine, dried over Na2SO4, filtered and concentrated in vacuo. Purification by flash chromatography on silica gel using ethyl acetate/Hexanes provides the title compound, m/z 352 [M+H+].

Amide coupling procedure 4: Synthesis of (S)-2-(5-tert-Butyl-1,3,4-thiadiazol-2-ylcarbamoyl)-piperidine-1-carboxylic acid tert-butyl ester To a suspension of (S)-piperidine-2-carboxylic acid (0.4 g; 1.745 mmol) in THF (5 mL) is added N,N-diisopropylethylamine (0.608 mL; 3.49 mmol) and 3-(diethoxyphosphoryloxy)-1,2,3-benzotrizin-4(3H)-one (1.044 g; 3.49 mmol) at room temperature. After 30 minutes of stirring, 2-amino-5-t-butyl-1,3,4-thiadiazole (0.274 g; 1.745 mmol) is added and the reaction is stirred at room temperature for 18 hours. The reaction is quenched with saturated NH4Cl aqueous solution and extracted with ethyl acetate 3 times. The organics are combined and washed with water, then brine, dried over Na2SO4, filtered and concentrated in vacuo. Purification by flash chromatography on silica gel using ethyl acetate/Hexanes provides the title compound, m/z 369 [M+H$^+$].

Amide coupling procedure 5: Synthesis of (S)-2-(5-tert-Butyl-1,3,4-thiadiazol-2-ylcarbamoyl)-piperidine-1-carboxylic acid tert-butyl ester To a solution of (S)-piperidine-2-carboxylic acid (1 g; 4.362 mmol) and 2-amino-5-t-butyl-1,3,4-thiadiazole (0.686 g; 4.362 mmol) in dichloromethane (35 mL) is added 2-isobutoxy-1-isobutoxycarbonyl-1,2-dihydroquinoline (1.304 mL; 4.5 mmol). The mixture is stirred at room temperature for 2.5 hours. The reaction mixture was concentrated in vacuo. Purification by flash chromatography on silica gel using ethyl acetate/Hexanes provides the title compound, m/z 369 [M+H$^+$].

TABLE 4

Amide intermediates

| Structure | Name | m/z [M + H$^+$] | Coupling procedure |
|---|---|---|---|
| 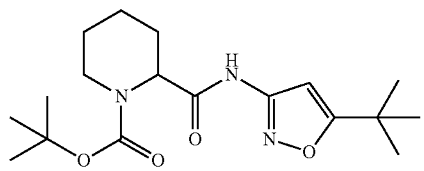 [SMILES: CC(C)(C)OC(=O)N1CCCCC1C(=O)Nc1cc(C(C)(C)C)on1] | 2-(5-tert-Butyl-isoxazol-3-ylcarbamoyl)-piperidine-1-carboxylic acid tert-butyl ester | 352 | 1 |
| 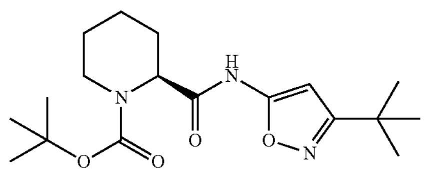 [SMILES: CC(C)(C)OC(=O)N1CCCC[C@H]1C(=O)Nc1cc(C(C)(C)C)no1] | (S)-2-(3-tert-Butyl-isoxazol-5-ylcarbamoyl)-piperidine-1-carboxylic acid tert-butyl ester | 352 | 2 |
| 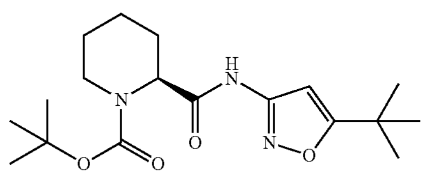 [SMILES: CC(C)(C)OC(=O)N1CCCC[C@H]1C(=O)Nc1cc(C(C)(C)C)on1] | (S)-2-(5-tert-Butyl-isoxazol-3-ylcarbamoyl)-piperidine-1-carboxylic acid tert-butyl ester | 352 | 1, 2 and 3 |
| 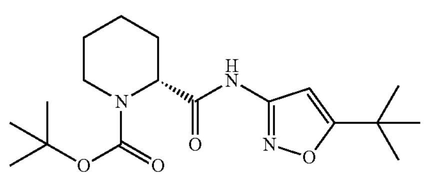 [SMILES: CC(C)(C)OC(=O)N1CCCC[C@@H]1C(=O)Nc1cc(C(C)(C)C)on1] | (R)-2-(5-tert-Butyl-isoxazol-3-ylcarbamoyl)-piperidine-1-carboxylic acid tert-butyl ester | 352 | 1 |
| 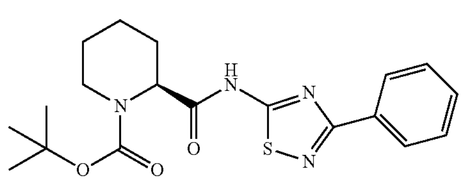 [SMILES: CC(C)(C)OC(=O)N1CCCC[C@H]1C(=O)Nc1nc(-c2ccccc2)ns1] | (S)-2-(3-Phenyl-1,2,4-thiadiazol-5-ylcarbamoyl)-piperidine-1-carboxylic acid tert-butyl ester | 389 | 2 |
| 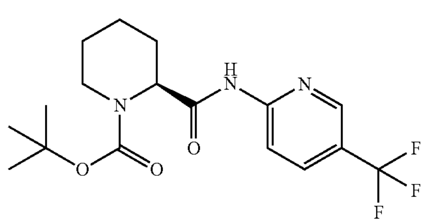 [SMILES: CC(C)(C)OC(=O)N1CCCC[C@H]1C(=O)Nc1ccc(C(F)(F)F)cn1] | (S)-2-(5-Trifluoromethyl-pyridin-2-ylcarbamoyl)-piperidine-1-carboxylic acid tert-butyl ester | 374 | 2 |

TABLE 4-continued

Amide intermediates

| Structure | Name | m/z [M + H⁺] | Coupling procedure |
|---|---|---|---|
| 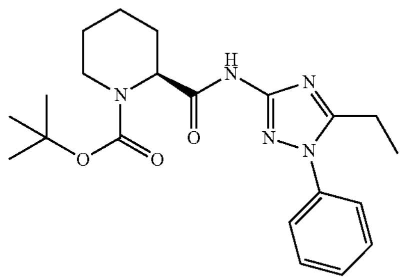 [SMILES: CCc1nc(NC(=O)[C@@H]2CCCCN2C(=O)OC(C)(C)C)nn1-c1ccccc1] | (S)-2-(5-Ethyl-1-phenyl-1H-1,2,4-triazol-3-ylcarbamoyl)-piperidine-1-carboxylic acid tert-butyl ester | 400 | 1 |
| 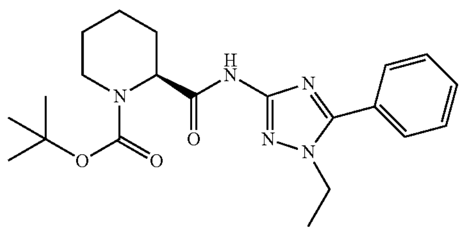 [SMILES: CCn1nc(NC(=O)[C@@H]2CCCCN2C(=O)OC(C)(C)C)nc1-c1ccccc1] | (S)-2-(1-Ethyl-5-phenyl-1H-1,2,4-triazol-3-ylcarbamoyl)-piperidine-1-carboxylic acid tert-butyl ester | 400 | 1 and 2 |
| 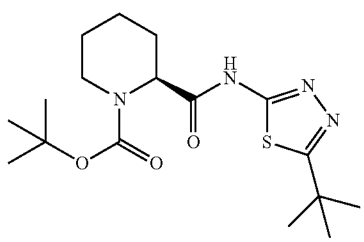 [SMILES: CC(C)(C)OC(=O)N1CCCC[C@H]1C(=O)Nc1nnc(C(C)(C)C)s1] | (S)-2-(5-tert-Butyl-1,3,4-thiadiazol-2-ylcarbamoyl)-piperidine-1-carboxylic acid tert-butyl ester | 369 | 1, 4 and 5 |
| 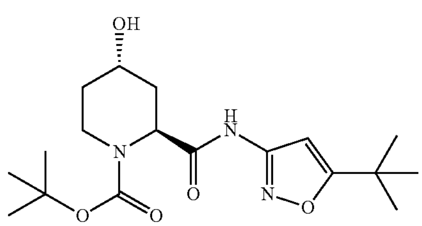 [SMILES: CC(C)(C)OC(=O)N1CC[C@H](O)C[C@H]1C(=O)Nc1cc(C(C)(C)C)on1] | (2S,4S)-2-(5-tert-Butyl-isoxazol-3-ylcarbamoyl)-4-hydroxy-piperidine-1-carboxylic acid tert-butyl ester | 368 | 2 |
| 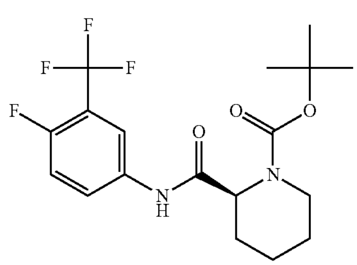 [SMILES: CC(C)(C)OC(=O)N1CCCC[C@H]1C(=O)Nc1ccc(F)c(C(F)(F)F)c1] | (S)-2-(4-Fluoro-3-trifluoromethyl-phenylcarbamoyl)-piperidine-1-carboxylic acid tert-butyl ester | 391 | 1 |
| 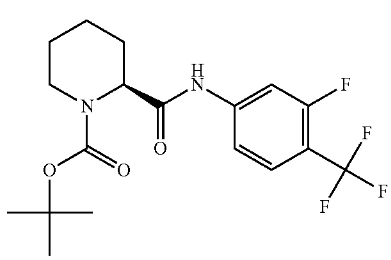 [SMILES: CC(C)(C)OC(=O)N1CCCC[C@H]1C(=O)Nc1ccc(C(F)(F)F)c(F)c1] | (S)-2-(3-Fluoro-4-trifluoromethyl-phenylcarbamoyl)-piperidine-1-carboxylic acid tert-butyl ester | 391 | 1 |

TABLE 4-continued

| Amide intermediates | | | |
|---|---|---|---|
| Structure | Name | m/z [M + H⁺] | Coupling procedure |
| | (S)-2-(5-Chloro-benzothiazol-2-ylcarbamoyl)-piperidine-1-carboxylic acid tert-butyl ester | 396 | 1 |
| | (S)-2-(3-Phenyl-isoxazol-5-ylcarbamoyl)-piperidine-1-carboxylic acid tert-butyl ester | 372 | 1 |
| | (S)-2-(3-Cyclopentyl-isoxazol-5-ylcarbamoyl)-piperidine-1-carboxylic acid tert-butyl ester | 364 | 1 |
| | (S)-2-[3-(1-Methyl-cyclopropyl)-isoxazol-5-ylcarbamoyl]-piperidine-1-carboxylic acid tert-butyl ester | 350 | 1 and 2 |
| | (S)-2-(5-Chloro-benzoxazol-2-ylcarbamoyl)-piperidine-1-carboxylic acid tert-butyl ester | 380 | 2 |
| | (S)-2-(4-Trifluoromethyl-pyridin-2-ylcarbamoyl)-piperidine-1-carboxylic acid tert-butyl ester | 374 | 2 |

TABLE 4-continued

Amide intermediates

| Structure | Name | m/z [M + H+] | Coupling procedure |
|---|---|---|---|
| 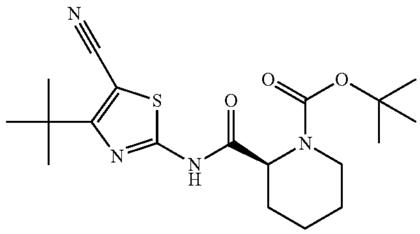 [SMILES: CC(C)(C)OC(=O)N1CCCC[C@H]1C(=O)Nc1nc(C(C)(C)C)c(C#N)s1] | (S)-2-(4-tert-Butyl-5-cyano-thiazol-2-ylcarbamoyl)-piperidine-1-carboxylic acid tert-butyl ester | 393 | 2 |
| 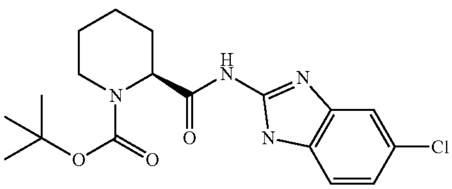 [SMILES: CC(C)(C)OC(=O)N1CCCC[C@H]1C(=O)Nc1nc2cc(Cl)ccc2[nH]1] | (S)-2-(5-Chloro-1H-benzimidazol-2-ylcarbamoyl)-piperidine-1-carboxylic acid tert-butyl ester | 379 | 2 |
| 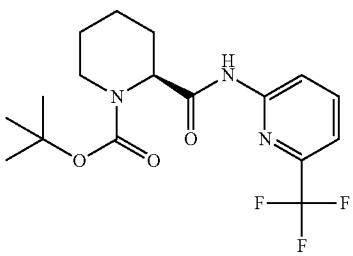 [SMILES: CC(C)(C)OC(=O)N1CCCC[C@H]1C(=O)Nc1cccc(C(F)(F)F)n1] | (S)-2-(6-Trifluoromethyl-pyridin-2-ylcarbamoyl)-piperidine-1-carboxylic acid tert-butyl ester | 374 | 2 |
| 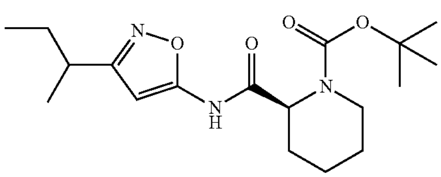 [SMILES: CCC(C)c1cc(NC(=O)[C@@H]2CCCCN2C(=O)OC(C)(C)C)on1] | (S)-2-(3-sec-Butyl-isoxazol-5-ylcarbamoyl)-piperidine-1-carboxylic acid tert-butyl ester | 352 | 2 |
| 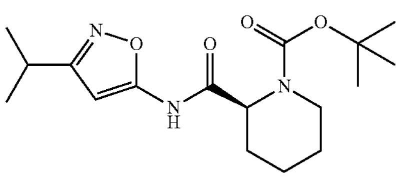 [SMILES: CC(C)c1cc(NC(=O)[C@@H]2CCCCN2C(=O)OC(C)(C)C)on1] | (S)-2-(3-Isopropyl-isoxazol-5-ylcarbamoyl)-piperidine-1-carboxylic acid tert-butyl ester | 338 | 2 |
| 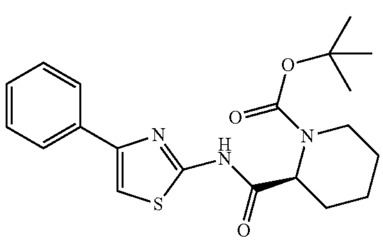 [SMILES: CC(C)(C)OC(=O)N1CCCC[C@H]1C(=O)Nc1nc(-c2ccccc2)cs1] | (S)-2-(4-Phenyl-thiazol-2-ylcarbamoyl)-piperidine-1-carboxylic acid tert-butyl ester | 388 | 2 |
| 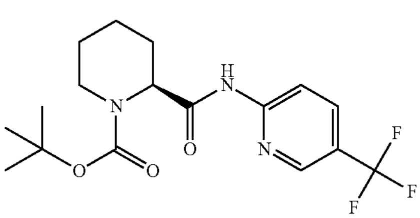 [SMILES: CC(C)(C)OC(=O)N1CCCC[C@H]1C(=O)Nc1ccc(C(F)(F)F)cn1] | (S)-2-(5-Trifluoromethyl-pyridin-2-ylcarbamoyl)-piperidine-1-carboxylic acid tert-butyl ester | 374 | 2 |

TABLE 4-continued

| Amide intermediates | | | |
|---|---|---|---|
| Structure | Name | m/z [M + H⁺] | Coupling procedure |
| | (S)-2-(5-Phenyl-1,3,4-thiadiazol-2-ylcarbamoyl)-piperidine-1-carboxylic acid tert-butyl ester | 389 | 2 |
| | (S)-2-(5-sec-Butyl-1,3,4-thiadiazol-2-ylcarbamoyl)-piperidine-1-carboxylic acid tert-butyl ester | 369 | 2 |
| | (S)-2-[5-(4-Chloro-phenyl)-1,3,4-thiadiazol-2-ylcarbamoyl]-piperidine-1-carboxylic acid tert-butyl ester | 423 | 2 |
| | (S)-2-(2-Phenoxy-ethylcarbamoyl)-piperidine-1-carboxylic acid tert-butyl ester | 349 | 2 |
| | (S)-2-(2-tert-Butylsulfanyl-ethylcarbamoyl)-piperidine-1-carboxylic acid tert-butyl ester | 345 | 2 |
| | (S)-2-(3-Cyclohexyl-isoxazol-5-ylcarbamoyl)-piperidine-1-carboxylic acid tert-butyl ester | 378 | 2 |

TABLE 4-continued

Amide intermediates

| Structure | Name | m/z [M + H+] | Coupling procedure |
|---|---|---|---|
| 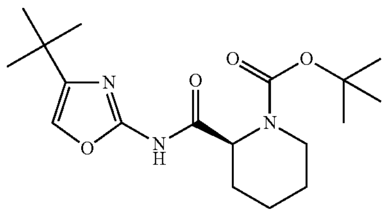 [SMILES: CC(C)(C)OC(=O)N1CCCC[C@H]1C(=O)Nc1nc(C(C)(C)C)co1] | (S)-2-(4-tert-Butyl-oxazol-2-ylcarbamoyl)-piperidine-1-carboxylic acid tert-butyl ester | 352 | 2 |
| 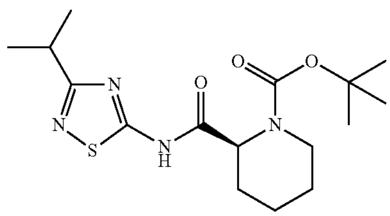 [SMILES: CC(C)c1nsc(NC(=O)[C@@H]2CCCCN2C(=O)OC(C)(C)C)n1] | (S)-2-(3-Isopropyl-1,2,4-thiadiazol-5-ylcarbamoyl)-piperidine-1-carboxylic acid tert-butyl ester | 355 | 2 |
| 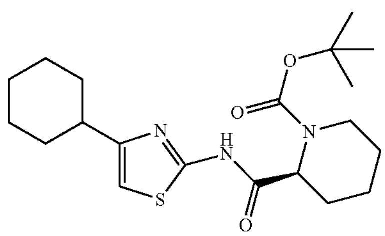 [SMILES: CC(C)(C)OC(=O)N1CCCC[C@H]1C(=O)Nc1nc(C2CCCCC2)cs1] | (S)-2-(4-Cyclohexyl-thiazol-2-ylcarbamoyl)-piperidine-1-carboxylic acid tert-butyl ester | 394 | 2 |
| 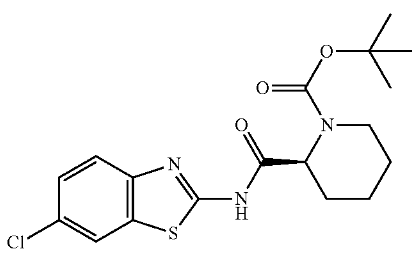 [SMILES: CC(C)(C)OC(=O)N1CCCC[C@H]1C(=O)Nc1nc2ccc(Cl)cc2s1] | (S)-2-(6-Chloro-benzothiazol-2-ylcarbamoyl)-piperidine-1-carboxylic acid tert-butyl ester | 396 | 2 |
| 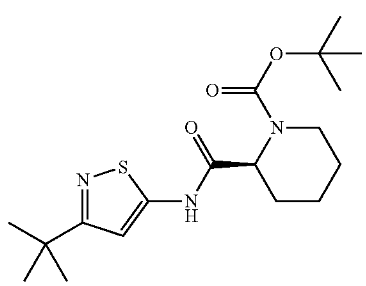 [SMILES: CC(C)(C)OC(=O)N1CCCC[C@H]1C(=O)Nc1cc(C(C)(C)C)ns1] | (S)-2-(3-tert-Butyl-isothiazol-5-ylcarbamoyl)-piperidine-1-carboxylic acid tert-butyl ester | 368 | 2 |
| 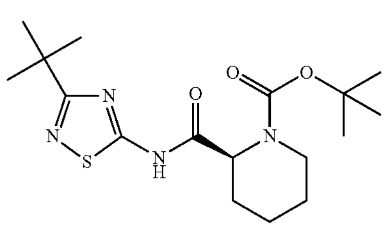 [SMILES: CC(C)(C)OC(=O)N1CCCC[C@H]1C(=O)Nc1nc(C(C)(C)C)ns1] | (S)-2-(3-tert-Butyl-1,2,4-thiadiazol-5-ylcarbamoyl)-piperidine-1-carboxylic acid tert-butyl ester | 369 | 2 |

TABLE 4-continued

| Amide intermediates | | | |
|---|---|---|---|
| Structure | Name | m/z [M + H+] | Coupling procedure |
| | (S)-2-[4-(3,4-Difluoro-phenyl)-thiazol-2-ylcarbamoyl]-piperidine-1-carboxylic acid tert-butyl ester | 424 | 2 |
| | (S)-2-(5-Phenyl-1,2,4-thiadiazol-3-ylcarbamoyl)-piperidine-1-carboxylic acid tert-butyl ester | 389 | 2 |
| | (S)-2-(4-Fluoro-benzothiazol-2-ylcarbamoyl)-piperidine-1-carboxylic acid tert-butyl ester | 380 | 2 |
| | (S)-2-(4-Trifluoromethyl-pyridin-2-ylcarbamoyl)-piperidine-1-carboxylic acid tert-butyl ester | 374 | 2 |
| | (S)-2-(5-Ethyl-4-phenyl-thiazol-2-ylcarbamoyl)-piperidine-1-carboxylic acid tert-butyl ester | 416 | 2 |
| | (S)-2-[3-(4-Methoxy-phenyl)-[1,2,4]thiadiazol-5-ylcarbamoyl]-piperidine-1-carboxylic acid tert-butyl ester | 419 | 4 |

TABLE 4-continued

Amide intermediates

| Structure | Name | m/z [M + H+] | Coupling procedure |
|---|---|---|---|
| 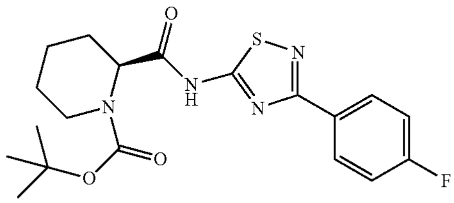 [SMILES: CC(C)(C)OC(=O)N1CCCC[C@H]1C(=O)Nc1nc(-c2ccc(F)cc2)ns1] | (S)-2-[3-(4-Fluoro-phenyl)-[1,2,4]thiadiazol-5-ylcarbamoyl]-piperidine-1-carboxylic acid tert-butyl ester | 407 | 4 |
| 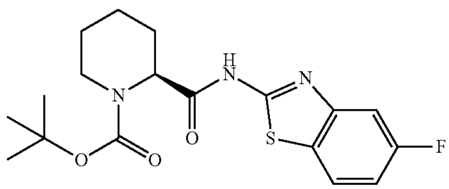 [SMILES: CC(C)(C)OC(=O)N1CCCC[C@H]1C(=O)Nc1nc2cc(F)ccc2s1] | (S)-2-(5-Fluoro-benzothiazol-2-ylcarbamoyl)-piperidine-1-carboxylic acid tert-butyl ester | 380 | 4 |
| 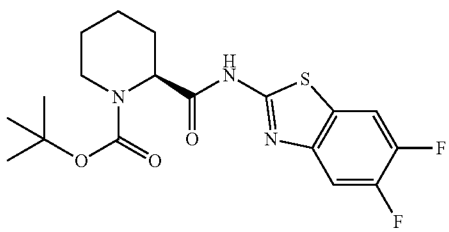 [SMILES: CC(C)(C)OC(=O)N1CCCC[C@H]1C(=O)Nc1nc2cc(F)c(F)cc2s1] | (S)-2-(5,6-Difluoro-benzothiazol-2-ylcarbamoyl)-piperidine-1-carboxylic acid tert-butyl ester | 398 | 4 |
| 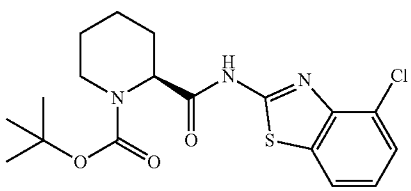 [SMILES: CC(C)(C)OC(=O)N1CCCC[C@H]1C(=O)Nc1nc2c(Cl)cccc2s1] | (S)-2-(4-Chloro-benzothiazol-2-ylcarbamoyl)-piperidine-1-carboxylic acid tert-butyl ester | 396 | 4 |
| 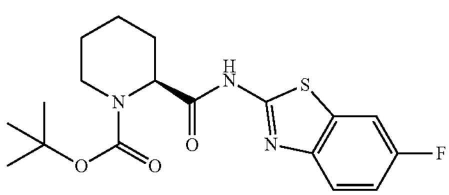 [SMILES: CC(C)(C)OC(=O)N1CCCC[C@H]1C(=O)Nc1nc2ccc(F)cc2s1] | (S)-2-(6-Fluoro-benzothiazol-2-ylcarbamoyl)-piperidine-1-carboxylic acid tert-butyl ester | 380 | 4 |
| 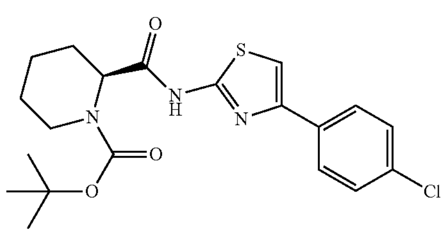 [SMILES: CC(C)(C)OC(=O)N1CCCC[C@H]1C(=O)Nc1nc(-c2ccc(Cl)cc2)cs1] | (S)-2-[4-(4-Chloro-phenyl)-thiazol-2-ylcarbamoyl]-piperidine-1-carboxylic acid tert-butyl ester | 422 | 4 |
| 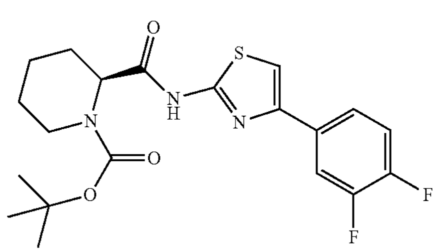 [SMILES: CC(C)(C)OC(=O)N1CCCC[C@H]1C(=O)Nc1nc(-c2ccc(F)c(F)c2)cs1] | (S)-2-[4-(3,4-Difluoro-phenyl)-thiazol-2-ylcarbamoyl]-piperidine-1-carboxylic acid tert-butyl ester | 424 | 4 |

TABLE 4-continued

Amide intermediates

| Structure | Name | m/z [M + H⁺] | Coupling procedure |
|---|---|---|---|
| 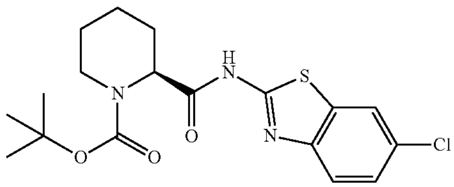 [SMILES: CC(C)(C)OC(=O)N1CCCC[C@H]1C(=O)Nc1nc2ccc(Cl)cc2s1] | (S)-2-(6-Chloro-benzothiazol-2-ylcarbamoyl)-piperidine-1-carboxylic acid tert-butyl ester | 396 | 4 |
| 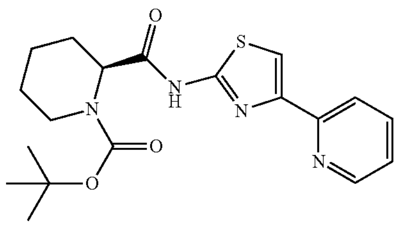 [SMILES: CC(C)(C)OC(=O)N1CCCC[C@H]1C(=O)Nc1nc(-c2ccccn2)cs1] | (S)-2-(4-Pyridin-2-yl-thiazol-2-ylcarbamoyl)-piperidine-1-carboxylic acid tert-butyl ester | 389 | 4 |
| 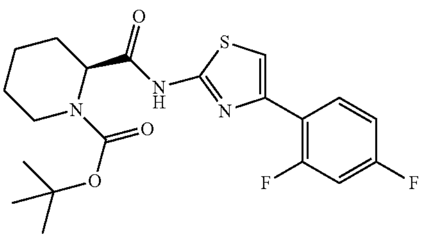 [SMILES: CC(C)(C)OC(=O)N1CCCC[C@H]1C(=O)Nc1nc(-c2ccc(F)cc2F)cs1] | (S)-2-[4-(2,4-Difluoro-phenyl)-thiazol-2-ylcarbamoyl]-piperidine-1-carboxylic acid tert-butyl ester | 424 | 4 |
| 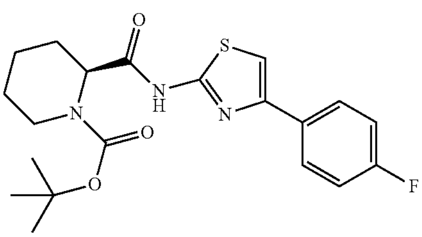 [SMILES: CC(C)(C)OC(=O)N1CCCC[C@H]1C(=O)Nc1nc(-c2ccc(F)cc2)cs1] | (S)-2-[4-(4-Fluoro-phenyl)-thiazol-2-ylcarbamoyl]-piperidine-1-carboxylic acid tert-butyl ester | 406 | 4 |
| 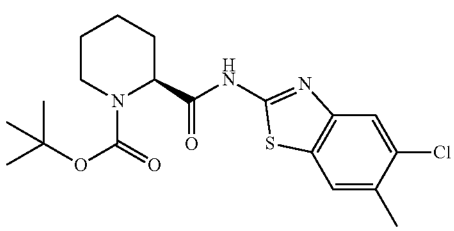 [SMILES: Cc1cc2sc(NC(=O)[C@@H]3CCCCN3C(=O)OC(C)(C)C)nc2cc1Cl] | (S)-2-(5-Chloro-6-methyl-benzothiazol-2-ylcarbamoyl)-piperidine-1-carboxylic acid tert-butyl ester | 410 | 4 |
| 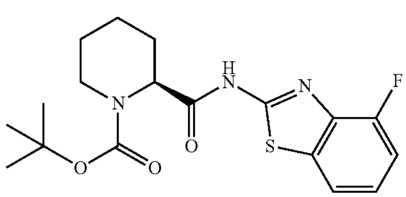 [SMILES: CC(C)(C)OC(=O)N1CCCC[C@H]1C(=O)Nc1nc2c(F)cccc2s1] | (S)-2-(4-Fluoro-benzothiazol-2-ylcarbamoyl)-piperidine-1-carboxylic acid tert-butyl ester | 380 | 4 |
| 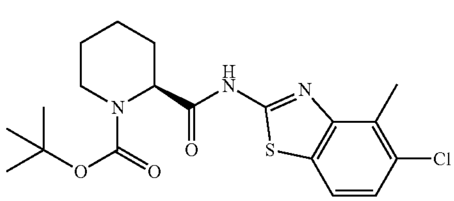 [SMILES: Cc1c(Cl)ccc2sc(NC(=O)[C@@H]3CCCCN3C(=O)OC(C)(C)C)nc12] | (S)-2-(5-Chloro-4-methyl-benzothiazol-2-ylcarbamoyl)-piperidine-1-carboxylic acid tert-butyl ester | 410 | 4 |

Step 2: Synthesis of (S)-Piperidine-2-carboxylic acid (5-tert-butyl-isoxazol-3-yl) amide; hydrochloride 4N HCl in dioxanes (0.675 mL; 2.7 mmol) is added to a solution of (S)-2-(5-tert-Butyl-isoxazol-3-ylcarbamoyl)-piperidine-1-carboxylic acid tert-butyl ester (235 mg; 0.669 mmol) in dichloromethane (5 mL). The reaction mixture is stirred at room temperature for 18 hour. The reaction is concentrated in vacuo to provide the title compound, m/z 252 [M+H$^+$].

Intermediates listed in Table 5 are made in a similar manner.

TABLE 5

| Structure | Name | m/z [M + H$^+$] |
|---|---|---|
| 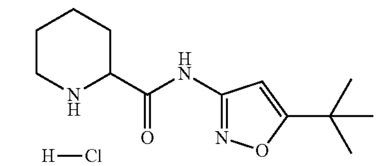 | Piperidine-2-carboxylic acid (5-tert-butyl-isoxazol-3-yl)-amide; hydrochloride | 252 |
| 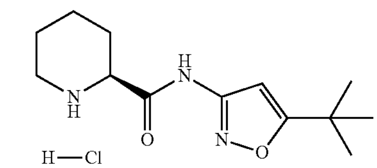 | (S)-Piperidine-2-carboxylic acid (5-tert-butyl-isoxazol-3-yl)-amide; hydrochloride | 252 |
| 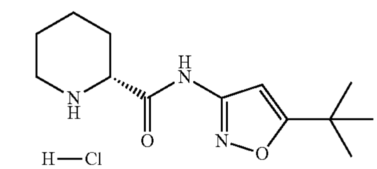 | (R)-Piperidine-2-carboxylic acid (5-tert-butyl-isoxazol-3-yl)-amide; hydrochloride | 252 |
| 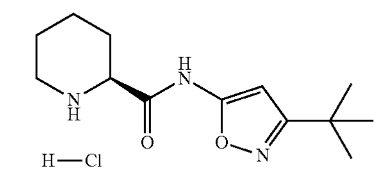 | (S)-Piperidine-2-carboxylic acid (3-tert-butyl-isoxazol-5-yl)-amide; hydrochloride | 252 |
| 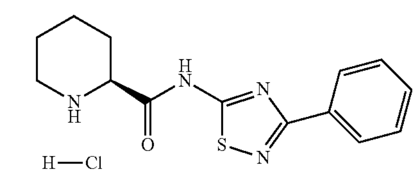 | (S)-Piperidine-2-carboxylic acid (3-phenyl-1,2,4-thiadiazol-5-yl)-amide; hydrochloride | 289 |
| 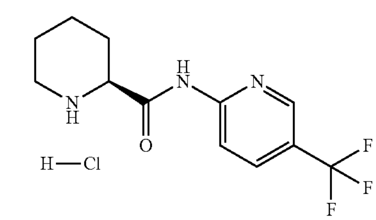 | (S)-Piperidine-2-carboxylic acid (5-trifluoromethyl-pyridin-2-yl)-amide; hydrochloride | 274 |
| 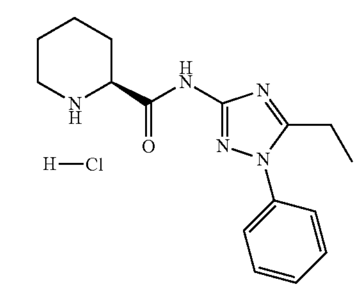 | (S)-Piperidine-2-carboxylic acid (5-ethyl-1-phenyl-1H-1,2,4-triazol-3-yl)-amide; hydrochloride | 300 |

TABLE 5-continued

| Structure | Name | m/z [M + H⁺] |
|---|---|---|
| 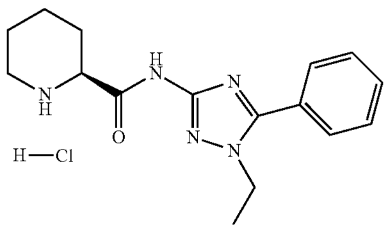 | (S)-Piperidine-2-carboxylic acid (1-ethyl-5-phenyl-1H-1,2,4-triazol-3-yl)-amide; hydrochloride | 300 |
| 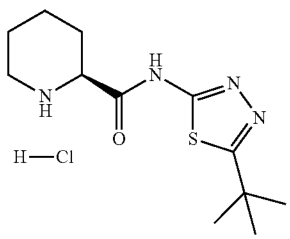 | (S)-Piperidine-2-carboxylic acid (5-tert-butyl-1,3,4-thiadiazol-2-yl)-amide; hydrochloride | 269 |
| 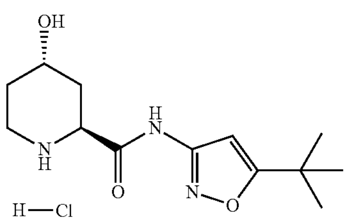 | (2S,4S)-4-Hydroxy-piperidine-2-carboxylic acid (5-tert-butyl-isoxazol-3-yl)-amide; hydrochloride | 268 |
| 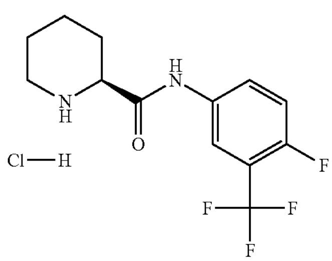 | (S)-Piperidine-2-carboxylic acid (4-fluoro-3-trifluoromethyl-phenyl)-amide; hydrochloride | 291 |
| 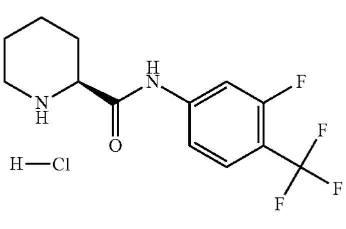 | (S)-Piperidine-2-carboxylic acid (3-fluoro-4-trifluoromethyl-phenyl)-amide; hydrochloride | 291 |
| 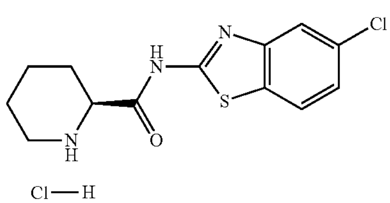 | (S)-Piperidine-2-carboxylic acid (5-chloro-benzothiazol-2-yl)-amide; hydrochloride | 296 |

TABLE 5-continued

| Structure | Name | m/z [M + H+] |
|---|---|---|
| 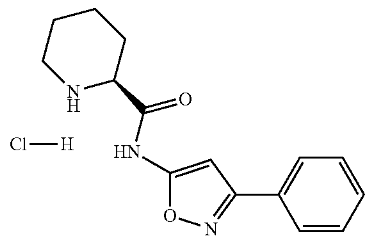 | (S)-Piperidine-2-carboxylic acid (3-phenyl-isoxazol-5-yl)-amide; hydrochloride | 272 |
| 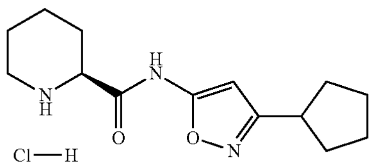 | (S)-Piperidine-2-carboxylic acid (3-cyclopentyl-isoxazol-5-yl)-amide; hydrochloride | 264 |
| 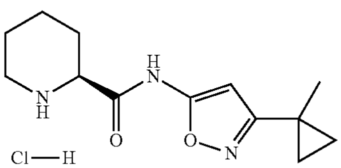 | (S)-Piperidine-2-carboxylic acid [3-(1-methyl-cyclopropyl)-isoxazol-5-yl]-amide; hydrochloride | 250 |
| 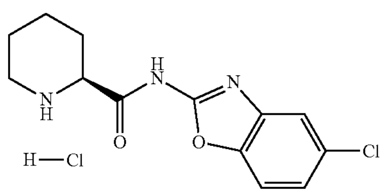 | (S)-Piperidine-2-carboxylic acid (5-chloro-benzoxazol-2-yl)-amide; hydrochloride | 280 |
| 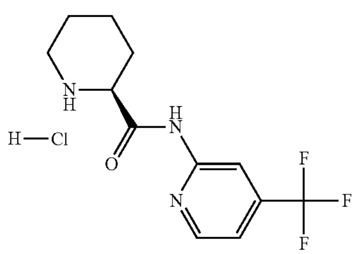 | (S)-Piperidine-2-carboxylic acid (4-trifluoromethyl-pyridin-2-yl)-amide; hydrochloride | 274 |
| 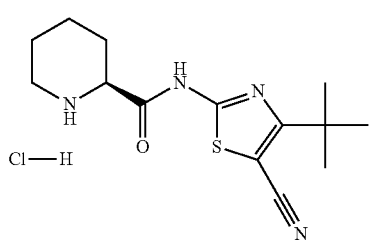 | (S)-Piperidine-2-carboxylic acid (4-tert-butyl-5-cyano-thiazol-2-yl)-amide; hydrochloride | 293 |
| 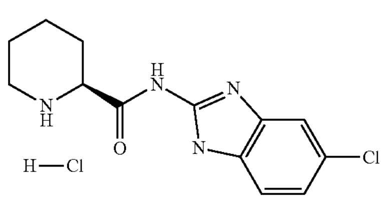 | (S)-Piperidine-2-carboxylic acid (5-chloro-1H-benzimidazol-2-yl)-amide; hydrochloride | 279 |

TABLE 5-continued

| Structure | Name | m/z [M + H⁺] |
|---|---|---|
| 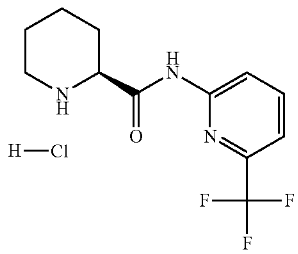 | (S)-Piperidine-2-carboxylic acid (6-trifluoromethyl-pyridin-2-yl)-amide; hydrochloride | 274 |
| 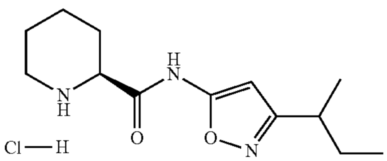 | (S)-Piperidine-2-carboxylic acid (3-sec-butyl-isoxazol-5-yl)-amide; hydrochloride | 252 |
| 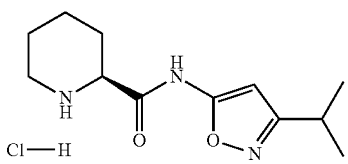 | (S)-Piperidine-2-carboxylic acid (3-isopropyl-isoxazol-5-yl)-amide; hydrochloride | 238 |
| 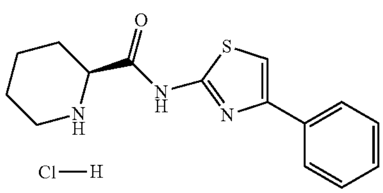 | (S)-Piperidine-2-carboxylic acid (4-phenyl-thiazol-2-yl)-amide; hydrochloride | 288 |
| 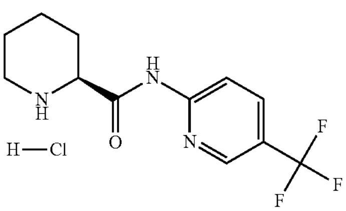 | (S)-Piperidine-2-carboxylic acid (5-trifluoromethyl-pyridin-2-yl)-amide; hydrochloride | 274 |
| 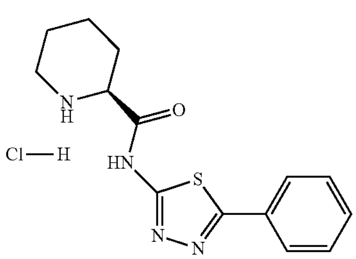 | (S)-Piperidine-2-carboxylic acid (5-phenyl-1,3,4-thiadiazol-2-yl)-amide; hydrochloride | 289 |
| 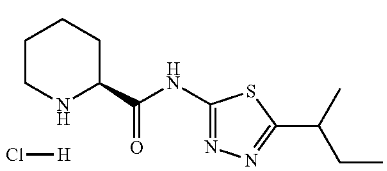 | (S)-Piperidine-2-carboxylic acid (5-sec-butyl-1,3,4-thiadiazol-2-yl)-amide; hydrochloride | 269 |

TABLE 5-continued

| Structure | Name | m/z [M + H⁺] |
|---|---|---|
| 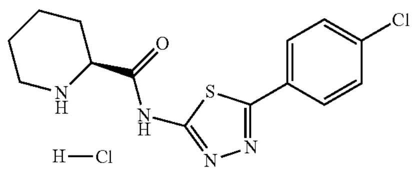 | (S)-Piperidine-2-carboxylic acid [5-(4-chloro-phenyl)-1,3,4-thiadiazol-2-yl]-amide; hydrochloride | 323 |
| 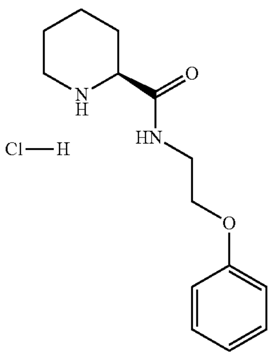 | (S)-Piperidine-2-carboxylic acid (2-phenoxy-ethyl)-amide; hydrochloride | 249 |
| 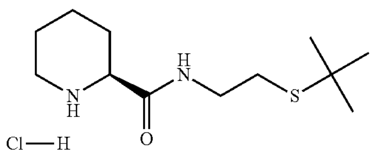 | (S)-Piperidine-2-carboxylic acid (2-tert-butylsulfanyl-ethyl)-amide; hydrochloride | 245 |
| 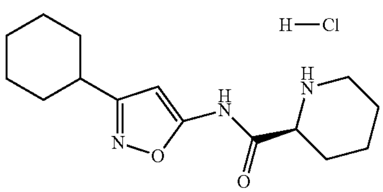 | (S)-Piperidine-2-carboxylic acid (3-cyclohexyl-isoxazol-5-yl)-amide; hydrochloride | 278 |
| 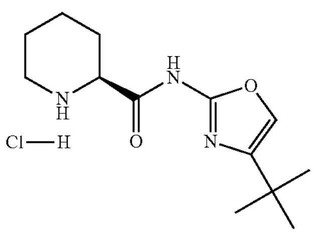 | (S)-Piperidine-2-carboxylic acid (4-tert-butyl-oxazol-2-yl)-amide; hydrochloride | 252 |
| 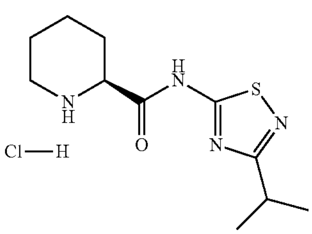 | (S)-Piperidine-2-carboxylic acid (3-isopropyl-1,2,4-thiadiazol-5-yl)-amide; hydrochloride | 255 |
| 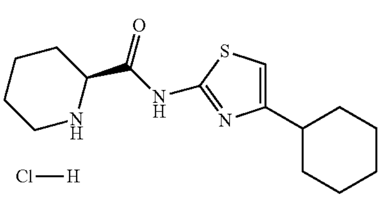 | (S)-Piperidine-2-carboxylic acid (4-cyclohexyl-thiazol-2-yl)-amide; hydrochloride | 294 |

TABLE 5-continued

| Structure | Name | m/z [M + H⁺] |
|---|---|---|
| 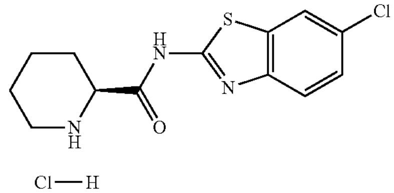 | (S)-Piperidine-2-carboxylic acid (6-chloro-benzothiazol-2-yl)-amide; hydrochloride | 296 |
| 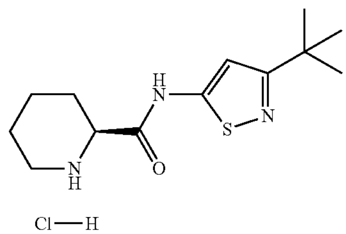 | (S)-Piperidine-2-carboxylic acid (3-tert-butyl-isothiazol-5-yl)-amide; hydrochloride | 268 |
| 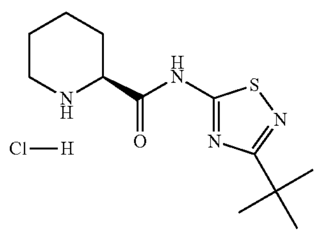 | (S)-Piperidine-2-carboxylic acid (3-tert-butyl-1,2,4-thiadiazol-5-yl)-amide; hydrochloride | 269 |
| 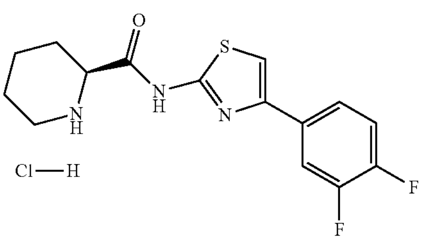 | (S)-Piperidine-2-carboxylic acid [4-(3,4-difluoro-phenyl)-thiazol-2-yl]-amide; hydrochloride | 324 |
| 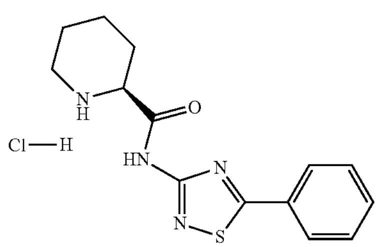 | (S)-Piperidine-2-carboxylic acid (5-phenyl-1,2,4-thiadiazol-3-yl)-amide; hydrochloride | 289 |
| 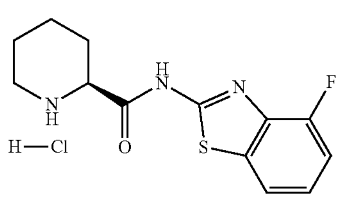 | (S)-Piperidine-2-carboxylic acid (4-fluoro-benzothiazol-2-yl)-amide; hydrochloride | 280 |
| 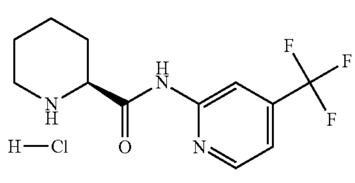 | (S)-Piperidine-2-carboxylic acid (4-trifluoromethyl-pyridin-2-yl)-amide; hydrochloride | 274 |

TABLE 5-continued

| Structure | Name | m/z [M + H⁺] |
|---|---|---|
| 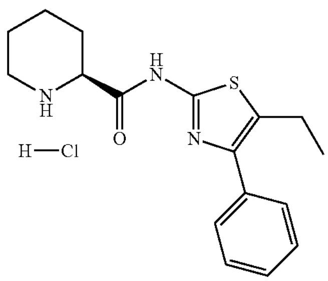 | (S)-Piperidine-2-carboxylic acid (5-ethyl-4-phenyl-thiazol-2-yl)-amide; hydrochloride | 316 |
| 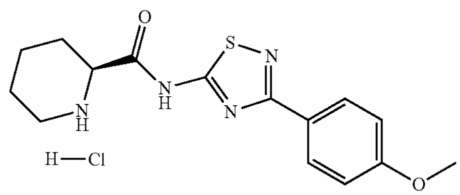 | (S)-Piperidine-2-carboxylic acid [3-(4-methoxy-phenyl)-[1,2,4]thiadiazol-5-yl]-amide; hydrochloride | not obtained |
| 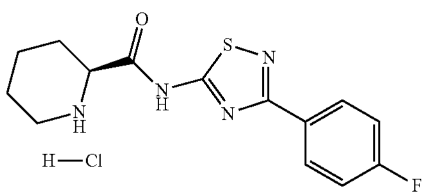 | (S)-Piperidine-2-carboxylic acid [3-(4-fluoro-phenyl)-[1,2,4]thiadiazol-5-yl]-amide; hydrochloride | not obtained |
| 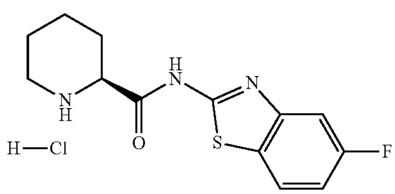 | (S)-Piperidine-2-carboxylic acid (5-fluoro-benzothiazol-2-yl)-amide; hydrochloride | not obtained |
| 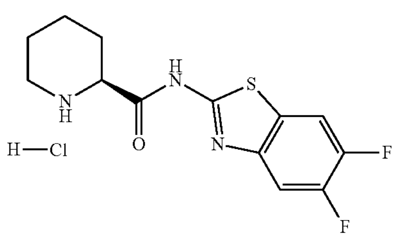 | (S)-Piperidine-2-carboxylic acid (5,6-difluoro-benzothiazol-2-yl)-amide; hydrochloride | not obtained |
| 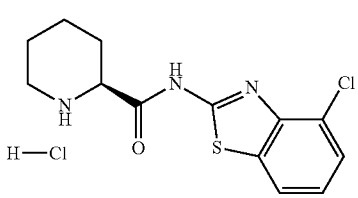 | (S)-Piperidine-2-carboxylic acid (4-chloro-benzothiazol-2-yl)-amide; hydrochloride | not obtained |
| 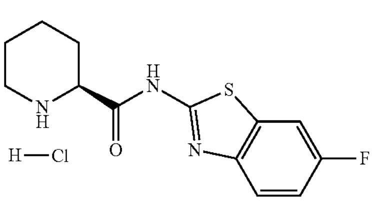 | (S)-Piperidine-2-carboxylic acid (6-fluoro-benzothiazol-2-yl)-amide; hydrochloride | not obtained |

TABLE 5-continued

| Structure | Name | m/z [M + H⁺] |
|---|---|---|
| 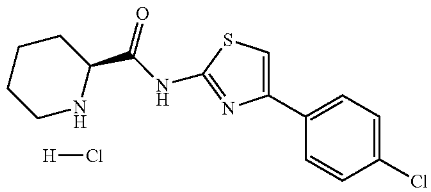 | (S)-Piperidine-2-carboxylic acid [4-(4-chloro-phenyl)-thiazol-2-yl]-amide; hydrochloride | not obtained |
| 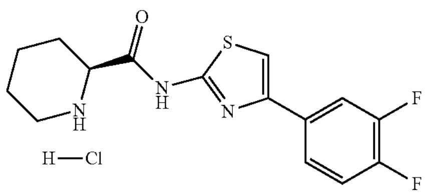 | (S)-Piperidine-2-carboxylic acid [4-(3,4-difluoro-phenyl)-thiazol-2-yl]-amide; hydrochloride | not obtained |
| 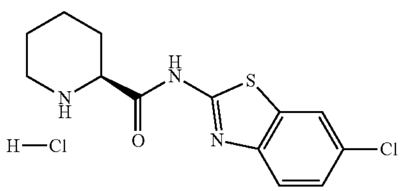 | (S)-Piperidine-2-carboxylic acid (6-chloro-benzothiazol-2-yl)-amide; hydrochloride | not obtained |
| 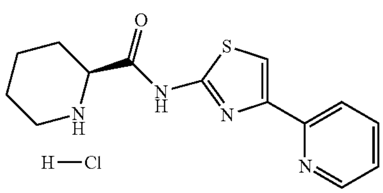 | (S)-Piperidine-2-carboxylic acid (4-pyridin-2-yl-thiazol-2-yl)-amide; hydrochloride | not obtained |
| 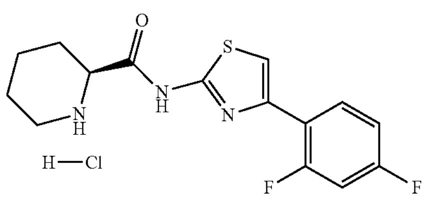 | (S)-Piperidine-2-carboxylic acid [4-(2,4-difluoro-phenyl)-thiazol-2-yl]-amide; hydrochloride | not obtained |
| 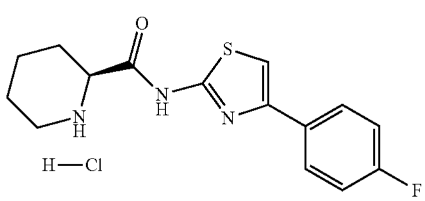 | (S)-Piperidine-2-carboxylic acid [4-(4-fluoro-phenyl)-thiazol-2-yl]-amide; hydrochloride | not obtained |
| 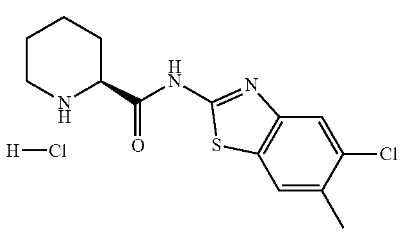 | (S)-Piperidine-2-carboxylic acid (5-chloro-6-methyl-benzothiazol-2-yl)-amide; hydrochloride | not obtained |

TABLE 5-continued

| Structure | Name | m/z [M + H⁺] |
|---|---|---|
| 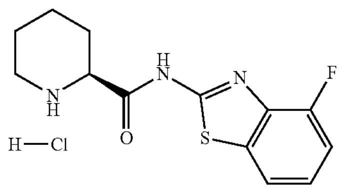 | (S)-Piperidine-2-carboxylic acid (4-fluoro-benzothiazol-2-yl)-amide; hydrochloride | not obtained |
| 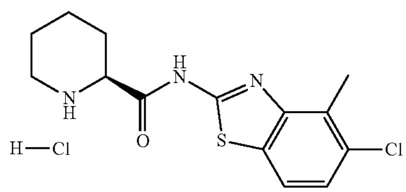 | (S)-Piperidine-2-carboxylic acid (5-chloro-4-methyl-benzothiazol-2-yl)-amide; hydrochloride | not obtained |

Step 3: Two amide coupling procedures can be used.

Amide coupling procedure 1: Synthesis of (S)-1-(4,4-Difluoro-cyclohexanecarbonyl)-piperidine-2-carboxylic acid (5-tert-butyl-isoxazol-3-yl)-amide (Example 18)

To a solution of 4,4-difluorocyclohexanecarboxylic acid (118.2 mg; 0.72 mmol) and 1-hydroxybenzotriazole hydrate (97.3 mg; 0.72 mmol) in DMF (2 mL) is added 1-(3-dimethylaminopropyl)-3-ethylcarbodiimide hydrochloride (138 mg; 0.72 mmol). After 15 minutes of stirring, (S)-Piperidine-2-carboxylic acid (5-tert-butyl-isoxazol-3-yl) amide; hydrochloride (190 mg; 0.66 mmol) is added, followed by triethylamine (0.093 mL; 0.67 mmol) and 4-dimethylaminopyridine (4 mg; 0.033 mmol). The reaction mixture is stirred at room temperature for 18 hours. The reaction mixture is quenched with water and the crude product is collected by filtration. Purification by flash chromatography on silica gel using methanol/methylene chloride provides the title compound, m/z 398 [M+H⁺].

Compounds in Table 7 Method F1 are prepared in a similar manner.

Amide coupling procedure 2: Synthesis of 1-(4-Trifluoromethyl-benzoyl)-piperidine-2-carboxylic acid (5-tert-butyl-isoxazol-3-yl)-amide (Example 17)

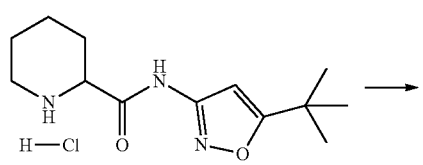

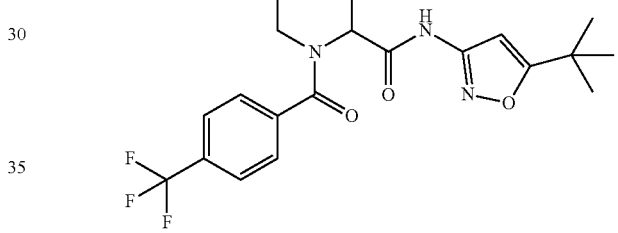

-continued

To a solution of piperidine-2-carboxylic acid (5-tert-butyl-isoxazol-3-yl) amide; hydrochloride (100 mg; 0.347 mmol) and 4-(trifluoromethyl)benzoic acid (66 mg; 0.347 mmol) in pyridine (1 mL) at 0° C. is added phosphorous oxychloride (0.032 mL; 0.347 mmol) and the reaction mixture is left stirring at room temperature for 3 hours. After this time, the reaction mixture is quenched with saturated NH4Cl aqueous solution and extracted with ethyl acetate 3 times. The combined organics are washed with brine, dried over Na2SO4, filtered and concentrated in vacuo. Purification by flash chromatography on silica gel using methanol/methylene chloride provides the title compound, m/z 424 [M+H⁺].

Compounds in Table 7 Method F2 are prepared in a similar manner.

Amide coupling procedure 3: Synthesis of (S)-1-(2,2,2-Trifluoro-acetyl)-piperidine-2-carboxylic acid (5-tert-butyl-isoxazol-3-yl)-amide (Example 137)

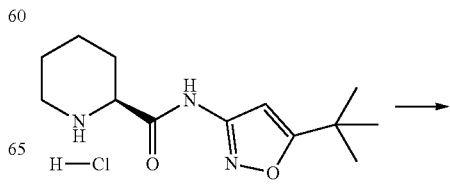

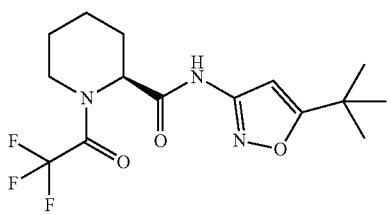

To a solution of (S)-Piperidine-2-carboxylic acid (5-tert-butyl-isoxazol-3-yl) amide; hydrochloride (126 mg; 0.438 mmol) in DMF (2 mL) is added N,N-diisopropylethylamine (0.153 mL; 0.876 mmol), followed by trifluoroacetic anhydride (0.061 mL; 0.438 mmol). The reaction mixture is stirred at room temperature for 48 hours. The mixture is diluted with ethyl acetate and washed with water twice then brine, dried over Na2SO4, filtered and concentrated in vacuo. Purification by flash chromatography on silica gel using ethyl acetate/Hexanes provides the title compound, m/z 348 [M+H$^+$].

Compounds in Table 7 Method F3 are prepared in a similar manner.

Amide coupling procedure 4: Synthesis of Synthesis of (S)-1-(1,1-Dioxo-1λ$^6$-thiomorpholine-4-carbonyl)-piperidine-2-carboxylic acid (4-chloro-benzothiazol-2-yl)-amide (Example 158)

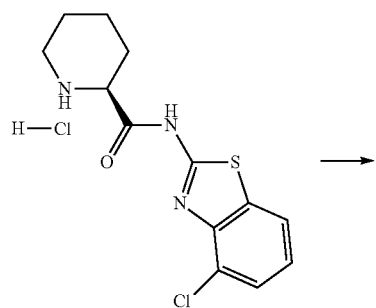

To the thiomorpholine dioxide carbonyl chloride (75 mg, 0.38 mmol) is added the amine (83 mg, 0.25 mmol) and N-methyl morpholine (139 μL, 1.27 mmol) in dichloromethane (1 mL). The reaction is shaken at room temperature for 16 hours then concentrated under reduced pressure. Purification by preparative HPLC provides the desired final compound (19 mg, 0.04 mmol, 17% yield).

Compounds in Table 7 Method F4 are prepared in a similar manner

Method G:

Synthesis of (S)-1-(1,1-Dioxo-1λ6-thiomorpholine-4-carbonyl)-piperidine-2-carboxylic acid (5-tert-butyl-isoxazol-3-yl)-amide (Example 22)

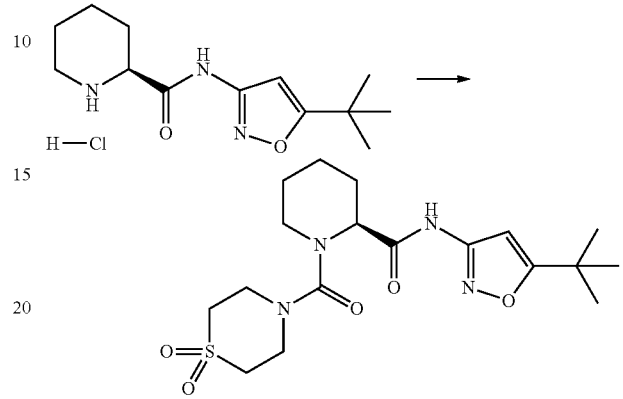

To a suspension of (S)-Piperidine-2-carboxylic acid (5-tert-butyl-isoxazol-3-yl) amide hydrochloride (150 mg; 0.521 mmol) in THF (6 mL) is added 1,1-Dioxo-1λ$^6$-thiomorpholine-4-carbonyl chloride (102.97 mg; 0.521 mmol) and N,N-diisopropylethylamine (0.186 mL; 1.07 mmol). The reaction mixture is stirred at room temperature for 4 hours. The reaction mixture is quenched with water and extracted with methylene chloride twice. The combined organics were washed with brine, dried over Na2SO4, filtered and concentrated in vacuo. Purification by flash chromatography on silica gel using methanol/methylene chloride provides the title compound, m/z 413 [M+H$^+$].

Compounds found in Table 7 Method G are prepared in a similar manner.

Synthesis of (S)-1(1-Oxo-1λ6-thiomorpholine-4-carbonyl)-piperidine-2-carboxylic acid (5-tert-butyl-isoxazol-3-yl)-amide (Example 81)

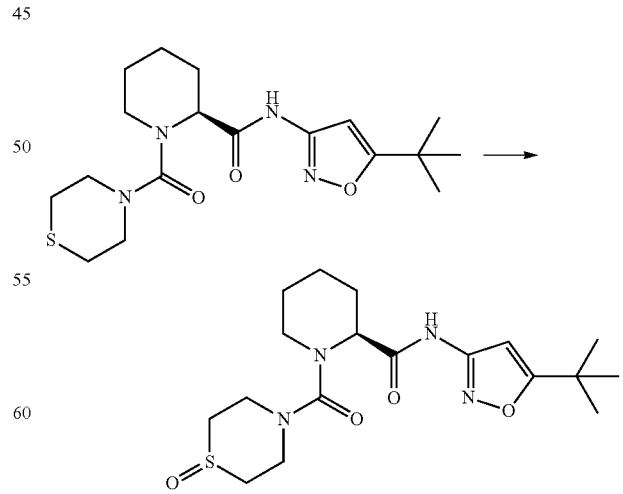

To a solution of (S)-1-(Thiomorpholine-4-carbonyl)-piperidine-2-carboxylic acid (5-tert-butyl-isoxazol-3-yl)-amide (150 mg; 0.394 mmol) in 50% methylene chloride in methanol (4 mL) is added oxone (122.8 mg; 0.2 mmol) and water (0.1 mL). The reaction mixture is stirred at room temperature for 2 hours. The reaction is quenched with water and extracted with dichloromethane 3 times. The organics are combined and dried over Na2SO4, filtered and concentrated in vacuo. Purification by flash chromatography on silica gel using methanol/methylene chloride provides the title compound, m/z 397 [M+H⁺].

Method H:

Synthesis of (S)-3'-Chloro-5'-trifluoromethyl-3,4,5,6-tetrahydro-2H-1,2'-bipyridinyl-2-carboxylic acid (3-phenyl-1,2,4-thiadiazol-5-yl)-amide (Example 25)

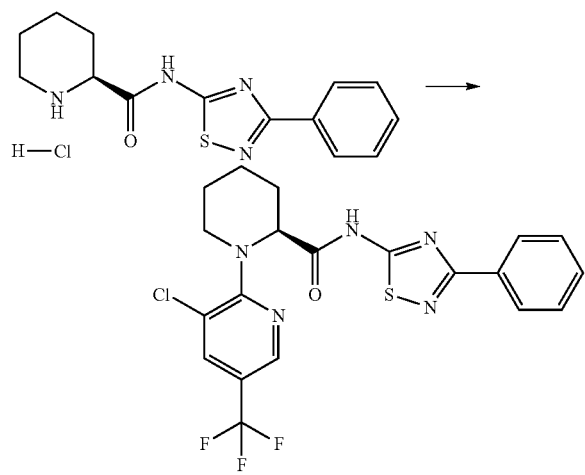

To a stirred solution of (S)-Piperidine-2-carboxylic acid (3-phenyl-1,2,4-thiadiazol-5-yl)-amide; hydrochloride (70 mg; 0.215 mmol) and N,N-diisopropylethylamine (0.037 mL; 0.215 mmol) in DMSO (1 mL) is added 3-chloro-2-fluoro-5-trifluoromethylpyridine (42.9 mg; 0.215 mmol). The reaction mixture is heated at 100° C. for 4 hours. Purification by flash chromatography on silica gel using methanol/methylene chloride provides the title compound, m/z 468 [M+H⁺].

Compounds in Table 7 Method H are prepared in a similar manner.

Method I:

Synthesis of (S)-1-(4-Chloro-phenyl)-piperidine-2-carboxylic acid (5-tert-butyl-isoxazol-3-yl)-amide (Example 92)

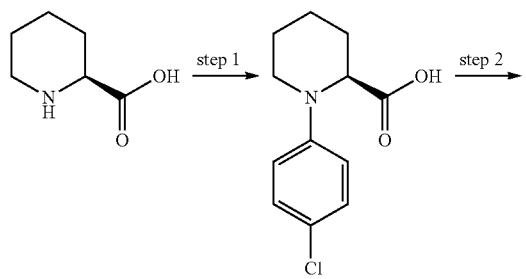

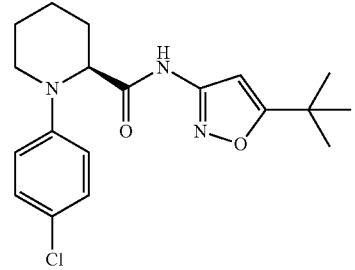

Step 1: Synthesis of (S)-1-(4-Chloro-phenyl)-piperidine-2-carboxylic acid

A reaction vessel containing L-(S)-pipecolic acid (200 mg; 1.549 mmol), 4-bromochlorobenzene (296.56 mg; 1.549 mmol), potassium carbonate (324.79 mg; 2.35 mmol) and copper iodide (29.5 mg; 0.155 mmol) is evacuated and purged with Argon several times. Dimethylacetamide (3 mL) is added and the mixture is heated at 100° C. for 3 days in a sealed vessel. After this time, the mixture is cooled to room temperature and diluted with ethyl acetate and water. The two layers are separated and the aqueous later is acidified to PH~1 by adding 1N HCl aqueous solution and extracted with ethyl acetate twice. The organics are combined and dried over Na2SO4, filtered and concentrated. Purification by flash chromatography on silica gel using ethyl acetate/Hexanes provides the title compound, m/z 240 [M+H⁺].

Step 2: Synthesis of (S)-1-(4-Chloro-phenyl)-piperidine-2-carboxylic acid (5-tert-butyl-isoxazol-3-yl)-amide Amide bond coupling method described in Example 1 coupling method A is used to synthesize the title compound, m/z 362 [M+H⁺].

Method J:

Three different reductive amination procedures can be used

Reductive amination procedure 1: Synthesis of (S)-1-(Tetrahydro-pyran-4-ylmethyl)-piperidine-2-carboxylic acid (5-tert-butyl-isoxazol-3-yl)-amide (Example 100)

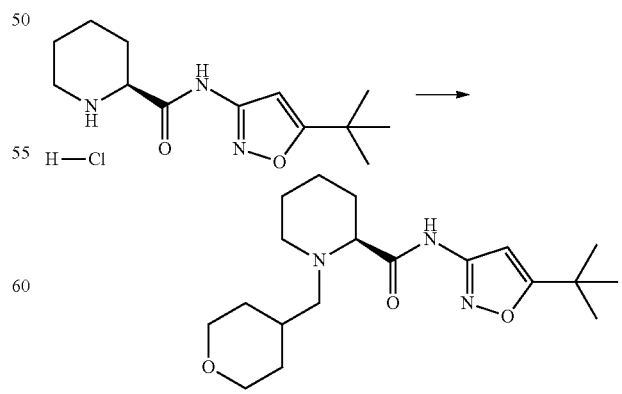

To a solution of (S)-Piperidine-2-carboxylic acid (5-tert-butyl-isoxazol-3-yl) amide; hydrochloride (110 mg; 0.382 mmol) in DMF (1.5 mL) is added tetrahydro-pyran-4-carbaldehyde (87.2 mg; 0.764 mmol), acetic acid (0.022 mL; 0.382 mmol) and sodium sulfate (5-10 equivalents). The mixture is stirred at room temperature for 30 minutes before adding sodium cyanoborohydride (24 mg; 0.382 mmol). The mixture is stirred at room temperature for 18 hours. The mixture is diluted with dichloromethane and washed with saturated NaHCO3 aqueous solution. The organic layer is dried over Na2SO4, filtered and concentrated in vacuo. Crude product is purified by preparative HPLC. Product fractions are pooled and concentrated in vacuo to afford the title compound, m/z 350 [M+H$^+$].

Compounds in Table 7 Method J1 are prepared in a similar manner.

Reductive amination procedure 2: Synthesis of (S)-1-Cyclopropyl-piperidine-2-carboxylic acid (5-tert-butyl-1,3,4-thiadiazol-2-yl)-amide (Example 142)

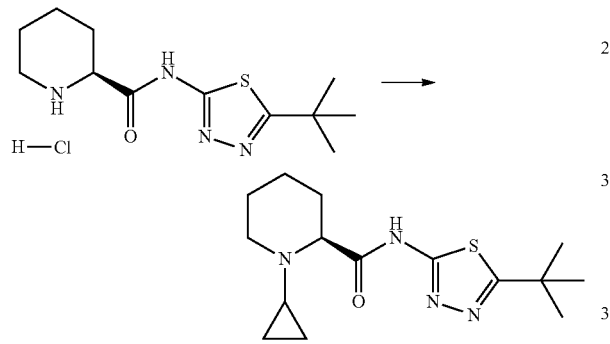

To a solution of (S)-Piperidine-2-carboxylic acid (5-tert-butyl-1,3,4-thiadiazol-2-yl)-amide; hydrochloride (125 mg; 0.41 mmol) in methanol (3 mL) is added acetic acid (0.235 mL; 4.1 mmol), [(1-ethoxycyclopropyl)oxy]trimethylsilane (0.48 mL; 2.4 mmol) and sodium cyanoborohydride (116.25 mg; 1.85 mmol). The reaction mixture is heated at reflux for 5 hours. After cooling, the mixture is diluted with ethyl acetate and washed with saturated NaHCO3 aqueous solution then brine, dried over Na2SO4, filtered and concentrated in vacuo. Purification by preparative HPLC affords the title compound, m/z 309 [M+H$^+$].

Compounds in Table 7 Method J2 are prepared in a similar manner.

Reductive amination procedure 3: Synthesis of (S)-1-(Tetrahydro-pyran-4-ylmethyl)-piperidine-2-carboxylic acid (3-tert-butyl-isothiazol-5-yl)-amide (Example 68)

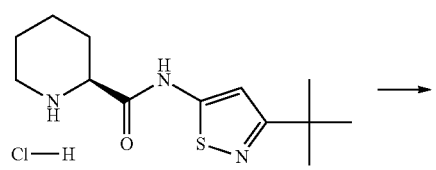

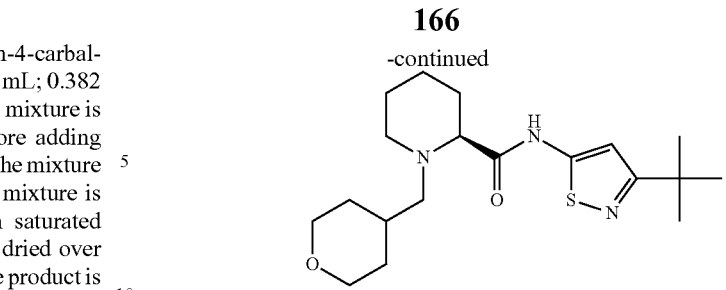

To a solution of (S)-Piperidine-2-carboxylic acid (3-tert-butyl-isothiazol-5-yl)-amide; hydrochloride (40.4 mg; 0.11 mmol) in DMF (1 mL) is added acetic acid (0.05 mL; 0.87 mmol) and a solution of tetrahydropyranyl-4-carboxaldehyde (37.7 mg; 0.33 mmol) in DMF (1 mL). The reaction is shaken for 4 hours. To the mixture is added a solution of sodium triacetoxyborohydride (93.2 mg; 0.44 mmol) in DMF (0.4 mL). The reaction mixture is shaken for 16 hours at room temperature. After this time, the reaction is quenched with water (0.1 mL) and the mixture is concentrated in vacuo. Purification by preparative HPLC provides the title compound, m/z 366 [M+H$^+$].

Compounds in Table 7 Method J3 are prepared in a similar manner.

Method K:

Synthesis of (S)-1-(4-Acetyl-piperazine-1-carbonyl)-piperidine-2-carboxylic acid (5-tert-butyl-isoxazol-3-yl)-amide (Example 85)

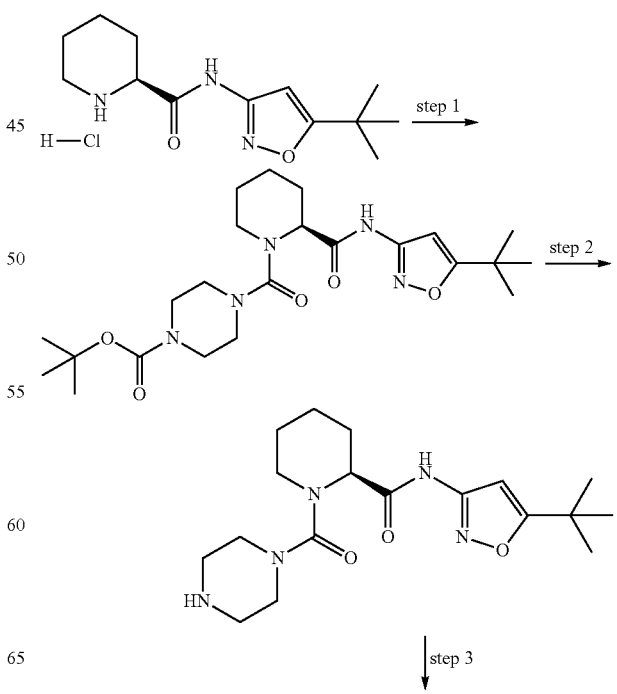

-continued

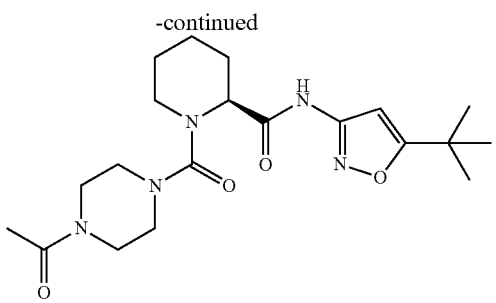

Step 1: Synthesis 4-[(S)-2-(5-tert-Butyl-isoxazol-3-ylcarbamoyl)-piperidine-1-carbonyl]-piperazine-1-carboxylic acid tert-butyl ester To a solution of (S)-Piperidine-2-carboxylic acid (5-tert-butyl-isoxazol-3-yl) amide; hydrochloride (675 mg; 2.345 mmol) in THF (18 mL) is added N,N-diisopropylethylamine (0.81 mL; 4.65 mmol) and 4-chlorocarbonyl-piperazine-1-carboxylic acid tert-butyl ester (609 mg; 2.45 mmol). The reaction mixture is left stirring at room temperature for 18 hours. After this time, the reaction mixture is diluted with ethyl acetate and washed with water then brine, dried over Na2SO4, filtered and concentrated in vacuo. Purification by flash chromatography on silica gel using ethyl acetate/Hexanes provides the title compound, m/z 464 [M+H$^+$].

Step 2: Synthesis of (S)-1-(piperazine-1-carbonyl)-piperidine-2-carboxylic acid (5-tert-butyl-isoxazol-3-yl)-amide To a solution of 4-[(S)-2-(5-tert-Butyl-isoxazol-3-ylcarbamoyl)-piperidine-1-carbonyl]-piperazine-1-carboxylic acid tert-butyl ester (655 mg; 1.413 mmol) in dichloromethane (100 mL) is added 4N hydrochloric acid in dioxane (1.25 mL; 5 mmol) and the reaction mixture is stirred at room temperature for 3 hours. More 4N hydrochloric acid in dioxane (1.25 mL; 5 mmol) is added and the stirring is continued for another 3 hours. After this time, the reaction mixture is concentrated to afford the product. The product is taken up in the mixture of ethyl acetate and saturated NaHCO3 aqueous solution to free base the product. The aqueous layer is extracted with ethyl acetate twice. The combined organics are washed with brine, dried over Na2SO4, filtered and concentrated to afford the title compound, m/z 364 [M+H$^+$].

Step 3: Synthesis of (S)-1-(4-Acetyl-piperazine-1-carbonyl)-piperidine-2-carboxylic acid (5-tert-butyl-isoxazol-3-yl)-amide (Example 85)

To a solution of (S)-Piperidine-2-carboxylic acid (5-tert-butyl-isoxazol-3-yl) amide (60 mg; 0.165 mmol) in THF (1 mL) is added acetic anhydride (0.016 mL; 0.17 mmol), followed by N,N-diisopropylethylamine (0.03 mL; 0.17 mmol) and 4-dimethylaminopyridine (4 mg; 0.033 mmol). The reaction mixture is stirred at room temperature for 18 hours. The mixture is diluted with ethyl acetate and water. The layers are separated and the organic layer is concentrated in vacuo. Purification by flash chromatography on silica gel using ethyl acetate/Hexanes provides the title compound, m/z 406 [M+H$^+$].

Synthesis of (S)-1-(4-Methanesulfonyl-piperazine-1-carbonyl)-piperidine-2-carboxylic acid (5-tert-butyl-isoxazol-3-yl)-amide (Example 84)

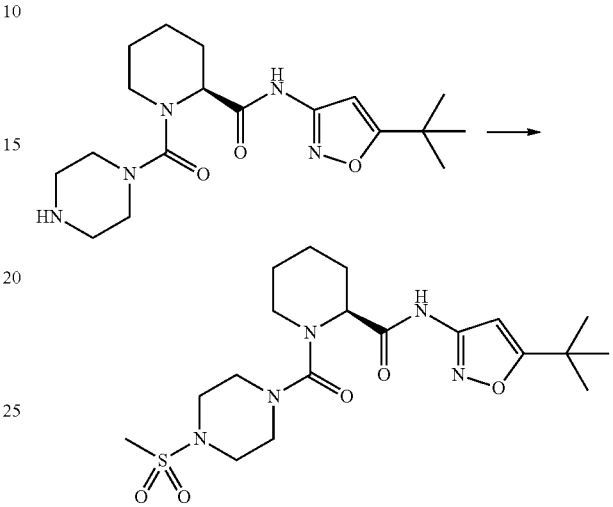

To a solution of (S)-1-(piperazine-1-carbonyl)-piperidine-2-carboxylic acid (5-tert-butyl-isoxazol-3-yl)-amide (60 mg; 0.165 mmol) in THF (1 mL) is added methane sulfonyl chloride (0.013 mL; 0.17 mmol), followed by N,N-diisopropylethylamine (0.03 mL; 0.17 mmol). The mixture is stirred at room temperature for 18 hours. The mixture is diluted with ethyl acetate and water. The layers are separated and the organic layer is concentrated in vacuo. Purification by flash chromatography on silica gel using ethyl acetate/Hexanes provides the title compound, m/z 442 [M+H$^+$].

Synthesis of (S)-1-(4-Propionyl-piperazine-1-carbonyl)-piperidine-2-carboxylic acid (5-tert-butyl-isoxazol-3-yl)-amide (Example 86)

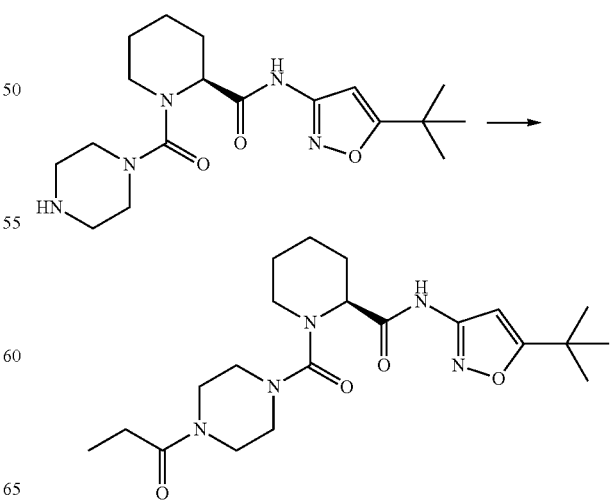

To a solution of (S)-1-(piperazine-1-carbonyl)-piperidine-2-carboxylic acid (5-tert-butyl-isoxazol-3-yl)-amide (60 mg; 0.165 mmol) in THF (1 mL) is added propionyl chloride (0.015 mL; 0.17 mmol), followed by N,N-diisopropylethylamine (0.03 mL; 0.17 mmol). The mixture is stirred at room temperature for 18 hours. The mixture is diluted with ethyl acetate and water. The layers are separated and the organic layer is concentrated in vacuo. Purification by flash chromatography on silica gel using ethyl acetate/Hexanes provides the title compound, m/z 420 [M+H$^+$].

Compounds in Table 7 Method K are prepared in a similar manner.

Method L:

Synthesis of (S)-1-(2-Pyrrolidin-1-yl-acetyl)-piperidine-2-carboxylic acid (5-tert-butyl-isoxazol-3-yl)-amide (Example 93)

Step 1: Synthesis of (S)-1-(2-Chloro-acetyl)-piperidine-2-carboxylic acid (5-tert-butyl-isoxazol-3-yl)-amide To a solution of (S)-Piperidine-2-carboxylic acid (5-tert-butyl-isoxazol-3-yl) amide; hydrochloride (611 mg; 2.123 mmol) in THF (15 mL) is added N,N-diisopropylethylamine (0.74 mL; 4.246 mmol), followed by alpha-chloroacetyl chloride (0.17 mL; 2.134 mmol). The reaction mixture is stirred at room temperature for 18 hours.

The reaction mixture is diluted with ethyl acetate and washed with water then brine, dried over Na2SO4, filtered and concentrated in vacuo. Purification by flash chromatography on silica gel using ethyl acetate/Hexanes provides the title compound, m/z 328 [M+H$^+$].

Step 2: Synthesis of (S)-1-(2-Pyrrolidin-1-yl-acetyl)-piperidine-2-carboxylic acid (5-tert-butyl-isoxazol-3-yl)-amide A mixture of pyrrolidine (33.43 mg; 0.47 mmol) and 4-dimethylaminopyridine (2 mg; 0.016 mmol) in DMF (1 mL) is added to (S)-1-(2-Chloro-acetyl)-piperidine-2-carboxylic acid (5-tert-butyl-isoxazol-3-yl)-amide (77 mg; 0.235 mmol). The reaction mixture is heated at 60° C. for 18 hours. Purification by preparative HPLC provides the title compound, m/z 363 [M+H$^+$].

Compounds in Table 7 Method L are prepared in a similar manner.

Method M:

Synthesis of (S)-1-(1,1-Dioxo-1λ6-thiomorpholine-4-carbonyl)-piperidine-2-carboxylic acid (5-ethyl-4-phenyl-thiazol-2-yl)-amide (Example 113)

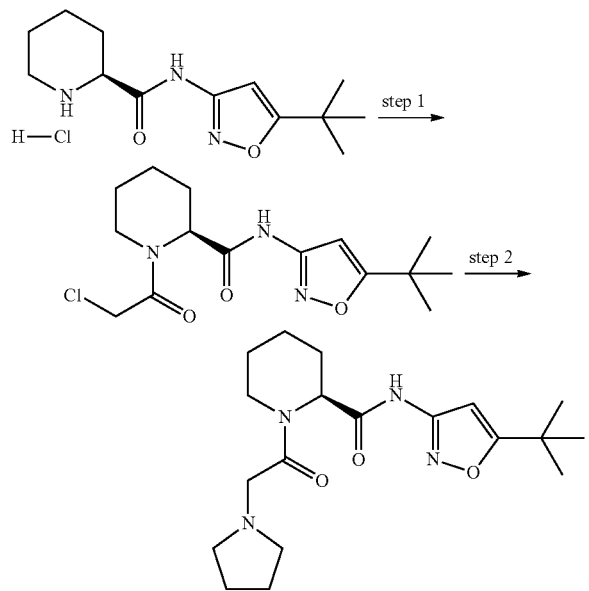

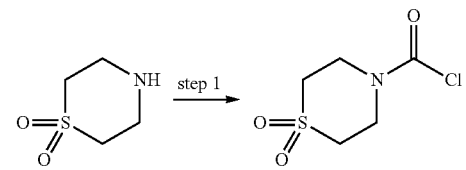

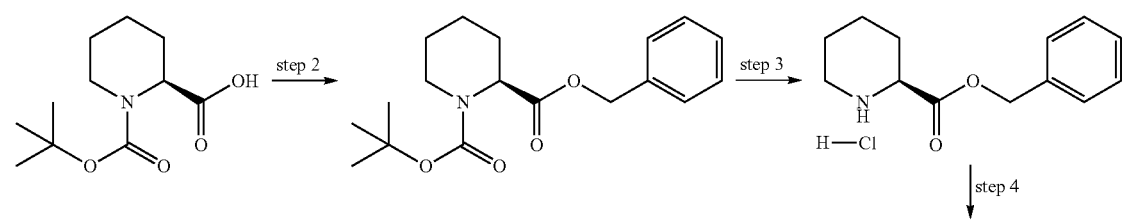

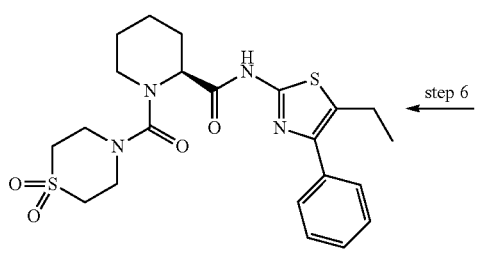 step 6 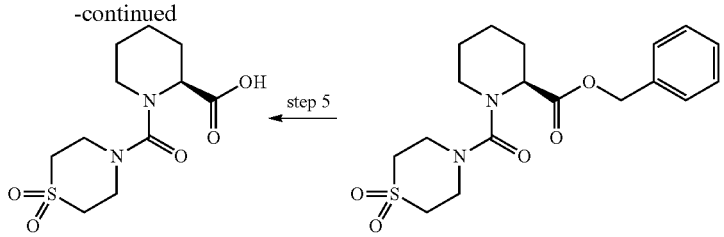 step 5

-continued

Step 1: Synthesis of 1,1-dioxo-1λ⁶-thiomorpholine-4-carbonyl chloride

Thiomorpholine 1,1-dioxide (3 g; 22.192 mmol) is dissolved in THF (70 mL) and cooled to 0° C. Triethylamine (3.708 mL; 26.6 mmol) is added, followed by 20% phosgene in toluene (35.229 mL; 66.6 mmol). The reaction mixture is stirred at room temperature for 18 hours. After this time, the reaction mixture is poured into ethyl ether (200 mL), then filtered through Celite®. The Celite® is washed with ethyl ether several times and the combined filtrates are concentrated in vacuo to afford the title compound as a white solid. $^1$H NMR (400 MHz, d-CDCl$_3$): δ 3.1-3.2 (m; 4H), 4.1-4.3 (d, 4H).

Intermediates in Table 6 are made in a similar manner.

TABLE 6

| Structure | Name |
|---|---|
| 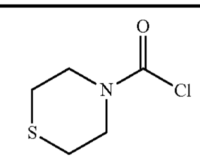 | Thiomorpholine-4-carbonyl chloride |
| 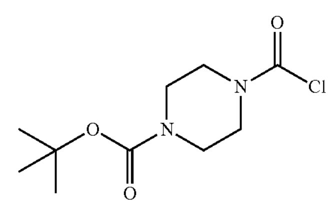 [SMILES: CC(C)(C)OC(=O)N1CCN(C(=O)Cl)CC1] | 4-Chlorocarbonyl-piperazine-1-carboxylic acid tert-butyl ester |
| 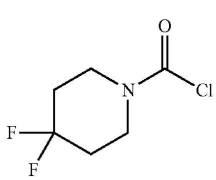 [SMILES: O=C(Cl)N1CCC(F)(F)CC1] | 4,4-Difluoro-piperidine-1-carbonyl chloride |

Step 2: Synthesis of (S)-Piperidine-1,2-dicarboxylic acid 2-benzyl ester 1-tert-butyl ester To a suspension of (S)-piperidine-2-carboxylic acid (5.159 g; 22.5 mmol) in acetonitrile (50 mL) at 0° C. is added benzyl bromide (2.5 mL; 21.019 mmol), followed by 1,5-diazabicyclo[4.3.0]non-5-ene (2.6 mL; 21.04 mmol). The reaction mixture is left stirring and slowly warm to room temperature overnight. The reaction mixture is diluted with ethyl acetate and washed with water, saturated NH4Cl aqueous solution then brine, dried over Na2SO4, filtered and concentrated in vacuo to afford the title compound, m/z 320 [M+H$^+$].

Step 3 is the same as Method F step 2.

Step 4 is the same as Method G.

Step 5: Synthesis of (S)-1-(1,1-Dioxo-1λ⁶-thiomorpholine-4-carbonyl)-piperidine-2-carboxylic acid To a solution of (S)-1-(1,1-Dioxo-1λ⁶-thiomorpholine-4-carbonyl)-piperidine-2-carboxylic acid benzyl ester (1.53 g; 4.021 mmol) in ethyl acetate (100 mL) is added 10% palladium on carbon (500 mg) and the reaction mixture is placed under an atmosphere of hydrogen and stirred at room temperature overnight. After this time, the mixture is filtered through Celite®. The Celite® is washed with 50% ethyl acetate in ethanol then ethanol and the combined filtrates are concentrated in vacuo to afford the title compound as a white solid, m/z 291 [M+H$^+$].

Step 6: Various Amide Coupling Procedures can be Used

Amide coupling procedure 1: is the same as Method F, step 1, amide coupling procedure 2.

Synthesis of (S)-1-(1,1-Dioxo-1λ⁶-thiomorpholine-4-carbonyl)-piperidine-2-carboxylic acid (5-ethyl-4-phenyl-thiazol-2-yl)-amide To a solution of (S)-1-(1,1-Dioxo-1λ⁶-thiomorpholine-4-carbonyl)-piperidine-2-carboxylic acid (92 mg; 0.317 mmol) and 2-amino-5-ethyl-4-phenyl-1,3-thiazole (64.8 mg; 0.317 mmol) in dichloromethane (4 mL) is added 2-ethoxy-1-ethoxycarbonyl-1,2-dihydroquinoline (79.1 mg; 0.32 mmol). The reaction mixture is left stirring at room temperature for 18 hours. The reaction mixture is directly purified by preparative HPLC provides the title compound, m/z 477 [M+H$^+$].

Compounds in Table 7 Method M1 are prepared in a similar manner.

Amide coupling procedure 2: is the same as Method F, step 1, coupling procedure 4:

Compounds in Table 7 Method M2 are prepared in a similar manner.

Amide coupling procedure 3: Synthesis of (S)-1-(1,1-Dioxo-1λ⁶-thiomorpholine-4-carbonyl)-piperidine-2-carboxylic acid cyclohexylmethyl-amide (Example 33)

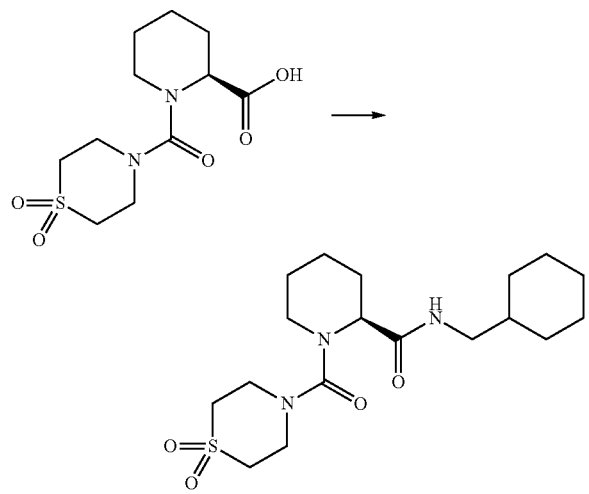

To a solution of (S)-1-(1,1-Dioxo-1λ⁶-thiomorpholine-4-carbonyl)-piperidine-2-carboxylic acid (58.07 mg; 0.2 mmol), N,N-diisopropylethylamine (142 mg; 1.1 mmol) and cyclohexanemethylamine (33.96 mg; 0.3 mmol) in dichloromethane (0.4 mL) at room temperature is added bromotripyrrolidinophosphonium hexafluorophosphate (279.7 mg; 0.6 mmol). The reaction mixture is shaken on an orbital shaker for 16 hours. The reaction mixture is concentrated in vacuo. Purification by preparative HPLC affords the title compound, m/z 386 [M+H⁺].

Compounds in Table 7 Method M3 are prepared in a similar manner.

Synthesis of (S)-1-(1,1-Dioxo-1λ⁶-thiomorpholine-4-carbonyl)-piperidine-2-carboxylic acid [5-(2-hydroxy-1,1-dimethyl-ethyl)-isoxazol-3-yl]-amide (Example 145)

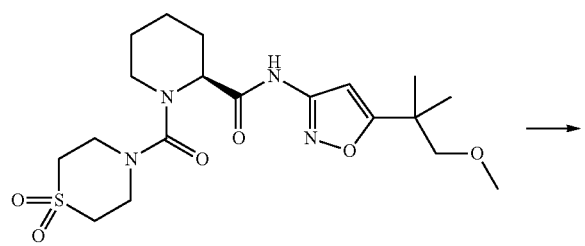

-continued

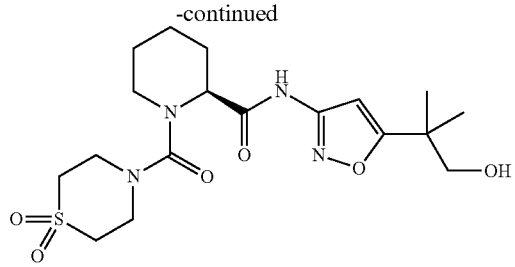

(S)-1-(1,1-Dioxo-1λ⁶-thiomorpholine-4-carbonyl)-piperidine-2-carboxylic acid [5-(2-methoxy-1,1-dimethyl-ethyl)-isoxazol-3-yl]-amide (110 mg; 0.249 mmol) is dissolved in ethanethiol (2 mL) and cooled to 0° C. Aluminum chloride (498 mg; 3.735 mmol) is added to the solution and the reaction mixture is stirred at room temperature for 2 hours. The mixture is quenched with water (10 mL) and 3 drops of concentrated HCl aqueous solution and extracted with ethyl acetate 3 times. The organics are combined and washed with brine, dried over Na2SO4, filtered and concentrated. Purification by preparative HPLC affords title compound, m/z 429 [M+H⁺].

Method N:

Synthesis of (S)-1-(4-Chloro-phenyl)-6-oxo-piperidine-2-carboxylic acid (3-tert-butyl-isoxazol-5-yl)-amide (Example 131)

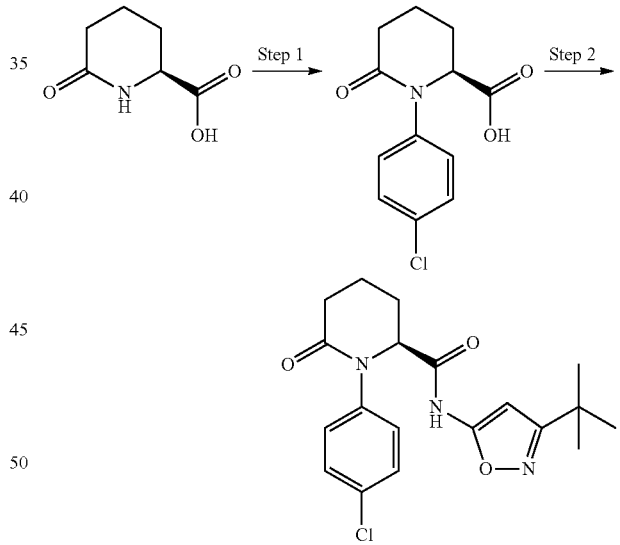

Step 1: Synthesis of (S)-1-(4-Chloro-phenyl)-6-oxo-piperidine-2-carboxylic acid

To a stirred suspension of (S)-1-(4-chloro-phenyl)-6-oxo-piperidine-2-carboxylic acid (1.368 g, 9.558 mmol) in 1,2-dichloroethane (35 mL) 1,8-diazabicyclo[5,4,0]undec-7-ene (DBU) (3.1 mL, 20.854 mmol) is added at room temperature. After 10 min di-µ-hydroxy-bis[N,N,N',N'-tetramethylenediamine)-copper (II) chloride (Cu-TMEDA) (1.614 g, 3.476 mmol) is added to the clear solution. The mixture is stirred for 10 min and 4-chlorophenylboronic acid (1.495 g, 9.558 mmol) is added. After 20 h solvent is evaporated in vacuo, the concentrate taken up in saturated sodium bicarbonate solution (150 mL) and the aqueous layer is washed with ethyl acetate (3×100 mL). The aqueous layer is treated with 1 N hydrochloric acid to pH 2 and extracted with ethyl acetate (3×100 mL). Combined organic extracts washed with brine (2×50 mL), dried over anhydrous sodium sulfate and solvent removed in vacuo to give the title compound as an off-white solid, m/z 254 [M+H⁺].

Step 2: Synthesis of (S)-1-(4-Chloro-phenyl)-6-oxo-piperidine-2-carboxylic acid (3-tert-butyl-isoxazol-5-yl)-amide To a cold slurry of (S)-1-(4-Chloro-phenyl)-6-oxo-piperidine-2-carboxylic acid (0.2 g; 0.788 mmol) and 5-amino-3-tert-butylisoxazole (0.110 g; 0.788 mmol) in pyridine (0.956 mL; 11.820 mmol) is added phosphorous oxychloride (0.088 mL; 0.946 mmol). The mixture is stirred at 0° C. for 30 minutes and then diluted with water and extracted with ethyl acetate several times. The organics are combined and washed with water and brine, dried (Na₂SO₄), filtered and concentrated in vacuo. Purification by preparative HPLC affords title compound, m/z 376 [M+H⁺].

Compounds in Table 7 Method N are prepared in a similar manner.

Method O:

Synthesis of (S)-1-(4-chloro-benzenesulfonyl)-piperidine-2-carboxylic acid (5-tert-butyl-isoxazol-3-yl)-amide (Example 99)

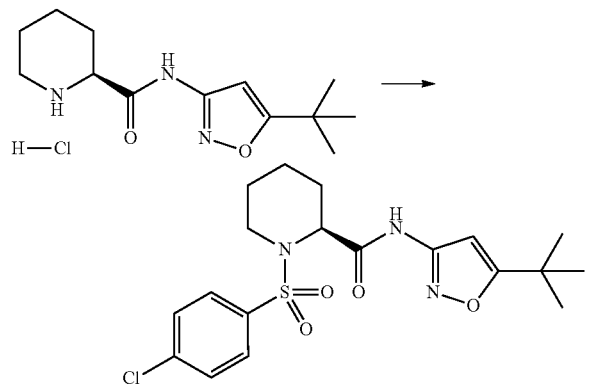

To a solution of (S)-Piperidine-2-carboxylic acid (5-tert-butyl-isoxazol-3-yl) amide; hydrochloride (110 mg; 0.382 mmol) in DMF (1.5 mL) is added 4-chlorobenzenesulfonyl chloride (80.6 mg; 0.382 mmol) and N,N-diisopropylethylamine (0.133 mL; 0.764 mmol). The reaction mixture is left stirring at room temperature for 18 hours in the presence of catalytic amount of 4-dimethylaminopyridine. The reaction mixture is quenched with water and extracted with ethyl acetate twice. The combined organics are washed with water then brine, dried over Na2SO4, filtered and concentrated in vacuo. Purification by flash chromatography on silica gel using ethyl acetate/Hexanes provides the title compound, m/z 426 [M+H⁺].

Compounds in Table 7 Method O are prepared in a similar manner.

Synthesis of Intermediates:

Synthesis of (S)-1-(1,1-Dioxo-hexahydro-1λ⁶-thiopyran-4-carbonyl)-piperidine-2-carboxylic acid (5-tert-butyl-isoxazol-3-yl)-amide (Intermediate for Example 108)

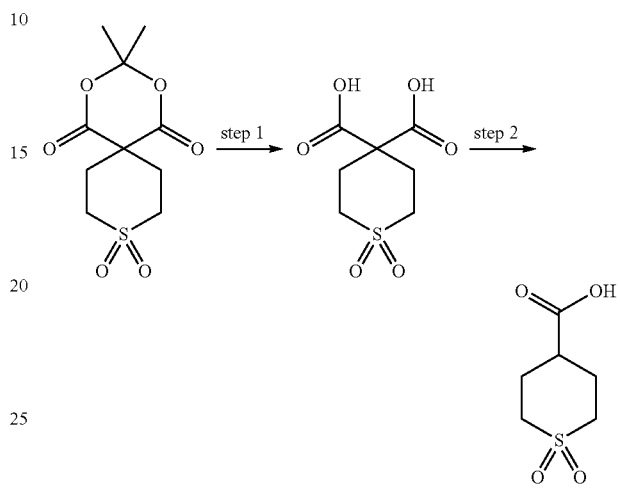

Step 1: Synthesis of 1,1-Dioxo-tetrahydro-1λ⁶-thiopyran-4,4-dicarboxylic acid 3,3-Dimethyl-9,9-dioxo-2,4-dioxa-9λ⁶-thia-spiro[5.5]undecane-1,5-dione (200 mg; 0.763 mmol) is dispersed in 2M HCl aqueous solution (2 mL) and the vial is placed into microwave oven for 23 minutes at 100° C. After cooling, the reaction mixture is extracted with diethyl ether once. The aqueous layer is saturated with solid sodium chloride and extracted with 50% THF in ethyl acetate three times. The organics are combined and dried over Na2SO4, filtered and concentrated in vacuo to afford the title compound.

Step 2: Synthesis of 1,1-Dioxo-hexahydro-1λ⁶-thiopyran-4-carboxylic acid

In a microwave vial is added 1,1-Dioxo-tetrahydro-1λ⁶-thiopyran-4,4-dicarboxylic acid (112 mg; 0.504 mmol), 2% cross-linked poly-4-vinylpyridine (225 mg) and DMF (2.1 mL). The vial is sealed and placed into microwave oven for 10 minutes at 95° C. After cooling, the mixture is filtered through filter paper and washed the paper with diethyl ether. The filtrate is concentrated in vacuo to afford the title compound.

Synthesis of 5-(2-Methoxy-1,1-dimethyl-ethyl)-isoxazol-3-ylamine (Intermediate for Example 144)

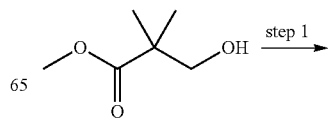

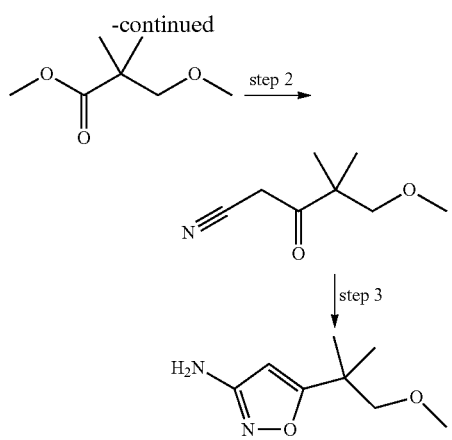

Step 1: Synthesis of 3-Methoxy-2,2-dimethyl-propionic acid methyl ester

Powdered potassium hydroxide (3.519 g; 62.712 mmol) is stirred in DMSO (30 mL) for 5 minutes before adding hydroxypivalic acid methyl eater (2 mL; 15.678 mmol) and methyl iodide (3.904 mL; 62.712 mmol). The reaction mixture is stirred at room temperature for 30 minutes. The mixture is quenched with water and extracted with dichloromethane 3 times. The organics are combined and washed with water twice then brine, dried over Na2SO4, filtered and concentrated in vacuo to provide the title compound.

Step 2: Synthesis of 5-Methoxy-4,4-dimethyl-3-oxo-pentanenitrile

60% sodium hydride in mineral oil (667.2 mg, 16.68 mmol) in toluene (15 mL) is heated to reflux. A solution of 3-methoxy-2,2-dimethyl-propionic acid methyl ester (1.742 g, 11.916 mmol) and acetonitrile (0.878 mL, 16.68 mmol) in toluene (5 mL) is added dropwise through an additional funnel into the NaH suspension in toluene. After the addition, the reaction is stirred at reflux for 3 hours. After cooling, the reaction mixture is neutralized to PH~7 by adding 1N HCl aqueous solution. The mixture is extracted with ethyl acetate 3 times. The organics are combined and washed with brine, dried over Na2SO4, filtered and concentrated in vacuo to afford the title compound.

Step 3: Synthesis of 5-(2-Methoxy-1,1-dimethyl-ethyl)-isoxazol-3-ylamine

A solution of hydroxylamine sulfate (976 mg; 5.947 mmol) in water (4 mL) is added to a stirred solution of 5-methoxy-4,4-dimethyl-3-oxo-pentanenitrile (1.678 g; 10.812 mmol) and sodium hydroxide (490.3 mg; 11.89 mmol) in water (13 mL). The reaction mixture is heated to reflux over 30 minutes and kept at reflux for 1 hour. After cooling, 37% HCl aqueous solution (0.8 mL; 9.73 mmol) is added and the mixture is heated to reflux for 20 minutes. After cooling, the mixture's pH is adjusted to ~12 by adding 40% sodium hydroxide aqueous solution. The mixture is extracted with methylene chloride 3 times. The organics are combined and washed with brine, dried over Na2SO4, filtered and concentrated in vacuo to afford the title compound, m/z 171 [M+H$^+$].

TABLE 7

Examples

| Example | Structure | Name | m/z [M + H$^+$] | Method |
|---|---|---|---|---|
| 14 | 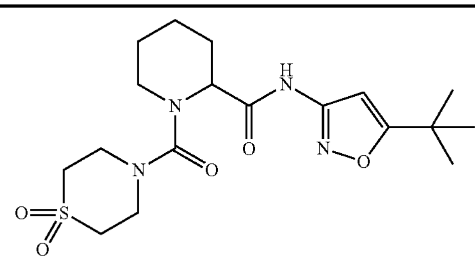 | 1-(1,1-Dioxo-1λ$^6$-thiomorpholine-4-carbonyl)-piperidine-2-carboxylic acid (5-tert-butyl-isoxazol-3-yl)-amide | 413 | G |
| 15 | 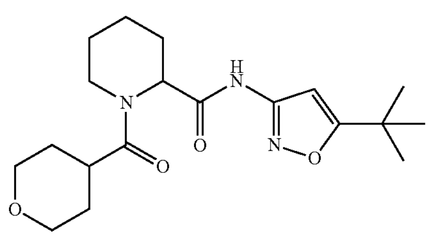 [SMILES: CC(C)(C)c1cc(NC(=O)C2CCCCN2C(=O)C2CCOCC2)no1] | 1-(Tetrahydro-pyran-4-carbonyl)-piperidine-2-carboxylic acid (5-tert-butyl-isoxazol-3-yl)-amide | 364 | F1 |
| 16 | 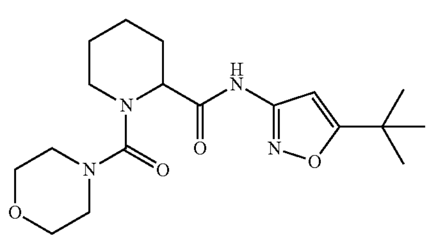 [SMILES: CC(C)(C)c1cc(NC(=O)C2CCCCN2C(=O)N2CCOCC2)no1] | 1-(1,1-Dioxo-1λ6-thiomorpholine-4-carbonyl)-piperidine-2-carboxylic acid (5-tert-butyl-isoxazol-3-yl)-amide | 413 | G |

TABLE 7-continued

Examples

| Example | Structure | Name | m/z [M + H+] | Method |
|---|---|---|---|---|
| 17 | 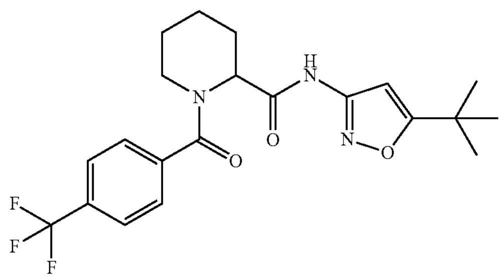 [SMILES: CC(C)(C)c1cc(NC(=O)C2CCCCN2C(=O)c2ccc(C(F)(F)F)cc2)no1] | 1-(4-Trifluoromethyl-benzoyl)-piperidine-2-carboxylic acid (5-tert-butyl-isoxazol-3-yl)-amide | 424 | F2 |
| 18 | 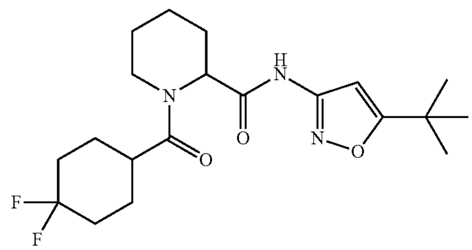 [SMILES: CC(C)(C)c1cc(NC(=O)C2CCCCN2C(=O)C2CCC(F)(F)CC2)no1] | 1-(4,4-Difluoro-cyclohexanecarbonyl)-piperidine-2-carboxylic acid (5-tert-butyl-isoxazol-3-yl)-amide | 398 | F2 |
| 19 | 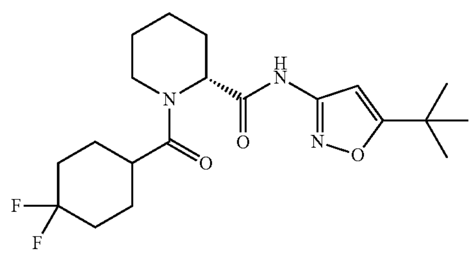 [SMILES: CC(C)(C)c1cc(NC(=O)[C@H]2CCCCN2C(=O)C2CCC(F)(F)CC2)no1] | (R)-1-(4,4-Difluoro-cyclohexanecarbonyl)-piperidine-2-carboxylic acid (5-tert-butyl-isoxazol-3-yl)-amide | 398 | F1 |
| 20 | 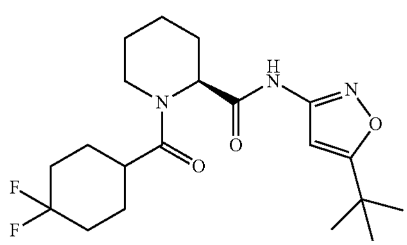 [SMILES: CC(C)(C)c1cc(NC(=O)[C@@H]2CCCCN2C(=O)C2CCC(F)(F)CC2)no1] | (S)-1-(4,4-Difluoro-cyclohexanecarbonyl)-piperidine-2-carboxylic acid (5-tert-butyl-isoxazol-3-yl)-amide | 398 | F1 |
| 21 | 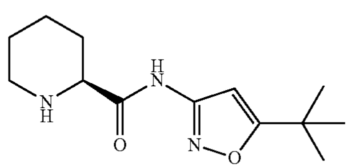 [SMILES: CC(C)(C)c1cc(NC(=O)[C@@H]2CCCCN2)no1] | (S)-Piperidine-2-carboxylic acid (5-tert-butyl-isoxazol-3-yl)-amide | 252 | F |
| 22 | 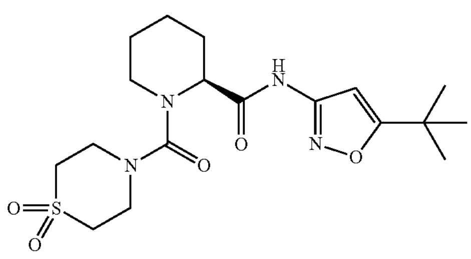 [SMILES: CC(C)(C)c1cc(NC(=O)[C@@H]2CCCCN2C(=O)N2CCS(=O)(=O)CC2)no1] | (S)-1-(1,1-Dioxo-1$\lambda^6$-thiomorpholine-4-carbonyl)-piperidine-2-carboxylic acid (5-tert-butyl-isoxazol-3-yl)-amide | 413 | G |

| Example | Name | m/z [M + H+] | Method |
|---|---|---|---|
| 23 | (R)-1-(1,1-Dioxo-1λ6-thiomorpholine-4-carbonyl)-piperidine-2-carboxylic acid (5-tert-butyl-isoxazol-3-yl)-amide | 413 | G |
| 24 | (S)-1-(4,4-Difluoro-cyclohexanecarbonyl)-piperidine-2-carboxylic acid (3-tert-butyl-isoxazol-5-yl)-amide | 398 | F1 |
| 25 | (S)-3'-Chloro-5'-trifluoromethyl-3,4,5,6-tetrahydro-2H-1,2'-bipyridinyl-2-carboxylic acid (3-phenyl-1,2,4-thiadiazol-5-yl)-amide | 468 | H |
| 26 | (S)-1-(4,4-Difluoro-cyclohexanecarbonyl)-piperidine-2-carboxylic acid (5-trifluoromethyl-pyridin-2-yl)-amide | 420 | F1 |
| 27 | (S)-1-Benzoyl-piperidine-2-carboxylic acid (5-tert-butyl-isoxazol-3-yl)-amide | 356 | F1 |
| 28 | (S)-1-(4-Fluoro-benzoyl)-piperidine-2-carboxylic acid (5-tert-butyl-isoxazol-3-yl)-amide | 374 | F1 |

TABLE 7-continued

Examples

| Example | Structure | Name | m/z [M + H⁺] | Method |
|---|---|---|---|---|
| 29 | 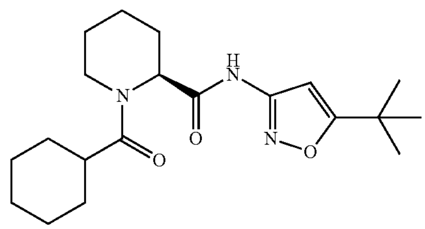 | S)-1-Cyclohexanecarbonyl-piperidine-2-carboxylic acid (5-tert-butyl-isoxazol-3-yl)-amide | 362 | F1 |
| 30 | 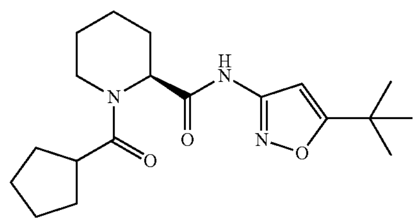 [SMILES: CC(C)(C)c1cc(NC(=O)[C@@H]2CCCCN2C(=O)C2CCCC2)no1] | (S)-1-Cyclopentanecarbonyl-piperidine-2-carboxylic acid (5-tert-butyl-isoxazol-3-yl)-amide | 348 | F1 |
| 31 | 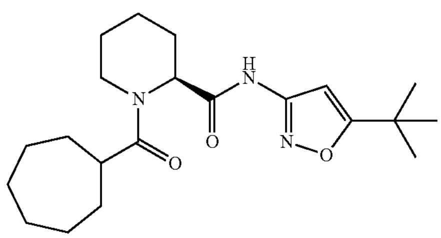 [SMILES: CC(C)(C)c1cc(NC(=O)[C@@H]2CCCCN2C(=O)C2CCCCCC2)no1] | (S)-1-Cycloheptanecarbonyl-piperidine-2-carboxylic acid (5-tert-butyl-isoxazol-3-yl)-amide | 376 | F1 |
| 32 | 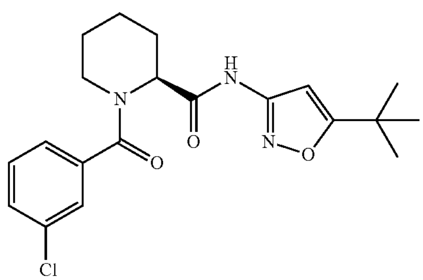 [SMILES: CC(C)(C)c1cc(NC(=O)[C@@H]2CCCCN2C(=O)c2cccc(Cl)c2)no1] | (S)-1-(3-Chloro-benzoyl)-piperidine-2-carboxylic acid (5-tert-butyl-isoxazol-3-yl)-amide | 390/392 | F1 |
| 33 | 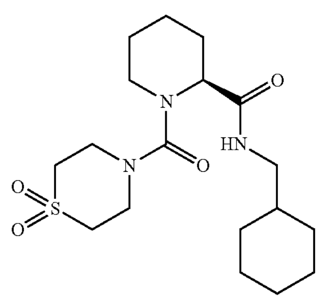 [SMILES: O=C(NCC1CCCCC1)[C@@H]1CCCCN1C(=O)N1CCS(=O)(=O)CC1] | (S)-1-(1,1-Dioxo-1$\lambda^6$-thiomorpholine-4-carbonyl)-piperidine-2-carboxylic acid cyclohexylmethyl-amide | 386 | M3 |
| 34 | 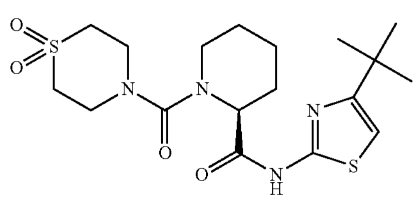 [SMILES: CC(C)(C)c1csc(NC(=O)[C@@H]2CCCCN2C(=O)N2CCS(=O)(=O)CC2)n1] | (S)-1-(1,1-Dioxo-1$\lambda^6$-thiomorpholine-4-carbonyl)-piperidine-2-carboxylic acid (4-tert-butyl-thiazol-2-yl)-amide | 429 | M3 |

TABLE 7-continued

Examples

| Example | Structure | Name | m/z [M + H⁺] | Method |
|---|---|---|---|---|
| 35 | 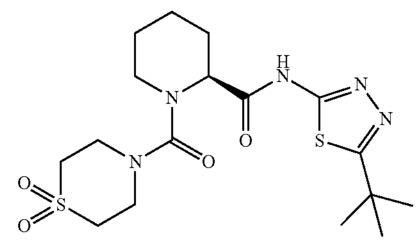 [SMILES: CC(C)(C)c1nnc(NC(=O)[C@@H]2CCCCN2C(=O)N2CCS(=O)(=O)CC2)s1] | (S)-1-(1,1-Dioxo-1λ⁶-thiomorpholine-4-carbonyl)-piperidine-2-carboxylic acid (5-tert-butyl-1,3,4-thiadiazol-2-yl)-amide | 430 | M3 |
| 36 | 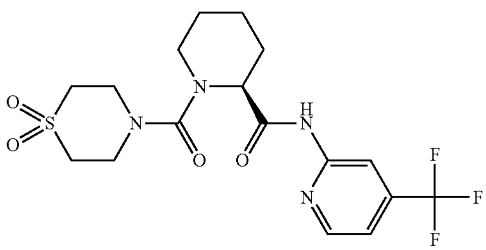 [SMILES: O=C(Nc1cc(C(F)(F)F)ccn1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (4-trifluoromethyl-pyridin-2-yl)-amide | 435 | G |
| 37 | 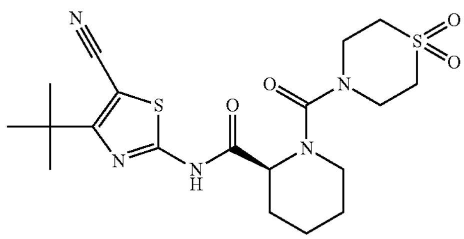 [SMILES: CC(C)(C)c1nc(NC(=O)[C@@H]2CCCCN2C(=O)N2CCS(=O)(=O)CC2)sc1C#N] | (S)-1-(1,1-Dioxo-1λ⁶-thiomorpholine-4-carbonyl)-piperidine-2-carboxylic acid (4-tert-butyl-5-cyano-thiazol-2-yl)-amide | 454 | G |
| 38 | 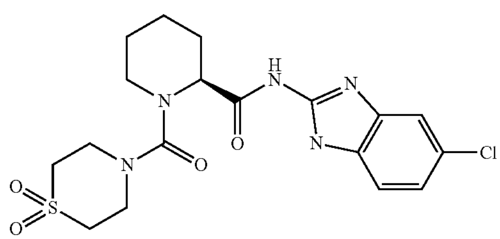 [SMILES: O=C(Nc1nc2cc(Cl)ccc2[nH]1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (5-chloro-1H-benzimidazol-2-yl)-amide | 440 | G |
| 39 | 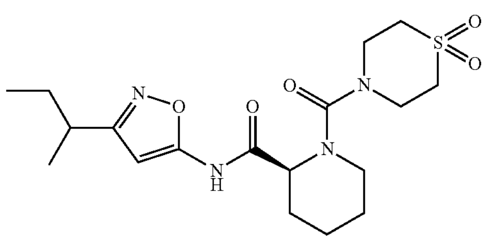 [SMILES: CCC(C)c1cc(NC(=O)[C@@H]2CCCCN2C(=O)N2CCS(=O)(=O)CC2)on1] | (S)-1-(1,1-Dioxo-1λ⁶-thiomorpholine-4-carbonyl)-piperidine-2-carboxylic acid (3-sec-butyl-isoxazol-5-yl)-amide | 413 | G |
| 40 | 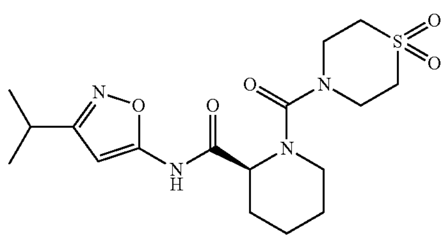 [SMILES: CC(C)c1cc(NC(=O)[C@@H]2CCCCN2C(=O)N2CCS(=O)(=O)CC2)on1] | (S)-1-(1,1-Dioxo-1λ⁶-thiomorpholine-4-carbonyl)-piperidine-2-carboxylic acid (3-isopropyl-isoxazol-5-yl)-amide | 399 | G |

TABLE 7-continued

Examples

| Example | Structure | Name | m/z [M + H⁺] | Method |
|---|---|---|---|---|
| 41 | 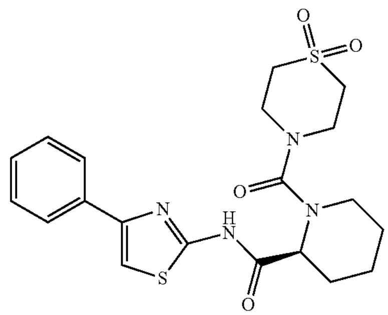 [SMILES: O=C(Nc1nc(-c2ccccc2)cs1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (4-phenyl-thiazol-2-yl)-amide | 449 | G |
| 42 | 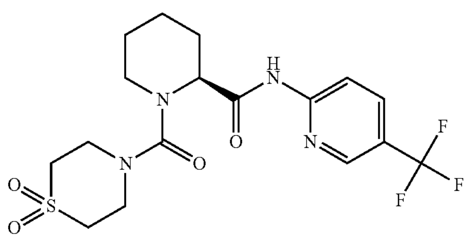 [SMILES: O=C(Nc1ccc(C(F)(F)F)cn1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (5-trifluoromethyl-pyridin-2-yl)-amide | 435 | F |
| 43 | 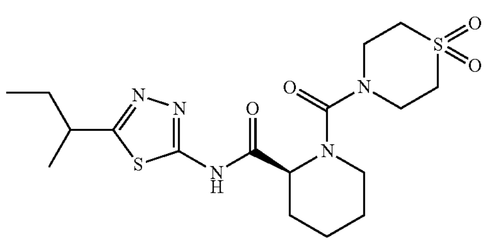 [SMILES: CCC(C)c1nnc(NC(=O)[C@@H]2CCCCN2C(=O)N2CCS(=O)(=O)CC2)s1] | (S)-1-(1,1-Dioxo-1λ⁶-thiomorpholine-4-carbonyl)-piperidine-2-carboxylic acid (5-sec-butyl-1,3,4-thiadiazol-2-yl)-amide | 430 | G |
| 44 | 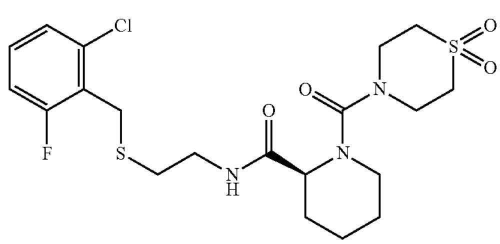 [SMILES: O=C(NCCSCc1c(F)cccc1Cl)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid [2-(2-chloro-6-fluoro-benzylsulfanyl)-ethyl]-amide | 493 | M1 |
| 45 | 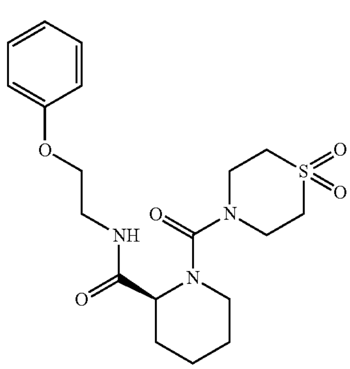 [SMILES: O=C(NCCOc1ccccc1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (2-phenoxy-ethyl)-amide | 410 | G |

TABLE 7-continued

Examples

| Example | Structure | Name | m/z [M + H+] | Method |
|---|---|---|---|---|
| 46 | 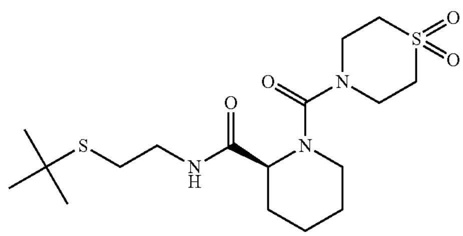 [SMILES: CC(C)(C)SCCNC(=O)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (2-tert-butylsulfanyl-ethyl)-amide | 406 | G |
| 47 | 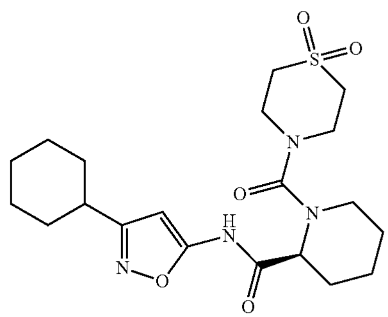 [SMILES: O=C(Nc1cc(C2CCCCC2)no1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-cyclohexyl-isoxazol-5-yl)-amide | 439 | G |
| 48 | 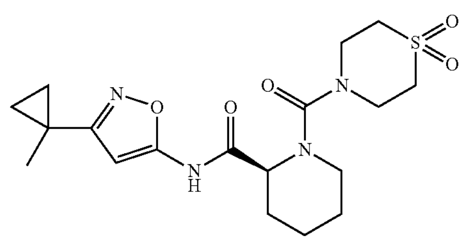 [SMILES: CC1(c2cc(NC(=O)[C@@H]3CCCCN3C(=O)N3CCS(=O)(=O)CC3)on2)CC1] | (S)-1-(1,1-Dioxo-1λ6-thiomorpholine-4-carbonyl)-piperidine-2-carboxylic acid [3-(1-methyl-cyclopropyl)-isoxazol-5-yl]-amide | 411 | G |
| 49 | 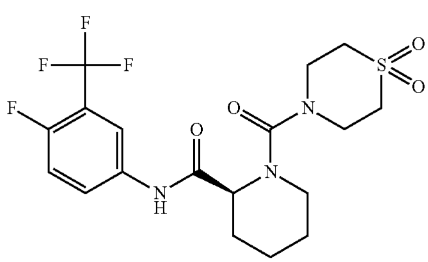 [SMILES: O=C(Nc1ccc(F)c(C(F)(F)F)c1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (4-fluoro-3-trifluoromethyl-phenyl)-amide | 452 | G |
| 50 | 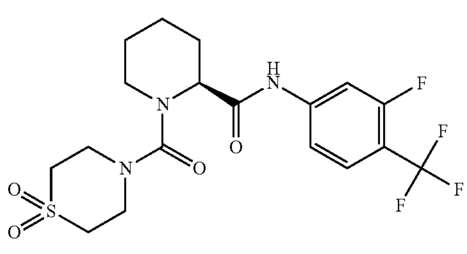 [SMILES: O=C(Nc1ccc(C(F)(F)F)c(F)c1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (3-fluoro-4-trifluoromethyl-phenyl)-amide | 452 | G |
| 51 | 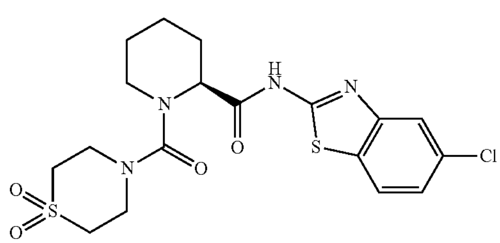 | (S)-1-(1,1-Dioxo-1λ6-thiomorpholine-4-carbonyl)-piperidine-2-carboxylic acid (5-chloro-benzothiazol-2-yl)-amide | 457 | G |

TABLE 7-continued

Examples

| Example | Structure | Name | m/z [M + H⁺] | Method |
|---|---|---|---|---|
| 52 | 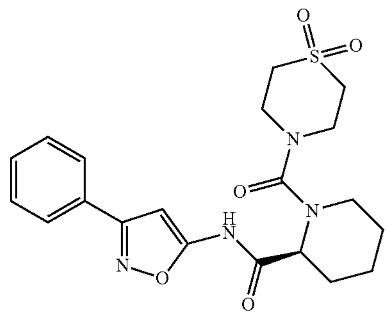 [SMILES: O=C(Nc1cc(-c2ccccc2)no1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (3-phenyl-isoxazol-5-yl)-amide | 433 | G |
| 53 | 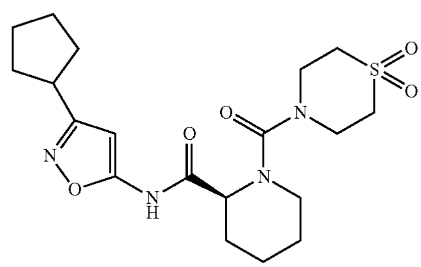 [SMILES: O=C(Nc1cc(C2CCCC2)no1)[C@@H]1CCCCN1C(=O)N1CCS(=O)(=O)CC1] | (S)-1-(1,1-Dioxo-1λ⁶-thiomorpholine-4-carbonyl)-piperidine-2-carboxylic acid (3-cyclopentyl-isoxazol-5-yl)-amide | 425 | G |
| 54 | 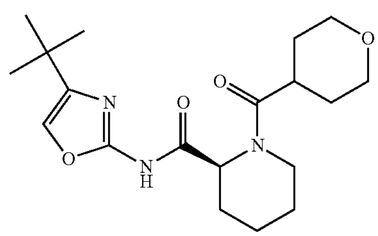 [SMILES: CC(C)(C)c1coc(NC(=O)[C@@H]2CCCCN2C(=O)C2CCOCC2)n1] | (S)-1-(Tetrahydro-pyran-4-ylmethyl)-piperidine-2-carboxylic acid (4-tert-butyl-oxazol-2-yl)-amide | 350 | J1 |
| 55 | 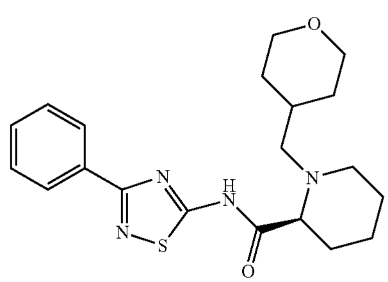 [SMILES: O=C(Nc1nc(-c2ccccc2)ns1)[C@@H]1CCCCN1CC1CCOCC1] | (S)-1-(Tetrahydro-pyran-4-ylmethyl)-piperidine-2-carboxylic acid (3-phenyl-1,2,4-thiadiazol-5-yl)-amide | 387 | J1 |
| 56 | 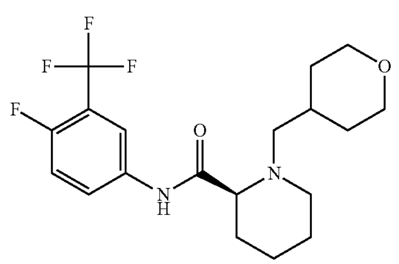 [SMILES: O=C(Nc1ccc(F)c(C(F)(F)F)c1)[C@@H]1CCCCN1CC1CCOCC1] | (S)-1-(Tetrahydro-pyran-4-ylmethyl)-piperidine-2-carboxylic acid (4-fluoro-3-trifluoromethyl-phenyl)-amide | 389 | J1 |

TABLE 7-continued

Examples

| Example | Structure | Name | m/z [M + H⁺] | Method |
|---|---|---|---|---|
| 57 | 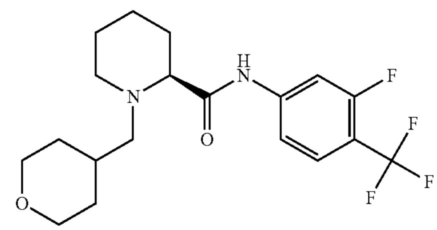 [SMILES: O=C(Nc1ccc(C(F)(F)F)c(F)c1)[C@@H]1CCCCN1CC1CCOCC1] | (S)-1-(Tetrahydro-pyran-4-ylmethyl)-piperidine-2-carboxylic acid (3-fluoro-4-trifluoromethyl-phenyl)-amide | 389 | J1 |
| 58 | 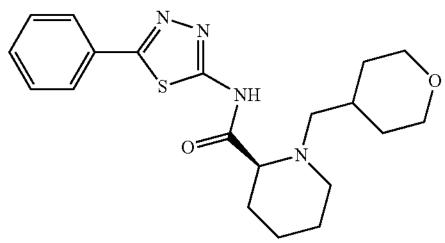 [SMILES: O=C(Nc1nnc(-c2ccccc2)s1)[C@@H]1CCCCN1CC1CCOCC1] | (S)-1-(Tetrahydro-pyran-4-ylmethyl)-piperidine-2-carboxylic acid (5-phenyl-1,3,4-thiadiazol-2-yl)-amide | 387 | J1 |
| 59 | 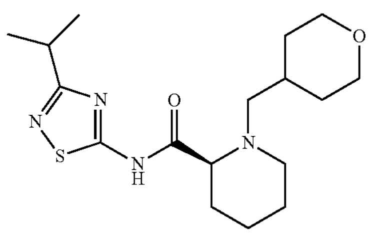 [SMILES: CC(C)c1nsc(NC(=O)[C@@H]2CCCCN2CC2CCOCC2)n1] | (S)-1-(Tetrahydro-pyran-4-ylmethyl)-piperidine-2-carboxylic acid (3-isopropyl-1,2,4-thiadiazol-5-yl)-amide | 353 | J1 |
| 60 | 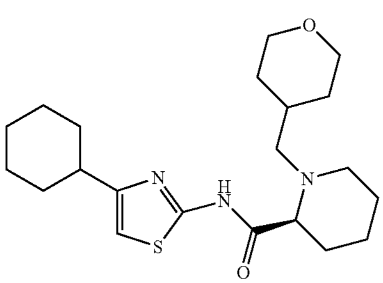 [SMILES: O=C(Nc1nc(C2CCCCC2)cs1)[C@@H]1CCCCN1CC1CCOCC1] | (S)-1-(Tetrahydro-pyran-4-ylmethyl)-piperidine-2-carboxylic acid (4-cyclohexyl-thiazol-2-yl)-amide | 392 | J1 |
| 61 | 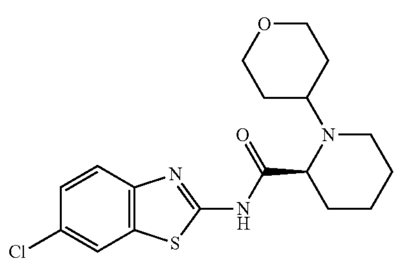 [SMILES: O=C(Nc1nc2ccc(Cl)cc2s1)[C@@H]1CCCCN1C1CCOCC1] | (S)-1-(Tetrahydro-pyran-4-yl)-piperidine-2-carboxylic acid (6-chloro-benzothiazol-2-yl)-amide | 380 | J1 |
| 62 | 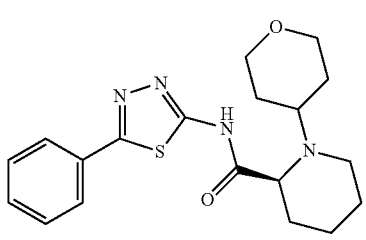 [SMILES: O=C(Nc1nnc(-c2ccccc2)s1)[C@@H]1CCCCN1C1CCOCC1] | (S)-1-(Tetrahydro-pyran-4-yl)-piperidine-2-carboxylic acid (5-phenyl-1,3,4-thiadiazol-2-yl)-amide | 373 | J1 |

TABLE 7-continued

Examples

| Example | Structure | Name | m/z [M + H+] | Method |
|---|---|---|---|---|
| 63 | 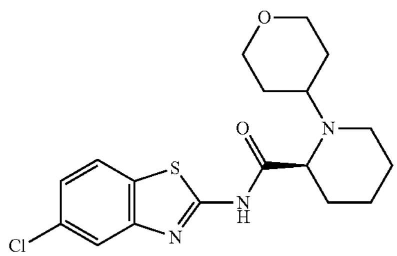 [SMILES: O=C(Nc1nc2cc(Cl)ccc2s1)[C@@H]1CCCCN1C1CCOCC1] | (S)-1-(Tetrahydro-pyran-4-yl)-piperidine-2-carboxylic acid (5-chloro-benzothiazol-2-yl)-amide | 380 | J1 |
| 64 | 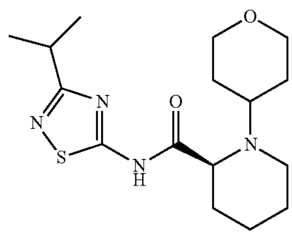 [SMILES: CC(C)c1nsc(NC(=O)[C@@H]2CCCCN2C2CCOCC2)n1] | (S)-1-(Tetrahydro-pyran-4-yl)-piperidine-2-carboxylic acid (3-isopropyl-1,2,4-thiadiazol-5-yl)-amide | 339 | J1 |
| 65 | 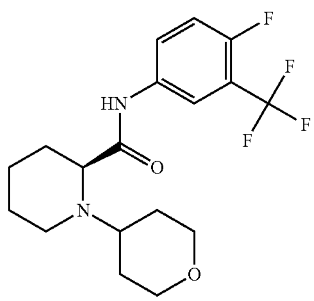 [SMILES: O=C(Nc1ccc(F)c(C(F)(F)F)c1)[C@@H]1CCCCN1C1CCOCC1] | (S)-1-(Tetrahydro-pyran-4-yl)-piperidine-2-carboxylic acid (4-fluoro-3-trifluoromethyl-phenyl)-amide | 375 | J3 |
| 66 | 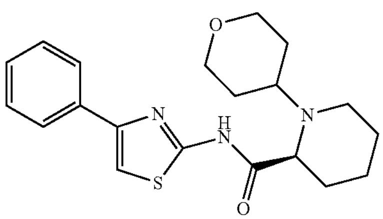 [SMILES: O=C(Nc1nc(-c2ccccc2)cs1)[C@@H]1CCCCN1C1CCOCC1] | (S)-1-(Tetrahydro-pyran-4-yl)-piperidine-2-carboxylic acid (4-phenyl-thiazol-2-yl)-amide | 372 | J3 |
| 67 | 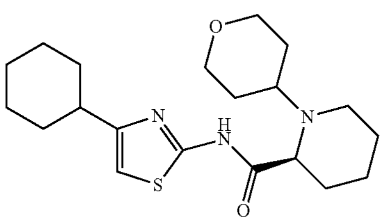 [SMILES: O=C(Nc1nc(C2CCCCC2)cs1)[C@@H]1CCCCN1C1CCOCC1] | (S)-1-(Tetrahydro-pyran-4-yl)-piperidine-2-carboxylic acid (4-cyclohexyl-thiazol-2-yl)-amide | 378 | J3 |
| 68 | 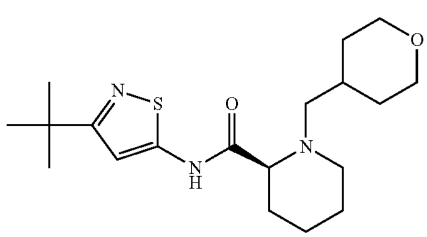 [SMILES: CC(C)(C)c1cc(NC(=O)[C@@H]2CCCCN2CC2CCOCC2)sn1] | (S)-1-(Tetrahydro-pyran-4-ylmethyl)-piperidine-2-carboxylic acid (3-tert-butyl-isothiazol-5-yl)-amide | 366 | J3 |

TABLE 7-continued

Examples

| Example | Structure | Name | m/z [M + H+] | Method |
|---|---|---|---|---|
| 69 | 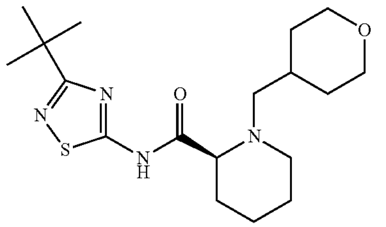 [SMILES: CC(C)(C)c1nsc(NC(=O)[C@@H]2CCCCN2CC2CCOCC2)n1] | (S)-1-(Tetrahydro-pyran-4-ylmethyl)-piperidine-2-carboxylic acid (3-tert-butyl-1,2,4-thiadiazol-5-yl)-amide | 367 | J3 |
| 70 | 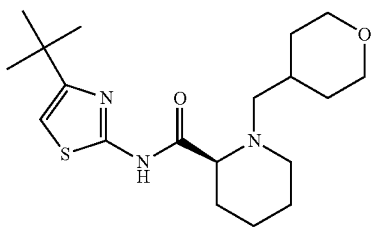 [SMILES: CC(C)(C)c1csc(NC(=O)[C@@H]2CCCCN2CC2CCOCC2)n1] | (S)-1-(Tetrahydro-pyran-4-ylmethyl)-piperidine-2-carboxylic acid (4-tert-butyl-thiazol-2-yl)-amide | 366 | J3 |
| 71 | 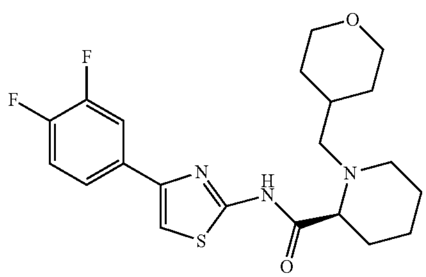 [SMILES: O=C(Nc1nc(-c2ccc(F)c(F)c2)cs1)[C@@H]1CCCCN1CC1CCOCC1] | (S)-1-(Tetrahydro-pyran-4-ylmethyl)-piperidine-2-carboxylic acid [4-(3,4-difluoro-phenyl)-thiazol-2-yl]-amide | 422 | J3 |
| 72 | 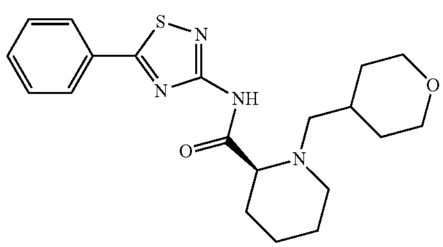 [SMILES: O=C(Nc1nsc(-c2ccccc2)n1)[C@@H]1CCCCN1CC1CCOCC1] | (S)-1-(Tetrahydro-pyran-4-ylmethyl)-piperidine-2-carboxylic acid (5-phenyl-1,2,4-thiadiazol-3-yl)-amide | 387 | J3 |
| 73 | 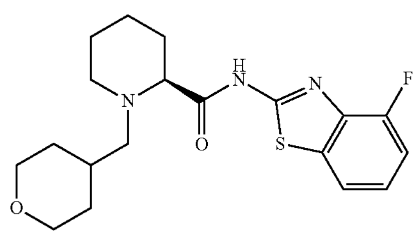 [SMILES: O=C(Nc1nc2c(F)cccc2s1)[C@@H]1CCCCN1CC1CCOCC1] | (S)-1-(Tetrahydro-pyran-4-ylmethyl)-piperidine-2-carboxylic acid (4-fluoro-benzothiazol-2-yl)-amide | 378 | J3 |
| 74 | 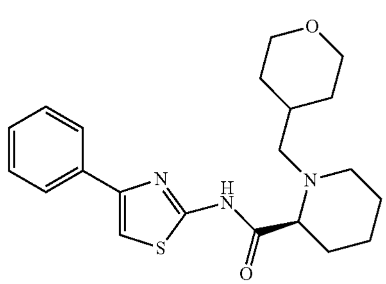 [SMILES: O=C(Nc1nc(-c2ccccc2)cs1)[C@@H]1CCCCN1CC1CCOCC1] | (S)-1-(Tetrahydro-pyran-4-ylmethyl)-piperidine-2-carboxylic acid (4-phenyl-thiazol-2-yl)-amide | 386 | J3 |

TABLE 7-continued

Examples

| Example | Structure | Name | m/z [M + H+] | Method |
|---|---|---|---|---|
| 75 | 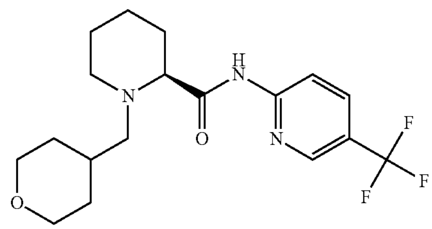 [SMILES: O=C(Nc1ccc(C(F)(F)F)cn1)[C@@H]1CCCCN1CC1CCOCC1] | (S)-1-(Tetrahydro-pyran-4-ylmethyl)-piperidine-2-carboxylic acid (5-trifluoromethyl-pyridin-2-yl)-amide | 372 | J3 |
| 76 | 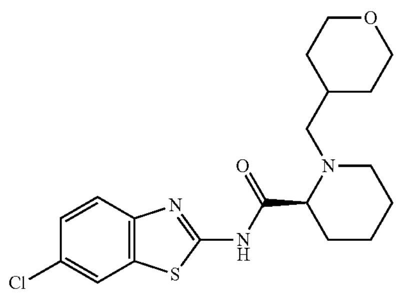 [SMILES: O=C(Nc1nc2ccc(Cl)cc2s1)[C@@H]1CCCCN1CC1CCOCC1] | (S)-1-(Tetrahydro-pyran-4-ylmethyl)-piperidine-2-carboxylic acid (6-chloro-benzothiazol-2-yl)-amide | 394 | J3 |
| 77 | 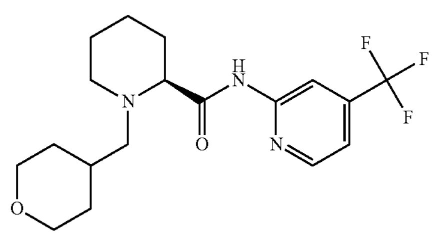 [SMILES: O=C(Nc1cc(C(F)(F)F)ccn1)[C@@H]1CCCCN1CC1CCOCC1] | (S)-1-(Tetrahydro-pyran-4-ylmethyl)-piperidine-2-carboxylic acid (4-trifluoromethyl-pyridin-2-yl)-amide | 372 | J3 |
| 78 | 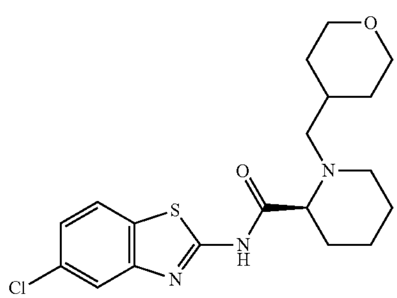 [SMILES: O=C(Nc1nc2cc(Cl)ccc2s1)[C@@H]1CCCCN1CC1CCOCC1] | (S)-1-(Tetrahydro-pyran-4-ylmethyl)-piperidine-2-carboxylic acid (5-chloro-benzothiazol-2-yl)-amide | 394 | J3 |
| 79 | 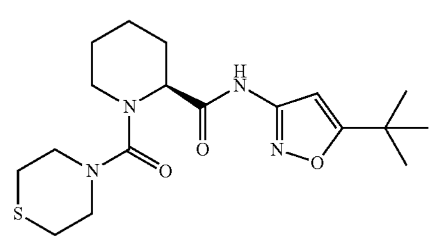 [SMILES: CC(C)(C)c1cc(NC(=O)[C@@H]2CCCCN2C(=O)N2CCSCC2)no1] | (S)-1-(Thiomorpholine-4-carbonyl)-piperidine-2-carboxylic acid (5-tert-butyl-isoxazol-3-yl)-amide | 381 | G |
| 80 | 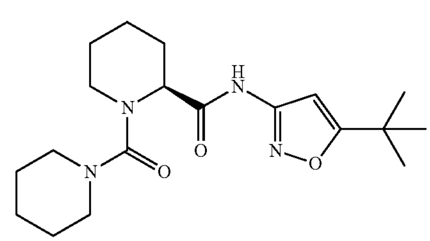 | (S)-1-(Piperidine-1-carbonyl)-piperidine-2-carboxylic acid (5-tert-butyl-isoxazol-3-yl)-amide | 363 | G |

TABLE 7-continued

Examples

| Example | Structure | Name | m/z [M + H⁺] | Method |
|---|---|---|---|---|
| 81 | 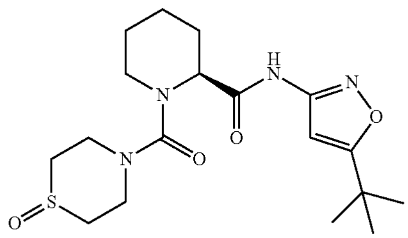 [SMILES: CC(C)(C)c1cc(NC(=O)[C@@H]2CCCCN2C(=O)N2CCS(=O)CC2)no1] | (S)-1-(1-Oxo-1λ4-thiomorpholine-4-carbonyl)-piperidine-2-carboxylic acid (5-tert-butyl-isoxazol-3-yl)-amide | 397 | G |
| 82 | 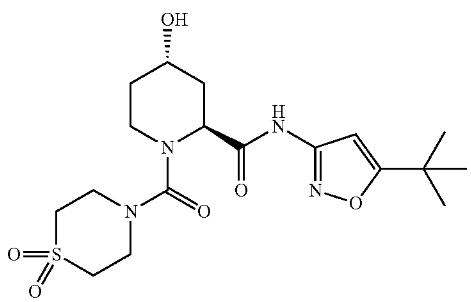 [SMILES: CC(C)(C)c1cc(NC(=O)[C@@H]2C[C@@H](O)CCN2C(=O)N2CCS(=O)(=O)CC2)no1] | (2S,4S)-1-(1,1-Dioxo-1λ⁶-thiomorpholine-4-carbonyl)-4-hydroxy-piperidine-2-carboxylic acid (5-tert-butyl-isoxazol-3-yl)-amide | 429 | G |
| 83 | 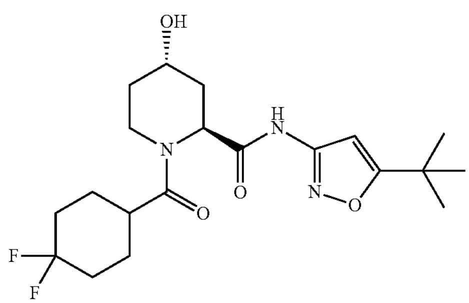 [SMILES: CC(C)(C)c1cc(NC(=O)[C@@H]2C[C@@H](O)CCN2C(=O)C2CCC(F)(F)CC2)no1] | (2S,4S)-1-(4,4-Difluoro-cyclohexanecarbonyl)-4-hydroxy-piperidine-2-carboxylic acid (5-tert-butyl isoxazol-3-yl)-amide | 414 | F1 |
| 84 | 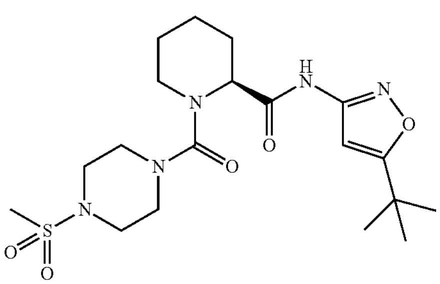 [SMILES: CC(C)(C)c1cc(NC(=O)[C@@H]2CCCCN2C(=O)N2CCN(S(C)(=O)=O)CC2)no1] | (S)-1-(4-Methanesulfonyl-piperazine-1-carbonyl)-piperidine-2-carboxylic acid (5-tert-butyl-isoxazol-3-yl)-amide | 442 | K |
| 85 | 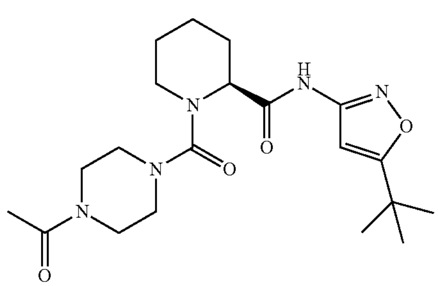 [SMILES: CC(=O)N1CCN(C(=O)N2CCCC[C@H]2C(=O)Nc2cc(C(C)(C)C)on2)CC1] | (S)-1-(4-Acetyl-piperazine-1-carbonyl)-piperidine-2-carboxylic acid (5-tert-butyl-isoxazol-3-yl)-amide | 406 | K |

TABLE 7-continued

Examples

| Example | Name | m/z [M + H+] | Method |
|---|---|---|---|
| 86 | (S)-1-(4-Propionyl-piperazine-1-carbonyl)-piperidine-2-carboxylic acid (5-tert-butyl-isoxazol-3-yl)-amide | 420 | K |
| 87 | (S)-2-(5-tert-Butyl-isoxazol-3-ylcarbamoyl)-piperidine-1-carboxylic acid tert-butyl ester | 352 | F |
| 88 | (S)-5'-trifluoromethyl-3,4,5,6-tetrahydro-2H-[1,2']bipyridinyl-2-carboxylic acid (5-tert-butyl-isoxazol-3-yl)-amide | 397 | H |
| 89 | (S)-3'-Chloro-5'-trifluoromethyl-3,4,5,6-tetrahydro-2H-[1,2']bipyridinyl-2-carboxylic acid (5-tert-butyl-isoxazol-3-yl)-amide | 431 | H |
| 90 | (S)-1-(Tetrahydro-pyran-4-carbonyl)-piperidine-2-carboxylic acid (5-tert-butyl-isoxazol-3-yl)-amide | 364 | F1 |

TABLE 7-continued

Examples

| Example | Structure | Name | m/z [M + H⁺] | Method |
|---|---|---|---|---|
| 91 | 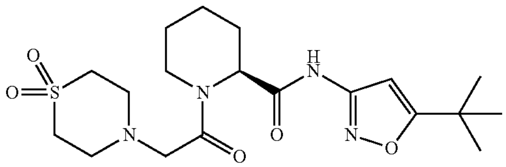 [SMILES: CC(C)(C)c1cc(NC(=O)[C@@H]2CCCCN2C(=O)CN2CCS(=O)(=O)CC2)no1] | (S)-1-[2-(1,1-Dioxo-1λ⁶-thiomorpholin-4-yl)-acetyl]-peridine-2-carboxylic acid (5-tert-butyl-isoxazol-3-yl)-amide | 427 | F1 |
| 92 | 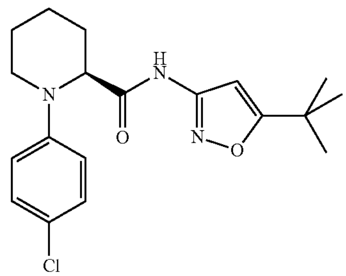 [SMILES: CC(C)(C)c1cc(NC(=O)[C@@H]2CCCCN2c2ccc(Cl)cc2)no1] | (S)-1-(4-Chloro-phenyl)-piperidine-2-carboxylic acid (5-tert-butyl-isoxazol-3-yl)-amide | 362 | I |
| 93 | 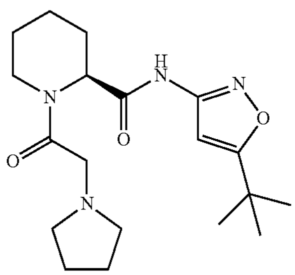 [SMILES: CC(C)(C)c1cc(NC(=O)[C@@H]2CCCCN2C(=O)CN2CCCC2)no1] | (S)-1-(2-Pyrrolidin-1-yl-acetyl)-piperidine-2-carboxylic acid (5-tert-butyl-isoxazol-3-yl)-amide | 363 | L |
| 94 | 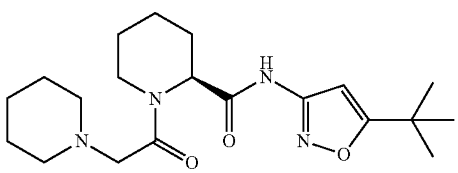 [SMILES: CC(C)(C)c1cc(NC(=O)[C@@H]2CCCCN2C(=O)CN2CCCCC2)no1] | (S)-1-(2-Piperidinyl-acetyl)-piperidine-2-carboxylic acid (5-tert-butyl-isoxazol-3-yl)-amide | 377 | L |
| 95 | 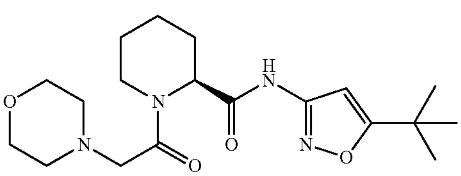 [SMILES: CC(C)(C)c1cc(NC(=O)[C@@H]2CCCCN2C(=O)CN2CCOCC2)no1] | (S)-1-(2-Morpholin-4-yl-acetyl)-piperidine-2-carboxylic acid (5-tert-butyl-isoxazol-3-yl)-amide | 379 | L |
| 96 | 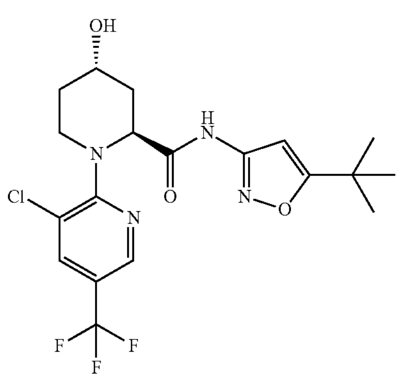 [SMILES: CC(C)(C)c1cc(NC(=O)[C@@H]2C[C@@H](O)CCN2c2ncc(C(F)(F)F)cc2Cl)no1] | (2S,4S)-3'-Chloro-4-hydroxy-5'-trifluoromethyl-3,4,5,6-tetrahydro-2H-[1,2']bipyridinyl-2-carboxylic acid (5-tert-butyl-isoxazol-3-yl)-amide | 447/449 | H |

TABLE 7-continued

Examples

| Example | Structure | Name | m/z [M + H⁺] | Method |
|---|---|---|---|---|
| 97 | 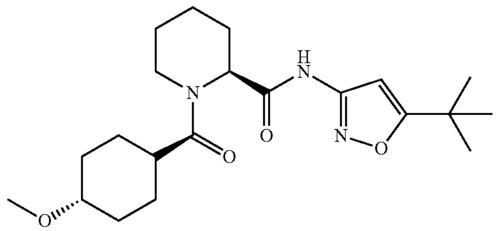 | (S)-1-(4-trans-Methoxy-cyclohexanecarbonyl)-piperidine-2-carboxylic acid (5-tert-butyl-isoxazol-3-yl)-amide | 392 | F1 |
| 98 | 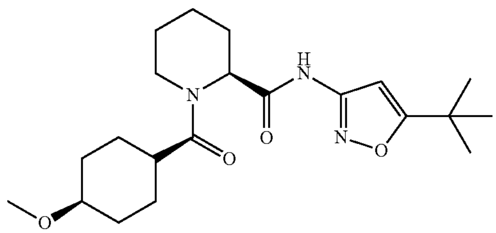 | (S)-1-(4-cis-Methoxy-cyclohexanecarbonyl)-piperidine-2-carboxylic acid (5-tert-butyl-isoxazol-3-yl)-amide | 392 | F1 |
| 99 | 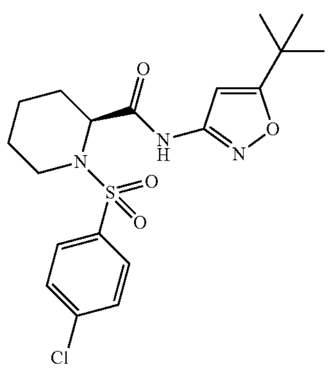 [SMILES: CC(C)(C)c1cc(NC(=O)[C@@H]2CCCCN2S(=O)(=O)c2ccc(Cl)cc2)no1] | (S)-1-(4-Chloro-benzenesulfonyl)-piperidine-2-carboxylic acid (5-tert-butyl-isoxazol-3-yl)-amide | 426 | O |
| 100 | 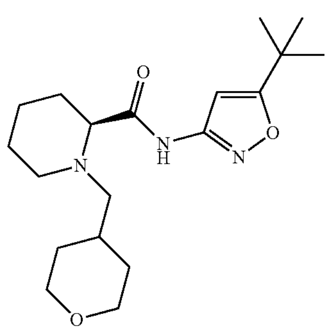 [SMILES: CC(C)(C)c1cc(NC(=O)[C@@H]2CCCCN2CC2CCOCC2)no1] | (S)-1-(Tetrahydro-pyran-4-ylmethyl)-piperidine-2-carboxylic acid (5-tert-butyl-isoxazol-3-yl)-amide | 350 | J1 |
| 101 | 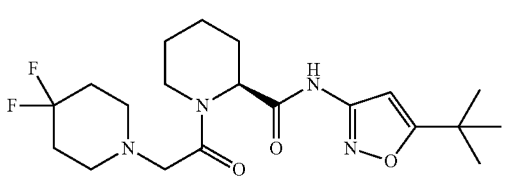 [SMILES: CC(C)(C)c1cc(NC(=O)[C@@H]2CCCCN2C(=O)CN2CCC(F)(F)CC2)no1] | (S)-1-[2-(4,4-Difluoro-piperidin-1-yl)-acetyl]-piperidine-2-carboxylic acid (5-tert-butyl-isoxazol-3-yl)-amide | 413 | L |

TABLE 7-continued

Examples

| Example | Name | m/z [M + H⁺] | Method |
|---|---|---|---|
| 102 | (S)-1-(Tetrahydro-pyran-4-yl)-piperidine-2-carboxylic acid (5-tert-butyl-isoxazol-3-yl)-amide | 336 | J1 |
| 103 | (S)-1-(2-Tetrahydro-pyran-4-yl-acetyl)-piperidine-2-carboxylic acid (5-tert-butyl-isoxazol-3-yl)-amide | 378 | F1 |
| 104 | (S)-1-((R)-2-Tetrahydro-furan-2-yl-acetyl)-piperidine-2-carboxylic acid (5-tert-butyl-isoxazol-3-yl)-amide | 364 | F1 |
| 105 | (S)-1-(1,1-Dioxo-1λ6-thiomorpholine-4-carbonyl)-piperidine-2-carboxylic acid (3-tert-butyl-isoxazol-5-yl)-amide | 413 | G |
| 106 | (S)-1-(4-Chloro-benzoyl)-piperidine-2-carboxylic acid (5-tert-butyl-isoxazol-3-yl)-amide | 390 | F1 |
| 107 | (S)-1-(4,4-Difluoro-piperidine-1-carbonyl)-piperidine-2-carboxylic acid (5-tert-butyl-isoxazol-3-yl)-amide | 399 | G |

TABLE 7-continued

Examples

| Example | Structure | Name | m/z [M + H⁺] | Method |
|---|---|---|---|---|
| 108 | 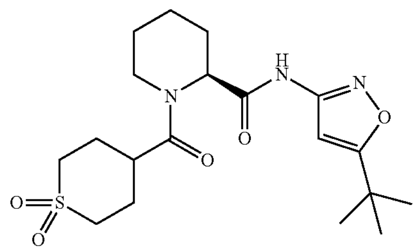 [SMILES: CC(C)(C)c1cc(NC(=O)[C@@H]2CCCCN2C(=O)C2CCS(=O)(=O)CC2)no1] | (S)-1-(1,1-Dioxo-hexahydro-1$\lambda^6$-thiopyran-4-carbonyl)-piperidine-2-carboxylic acid (5-tert-butyl-isoxazol-3-yl)-amide | 412 | F1 |
| 109 | 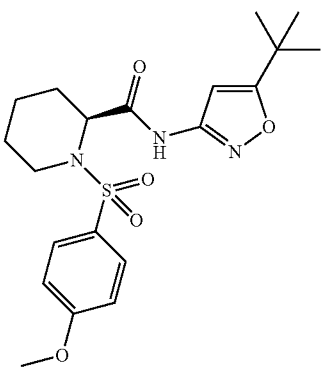 [SMILES: COc1ccc(S(=O)(=O)N2CCCC[C@H]2C(=O)Nc2cc(C(C)(C)C)on2)cc1] | (S)-1-(4-Methoxy-benzenesulfonyl)-piperidine-2-carboxylic acid (5-tert-butyl-isoxazol-3-yl)-amide | 442 | O |
| 110 | 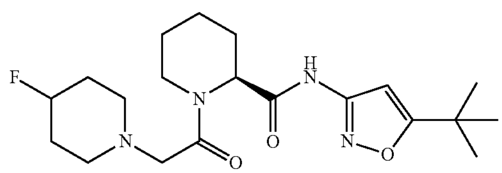 [SMILES: CC(C)(C)c1cc(NC(=O)[C@@H]2CCCCN2C(=O)CN2CCC(F)CC2)no1] | (S)-1-[2-(4-Fluoro-piperidin-1-yl)-acetyl]-piperidine-2-carboxylic acid (5-tert-butyl-isoxazol-3-yl)-amide | 395 | L |
| 111 | 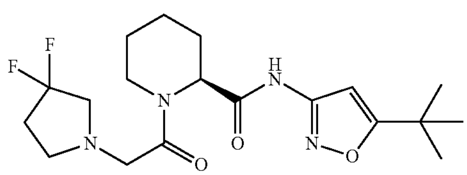 [SMILES: CC(C)(C)c1cc(NC(=O)[C@@H]2CCCCN2C(=O)CN2CCC(F)(F)C2)no1] | (S)-1-[2-(3,3-Difluoro-pyrrolidin-1-yl)-acetyl]-piperidine-2-carboxylic acid (5-tert-butyl-isoxazol-3-yl)-amide | 399 | L |
| 112 | 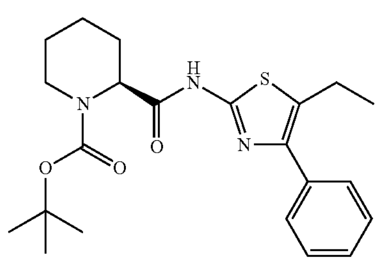 [SMILES: CCc1sc(NC(=O)[C@@H]2CCCCN2C(=O)OC(C)(C)C)nc1-c1ccccc1] | (S)-2-(5-Ethyl-4-phenyl-thiazol-2-ylcarbamoyl)-piperidine-1-carboxylic acid tert-butyl ester | 416 | F |
| 113 | 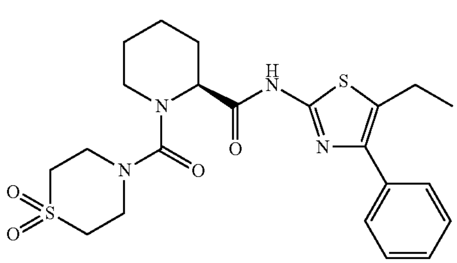 [SMILES: CCc1sc(NC(=O)[C@@H]2CCCCN2C(=O)N2CCS(=O)(=O)CC2)nc1-c1ccccc1] | (S)-1-(1,1-Dioxo-1$\lambda^6$-thiomorpholine-4-carbonyl)-piperidine-2-carboxylic acid (5-ethyl-4-phenyl-thiazol-2-yl)-amide | 477 | M1 |

TABLE 7-continued

Examples

| Example | Structure | Name | m/z [M + H⁺] | Method |
|---|---|---|---|---|
| 114 | 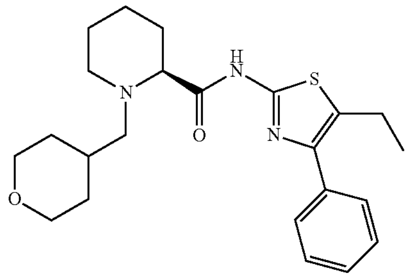 [SMILES: CCc1sc(NC(=O)[C@@H]2CCCCN2CC2CCOCC2)nc1-c1ccccc1] | (S)-1-(Tetrahydro-pyran-4-ylmethyl)-piperidine-2-carboxylic acid (5-ethyl-4-phenyl-thiazol-2-yl)-amide | 414 | J1 |
| 115 | 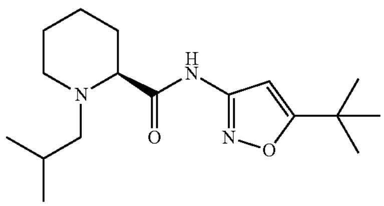 [SMILES: CC(C)CN1CCCC[C@H]1C(=O)Nc1cc(C(C)(C)C)on1] | (S)-1-Isobutyl-piperidine-2-carboxylic acid (5-tert-butyl-isoxazol-3-yl)-amide | 308 | J1 |
| 116 | 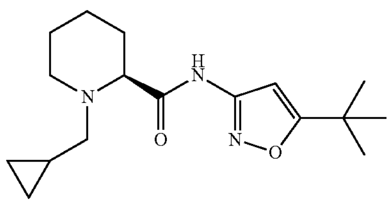 [SMILES: CC(C)(C)c1cc(NC(=O)[C@@H]2CCCCN2CC2CC2)no1] | (S)-1-Cyclopropylmethyl-piperidine-2-carboxylic acid (5-tert-butyl-isoxazol-3-yl)-amide | 306 | J1 |
| 117 | 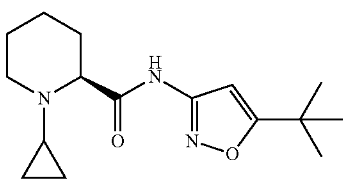 [SMILES: CC(C)(C)c1cc(NC(=O)[C@@H]2CCCCN2C2CC2)no1] | (S)-1-Cyclopropyl-piperidine-2-carboxylic acid (5-tert-butyl-isoxazol-3-yl)-amide | 292 | J2 |
| 118 | 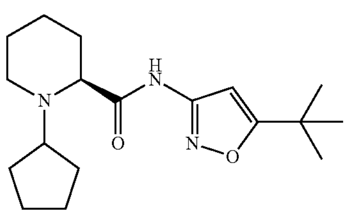 [SMILES: CC(C)(C)c1cc(NC(=O)[C@@H]2CCCCN2C2CCCC2)no1] | (S)-1-Cyclopentyl-piperidine-2-carboxylic acid (5-tert-butyl-isoxazol-3-yl)-amide | 320 | J1 |
| 119 | 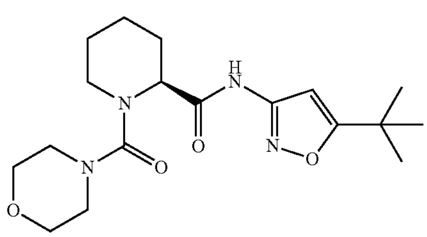 | (S)-1-(Morpholine-4-carbonyl)-piperidine-2-carboxylic acid (5-tert-butyl-isoxazol-3-yl)-amide | 365 | G |

TABLE 7-continued

Examples

| Example | Name | m/z [M + H+] | Method |
|---|---|---|---|
| 120 | (S)-1-(benzyl)-piperidine-2-carboxylic acid (5-tert-butyl-isoxazol-3-yl)-amide | 342 | J1 |
| 121 | (S)-1-(4-Chloro-benzyl)-piperidine-2-carboxylic acid (5-tert-butyl-isoxazol-3-yl)-amide | 376/378 | J1 |
| 122 | (S)-1-(3,4-Difluoro-benzyl)-piperidine-2-carboxylic acid (5-tert-butyl-isoxazol-3-yl)-amide | 378 | J1 |
| 123 | (S)-1-(Tetrahydro-pyran-4-ylmethyl)-piperidine-2-carboxylic acid (5-ethyl-1-phenyl-1H-1,2,4-triazol-3-yl)-amide | 398 | J1 |
| 124 | (S)-1-(1,1-Dioxo-1$\lambda^6$-thiomorpholine-4-carbonyl)-piperidine-2-carboxylic acid (5-ethyl-1-phenyl-1H-1,2,4-triazol-3-yl)-amide | 461 | G |

TABLE 7-continued

| Example | Name | m/z [M + H⁺] | Method |
|---|---|---|---|
| 125 | (S)-1-(1,1-Dioxo-tetrahydro-1$\lambda$6-thiophene-3-carbonyl)-piperidine-2-carboxylic acid (5-tert-butyl-isoxazol-3-yl)-amide | 398 | F1 |
| 126 | (S)-1-[2-(1,1-Dioxo-tetrahydro-1$\lambda^6$-thiophen-3-yl)-acetyl]-piperidine-2-carboxylic acid (5-tert-butyl-isoxazol-3-yl)-amide | 412 | F1 |
| 127 | (S)-2-(1-Ethyl-5-phenyl-1H-1,2,4-triazol-3-ylcarbamoyl)-piperidine-1-carboxylic acid tert-butyl ester | 400 | F |
| 128 | (S)-1-(1,1-Dioxo-1$\lambda^6$-thiomorpholine-4-carbonyl)-piperidine-2-carboxylic acid (1-ethyl-5-phenyl-1H-1,2,4-triazol-3-yl)-amide | 461 | G |
| 129 | (S)-1-(Tetrahydro-pyran-4-ylmethyl)-piperidine-2-carboxylic acid (1-ethyl-5-phenyl-1H-1,2,4-triazol-3-yl)-amide | 398 | J1 |
| 130 | (S)-1-(Tetrahydro-pyran-4-ylmethyl)-piperidine-2-carboxylic acid (5-tert-butyl-1,3,4-thiadiazol-2-yl)-amide | 367 | J1 |

TABLE 7-continued

| Example | Structure | Name | m/z [M + H+] | Method |
|---|---|---|---|---|
| 131 | 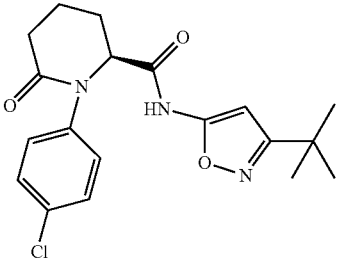 [SMILES: CC(C)(C)c1cc(NC(=O)[C@@H]2CCCC(=O)N2c2ccc(Cl)cc2)on1] | (S)-1-(4-Chloro-phenyl)-6-oxo-piperidine-2-carboxylic acid (3-tert-butyl-isoxazol-5-yl)-amide | 376/378 | N |
| 132 | 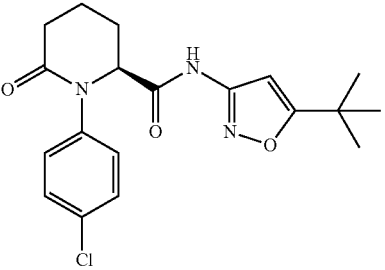 [SMILES: CC(C)(C)c1cc(NC(=O)[C@@H]2CCCC(=O)N2c2ccc(Cl)cc2)no1] | (S)-1-(4-Chloro-phenyl)-6-oxo-piperidine-2-carboxylic acid (5-tert-butyl-isoxazol-3-yl)-amide | 376/378 | N |
| 133 | 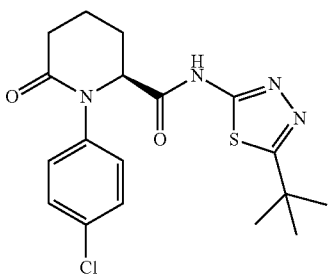 [SMILES: CC(C)(C)c1nnc(NC(=O)[C@@H]2CCCC(=O)N2c2ccc(Cl)cc2)s1] | (S)-1-(4-Chloro-phenyl)-6-oxo-piperidine-2-carboxylic acid (5-tert-butyl-1,3,4-thiadiazol-2-yl)-amide | 393/395 | N |
| 134 | 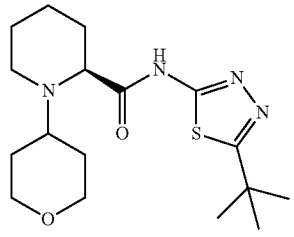 [SMILES: CC(C)(C)c1nnc(NC(=O)[C@@H]2CCCCN2C2CCOCC2)s1] | (S)-1-(Tetrahydro-pyran-4-yl)-piperidine-2-carboxylic acid (5-tert-butyl-1,3,4-thiadiazol-2-yl)-amide | 353 | J1 |
| 135 | 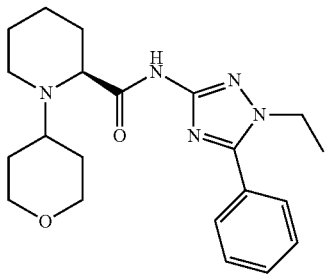 [SMILES: CCn1nc(NC(=O)[C@@H]2CCCCN2C2CCOCC2)nc1-c1ccccc1] | (S)-1-(Tetrahydro-pyran-4-yl)-piperidine-2-carboxylic acid (1-ethyl-5-phenyl-1H-1,2,4-triazol-3-yl)-amide | 384 | J1 |

TABLE 7-continued

Examples

| Example | Structure | Name | m/z [M + H+] | Method |
|---|---|---|---|---|
| 136 | 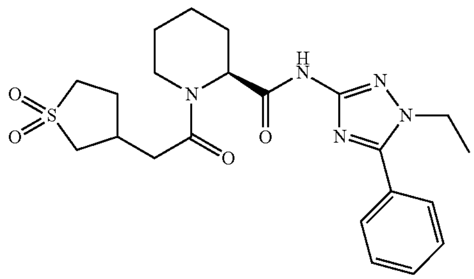 [SMILES: CCn1nc(NC(=O)[C@@H]2CCCCN2C(=O)CC2CCS(=O)(=O)C2)nc1-c1ccccc1] | (S)-1-[2-(1,1-Dioxo-tetrahydro-1λ6-thiophen-3-yl)-acetyl]-piperidine-2-carboxylic acid (1-ethyl-5-phenyl-1H-1,2,4-triazol-3-yl)-amide | 460 | F1 |
| 137 | 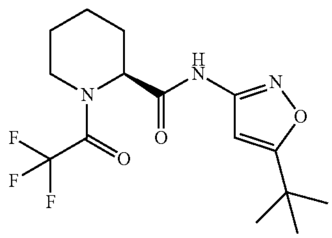 [SMILES: CC(C)(C)c1cc(NC(=O)[C@@H]2CCCCN2C(=O)C(F)(F)F)no1] | (S)-1-(2,2,2-Trifluoro-acetyl)-piperidine-2-carboxylic acid (5-tert-butyl-isoxazol-3-yl)-amide | 348 | F3 |
| 138 | 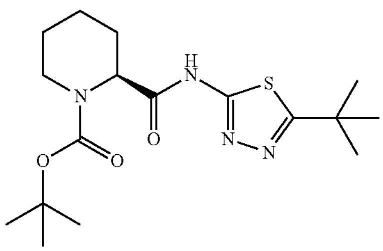 [SMILES: CC(C)(C)OC(=O)N1CCCC[C@H]1C(=O)Nc1nnc(C(C)(C)C)s1] | (S)-2-(5-tert-Butyl-1,3,4-thiadiazol-2-ylcarbamoyl)-piperidine-1-carboxylic acid tert-butyl ester | 369 | F |
| 139 | 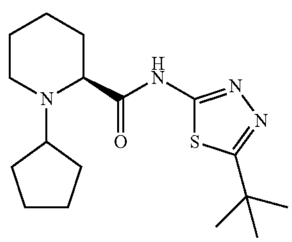 [SMILES: CC(C)(C)c1nnc(NC(=O)[C@@H]2CCCCN2C2CCCC2)s1] | (S)-1-Cyclopentyl-piperidine-2-carboxylic acid (5-tert-butyl-1,3,4-thiadiazol-2-yl)-amide | 337 | J1 |
| 140 | 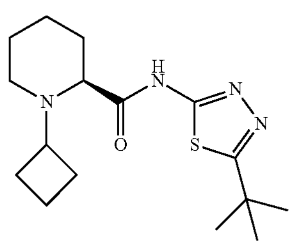 [SMILES: CC(C)(C)c1nnc(NC(=O)[C@@H]2CCCCN2C2CCC2)s1] | (S)-1-Cyclobutyl-piperidine-2-carboxylic acid (5-tert-butyl-1,3,4-thiadiazol-2-yl)-amide | 323 | J1 |
| 141 | 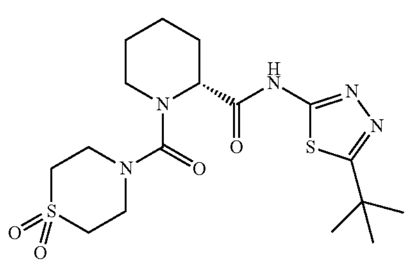 [SMILES: CC(C)(C)c1nnc(NC(=O)[C@H]2CCCCN2C(=O)N2CCS(=O)(=O)CC2)s1] | (R)-1-(1,1-Dioxo-1λ6-thiomorpholine-4-carbonyl)-piperidine-2-carboxylic acid (5-tert-butyl-1,3,4-thiadiazol-2-yl)-amide | 430 | G |

TABLE 7-continued

Examples

| Example | Name | m/z [M + H⁺] | Method |
|---|---|---|---|
| 142 | (S)-1-Cyclopropyl-piperidine-2-carboxylic acid (5-tert-butyl-1,3,4-thiadiazol-2-yl)-amide | 309 | J2 |
| 143 | (S)-1-[2-(3,3-Difluoro-pyrrolidin-1-yl)-acetyl]-piperidine-2-carboxylic acid (1-ethyl-5-phenyl-1H-1,2,4-triazol-3-yl)-amide | 447 | L |
| 144 | (S)-1-(1,1-Dioxo-1$\lambda^6$-thiomorpholine-4-carbonyl)-piperidine-2-carboxylic acid [5-(2-methoxy-1,1-dimethyl-ethyl)-isoxazol-3-yl]-amide | 443 | M2 |
| 145 | (S)-1-(1,1-Dioxo-1$\lambda^6$-thiomorpholine-4-carbonyl)-piperidine-2-carboxylic acid [5-(2-hydroxy-1,1-dimethyl-ethyl)-isoxazol-3-yl]-amide | 429 | M2 |
| 146 | (S)-1-(1,1-Dioxo-1$\lambda^6$-thiomorpholine-4-carbonyl)-piperidine-2-carboxylic acid (3-phenyl-1,2,4-thiadiazol-5-yl)-amide | 450 | G |
| 154 | (S)-1-(1,1-Dioxo-1$\lambda^6$-thiomorpholine-4-carbonyl)-piperidine-2-carboxylic acid [3-(4-methoxy-phenyl)-[1,2,4]thiadiazol-5-yl]-amide | 480 | F4 |

TABLE 7-continued

Examples

| Example | Structure | Name | m/z [M + H+] | Method |
|---|---|---|---|---|
| 155 | 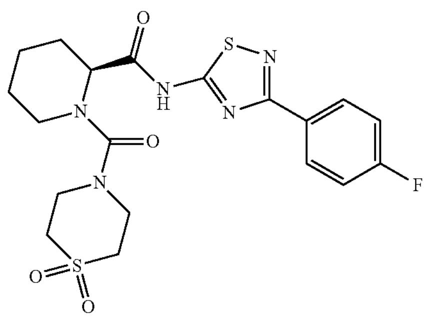 [SMILES: O=C(Nc1nc(-c2ccc(F)cc2)ns1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid [3-(4-fluoro-phenyl)-[1,2,4]thiadiazolo-5-yl]-amide | 468 | F4 |
| 156 | 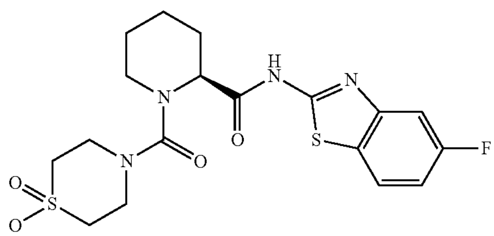 | (S)-1-(1,1-Dioxo-1λ6-thiomorpholine-4-carbonyl)-piperidine-2-carboxylic acid (5-fluoro-benzothiazol-2-yl)-amide | 441 | F4 |
| 157 | 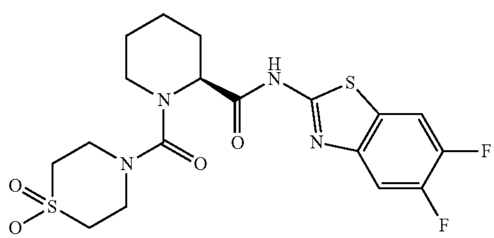 | (S)-1-(1,1-Dioxo-1λ6-thiomorpholine-4-carbonyl)-piperidine-2-carboxylic acid (5,6-difluoro-benzothiazol-2-yl)-amide | 459 | F4 |
| 158 | 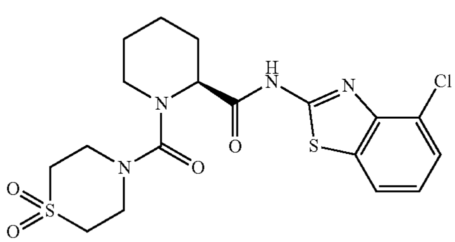 [SMILES: O=C(Nc1nc2c(Cl)cccc2s1)[C@@H]1CCCCN1C(=O)N1CCS(=O)(=O)CC1] | (S)-1-(1,1-Dioxo-1λ6-thiomorpholine-4-carbonyl)-piperidine-2-carboxylic acid (4-chloro-benzothiazol-2-yl)-amide | 457 | F4 |
| 159 | 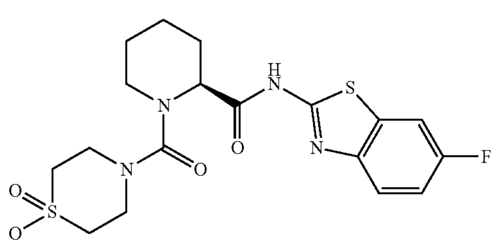 | (S)-1-(1,1-Dioxo-1λ6-thiomorpholine-4-carbonyl)-piperidine-2-carboxylic acid (6-fluoro-benzothiazol-2-yl)-amide | 441 | F4 |

TABLE 7-continued

Examples

| Example | Name | m/z [M + H+] | Method |
|---|---|---|---|
| 160 | (S)-1-(1,1-Dioxo-1λ$^6$-thiomorpholine-4-carbonyl)-piperidine-2-carboxylic acid [4-(4-chloro-phenyl)-thiazol-2-yl]-amide | 483 | F4 |
| 161 | (S)-1-(1,1-Dioxo-1λ$^6$-thiomorpholine-4-carbonyl)-piperidine-2-carboxylic acid [4-(3,4-difluoro-phenyl)-thiazol-2-yl]-amide | 485 | F4 |
| 162 | (S)-1-(1,1-Dioxo-1λ$^6$-thiomorpholine-4-carbonyl)-piperidine-2-carboxylic acid (6-chloro-benzothiazol-2-yl)-amide | 457 | F4 |
| 163 | (S)-1-(1,1-Dioxo-1λ$^6$-thiomorpholine-4-carbonyl)-piperidine-2-carboxylic acid (4-pyridin-2-yl-thiazol-2-yl)-amide | 451 | F4 |
| 164 | (S)-1-(1,1-Dioxo-1λ$^6$-thiomorpholine-4-carbonyl)-piperidine-2-carboxylic acid [4-(2,4-difluoro-phenyl)-thiazol-2-yl]-amide | 485 | F4 |

TABLE 7-continued

Examples

| Example | Name | m/z [M + H⁺] | Method |
|---|---|---|---|
| 165 | (S)-1-(1,1-Dioxo-1λ⁶-thiomorpholine-4-carbonyl)-piperidine-2-carboxylic acid [4-(4-fluoro-phenyl)-thiazol-2-yl]-amide | 467 | F4 |
| 166 | (S)-1-(1,1-Dioxo-1λ⁶-thiomorpholine-4-carbonyl)-piperidine-2-carboxylic acid (5-chloro-6-methyl-benzothiazol-2-yl)-amide | 471 | F4 |
| 167 | (S)-1-(1,1-Dioxo-1λ⁶-thiomorpholine-4-carbonyl)-piperidine-2-carboxylic acid (4-fluoro-benzothiazol-2-yl)-amide | 441 | F4 |
| 168 | (S)-1-(1,1-Dioxo-1λ⁶-thiomorpholine-4-carbonyl)-piperidine-2-carboxylic acid (5-chloro-4-methyl-benzothiazol-2-yl)-amide | 471 | F4 |

Compounds of Formula (IB)
Method P:

Synthesis of 4-(4-Trifluoromethyl-benzoyl)-morpholine-2-carboxylic acid (5-tert-butyl-isoxazol-3-yl)-amide (Example 147)

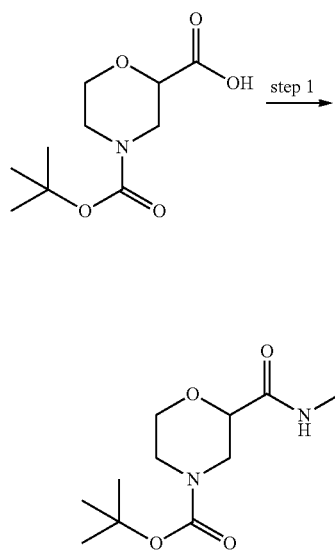

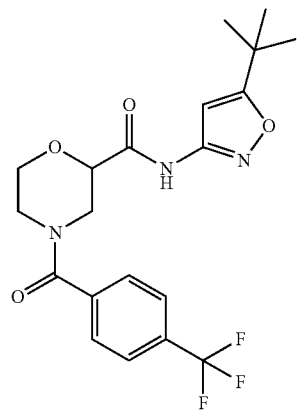

Step 1: Synthesis of 2-(5-tert-Butyl-isoxazol-3-ylcarbamoyl)-morpholine-4-carboxylic acid tert-butyl ester To a cold (0° C.) solution of morpholine-2,4-dicarboxylic acid 4-tert-butyl ester (1 g; 4.424 mmol) and 3-amino-5-t-butylisoxazole (606 mg; 4.324 mmol) and N,N-diisopropylethylamine (1.521 mL; 8.732 mmol) in anhydrous acetonitrile (12 mL) is added phosphorous oxychloride (0.39 mL; 4.424 mmol). The reaction mixture is stirred at room temperature for 18 hours. After this time, the reaction mixture is quenched with saturated NH4Cl aqueous solution and extracted with ethyl acetate twice. The organics are combined and washed with brine, dried over Na2SO4, filtered and concentrated under reduced pressure. Purification by flash chromatography on silica gel using ethyl acetate/Hexanes provides the title compound, m/z 354 [M+H⁺].

Amide intermediate in Table 8 is made in a similar manner.

TABLE 8

| Structure | Name | m/z [M + H⁺] |
| --- | --- | --- |
| 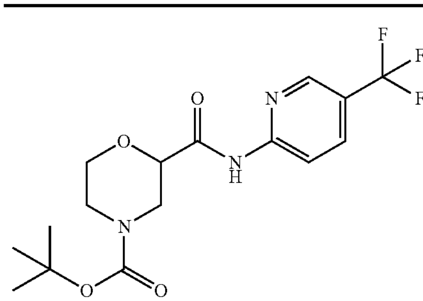 | 2-(5-Trifluoromethyl-pyridin-2-ylcarbamoyl)-morpholine-4-carboxylic acid tert-butyl ester | 376 |

Step 2: Synthesis of Morpholine-2-carboxylic acid (5-tert-butyl-isoxazol-3-yl)-amide; hydrochloride To a solution of 2-(5-tert-Butyl-isoxazol-3-ylcarbamoyl)-morpholine-4-carboxylic acid tert-butyl ester (1.143 g; 3.234 mmol) in methylene chloride (10 mL) is added 4N HCl in dioxanes (4 mL; 16 mmol). The reaction mixture is left stirring at room temperature for 18 hours. After this time, the reaction mixture is concentrated in vacuo to provide the title compound, m/z 254 [M+H$^+$].

Intermediate in Table 9 is made in a similar manner.

TABLE 9

| Structure | Name | m/z [M + H$^+$] |
|---|---|---|
| 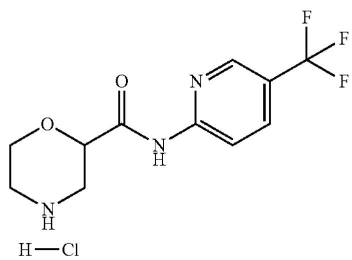 | Morpholine-2-carboxylic acid (5-trifluoromethyl-pyridin-2-yl)-amide; hydrochloride | 276 |

Step 3: Synthesis of 4-(4-Trifluoromethyl-benzoyl)-morpholine-2-carboxylic acid (5-tert-butyl-isoxazol-3-yl)-amide To a cold (0° C.) solution of morpholine-2-carboxylic acid (5-tert-butyl-isoxazol-3-yl)-amide; hydrochloride (75 mg; 0.259 mmol), 4-(trifluoromethyl)benzoic acid (49.2 mg; 0.259 mmol) and N,N-diisopropylethylamine (0.099 mL; 0.57 mmol) in anhydrous acetonitrile (2 mL) is added phosphorous oxychloride (0.023 mL; 0.259 mmol). The reaction mixture is left stirring at room temperature for 3.5 hours. After this time, the reaction mixture is quenched with saturated NH4Cl aqueous solution and extracted with ethyl acetate twice. The organics are combined and washed with brine, dried over Na2SO4, filtered and concentrated under reduced pressure. Purification by flash chromatography on silica gel using methanol/methylene chloride then trituation from hot methanol provides the title compound, m/z 426 [M+H$^+$].

Compounds in Table 10 Method P are prepared in a similar manner.

Method Q:

Synthesis of 4-(5-Trifluoromethyl-pyridin-2-yl)-morpholine-2-carboxylic acid (5-tert-butyl-isoxazol-3-yl)-amide (Example 149)

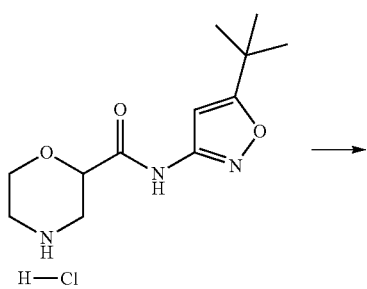

→

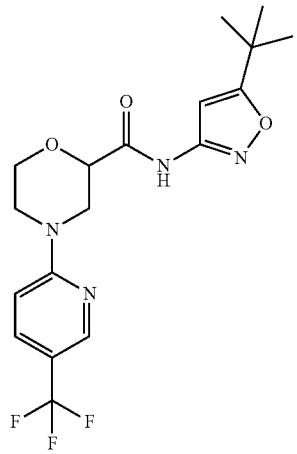

A microwave vial is charged with morpholine-2-carboxylic acid (5-tert-butyl-isoxazol-3-yl)-amide; hydrochloride (75 mg; 0.259 mmol), 2-bromo-5-trifluoromethylpyridine (58.8 mg; 0.26 mmol), triethylamine (0.072 mL; 0.52 mmol) and t-butanol (0.5 mL). The vial is heated in microwave at 175° C. for 1 hour then left standing at room temperature for 18 hours. After this time, the reaction mixture is concentrated in vacuo. Purification by flash chromatography using methanol/methylene chloride provides the title compound, m/z 399 [M+H$^+$].

Compounds in Table 10 Method Q are prepared in a similar manner.

TABLE 10

Examples

| Example | Structure | Name | m/z [M + H+] | Patent Method |
|---|---|---|---|---|
| 147 | 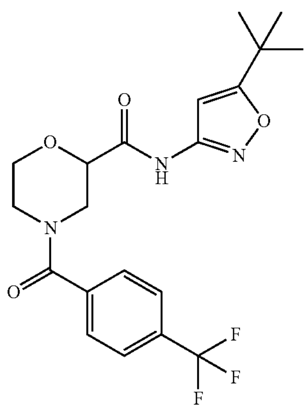 [SMILES: CC(C)(C)c1cc(NC(=O)C2CN(C(=O)c3ccc(C(F)(F)F)cc3)CCO2)no1] | 4-(4-Trifluoromethyl-benzoyl)-morpholine-2-carboxylic acid (5-tert-butyl-isoxazol-3-yl)-amide | 426 | P |
| 148 | 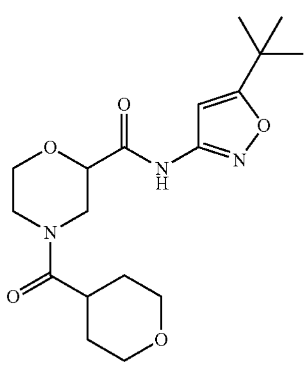 [SMILES: CC(C)(C)c1cc(NC(=O)C2CN(C(=O)C3CCOCC3)CCO2)no1] | 4-(Tetrahydro-pyran-4-carbonyl)-morpholine-2-carboxylic acid (5-tert-butyl-isoxazol-3-yl)-amide | 366 | P |
| 149 | 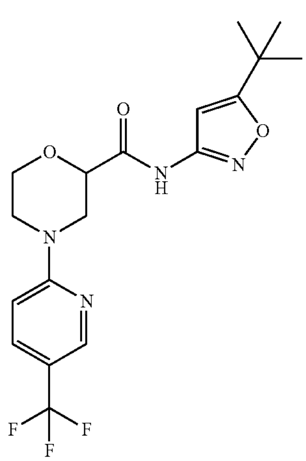 [SMILES: CC(C)(C)c1cc(NC(=O)C2CN(c3ccc(C(F)(F)F)cn3)CCO2)no1] | 4-(5-Trifluoromethyl-pyridin-2-yl)-morpholine-2-carboxylic acid (5-tert-butyl-isoxazol-3-yl)-amide | 399 | Q |

TABLE 10-continued

Examples

| Example | Structure | Name | m/z [M + H+] | Patent Method |
|---|---|---|---|---|
| 150 | 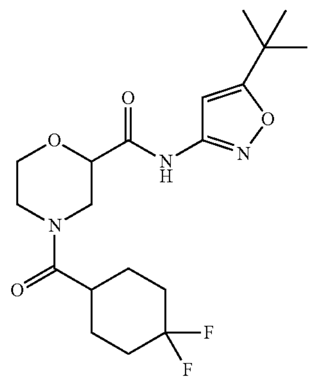 [SMILES: CC(C)(C)c1cc(NC(=O)C2CN(C(=O)C3CCC(F)(F)CC3)CCO2)no1] | 4-(4,4-Difluoro-cyclohexanecarbonyl)-morpholine-2-carboxylic acid (5-tert-butyl-isoxazol-3-yl)-amide | 400 | P |
| 151 | 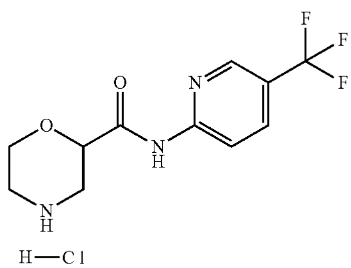 | Morpholine-2-carboxylic acid (5-trifluoromethyl-pyridin-2-yl)-amide; hydrochloride | 276 | P |

Compounds of Formula (IIB)

Method R:

Synthesis of 4-(4,4-Difluoro-cyclohexanecarbonyl)-morpholine-3-carboxylic acid (5-tert-butyl-isoxazol-3-yl)-amide (Example 152)

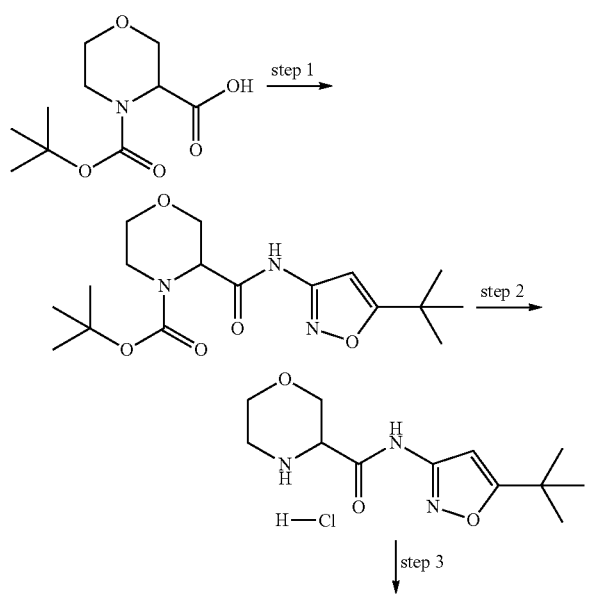

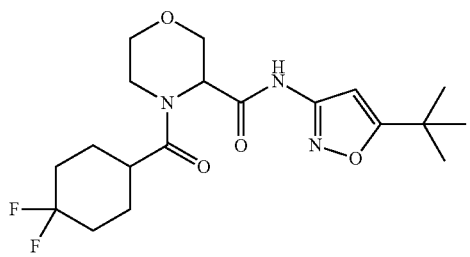 [SMILES: CC(C)(C)c1cc(NC(=O)C2COCCN2C(=O)C2CCC(F)(F)CC2)no1]

Step 1: Synthesis of 3-(5-tert-Butyl-isoxazol-3-ylcarbamoyl)-morpholine-4-carboxylic acid tert-butyl ester To a cold (0° C.) solution of morpholine-3,4-dicarboxylic acid 4-tert-butyl ester (100 mg; 0.432 mmol) and 3-amino-5-t-butylisoxazole (58.9 mg; 0.42 mmol) in anhydrous pyridine (1.2 mL) is added phosphorous oxychloride (0.039 mL; 0.432 mmol). The reaction mixture is left stirring at room temperature for 1 hour. After this time, the reaction mixture is quenched with saturated NH4Cl aqueous solution and extracted with ethyl acetate twice. The organics are combined and washed with brine, dried over Na2SO4, filtered and concentrated under reduced pressure. Purification by flash chromatography on silica gel using methanol/methylene chloride provides the title compound, m/z 354 [M+H+].

Step 2: Synthesis of Morpholine-3-carboxylic acid (5-tert-butyl-isoxazol-3-yl)-amide; hydrochloride To a solution of 3-(5-tert-butyl-isoxazol-3-ylcarbamoyl)-morpholine-4-carboxylic acid tert-butyl ester (87 mg; 0.246 mmol) in methylene chloride (2 mL) is added 4N HCl in dioxanes (0.615 mL; 2.46 mmol). The reaction mixture is left stirring at room temperature for 18 hours. After this time, the reaction mixture is concentrated in vacuo to provide the title compound, m/z 254 [M+H$^+$].

Step 3: Synthesis of 4-(4,4-Difluoro-cyclohexanecarbonyl)-morpholine-3-carboxylic acid (5-tert-butyl-isoxazol-3-yl)-amide To a cold (0° C.) solution of morpholine-3-carboxylic acid (5-tert-butyl-isoxazol-3-yl)-amide; hydrochloride (50 mg; 0.115 mmol), 4,4-difluorocyclohexanecarboxylic acid (18.9 mg, 0.115 mmol) and N,N-diisopropylethylamine (0.052 mL; 0.3 mmol) in anhydrous acetonitrile (2 mL) is added phosphorous oxychloride (0.01 mL; 0.115 mmol). The reaction mixture is left stirring at room temperature for 18 hours. After this time, the reaction mixture is quenched with saturated NH4Cl aqueous solution and extracted with ethyl acetate twice. The organics are combined and washed with brine, dried over Na2SO4, filtered and concentrated under reduced pressure. Purification by preparative LC-MS provides the title compound, m/z 400 [M+H$^+$].

Compounds in Table 11 Method R are prepared in a similar manner.

Method S:

Synthesis of 4-(4-Chloro-benzenesulfonyl)-morpholine-3-carboxylic acid (5-tert-butyl-isoxazol-3-yl)-amide (Example 153)

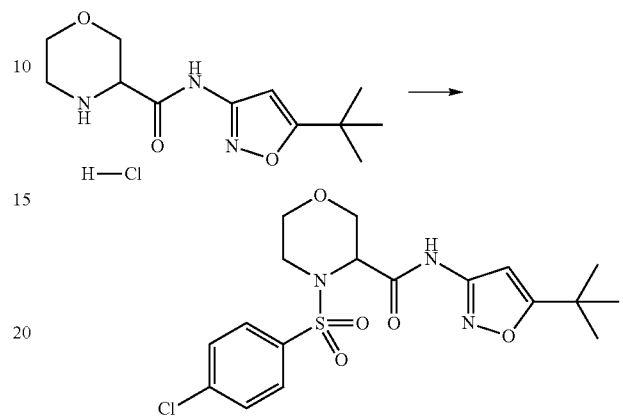

To a solution of morpholine-3-carboxylic acid (5-tert-butyl-isoxazol-3-yl)-amide; hydrochloride (55 mg; 0.19 mmol) in anhydrous DMF (1 mL) is added 4-chlorobenzenesulfonyl chloride (40.1 mg; 0.19 mmol) and N,N-diisopropylethylamine (0.089 mL; 0.513 mmol). The reaction mixture is left stirring at room temperature for 18 hours in the presence of catalytic amount of 4-dimethylaminopyridine. After this time, the reaction mixture is diluted with ethyl acetate and washed with eater 3 times, then brine, dried over Na2SO4, filtered and concentrated in vacuo. Recrystallization from hot methanol provides the title compound, m/z 428 [M+H$^+$].

Compounds in Table 11 Method S are prepared in a similar manner.

TABLE 11

| Example | Structure | Name | m/z [M + H$^+$] | Patent Method |
|---|---|---|---|---|
| 152 | 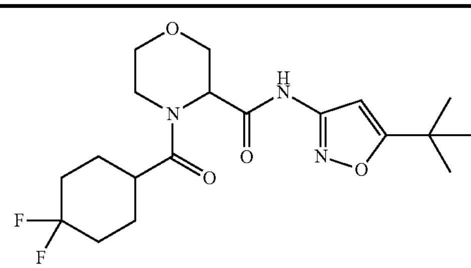 | 4-(4,4-Difluoro-cyclohexanecarbonyl)-morpholine-3-carboxylic acid (5-tert-butyl-isoxazol-3-yl)-amide | 400 | R |
| 153 | 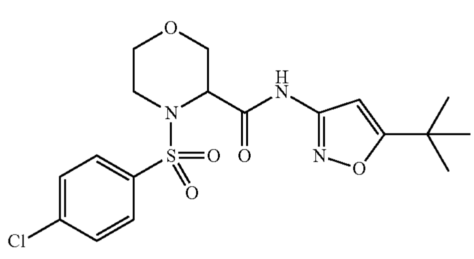 [SMILES: CC(C)(C)c1cc(NC(=O)C2COCCN2S(=O)(=O)c2ccc(Cl)cc2)no1] | 4-(4-Chloro-benzenesulfonyl)-morpholine-3-carboxylic acid (5-tert-butyl-isoxazol-3-yl)-amide | 428 | S |

Compounds of Formula (IC)
Method T

Synthesis of 1-(1,1-Dioxo-1λ⁶-thiomorpholine-4-carbonyl)-perhydro-azepine-2-carboxylic acid (5-tert-butyl-isoxazol-3-yl)-amide (Example 170)

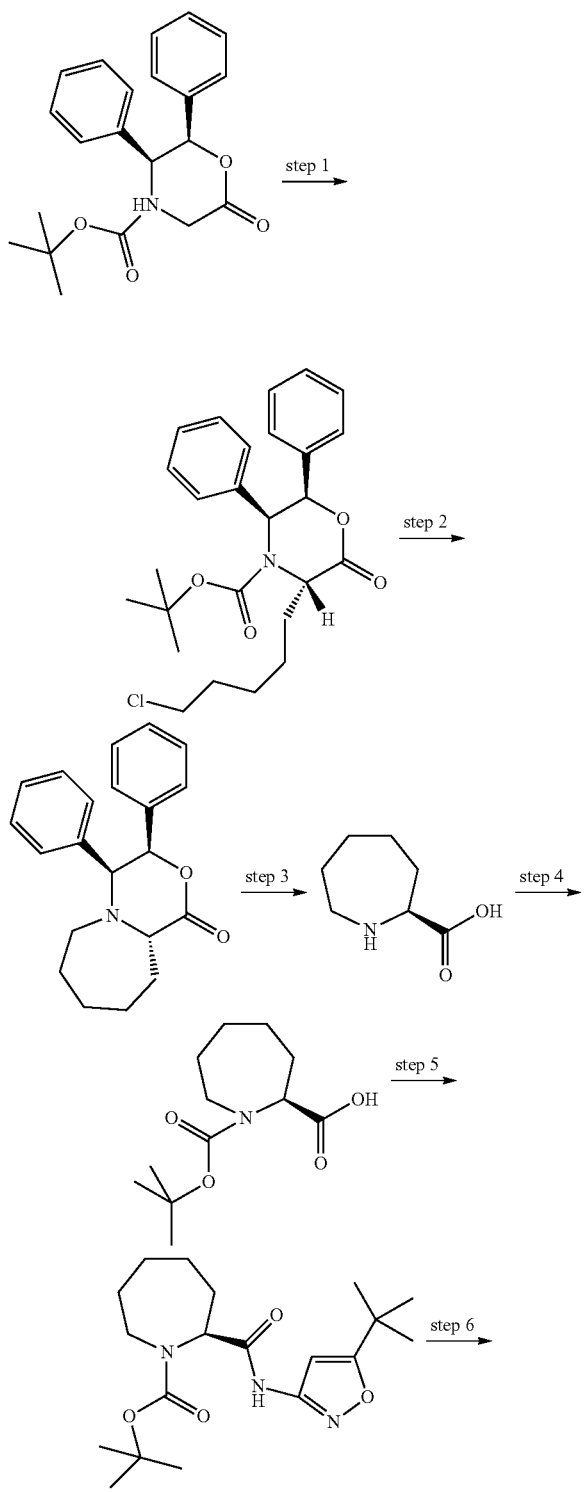

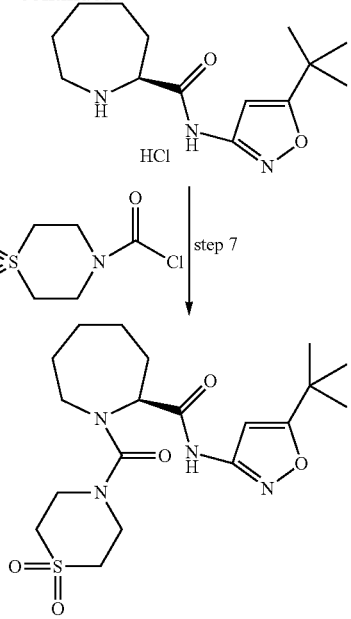

Step 1: Synthesis of (3S,5S,6R)-3-(5-Chloro-pentyl)-2-oxo-5,6-diphenyl-morpholine-4-carboxylic acid tert-butyl ester A 1.0M solution of sodium bis(trimethylsilyl)amide in THF (55.0 mL, 55.2 mmol) is added at −78° C. to a solution of (5S,6R)-5,6-diphenyl-4-tert-butoxycarbonyl-morpholin-2-one (13.0 g, 36.8 mmol), 1-chloro-5-iodo-pentane (25.0 g, 108.0 mmol) and HMPA (55.0 mL) in THF (200.0 mL). The reaction mixture is stirred at −78° C. for 2 hours and at room temperature for 1 hour. The reaction mixture is diluted with EtOAc, washed with water and brine. After drying the organic phase over anhydrous Na2SO4, the solvent is removed under reduced pressure to afford the crude product that is purified by silica gel column chromatography to afford the title compound; m/z 358 [M−Boc+H].

Step 2: Synthesis of (3R,4S,9aS)-3,4-Diphenyl-octahydro-2-oxa-4a-aza-benzocyclohepten-1-one A solution of TFA in DCM (20%, 60 mL) is added at 0° C. to (3S,5S,6R)-3-(5-chloro-pentyl)-2-oxo-5,6-diphenyl-morpholine-4-carboxylic acid tert-butyl ester (8.0 g, 17.5 mmol). The reaction mixture is slowly warmed up to room temperature and stirred for 4 hours. The reaction mixture is poured into a saturated $K_2CO_3$ solution, the two phases are separated and the water phase is extracted with DCM twice. The combined organic phases are dried over anhydrous $Na_2SO_4$ and removal of the solvent under reduced pressure affords 6.0 g of (3S,5S,6R)-3-(5-Chloro-pentyl)-5,6-diphenyl-morpholin-2-one trifluoroacetate.

A solution of the above crude, $K_2CO_3$ (2.89 g, 20.0 mmol) and KI (3.46 g, 20.9 mmol) in ACN (100.0 mL) is stirred under refluxing conditions for 24 hours. The reaction mixture is diluted with EtOAc and washed with water and brine. The organic phase is dried over anhydrous $Na_2SO_4$, and removal of the solvent under reduced pressure affords the crude that is purified via silica gel column chromatography to afford the title compound; m/z 322 [M+H].

Step 3: Synthesis of (S)-Perhydro-azepine-2-carboxylic acid

Palladium (II) chloride (800 mg, 4.51 mmol) is added to a solution of (3R,4S,9aS)-3,4-diphenyl-octahydro-2-oxa-4a-aza-benzocyclohepten-1-one (4.5 g, 14.0 mmol) in THF (140 mL) and EtOH (160 mL). The reaction mixture is stirred for 12 hours under $H_2$ atmosphere at 50 psi, then filtered through celite that is washed with EtOH. Removal of the solvent under reduced pressure affords the title compound m/z 144 [M+H].

Step 4: Synthesis of (S)-Perhydro-azepine-1,2-dicarboxylic acid 1-tert-butyl ester Triethylamine (3.46 g, 34.3 mmol) and di-tert-butyl dicarbonate (3.74 g, 17.2 mmol) are added in sequence at 0° C. to a solution of (S)-perhydro-azepine-2-carboxylic acid in THF (105 mL) and water (46 mL). After stirring at room temperature for 12 hours, the reaction mixture is extracted with diethyl ether. The water phase is acidified with 1N HCl and then extracted with diethyl ether. The combined organic layer is dried over anhydrous $Na_2SO_4$, filtered and concentrated under reduced pressure to afford the title compound that is used in the next step without further purification; m/z 242 [M−H].

Step 5: Synthesis of (S)-2-(5-tert-Butyl-isoxazol-3-ylcarbamoyl)-perhydro-azepine-1-carboxylic acid tert-butyl ester Phosphorus oxychloride (0.88 g, 5.73 mmol) is added drop wise at 0° C. to a solution of perhydro-azepine-1,2-dicarboxylic acid 1-tert-butyl ester (0.93 g, 3.82 mmol) and 5-tert-butyl-isoxazol-3-ylamine (0.54 g, 3.82 mol) in pyridine (10.0 mL). The reaction mixture is slowly warmed up to room temperature and stirred for three hours. The mixture is diluted with EtOAc and washed twice with saturated $NH_4Cl$ solution. The organic phase is washed with 1N HCl, and after drying over anhydrous $Na_2SO_4$ the solvent is removed under reduced pressure to afford the crude product that is used in the next step without further purification; m/z 366 [M+H$^+$].

Step 6: Synthesis of (S)-Perhydro-azepine-2-carboxylic acid (5-tert-butyl-isoxazol-3-yl)-amide hydrochloride HCl in dioxane (10.0 mL) is added slowly at 0° C. to a solution of (S)-2-(5-tert-butyl-isoxazol-3-ylcarbamoyl)-perhydro-azepine-1-carboxylic acid tert-butyl ester (0.70 g, 1.90 mmol) in DCM (15.0 mL). After stirring the reaction mixture at 0° C. for 3 hours, the solvent is removed under reduced pressure to afford the title product that is used in the next step without further purification.

Step 7: Synthesis of (S)-1-(1,1-Dioxo-1λ$^6$-thiomorpholine-4-carbonyl)-perhydro-azepine-2-carboxylic acid (5-tert-butyl-isoxazol-3-yl)-amide A solution of (S)-perhydro-azepine-2-carboxylic acid (5-tert-butyl-isoxazol-3-yl)-amide hydrochloride (0.30 g, 1.13 mmol), DIPEA (0.32 g, 2.48 mmol) and DMAP (16.0 mg, 0.13 mmol) is stirred at room temperature for 15 minutes. 1,1-Dioxo-1λ$^6$-thiomorpholine-4-carbonyl chloride (0.27 g, 1.35 mmol) (prepared according to method M step 1) is added drop wise at 0° C. to the reaction mixture that is slowly warmed up to room temperature and stirred for 14 hours. The reaction mixture is diluted with EtOAc, washed with water and brine. After drying the organic phase over anhydrous $Na_2SO_4$, removal of the solvent under reduced pressured affords the crude product that is purified by prep TLC to afford the title product; m/z 427 [M+H$^+$].

Method U

Synthesis of (S)-1-(Tetrahydro-pyran-4-ylmethyl)-azepane-2-carboxylic acid (5-tert-butyl-isoxazol-3-yl)-amide (Example 172)

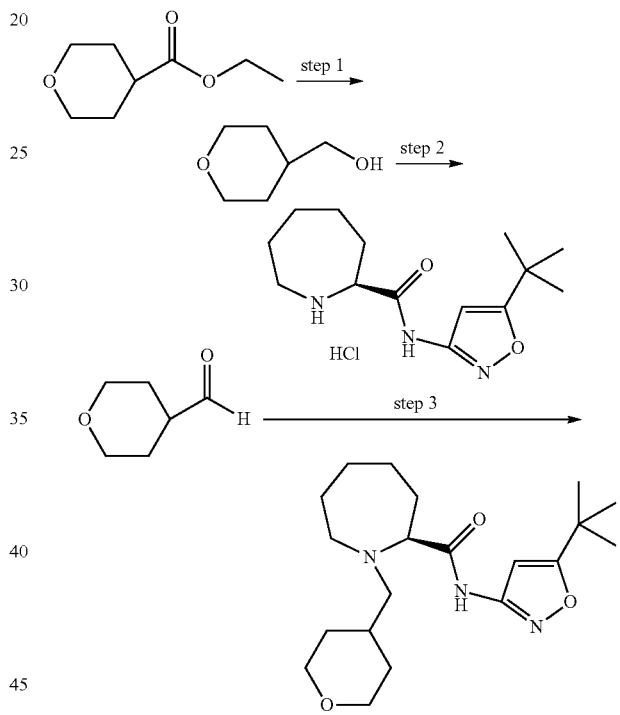

Step 1: Synthesis of (Tetrahydro-pyran-4-yl)-methanol

LiAlH$_4$ (1M in THF) (100.0 mL, mmol) is added at 0° C. to a solution of tetrahydro-pyran-4-carboxylic acid ethyl ester (25.0 g, 173.6 mmol) is THF (500.0 mL). The reaction mixture is warmed up to room temperature and stirred under reflux for five hours. The reaction mixture is cooled to room temperature and then 5.0 mL of water, 5.0 mL of 5N NaOH and 20.0 mL of water are added and the precipitated salts are filtered through a celite pad and washed with 1:1 Et$_2$O: MeOH. The filtrate is concentrated under reduced pressure to afford the title product.

Step 2: Synthesis of tetrahydro-pyran-4-carbaldehyde

Pyridinium chlorochromate (37.8 g, 175.0 mmol) is added to a solution of (tetrahydro-pyran-4-yl)-methanol (13.6 g, 117.0 mmol) in DCM (50.0 mL) at 0° C. The reaction mixture is stirred at room temperature for 12 hours. The reaction mixture is filtered through a pad of celite that is washed with diethyl ether. The filtrate is concentrated under reduced pressure to afford the title compound.

Step 3: Synthesis of (S)-1-(Tetrahydro-pyran-4-ylmethyl)-azepane-2-carboxylic acid (5-tert-butyl-isoxazol-3-yl)-amide Sodium cyanoborohydride (0.19 g, 3.02 mmol) and tetrahydro-pyran-4-carbaldehyde (0.26 g, 2.26 mmol) is added to a solution of (S)-perhydro-azepine-2-carboxylic acid (5-tert-butyl-isoxazol-3-yl)-amide hydrochloride (prepared according to Method T, step 6) (0.4 g, 1.51 mmol) in DMF (5.0 mL). After stirring for four hours, the reaction mixture is diluted with EtOAc and washed twice with water. The organic phase is dried over anhydrous Na₂SO₄ and after removal of the solvent under reduced pressure, the crude is purified by prep TLC to afford the title compound; m/z 364 [M+H].

Method V

Synthesis of (S)-1-(tetrahydro-pyran-4-yl)-azepane-2-carboxylic acid (5-tert-butyl-isoxazol-3-yl)-amide (Example 171)

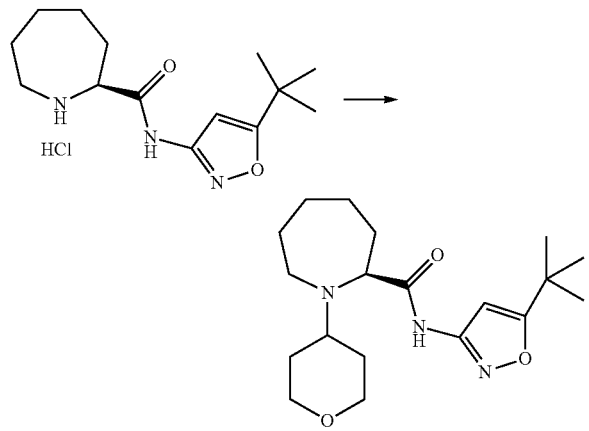

Sodium cyanoborohydride (71 mg, 1.13 mmol) and tetrahydro-pyran-4-one (75 mg, 0.75 mmol) are added to a solution of (S)-perhydro-azepine-2-carboxylic acid (5-tert-butyl-isoxazol-3-yl)-amide hydrochloride (prepared according to Method T, step 6) (0.2 g, 0.75 mmol) in DCM (8.0 mL). After stirring for four hours, the reaction mixture is diluted with EtOAc and washed twice with water. The organic phase is dried over anhydrous Na₂SO₄ and after removal of the solvent under reduced pressure, the crude is purified by prep TLC to afford the title compound; m/z 350 [M+H].

Method Z

Synthesis of (S)-1-(4-Chloro-phenyl)-azepane-2-carboxylic acid (5-tert-butyl-isoxazol-3-yl)-amide (Example 169)

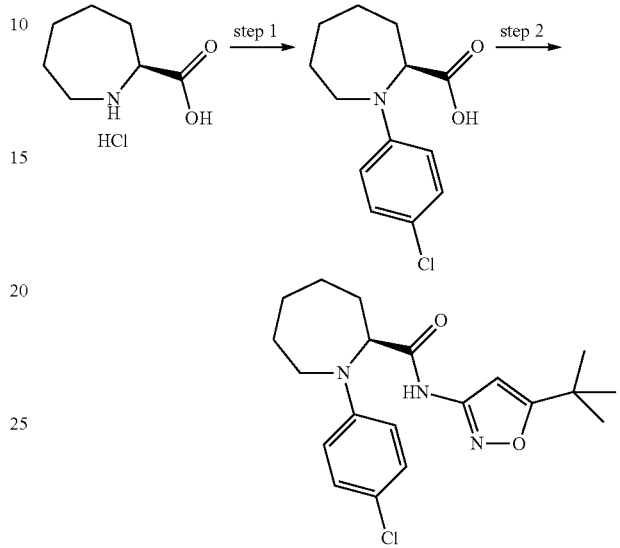

Step 1: Synthesis of (S)-1-(4-Chloro-phenyl)-azepane-2-carboxylic acid

A solution of (S)-perhydro-azepine-2-carboxylic acid (5-tert-butyl-isoxazol-3-yl)-amide hydrochloride (prepared according to Method T, step 6) (0.60 g, 4.20 mmol), 1-Bromo-4-chloro-benzene (0.80 g, 4.20 mmol), potassium carbonate (0.87 g, 6.29 mmol) and copper (I) iodide (0.08 g, 0.42 mmol) in DMA (10.0 mL), is heated at 100° C. in a sealed tube for 48 hours. The reaction mixture is diluted with EtOAc and washed with water. The water phase is acidified with 1N HCl and then extracted with EtOAc. The organic layers are combined, and after drying over anhydrous Na₂SO₄, removal of the solvent affords the title product that is used in the next step without any further purification. m/z 254 [M+H].

Step 2: Synthesis of (S)-1-(4-Chloro-phenyl)-azepane-2-carboxylic acid (5-tert-butyl-isoxazol-3-yl)-amide Phosphorus oxychloride (0.21 g, 1.38 mmol) is added drop wise at 0° C. to a solution of (S)-1-(4-chloro-phenyl)-azepane-2-carboxylic acid (0.23 g, 0.92 mmol) and 5-tert-butyl-isoxazol-3-ylamine (0.19 g, 1.38 mol) in pyridine. The reaction mixture is slowly warmed up to room temperature and stirred for three hours. The mixture is diluted with EtOAc and washed twice with saturated NH₄Cl solution. The organic phase is washed with 1N HCl, and after drying over anhydrous Na₂SO₄ the solvent is removed under reduced pressure to afford the crude product that is purified by prep TLC to afford the title compound; m/z 376 [M+H⁺].

TABLE 12

Examples

| Example | Structure | Name | m/z [M + H+] | Patent Method |
|---|---|---|---|---|
| 169 | 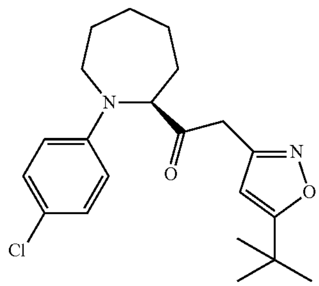 [SMILES: CC(C)(C)c1cc(CC(=O)[C@@H]2CCCCCN2c2ccc(Cl)cc2)no1] | (S)-1-(4-Chloro-phenyl)-azepane-2-carboxylic acid (5-tert-butyl-isoxazol-3-yl)-amide | 376 | Z |
| 170 | 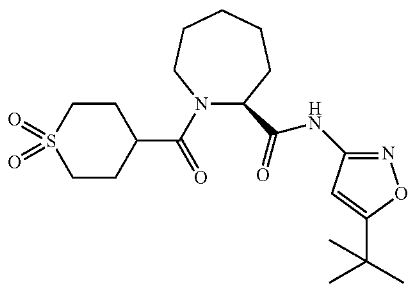 | (S)-1-(1,1-Dioxo-1$\lambda^6$-thiomorpholine-4-carbonyl)-azepane-2-carboxylic acid (5-tert-butyl-isoxazol-3-yl)-amide | 427 | T |
| 171 | 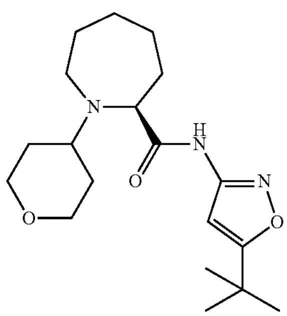 [SMILES: CC(C)(C)c1cc(NC(=O)[C@@H]2CCCCCN2C2CCOCC2)no1] | (S)-1-(Tretrahydro-pyran-4-yl)-azepane-2-carboxylic acid (5-tert-butyl-isoxazol-3-yl)-amide | 350 | V |
| 172 | 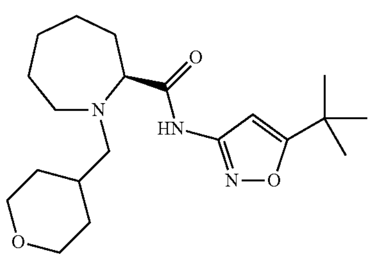 [SMILES: CC(C)(C)c1cc(NC(=O)[C@@H]2CCCCCN2CC2CCOCC2)no1] | (S)-1-(Tetrahydro-pyran-4-ylmelhyl)-azepane-2-carboxylic acid (5-tert-butyl-isoxazol-3-yl)-amide | 364 | U |

Assessment of Biological Properties

The biological properties of the compounds of the invention were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). 1050 values for each compound were calculated as the concentration of compound that inhibits the specific binding of the radioactively labeled ligand to the receptor by 50% using the XLFit 4.1 four parameter logistic model. 1050 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays compounds were found to exhibit agonistic activity and thus to be particularly well suited for the treatment of pain as well as for the treatment of inflammation. Preferred compounds had EC 50 values<500 nM.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:
1. A compound of the formula (IIA)

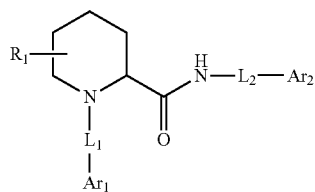

(IIA)

wherein
Ar$_1$ is chosen from phenyl, cyclopropyl, cyclobutyl, cyclopentyl, cyclohexyl, cycloheptyl, tetrahydrofuranyl, tetrahydropyranyl, tetrahydrothiopyranyl, tetrahydrothiopyran-1,1-dioxide, tetrahydrothiofuranyl, tetrahydrothiofuran-1,1-dioxide, thiomorpholinyl, 1-oxo-1λ$^4$-thiomorpholinyl, 1,1-dioxo-1λ$^6$-thiomorpholinyl, pyridinyl, pyrrolidinyl, piperidinyl and piperazinyl, each optionally substituted by 1-3 C$_{1-6}$ alkyl, trifluoromethyl, C$_{1-2}$ alkoxy, halogen, oxo, —C(O)—C$_{1-10}$ alkyl, —S(O)$_2$—C$_{1-3}$ alkyl or —CO$_2$—C$_{1-4}$ alkyl;
Ar$_2$ is chosen from cyclohexyl, benzothiazolyl, benzimidazolyl, oxazolyl, isoxazolyl, isothiazolyl, thiadiazolyl, triazolyl and pyridinyl, each optionally substituted by 1-3 C$_{1-6}$ alkyl, trifluoromethyl, cyclopropyl, cyclopentyl, cyclohexyl, phenyl optionally substituted by halogens, CN or halogen;

L$_1$ is chosen from a bond or C$_{1-3}$ alkyl chain wherein each —CH$_2$— of said chain is optionally replaced by C(O) or S(O)$_2$;

L$_2$ is chosen bond or C$_{2-3}$ alkyl chain wherein each —CH$_2$— of said chain is optionally replaced by S;

R$_1$ is chosen from hydrogen and oxo (=O);

or a pharmaceutically acceptable salt thereof.

2. The compound according to claim 1 and wherein:
R$_1$ is hydrogen.

3. A compound of the formula (IVA)

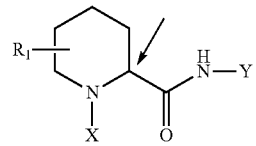

(IVA)

wherein

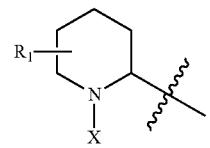

of the formula (IVA) is chosen from A1-A53 of Table II, and

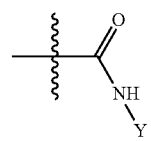

of the formula (IVA) is chosen from B1-B39 of Table II,

TABLE II

| | 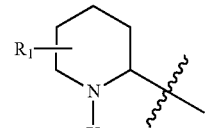 |
|---|---|
| A1 | 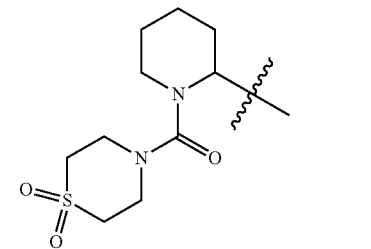 [SMILES: *C1CCCCN1C(=O)N1CCS(=O)(=O)CC1] |

TABLE II-continued
A2 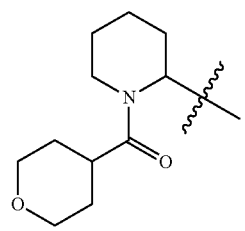
A3 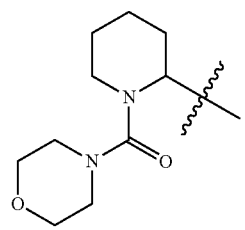
A4 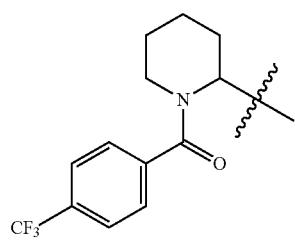 [SMILES: *C1CCCCN1C(=O)c1ccc(C(F)(F)F)cc1]
A5 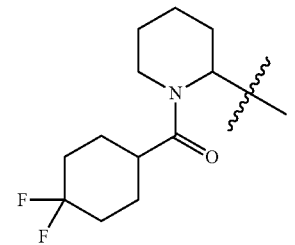 [SMILES: *C1CCCCN1C(=O)C1CCC(F)(F)CC1]
A6 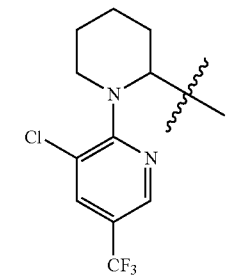 [SMILES: *C1CCCCN1c1ncc(C(F)(F)F)cc1Cl]
A7 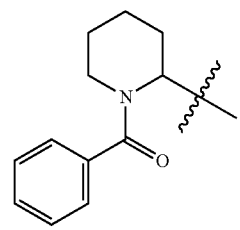 [SMILES: *C1CCCCN1C(=O)c1ccccc1]
TABLE II-continued
A8 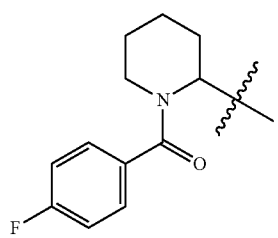 [SMILES: *C1CCCCN1C(=O)c1ccc(F)cc1]
A9 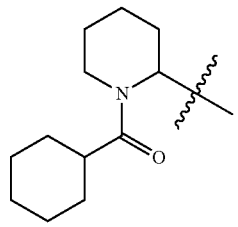 [SMILES: *C1CCCCN1C(=O)C1CCCCC1]
A10 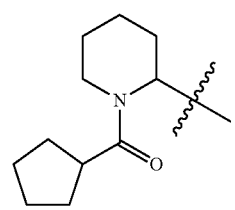 [SMILES: *C1CCCCN1C(=O)C1CCCC1]
A11 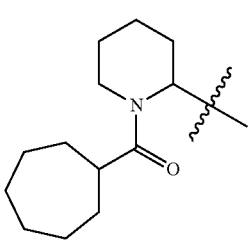 [SMILES: *C1CCCCN1C(=O)C1CCCCCC1]
A12 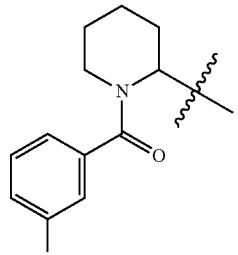
A13 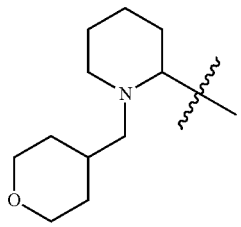 [SMILES: *C1CCCCN1CC1CCOCC1]

TABLE II-continued
A14 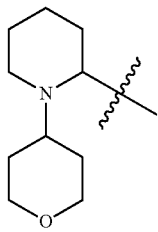 [SMILES: *C1CCCCN1C1CCOCC1]
A15 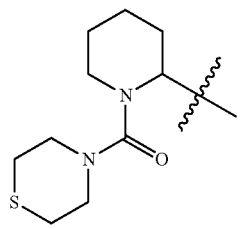 [SMILES: *C1CCCCN1C(=O)N1CCSCC1]
A16 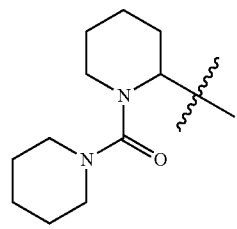 [SMILES: *C1CCCCN1C(=O)N1CCCCC1]
A17 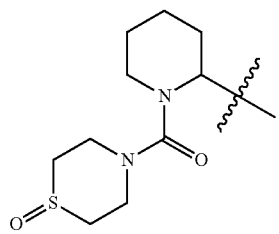 [SMILES: *C1CCCCN1C(=O)N1CCS(=O)CC1]
A18 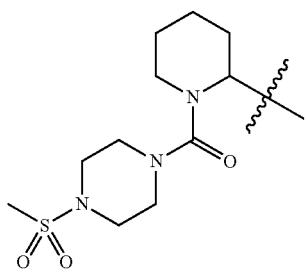 [SMILES: *C1CCCCN1C(=O)N1CCN(S(C)(=O)=O)CC1]
A19 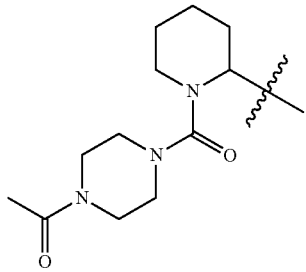 [SMILES: *C1CCCCN1C(=O)N1CCN(C(C)=O)CC1]
A20 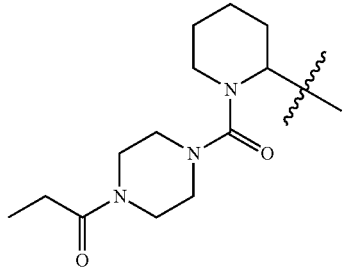 [SMILES: *C1CCCCN1C(=O)N1CCN(C(=O)CC)CC1]
A21 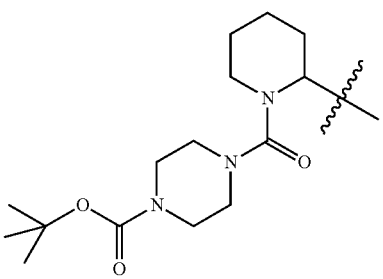 [SMILES: *C1CCCCN1C(=O)N1CCN(C(=O)OC(C)(C)C)CC1]
A22 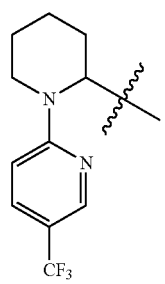 [SMILES: *C1CCCCN1c1ccc(C(F)(F)F)cn1]
A23 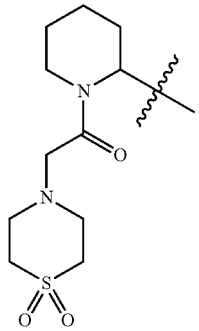 [SMILES: *C1CCCCN1C(=O)CN1CCS(=O)(=O)CC1]
A24 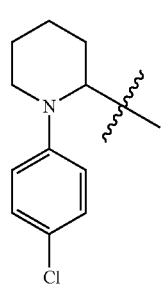 [SMILES: *C1CCCCN1c1ccc(Cl)cc1]

TABLE II-continued
| | |
|---|---|
| A25 | 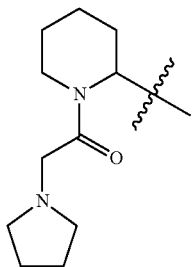 [SMILES: *C1CCCCN1C(=O)CN1CCCC1] |
| A26 | 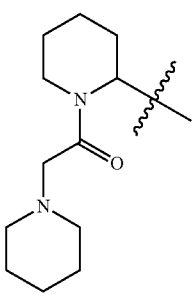 [SMILES: *C1CCCCN1C(=O)CN1CCCCC1] |
| A27 | 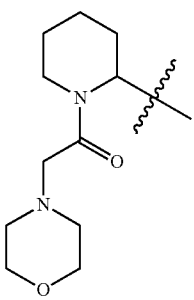 [SMILES: *C1CCCCN1C(=O)CN1CCOCC1] |
| A28 | 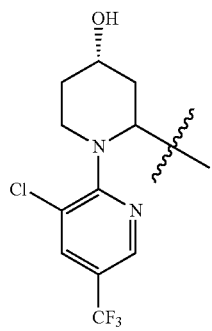 [SMILES: *C1C[C@@H](O)CCN1c1ncc(C(F)(F)F)cc1Cl] |
| A29 | 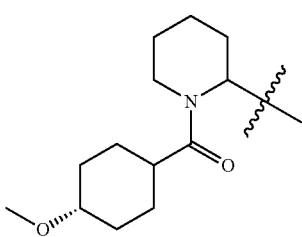 |
| A30 | 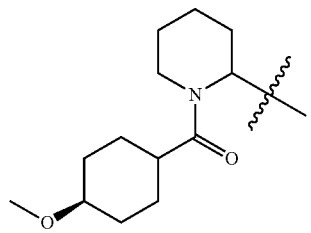 |
| A31 | 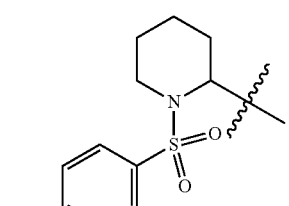 |
| A32 | 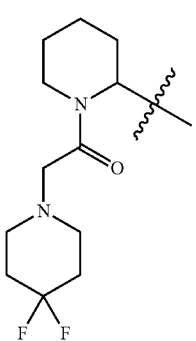 [SMILES: *C1CCCCN1C(=O)CN1CCC(F)(F)CC1] |
| A33 | 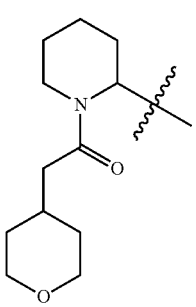 [SMILES: *C1CCCCN1C(=O)CC1CCOCC1] |
| A34 | 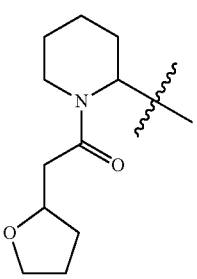 [SMILES: *C1CCCCN1C(=O)CC1CCCO1] |
| A35 | 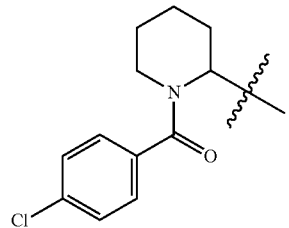 [SMILES: *C1CCCCN1C(=O)c1ccc(Cl)cc1] |

TABLE II-continued
| | |
|---|---|
| A36 | 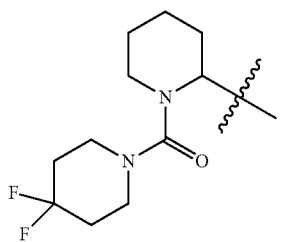 [SMILES: *C1CCCCN1C(=O)N1CCC(F)(F)CC1] |
| A37 | 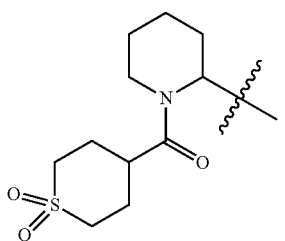 [SMILES: *C1CCCCN1C(=O)C1CCS(=O)(=O)CC1] |
| A38 | 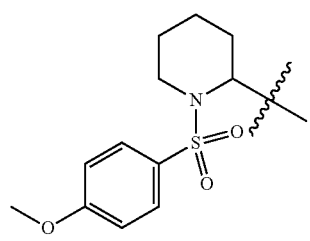 [SMILES: *C1CCCCN1S(=O)(=O)c1ccc(OC)cc1] |
| A39 | 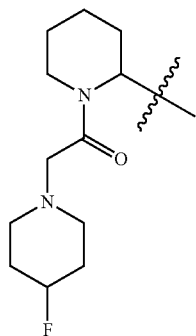 [SMILES: *C1CCCCN1C(=O)CN1CCC(F)CC1] |
| A40 | 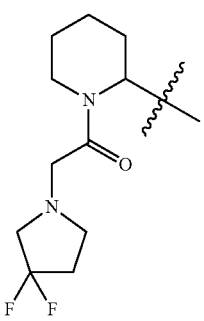 [SMILES: *C1CCCCN1C(=O)CN1CCC(F)(F)C1] |
| A41 | 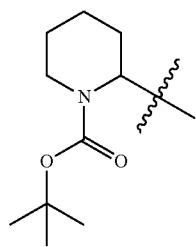 [SMILES: *C1CCCCN1C(=O)OC(C)(C)C] |
| A42 | 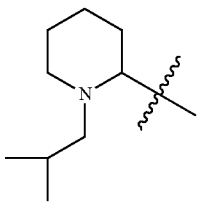 [SMILES: *C1CCCCN1CC(C)C] |
| A43 | 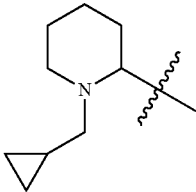 [SMILES: *C1CCCCN1CC1CC1] |
| A44 | 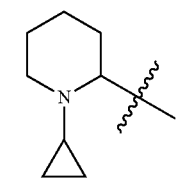 [SMILES: *C1CCCCN1C1CC1] |
| A45 | 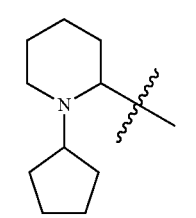 [SMILES: *C1CCCCN1C1CCCC1] |
| A46 | 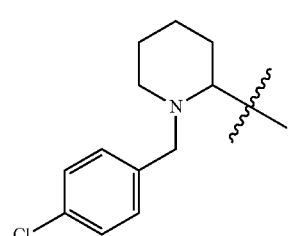 |
| A47 | 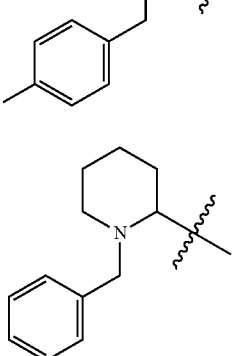 |
| A48 | 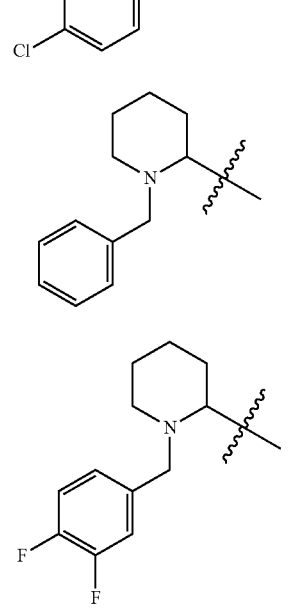 |

TABLE II-continued
A49 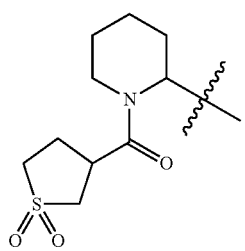 [SMILES: *C1CCCCN1C(=O)C1CCS(=O)(=O)C1]
A50 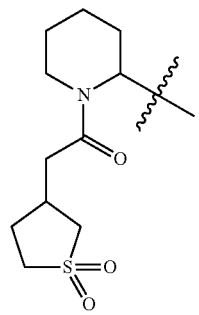 [SMILES: *C1CCCCN1C(=O)CC1CCS(=O)(=O)C1]
A51 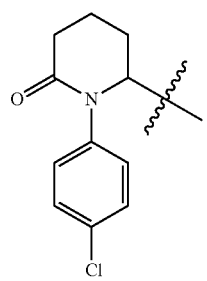 [SMILES: *C1CCCC(=O)N1c1ccc(Cl)cc1]
A52 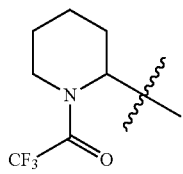
A53 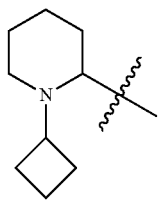 [SMILES: *C1CCCCN1C1CCC1]
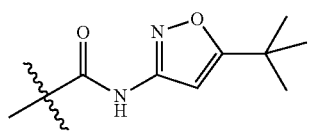 [SMILES: *C(=O)Nc1cc(C(C)(C)C)on1]
B1 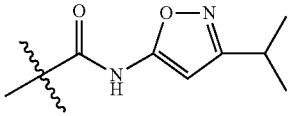 [SMILES: *C(=O)Nc1cc(C(C)C)no1]
TABLE II-continued
B2 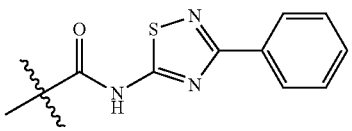
B3 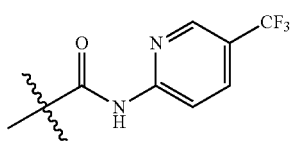 [SMILES: *C(=O)Nc1ccc(C(F)(F)F)cn1]
B4 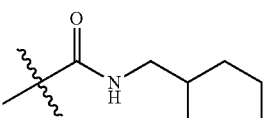
B5 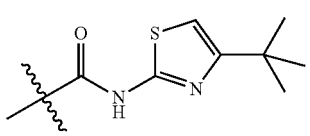 [SMILES: *C(=O)Nc1nc(C(C)(C)C)cs1]
B6 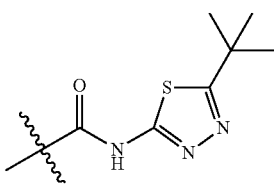 [SMILES: *C(=O)Nc1nnc(C(C)(C)C)s1]
B7 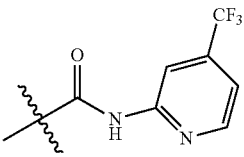 [SMILES: *C(=O)Nc1cc(C(F)(F)F)ccn1]
B8 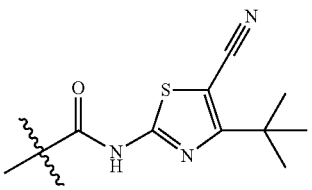 [SMILES: *C(=O)Nc1nc(C(C)(C)C)c(C#N)s1]
B9 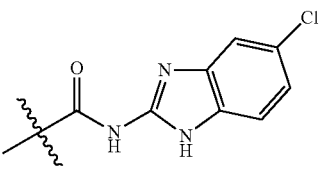 [SMILES: *C(=O)Nc1nc2cc(Cl)ccc2[nH]1]
B10 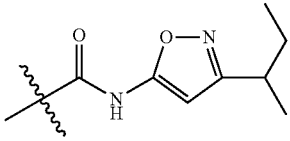 [SMILES: *C(=O)Nc1cc(C(C)CC)no1]
B11 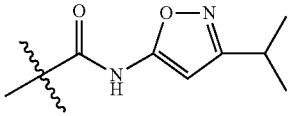 [SMILES: *C(=O)Nc1cc(C(C)C)no1]

TABLE II-continued
| | |
|---|---|
| B12 | 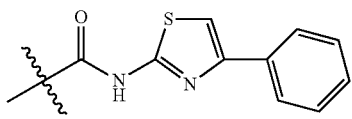 [SMILES: *C(=O)Nc1nc(-c2ccccc2)cs1] |
| B13 | 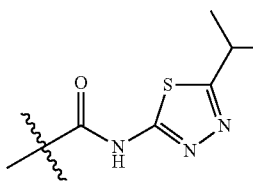 |
| B14 | 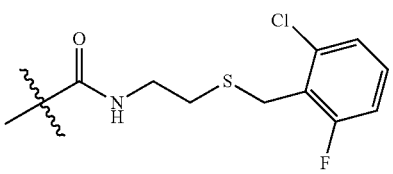 [SMILES: *C(=O)NCCSCc1c(F)cccc1Cl] |
| B15 | 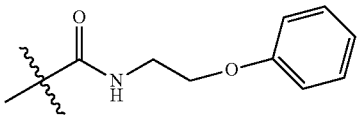 [SMILES: *C(=O)NCCOc1ccccc1] |
| B16 | 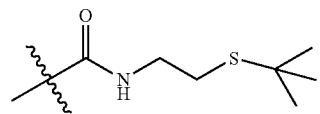 [SMILES: *C(=O)NCCSC(C)(C)C] |
| B17 | 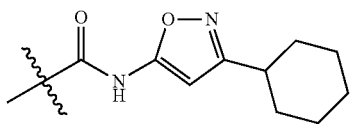 [SMILES: *C(=O)Nc1cc(C2CCCCC2)no1] |
| B18 | 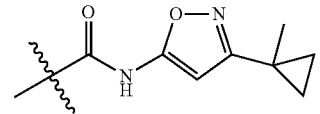 [SMILES: *C(=O)Nc1cc(C2(C)CC2)no1] |
| B19 | 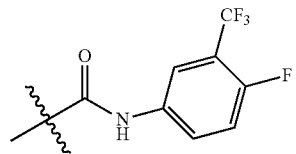 [SMILES: *C(=O)Nc1ccc(F)c(C(F)(F)F)c1] |
| B20 | 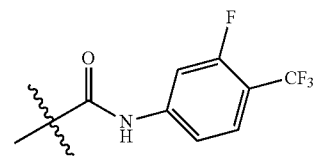 [SMILES: *C(=O)Nc1ccc(C(F)(F)F)c(F)c1] |
| B21 | 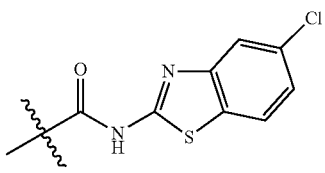 [SMILES: *C(=O)Nc1nc2cc(Cl)ccc2s1] |
TABLE II-continued
| | |
|---|---|
| B22 | 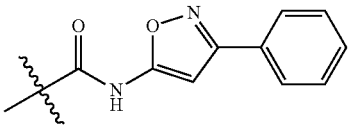 [SMILES: *C(=O)Nc1cc(-c2ccccc2)no1] |
| B23 | 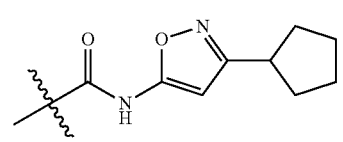 [SMILES: *C(=O)Nc1cc(C2CCCC2)no1] |
| B24 | 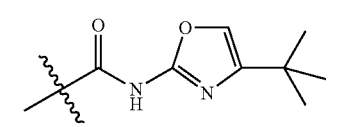 [SMILES: *C(=O)Nc1nc(C(C)(C)C)co1] |
| B25 | 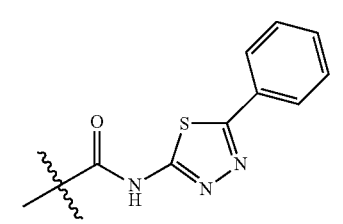 [SMILES: *C(=O)Nc1nnc(-c2ccccc2)s1] |
| B26 | 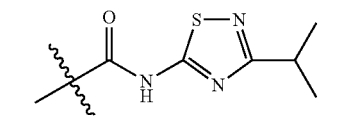 [SMILES: *C(=O)Nc1nc(C(C)C)ns1] |
| B27 | 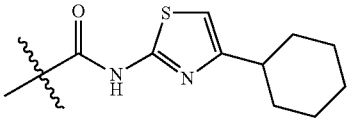 [SMILES: *C(=O)Nc1nc(C2CCCCC2)cs1] |
| B28 | 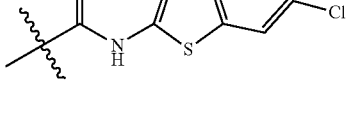 |
| B29 | 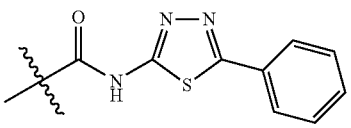 [SMILES: *C(=O)Nc1nnc(-c2ccccc2)s1] |
| B30 | 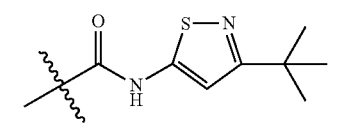 [SMILES: *C(=O)Nc1cc(C(C)(C)C)ns1] |
| B31 | 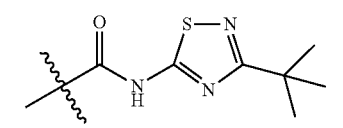 [SMILES: *C(=O)Nc1nc(C(C)(C)C)ns1] |
| B32 | 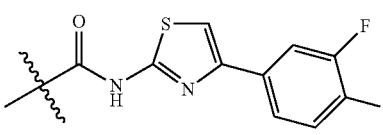 |

TABLE II-continued

| | |
|---|---|
| B33 | 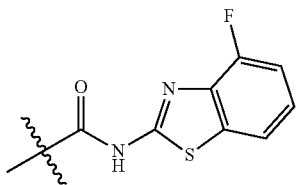 [SMILES: *C(=O)Nc1nc2c(F)cccc2s1] |
| B34 | 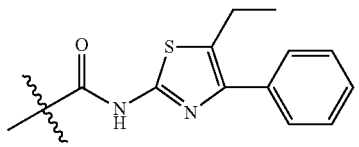 [SMILES: *C(=O)Nc1nc(-c2ccccc2)c(CC)s1] |
| B35 | 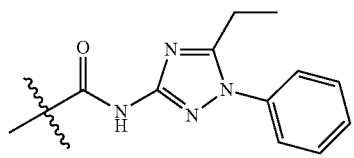 [SMILES: *C(=O)Nc1nc(CC)n(-c2ccccc2)n1] |
| B36 | 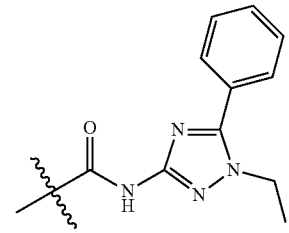 [SMILES: *C(=O)Nc1nc(-c2ccccc2)n(CC)n1] |
| B37 | 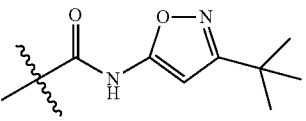 [SMILES: *C(=O)Nc1cc(C(C)(C)C)no1] |
| B38 | 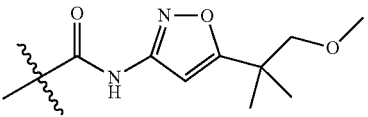 [SMILES: *C(=O)Nc1cc(C(C)(C)COC)on1] |

TABLE II-continued

| | |
|---|---|
| B39 | 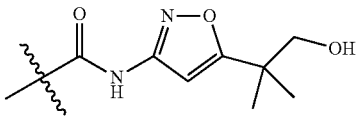 [SMILES: *C(=O)Nc1cc(C(C)(C)CO)on1] | or a pharmaceutically acceptable salt thereof.

4. The compounds according to claim 3 wherein the stereogenic carbon indicated with an arrow is in the (S) configuration.

5. The compound according to claim 1 wherein:
   $Ar_2$ is isoxazolyl substituted by 1-3 $C_{1-6}$ alkyl group.

6. The compound according to claim 1 wherein:
   $L_1$ is a bond or $C_{1-3}$ alkyl chain wherein each —$CH_2$— of said chain is optionally replaced by C(O);
   $L_2$ is a bond.

7. The compound according to claim 1 wherein:
   $Ar_1$ is chosen from phenyl, tetrahydropyranyl, thiomorpholinyl, 1-Oxo-1$\lambda^4$-thiomorpholinyl, and 1,1-dioxo-1$\lambda^6$-thiomorpholinyl, each optionally substituted chloro;
   $Ar_2$ is isoxazolyl substituted by 1-3 $C_{1-6}$ alkyl group;
   $L_1$ is a bond or $C_{1-2}$ alkyl chain wherein each —$CH_2$— of said chain is optionally replaced by C(O);
   $L_2$ is a bond.

8. The compound according to claim 1, wherein:
   $Ar_2$ is

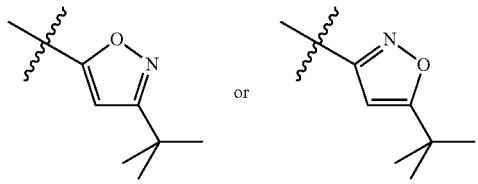

9. The compound according to claim 1 wherein:
   $Ar_1$ is chosen from phenyl optionally substituted chloro, tetrahydropyranyl, and 1,1-dioxo-1$\lambda^6$-thiomorpholinyl;
   $L_1$ is a bond or —$CH_2$—;
   $L_2$ is a bond.

10. A compound chosen from 1-(1,1-Dioxo-1$\lambda^6$-thiomorpholine-4-carbonyl)-piperidine-2-carboxylic acid (5-tert-butyl-isoxazol-3-yl)-amide
1-(Tetrahydro-pyran-4-carbonyl)-piperidine-2-carboxylic acid (5-tert-butyl-isoxazol-3-yl)-amide
1-(4-Trifluoromethyl-benzoyl)-piperidine-2-carboxylic acid (5-tert-butyl-isoxazol-3-yl)-amide
1-(4,4-Difluoro-cyclohexanecarbonyl)-piperidine-2-carboxylic acid (5-tert-butyl-isoxazol-3-yl)-amide
(R)-1-(4,4-Difluoro-cyclohexanecarbonyl)-piperidine-2-carboxylic acid (5-tert-butyl-isoxazol-3-yl)-amide
(S)-1-(4,4-Difluoro-cyclohexanecarbonyl)-piperidine-2-carboxylic acid (5-tert-butyl-isoxazol-3-yl)-amide
(S)-1-(1,1-Dioxo-1$\lambda^6$-thiomorpholine-4-carbonyl)-piperidine-2-carboxylic acid (5-tert-butyl-isoxazol-3-yl)-amide
(R)-1-(1,1-Dioxo-1$\lambda^6$-thiomorpholine-4-carbonyl)-piperidine-2-carboxylic acid (5-tert-butyl-isoxazol-3-yl)-amide
(S)-1-(4,4-Difluoro-cyclohexanecarbonyl)-piperidine-2-carboxylic acid (3-tert-butyl-isoxazol-5-yl)-amide
(S)-3'-Chloro-5'-trifluoromethyl-3,4,5,6-tetrahydro-2H-1,2'-bipyridinyl-2-carboxylic acid (3-phenyl-1,2,4-thiadiazol-5-yl)-amide
(S)-1-(4,4-Difluoro-cyclohexanecarbonyl)-piperidine-2-carboxylic acid (5-trifluoromethyl-pyridin-2-yl)-amide
(S)-1-Benzoyl-piperidine-2-carboxylic acid (5-tert-butyl-isoxazol-3-yl)-amide
(S)-1-(4-Fluoro-benzoyl)-piperidine-2-carboxylic acid (5-tert-butyl-isoxazol-3-yl)-amide S)-1-Cyclohexanecarbonyl-piperidine-2-carboxylic acid (5-tert-butyl-isoxazol-3-yl)-amide
(S)-1-Cyclopentanecarbonyl-piperidine-2-carboxylic acid (5-tert-butyl-isoxazol-3-yl)-amide
S)-1-Cycloheptanecarbonyl-piperidine-2-carboxylic acid (5-tert-butyl-isoxazol-3-yl)-amide
(S)-1-(3-Chloro-benzoyl)-piperidine-2-carboxylic acid (5-tert-butyl-isoxazol-3-yl)-amide
(S)-1-(1,1-Dioxo-1$\lambda^6$-thiomorpholine-4-carbonyl)-piperidine-2-carboxylic acid (5-tert-butyl-1,3,4-thiadiazol-2-yl)-amide
(S)-1-(1,1-Dioxo-1$\lambda^6$-thiomorpholine-4-carbonyl)-piperidine-2-carboxylic acid (5-chloro-1H-benzimidazol-2-yl)-amide
(S)-1-(1,1-Dioxo-1$\lambda^6$-thiomorpholine-4-carbonyl)-piperidine-2-carboxylic acid (3-sec-butyl-isoxazol-5-yl)-amide
(S)-1-(1,1-Dioxo-1$\lambda^6$-thiomorpholine-4-carbonyl)-piperidine-2-carboxylic acid (3-isopropyl-isoxazol-5-yl)-amide
(S)-1-(1,1-Dioxo-1$\lambda^6$-thiomorpholine-4-carbonyl)-piperidine-2-carboxylic acid (4-phenyl-thiazol-2-yl)-amide
(S)-1-(1,1-Dioxo-1$\lambda^6$-thiomorpholine-4-carbonyl)-piperidine-2-carboxylic acid [2-(2-chloro-6-fluoro-benzylsulfanyl)-ethyl]-amide
(S)-1-(1,1-Dioxo-1$\lambda^6$-thiomorpholine-4-carbonyl)-piperidine-2-carboxylic acid (3-cyclohexyl-isoxazol-5-yl)-amide
(S)-1-(1,1-Dioxo-1$\lambda^6$-thiomorpholine-4-carbonyl)-piperidine-2-carboxylic acid [3-(1-methyl-cyclopropyl)-isoxazol-5-yl]-amide
(S)-1-(1,1-Dioxo-1$\lambda^6$-thiomorpholine-4-carbonyl)-piperidine-2-carboxylic acid (5-chloro-benzothiazol-2-yl)-amide
(S)-1-(1,1-Dioxo-1$\lambda^6$-thiomorpholine-4-carbonyl)-piperidine-2-carboxylic acid (3-cyclopentyl-isoxazol-5-yl)-amide
(S)-1-(Tetrahydro-pyran-4-ylmethyl)-piperidine-2-carboxylic acid (4-tert-butyl-oxazol-2-yl)-amide
(S)-1-(Tetrahydro-pyran-4-ylmethyl)-piperidine-2-carboxylic acid (3-phenyl-1,2,4-thiadiazol-5-yl)-amide
(S)-1-(Tetrahydro-pyran-4-ylmethyl)-piperidine-2-carboxylic acid (4-fluoro-3-trifluoromethyl-phenyl)-amide
(S)-1-(Tetrahydro-pyran-4-ylmethyl)-piperidine-2-carboxylic acid (3-fluoro-4-trifluoromethyl-phenyl)-amide
(S)-1-(Tetrahydro-pyran-4-ylmethyl)-piperidine-2-carboxylic acid (3-isopropyl-1,2,4-thiadiazol-5-yl)-amide
(S)-1-(Tetrahydro-pyran-4-ylmethyl)-piperidine-2-carboxylic acid (4-cyclohexyl-thiazol-2-yl)-amide
(S)-1-(Tetrahydro-pyran-4-yl)-piperidine-2-carboxylic acid (5-chloro-benzothiazol-2-yl)-amide
(S)-1-(Tetrahydro-pyran-4-yl)-piperidine-2-carboxylic acid (4-cyclohexyl-thiazol-2-yl)-amide
(S)-1-(Tetrahydro-pyran-4-ylmethyl)-piperidine-2-carboxylic acid (3-tert-butyl-isothiazol-5-yl)-amide
(S)-1-(Tetrahydro-pyran-4-ylmethyl)-piperidine-2-carboxylic acid (3-tert-butyl-1,2,4-thiadiazol-5-yl)-amide
(S)-1-(Tetrahydro-pyran-4-ylmethyl)-piperidine-2-carboxylic acid (4-tert-butyl-thiazol-2-yl)-amide
(S)-1-(Tetrahydro-pyran-4-ylmethyl)-piperidine-2-carboxylic acid [4-(3,4-difluoro-phenyl)-thiazol-2-yl]-amide
(S)-1-(Tetrahydro-pyran-4-ylmethyl)-piperidine-2-carboxylic acid (5-phenyl-1,2,4-thiadiazol-3-yl)-amide
(S)-1-(Tetrahydro-pyran-4-ylmethyl)-piperidine-2-carboxylic acid (4-fluoro-benzothiazol-2-yl)-amide
(S)-1-(Tetrahydro-pyran-4-ylmethyl)-piperidine-2-carboxylic acid (4-phenyl-thiazol-2-yl)-amide
(S)-1-(Tetrahydro-pyran-4-ylmethyl)-piperidine-2-carboxylic acid (5-trifluoromethyl-pyridin-2-yl)-amide
(S)-1-(Tetrahydro-pyran-4-ylmethyl)-piperidine-2-carboxylic acid (6-chloro-benzothiazol-2-yl)-amide
(S)-1-(Tetrahydro-pyran-4-ylmethyl)-piperidine-2-carboxylic acid (4-trifluoromethyl-pyridin-2-yl)-amide
(S)-1-(Tetrahydro-pyran-4-ylmethyl)-piperidine-2-carboxylic acid (5-chloro-benzothiazol-2-yl)-amide
(S)-1-(Thiomorpholine-4-carbonyl)-piperidine-2-carboxylic acid (5-tert-butyl-isoxazol-3-yl)-amide
(S)-1-(Piperidine-1-carbonyl)-piperidine-2-carboxylic acid (5-tert-butyl-isoxazol-3-yl)-amide
(S)-1-(1-Oxo-1$\lambda^4$-thiomorpholine-4-carbonyl)-piperidine-2-carboxylic acid (5-tert-butyl-isoxazol-3-yl)-amide
(S)-1-(4-Acetyl-piperazine-1-carbonyl)-piperidine-2-carboxylic acid (5-tert-butyl-isoxazol-3-yl)-amide
(S)-1-(4-Propionyl-piperazine-1-carbonyl)-piperidine-2-carboxylic acid (5-tert-butyl-isoxazol-3-yl)-amide
(S)-2-(5-tert-Butyl-isoxazol-3-ylcarbamoyl)-piperidine-1-carboxylic acid tert-butyl ester (S)-5'-trifluoromethyl-3,4,5,6-tetrahydro-2H-[1,2']bipyridinyl-2-carboxylic acid (5-tert-butyl-isoxazol-3-yl)-amide
(S)-3'-Chloro-5'-trifluoromethyl-3,4,5,6-tetrahydro-2H-[1,2']bipyridinyl-2-carboxylic acid (5-tert-butyl-isoxazol-3-yl)-amide
(S)-1-(Tetrahydro-pyran-4-carbonyl)-piperidine-2-carboxylic acid (5-tert-butyl-isoxazol-3-yl)-amide
(S)-1-[2-(1,1-Dioxo-1$\lambda^6$-thiomorpholin-4-yl)-acetyl]-piperidine-2-carboxylic acid (5-tert-butyl-isoxazol-3-yl)-amide
(S)-1-(4-Chloro-phenyl)-piperidine-2-carboxylic acid (5-tert-butyl-isoxazol-3-yl)-amide
(S)-1-(2-Pyrrolidin-1-yl-acetyl)-piperidine-2-carboxylic acid (5-tert-butyl-isoxazol-3-yl)-amide
(S)-1-(2-Morpholin-4-yl-acetyl)-piperidine-2-carboxylic acid (5-tert-butyl-isoxazol-3-yl)-amide
(2S,4S)-3'-Chloro-4-hydroxy-5'-trifluoromethyl-3,4,5,6-tetrahydro-2H-[1,2']bipyridinyl-2-carboxylic acid (5-tert-butyl-isoxazol-3-yl)-amide
(S)-1-(4-cis-Methoxy-cyclohexanecarbonyl)-piperidine-2-carboxylic acid (5-tert-butyl-isoxazol-3-yl)-amide
(S)-1-(4-Chloro-benzenesulfonyl)-piperidine-2-carboxylic acid (5-tert-butyl-isoxazol-3-yl)-amide
(S)-1-(Tetrahydro-pyran-4-ylmethyl)-piperidine-2-carboxylic acid (5-tert-butyl-isoxazol-3-yl)-amide
(S)-1-[2-(4,4-Difluoro-piperidin-1-yl)-acetyl]-piperidine-2-carboxylic acid (5-tert-butyl-isoxazol-3-yl)-amide
(S)-1-(Tetrahydro-pyran-4-yl)-piperidine-2-carboxylic acid (5-tert-butyl-isoxazol-3-yl)-amide
(S)-1-(2-Tetrahydro-pyran-4-yl-acetyl)-piperidine-2-carboxylic acid (5-tert-butyl-isoxazol-3-yl)-amide
(S)-1-((R)-2-Tetrahydro-furan-2-yl-acetyl)-piperidine-2-carboxylic acid (5-tert-butyl-isoxazol-3-yl)-amide
(S)-1-(1,1-Dioxo-1$\lambda^6$-thiomorpholine-4-carbonyl)-piperidine-2-carboxylic acid (3-tert-butyl-isoxazol-5-yl)-amide
(S)-1-(4-Chloro-benzoyl)-piperidine-2-carboxylic acid (5-tert-butyl-isoxazol-3-yl)-amide
(S)-1-(4,4-Difluoro-piperidine-1-carbonyl)-piperidine-2-carboxylic acid (5-tert-butyl-isoxazol-3-yl)-amide
(S)-1-(1,1-Dioxo-hexahydro-1$\lambda$6-thiopyran-4-carbonyl)-piperidine-2-carboxylic acid (5-tert-butyl-isoxazol-3-yl)-amide
(S)-1-(4-Methoxy-benzenesulfonyl)-piperidine-2-carboxylic acid (5-tert-butyl-isoxazol-3-yl)-amide
(S)-1-[2-(4-Fluoro-piperidin-1-yl)-acetyl]-piperidine-2-carboxylic acid (5-tert-butyl-isoxazol-3-yl)-amide
(S)-1-[2-(3,3-Difluoro-pyrrolidin-1-yl)-acetyl]-piperidine-2-carboxylic acid (5-tert-butyl-isoxazol-3-yl)-amide
(S)-2-(5-Ethyl-4-phenyl-thiazol-2-ylcarbamoyl)-piperidine-1-carboxylic acid tert-butyl ester
(S)-1-(1,1-Dioxo-1$\lambda^6$-thiomorpholine-4-carbonyl)-piperidine-2-carboxylic acid (5-ethyl-4-phenyl-thiazol-2-yl)-amide
(S)-1-(Tetrahydro-pyran-4-ylmethyl)-piperidine-2-carboxylic acid (5-ethyl-4-phenyl-thiazol-2-yl)-amide
(S)-1-Isobutyl-piperidine-2-carboxylic acid (5-tert-butyl-isoxazol-3-yl)-amide
(S)-1-Cyclopropylmethyl-piperidine-2-carboxylic acid (5-tert-butyl-isoxazol-3-yl)-amide
(S)-1-Cyclopropyl-piperidine-2-carboxylic acid (5-tert-butyl-isoxazol-3-yl)-amide
(S)-1-Cyclopentyl-piperidine-2-carboxylic acid (5-tert-butyl-isoxazol-3-yl)-amide
(S)-1-(Morpholine-4-carbonyl)-piperidine-2-carboxylic acid (5-tert-butyl-isoxazol-3-yl)-amide
(S)-1-(benzyl)-piperidine-2-carboxylic acid (5-tert-butyl-isoxazol-3-yl)-amide
(S)-1-(4-Chloro-benzyl)-piperidine-2-carboxylic acid (5-tert-butyl-isoxazol-3-yl)-amide
(S)-1-(3,4-Difluoro-benzyl)-piperidine-2-carboxylic acid (5-tert-butyl-isoxazol-3-yl)-amide
(S)-1-(Tetrahydro-pyran-4-ylmethyl)-piperidine-2-carboxylic acid (5-ethyl-1-phenyl-1H-1,2,4-triazol-3-yl)-amide
(S)-1-(1,1-Dioxo-tetrahydro-1$\lambda^6$-thiophene-3-carbonyl)-piperidine-2-carboxylic acid (5-tert-butyl-isoxazol-3-yl)-amide
(S)-1-[2-(1,1-Dioxo-tetrahydro-1$\lambda^6$-thiophen-3-yl)-acetyl]-piperidine-2-carboxylic acid (5-tert-butyl-isoxazol-3-yl)-amide
(S)-1-(1,1-Dioxo-1$\lambda^6$-thiomorpholine-4-carbonyl)-piperidine-2-carboxylic acid (1-ethyl-5-phenyl-1H-1,2,4-triazol-3-yl)-amide
(S)-1-(Tetrahydro-pyran-4-ylmethyl)-piperidine-2-carboxylic acid (1-ethyl-5-phenyl-1H-1,2,4-triazol-3-yl)-amide
(S)-1-(Tetrahydro-pyran-4-ylmethyl)-piperidine-2-carboxylic acid (5-tert-butyl-1,3,4-thiadiazol-2-yl)-amide
(S)-1-(4-Chloro-phenyl)-6-oxo-piperidine-2-carboxylic acid (3-tert-butyl-isoxazol-5-yl)-amide
(S)-1-[2-(1,1-Dioxo-tetrahydro-1$\lambda^6$-thiophen-3-yl)-acetyl]-piperidine-2-carboxylic acid (1-ethyl-5-phenyl-1H-1,2,4-triazol-3-yl)-amide -continued (S)-1-(2,2,2-Trifluoro-acetyl)-piperidine-2-carboxylic acid (5-tert-butyl-isoxazol-3-yl)-amide
(S)-2-(5-tert-Butyl-1,3,4-thiadiazol-2-ylcarbamoyl)-piperidine-1-carboxylic acid tert-butyl ester
(S)-1-Cyclobutyl-piperidine-2-carboxylic acid (5-tert-butyl-1,3,4-thiadiazol-2-yl)-amide
(S)-1-Cyclopropyl-piperidine-2-carboxylic acid (5-tert-butyl-1,3,4-thiadiazol-2-yl)-amide
(S)-1-[2-(3,3-Difluoro-pyrrolidin-1-yl)-acetyl]-piperidine-2-carboxylic acid (1-ethyl-5-phenyl-1H-1,2,4-triazol-3-yl)-amide
(S)-1-(1,1-Dioxo-1$\lambda^6$-thiomorpholine-4-carbonyl)-piperidine-2-carboxylic acid [5-(2-methoxy-1,1-dimethyl-ethyl)-isoxazol-3-yl]-amide
(S)-1-(1,1-Dioxo-1$\lambda^6$-thiomorpholine-4-carbonyl)-piperidine-2-carboxylic acid (3-phenyl-1,2,4-thiadiazol-5-yl)-amide
(S)-1-(1,1-Dioxo-1$\lambda^6$-thiomorpholine-4-carbonyl)-piperidine-2-carboxylic acid [3-(4-methoxy-phenyl)-[1,2,4]thiadiazol-5-yl]-amide
(S)-1-(1,1-Dioxo-1$\lambda^6$-thiomorpholine-4-carbonyl)-piperidine-2-carboxylic acid [3-(4-fluoro-phenyl)-[1,2,4]thiadiazol-5-yl]-amide
(S)-1-(1,1-Dioxo-1$\lambda^6$-thiomorpholine-4-carbonyl)-piperidine-2-carboxylic acid (5-fluoro-benzothiazol-2-yl)-amide
(S)-1-(1,1-Dioxo-1$\lambda^6$-thiomorpholine-4-carbonyl)-piperidine-2-carboxylic acid (5,6-difluoro-benzothiazol-2-yl)-amide
(S)-1-(1,1-Dioxo-1$\lambda^6$-thiomorpholine-4-carbonyl)-piperidine-2-carboxylic acid (4-chloro-benzothiazol-2-yl)-amide
(S)-1-(1,1-Dioxo-1$\lambda^6$-thiomorpholine-4-carbonyl)-piperidine-2-carboxylic acid [4-(4-chloro-phenyl)-thiazol-2-yl]-amide
(S)-1-(1,1-Dioxo-1$\lambda^6$-thiomorpholine-4-carbonyl)-piperidine-2-carboxylic acid [4-(3,4-difluoro-phenyl)-thiazol-2-yl]-amide
(S)-1-(1,1-Dioxo-1$\lambda^6$-thiomorpholine-4-carbonyl)-piperidine-2-carboxylic acid [4-(2,4-difluoro-phenyl)-thiazol-2-yl]-amide
(S)-1-(1,1-Dioxo-1$\lambda^6$-thiomorpholine-4-carbonyl)-piperidine-2-carboxylic acid [4-(4-fluoro-phenyl)-thiazol-2-yl]-amide and
(S)-1-(1,1-Dioxo-1$\lambda^6$-thiomorpholine-4-carbonyl)-piperidine-2-carboxylic acid (4-fluoro-benzothiazol-2-yl)-amide or a pharmaceutically acceptable salt thereof.

11. A pharmaceutical composition comprising a therapeutically effective amount of a compound according to claim 1, and one or more pharmaceutically acceptable carriers and/or adjuvants.

12. A method of treating pain comprising administering a therapeutically effective amount of a compound according to 1.

13. The method according to claim 12 wherein the pain is acute pain, visceral pain, neuropathic pain, inflammatory and nociceptive pain, cancer pain and headache.

* * * * *